US006444425B1

(12) United States Patent
Reed et al.

(10) Patent No.: US 6,444,425 B1
(45) Date of Patent: Sep. 3, 2002

(54) COMPOUNDS FOR THERAPY AND DIAGNOSIS OF LUNG CANCER AND METHODS FOR THEIR USE

(75) Inventors: Steven G. Reed, Bellevue; Michael J. Lodes, Seattle; Raodoh Mohamath, Seattle; Heather Secrist, Seattle, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/370,838

(22) Filed: Aug. 9, 1999

Related U.S. Application Data

(63) Continuation-in-part of application No. 09/285,323, filed on Apr. 2, 1999.

(51) Int. Cl.[7] .................................................. C12Q 1/68
(52) U.S. Cl. ........................................... 435/6; 435/91.2
(58) Field of Search ...................... 435/6, 91.1; 436/63, 436/94

(56) References Cited

FOREIGN PATENT DOCUMENTS

| | | |
|---|---|---|
| WO | WO 96/02552 | 2/1996 |
| WO | WO 99/38973 | 8/1999 |

OTHER PUBLICATIONS

Chen et al., "Isolation and characterization of a novel gene expressed in multiple cancers," *Oncogene*, 12:741–751, Feb. 15, 1996.
El–Deiry W., "Role of oncogenes in resistance and killing by cancer therapeutic agents," *Current Opinion in Oncology* 9(1):79–87, Jan. 1997.
Gure et al., "Human lung cancer antigens recognized by autologous antibodies: definition of a novel cDNA dervied form the tumor suppressor gene locus on chromosome 3p21.3," *Cancer Research*, 58:1034–1041, Mar. 1, 1998.
Heller et al., "Discovery and analysis of inflammatory disease–related genes using cDNA micorarrays," *Proc. Natl. Acad. Sci. USA* 94;2150–2155, Mar. 1997.
Okamoto et al., "Overexpression of human mutT homologue gene messenger RNA in renal–cell carcinoma: evidence of persistent oxidative stress in cancer," *International Journal of Cancer* 65(4):437–441, Feb. 8, 1996.
Porter et al., "Mechanistic studies of the inhibition of MutT dGTPase by the carcinogenic metal Ni(II)," *Chem. Res. Toxicol.* 9(8):1375–1381, Dec. 1996.
Schena et al., "Parallel human genome analysis: mciroarray–based expression monitoring of 1000 genes," *Proc. Natl. Acad. Sci. USA* 93:10614–10619, Oct. 1996.
Wu et al., "Polymorphisms and probable lack of mutation in a human mutT homolog, hMTH1, in hereditary nonpoliposis colorectal cancer," *Biochemical and Biophysical Research Communications* 214(3): 1239–1245, Sep. 25, 1995.

*Primary Examiner*—James Martinell
(74) *Attorney, Agent, or Firm*—Seed Intellectual Property Law Group PLLC

(57) ABSTRACT

Compositions and methods for the therapy and diagnosis of cancer, such as lung cancer, are disclosed. Compositions may comprise one or more lung tumor proteins, immunogenic portions thereof, or polynucleotides that encode such portions. Alternatively, a therapeutic composition may comprise an antigen presenting cell that expresses a lung tumor protein, or a T cell that is specific for cells expressing such a protein. Such compositions may be used, for example, for the prevention and treatment of diseases such as lung cancer. Diagnostic methods based on detecting a lung tumor protein, or mRNA encoding such a protein, in a sample are also provided.

6 Claims, No Drawings

COMPOUNDS FOR THERAPY AND DIAGNOSIS OF LUNG CANCER AND METHODS FOR THEIR USE

REFERENCE TO RELATED APPLICATIONS

This application is a continuation-in-part of U.S. patent application Ser. No. 09/285,323, filed Apr. 2, 1999.

TECHNICAL FIELD

The present invention relates generally to compositions and methods for the treatment of lung cancer. The invention is more specifically related to nucleotide sequences that are preferentially expressed in lung tumor tissue, together with polypeptides encoded by such nucleotide sequences. The inventive nucleotide sequences and polypeptides may be used in vaccines and pharmaceutical compositions for the treatment of lung cancer.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compounds and methods for the therapy and diagnosis of cancer, such as lung cancer. In one aspect, the present invention provides polypeptides comprising at least a portion of a lung tumor protein, or a variant thereof. Certain portions and other variants are immunogenic, such that the ability of the variant to react with antigen-specific antisera is not substantially diminished. Within certain embodiments, the polypeptide comprises a sequence that is encoded by a polynucleotide sequence selected from the group consisting of: (a) sequences recited in SEQ ID NOS:218–222, 224–226, 249, 250, 253, 256, 266, 276, 277, 282 and 285; (b) variants of a sequence recited in SEQ ID NOS:218–222, 224–226, 249, 250, 253, 256, 266, 276, 277, 282 and 285; and (c) complements of a sequence of (a) or (b).

The present invention further provides polynucleotides that encode a polypeptide as described above, or a portion thereof (such as a portion encoding at least 15 contiguous amino acid residues of a lung tumor protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines are provided. Such vaccines comprise a polypeptide or polynucleotide as described above and a non-specific immune response enhancer.

The present invention further provides pharmaceutical compositions that comprise: (a) an antibody or antigen-binding fragment thereof that specifically binds to a lung tumor protein; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) a non-specific immune response enhancer.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a lung tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a lung tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a lung tumor protein; (ii) a polynucleotide encoding such a polypeptide;

and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be lung cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a lung tumor protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a lung tumor protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

Sequence Identifiers

SEQ ID NO:1 is the determined cDNA sequence for L363C1.cons

SEQ ID NO:2 is the determined cDNA sequence for L263C2.cons

SEQ ID NO:3 is the determined cDNA sequence for L263C2c

SEQ ID NO:4 is the determined cDNA sequence for L263C1.cons

SEQ ID NO:5 is the determined cDNA sequence for L263C1b

SEQ ID NO:6 is the determined cDNA sequence for L164C2.cons

SEQ ID NO:7 is the determined cDNA sequence for L164C1.cons

SEQ ID NO:8 is the determined cDNA sequence for L366C1a

SEQ ID NO:9 is the determined cDNA sequence for L260C1. cons

SEQ ID NO:10 is the determined cDNA sequence for L163C1c

SEQ ID NO:11 is the determined cDNA sequence for L163C1b

SEQ ID NO:12 is the determined cDNA sequence for L255C1.cons

SEQ ID NO:13 is the determined cDNA sequence for L255C1b

SEQ ID NO:14 is the determined cDNA sequence for L355C1.cons

SEQ ID NO:15 is the determined cDNA sequence for L366C1.cons

SEQ ID NO:16 is the determined cDNA sequence for L163C1a

SEQ ID NO:17 is the determined cDNA sequence for LT86-1

SEQ ID NO:18 is the determined cDNA sequence for LT86-2

SEQ ID NO:19 is the determined cDNA sequence for LT86-3

SEQ ID NO:20 is the determined cDNA sequence for LT86-4

SEQ ID NO:21 is the determined cDNA sequence for LT86-5

SEQ ID NO:22 is the determined cDNA sequence for LT86-6

SEQ ID NO:23 is the determined cDNA sequence for LT86-7

SEQ ID NO:24 is the determined cDNA sequence for LT86-8

SEQ ID NO:25 is the determined cDNA sequence for LT86-9

SEQ ID NO:26 is the determined cDNA sequence for LT86-10

SEQ ID NO:27 is the determined cDNA sequence for LT86-11

SEQ ID NO:28 is the determined cDNA sequence for LT86-12

SEQ ID NO:29 is the determined cDNA sequence for LT86-13

SEQ ID NO:30 is the determined cDNA sequence for LT86-14
SEQ ID NO:31 is the determined cDNA sequence for LT86-15
SEQ ID NO:32 is the predicted amino acid sequence for LT86-1
SEQ ID NO:33 is the predicted amino acid sequence for LT86-2
SEQ ID NO:34 is the predicted amino acid sequence for LT86-3
SEQ ID NO:35 is the predicted amino acid sequence for LT86-4
SEQ ID NO:36 is the predicted amino acid sequence for LT86-5
SEQ ID NO:37 is the predicted amino acid sequence for LT86-6
SEQ ID NO:38 is the predicted amino acid sequence for LT86-7
SEQ ID NO:39 is the predicted amino acid sequence for LT86-8
SEQ ID NO:40 is the predicted amino acid sequence for LT86-9
SEQ ID NO:41 is the predicted amino acid sequence for LT86-10
SEQ ID NO:42 is the predicted amino acid sequence for LT86-11
SEQ ID NO:43 is the predicted amino acid sequence for LT86-12
SEQ ID NO:44 is the predicted amino acid sequence for LT86-13
SEQ ID NO:45 is the predicted amino acid sequence for LT86-14
SEQ ID NO:46 is the predicted amino acid sequence for LT86-15
SEQ ID NO:47 is a $(dT)_{12}AG$ primer
SEQ ID NO:48 is a primer
SEQ ID NO:49 is the determined 5' cDNA sequence for L86S-3
SEQ ID NO:50 is the determined 5' cDNA sequence for L86S-12
SEQ ID NO:51 is the determined 5' cDNA sequence for L86S-16
SEQ ID NO:52 is the determined 5' cDNA sequence for L86S-25
SEQ ID NO:53 is the determined 5' cDNA sequence for L86S-36
SEQ ID NO:54 is the determined 5' cDNA sequence for L86S-40
SEQ ID NO:55 is the determined 5' cDNA sequence for L86S-46
SEQ ID NO:56 is the predicted amino acid sequence for L86S-3
SEQ ID NO:57 is the predicted amino acid sequence for L86S-12
SEQ ID NO:58 is the predicted amino acid sequence for L86S-16
SEQ ID NO:59 is the predicted amino acid sequence for L86S-25
SEQ ID NO:60 is the predicted amino acid sequence for L86S-36
SEQ ID NO:61 is the predicted amino acid sequence for L86S-40
SEQ ID NO:62 is the predicted amino acid sequence for L86S-46
SEQ ID NO:63 is the determined 5' cDNA sequence for L86S-30
SEQ ID NO:64 is the determined 5' cDNA sequence for L86S-41
SEQ ID NO:65 is the predicted amino acid sequence from the 5' end of LT86-9
SEQ ID NO:66 is the determined extended cDNA sequence for LT86-4
SEQ ID NO:67 is the predicted extended amino acid sequence for LT86-4
SEQ ID NO:68 is the determined 5' cDNA sequence for LT86-20
SEQ ID NO:69 is the determined 3' cDNA sequence for LT86-21
SEQ ID NO:70 is the determined 5' cDNA sequence for LT86-22
SEQ ID NO:71 is the determined 5' cDNA sequence for LT86-26
SEQ ID NO:72 is the determined 5' cDNA sequence for LT86-27
SEQ ID NO:73 is the predicted amino acid sequence for LT86-20
SEQ ID NO:74 is the predicted amino acid sequence for LT86-21
SEQ ID NO:75 is the predicted amino acid sequence for LT86-22
SEQ ID NO:76 is the predicted amino acid sequence for LT86-26
SEQ ID NO:77 is the predicted amino acid sequence for LT86-27
SEQ ID NO:78 is the determined extended cDNA sequence for L86S-12
SEQ ID NO:79 is the determined extended cDNA sequence for L86S-36
SEQ ID NO:80 is the determined extended cDNA sequence for L86S-46
SEQ ID NO:81 is the predicted extended amino acid sequence for L86S-12
SEQ ID NO:82 is the predicted extended amino acid sequence for L86S-36
SEQ ID NO:83 is the predicted extended amino acid sequence for L86S-46
SEQ ID NO:84 is the determined 5' cDNA sequence for L86S-6
SEQ ID NO:85 is the determined 5' cDNA sequence for L86S-11
SEQ ID NO:86 is the determined 5' cDNA sequence for L86S-14
SEQ ID NO:87 is the determined 5' cDNA sequence for L86S-29
SEQ ID NO:88 is the determined 5' cDNA sequence for L86S-34
SEQ ID NO:89 is the determined 5' cDNA sequence for L86S-39
SEQ ID NO:90 is the determined 5' cDNA sequence for L86S-47
SEQ ID NO:91 is the determined 5' cDNA sequence for L86S-49
SEQ ID NO:92 is the determined 5' cDNA sequence for L86S-51
SEQ ID NO:93 is the predict ed amino acid sequence for L86S-6
SEQ ID NO:94 is the predicted amino acid sequence for L86S-11
SEQ ID NO:95 is the predicted amino acid sequence for L86S-14
SEQ ID NO:96 is the predicted amino acid sequence for L86S-29
SEQ ID NO:97 is the predicted amino acid sequence for L86S-34
SEQ ID NO:98 is the predicted amino acid sequence for L86S-39

SEQ ID NO:99 is the predicted amino acid sequence for L86S-47

SEQ ID NO:100 is the predicted amino acid sequence for L86S-49

SEQ ID NO:101 is the predicted amino acid sequence for L86S-51

SEQ ID NO:102 is the determined DNA sequence for SLT-T1

SEQ ID NO:103 is the determined 5' cDNA sequence for SLT-T2

SEQ ID NO:104 is the determined 5' cDNA sequence for SLT-T3

SEQ ID NO:105 is the determined 5' cDNA sequence for SLT-T5

SEQ ID NO:106 is the determined 5' cDNA sequence for SLT-T7

SEQ ID NO:107 is the determined 5' cDNA sequence for SLT-T9

SEQ ID NO:108 is the determined 5' cDNA sequence for SLT-T10

SEQ ID NO:109 is the determined 5' cDNA sequence for SLT-T11

SEQ ID NO:110 is the determined 5' cDNA sequence for SLT-T12

SEQ ID NO:111 is the predicted amino acid sequence for SLT-T1

SEQ ID NO:112 is the predicted amino acid sequence for SLT-T2

SEQ ID NO:113 is the predicted amino acid sequence for SLT-T3

SEQ ID NO:114 is the predicted amino acid sequence for SLT-T10

SEQ ID NO:115 is the predicted amino acid sequence for SLT-T12

SEQ ID NO:116 is the determined 5' cDNA sequence for SALT-T3

SEQ ID NO:117 is the determined 5' cDNA sequence for SALT-T4

SEQ ID NO:118 is the determined 5' cDNA sequence for SALT-T7

SEQ ID NO:119 is the determined 5' cDNA sequence for SALT-T8

SEQ ID NO:120 is the determined 5' cDNA sequence for SALT-T9

SEQ ID NO:121 is the predicted amino acid sequence for SALT-T3

SEQ ID NO:122 is the predicted amino acid sequence for SALT-T4

SEQ ID NO:123 is the predicted amino acid sequence for SALT-T7

SEQ ID NO:124 is the predicted amino acid sequence for SALT-T8

SEQ ID NO:125 is the predicted amino acid sequence for SALT-T9

SEQ ID NO:126 is the determined cDNA sequence for PSLT-1

SEQ ID NO:127 is the determined cDNA sequence for PSLT-2

SEQ ID NO:128 is the determined cDNA sequence for PSLT-7

SEQ ID NO:129 is the determined cDNA sequence for PSLT-13

SEQ ID NO:130 is the determined cDNA sequence for PSLT-27

SEQ ID NO:131 is the determined cDNA sequence for PSLT-28

SEQ ID NO:132 is the determined cDNA sequence for PSLT-30

SEQ ID NO:133 is the determined cDNA sequence for PSLT-40

SEQ ID NO:134 is the determined cDNA sequence for PSLT-69

SEQ ID NO:135 is the determined cDNA sequence for PSLT-71

SEQ ID NO:136 is the determined cDNA sequence for PSLT-73

SEQ ID NO:137 is the determined cDNA sequence for PSLT-79

SEQ ID NO:138 is the determined cDNA sequence for PSLT-03

SEQ ID NO:139 is the determined cDNA sequence for PSLT-09

SEQ ID NO:140 is the determined cDNA sequence for PSLT-011

SEQ ID NO:141 is the determined cDNA sequence for PSLT-041

SEQ ID NO:142 is the determined cDNA sequence for PSLT-62

SEQ ID NO:143 is the determined cDNA sequence for PSLT-6

SEQ ID NO:144 is the determined cDNA sequence for PSLT-37

SEQ ID NO:145 is the determined cDNA sequence for PSLT-74

SEQ ID NO:146 is the determined cDNA sequence for PSLT-010

SEQ ID NO:147 is the determined cDNA sequence for PSLT-012

SEQ ID NO:148 is the determined cDNA sequence for PSLT-037

SEQ ID NO. 149 is the determined 5' cDNA sequence for SAL-3

SEQ ID NO:150 is the determined 5' cDNA sequence for SAL-24

SEQ ID NO:151 is the determined 5' cDNA sequence for SAL-25

SEQ ID NO:152 is the determined 5' cDNA sequence for SAL-33

SEQ ID NO:153 is the determined 5' cDNA sequence for SAL-50

SEQ ID NO:154 is the determined 5' cDNA sequence for SAL-57

SEQ ID NO:155 is the determined 5' cDNA sequence for SAL-66

SEQ ID NO:156 is the determined 5' cDNA sequence for SAL-82

SEQ ID NO:157 is the determined 5' cDNA sequence for SAL-99

SEQ ID NO:158 is the determined 5' cDNA sequence for SAL-104

SEQ ID NO:159 is the determined 5' cDNA sequence for SAL-109

SEQ ID NO:160 is the determined 5' cDNA sequence for SAL-5

SEQ ID NO:161 is the determined 5' cDNA sequence for SAL-8

SEQ ID NO:162 is the determined 5' cDNA sequence for SAL-12

SEQ ID NO:163 is the determined 5' cDNA sequence for SAL-14

SEQ ID NO:164 is the determined 5' cDNA sequence for SAL-16

SEQ ID NO:165 is the determined 5' cDNA sequence for SAL-23

SEQ ID NO:166 is the determined 5' cDNA sequence for SAL-26

SEQ ID NO:167 is the determined 5' cDNA sequence for SAL-29

SEQ ID NO:168 is the determined 5' cDNA sequence for SAL-32

SEQ ID NO:169 is the determined 5' cDNA sequence for SAL-39

SEQ ID NO:170 is the determined 5' cDNA sequence for SAL-42

SEQ ID NO:171 is the determined 5' cDNA sequence for SAL-43

SEQ ID NO:172 is the determined 5' cDNA sequence for SAL-44

SEQ ID NO:173 is the determined 5' cDNA sequence for SAL-48

SEQ ID NO:174 is the determined 5' cDNA sequence for SAL-68

SEQ ID NO:175 is the determined 5' cDNA sequence for SAL-72

SEQ ID NO:176 is the determined 5' cDNA sequence for SAL-77

SEQ ID NO:177 is the determined 5' cDNA sequence for SAL-86

SEQ ID NO:178 is the determined 5' cDNA sequence for SAL-88

SEQ ID NO:179 is the determined 5' cDNA sequence for SAL-93

SEQ ID NO:180 is the determined 5' cDNA sequence for SAL-100

SEQ ID NO:181 is the determined 5' cDNA sequence for SAL-105

SEQ ID NO:182 is the predicted amino acid sequence for SAL-3

SEQ ID NO:183 is the predicted amino acid sequence for SAL-24

SEQ ID NO:184 is a first predicted amino acid sequence for SAL-25

SEQ ID NO:185 is a second predicted amino acid sequence for SAL-25

SEQ ID NO:186 is the predicted amino acid sequence for SAL-33

SEQ ID NO:187 is a first predicted amino acid sequence for SAL-50

SEQ ID NO:188 is the predicted amino acid sequence for SAL-57

SEQ ID NO:189 is a first predicted amino acid sequence for SAL-66

SEQ ID NO:190 is a second predicted amino acid sequence for SAL-66

SEQ ID NO:191 is the predicted amino acid sequence for SAL-82

SEQ ID NO:192 is the predicted amino acid sequence for SAL-99

SEQ ID NO:193 is the predicted amino acid sequence for SAL-104

SEQ ID NO:194 is the predicted amino acid sequence for SAL-5

SEQ ID NO:195 is the predicted amino acid sequence for SAL-8

SEQ ID NO:196 is the predicted amino acid sequence for SAL-12

SEQ ID NO:197 is the predicted amino acid sequence for SAL-14

SEQ ID NO:198 is the predicted amino acid sequence for SAL-16

SEQ ID NO:199 is the predicted amino acid sequence for SAL-23

SEQ ID NO:200 is the predicted amino acid sequence for SAL-26

SEQ ID NO:201 is the predicted amino acid sequence for SAL-29

SEQ ID NO:202 is the predicted amino acid sequence for SAL-32

SEQ ID NO:203 is the predicted amino acid sequence for SAL-39

SEQ ID NO:204 is the predicted amino acid sequence for SAL-42

SEQ ID NO:205 is the predicted amino acid sequence for SAL-43

SEQ ID NO:206 is the predicted amino acid sequence for SAL-44

SEQ ID NO:207 is the predicted amino acid sequence for SAL-48

SEQ ID NO:208 is the predicted amino acid sequence for SAL-68

SEQ ID NO:209 is the predicted amino acid sequence for SAL-72

SEQ ID NO:210 is the predicted amino acid sequence for SAL-77

SEQ ID NO:211 is the predicted amino acid sequence for SAL-86

SEQ ID NO:212 is the predicted amino acid sequence for SAL-88

SEQ ID NO:213 is the predicted amino acid sequence for SAL-93

SEQ ID NO:214 is the predicted amino acid sequence for SAL-100

SEQ ID NO:215 is the predicted amino acid sequence for SAL-105

SEQ ID NO:216 is a second predicted amino acid sequence for SAL-50

SEQ ID NO:217 is the determined cDNA sequence for SSLT-4

SEQ ID NO:218 is the determined cDNA sequence for SSLT-9

SEQ ID NO:219 is the determined cDNA sequence for SSLT-10

SEQ ID NO:220 is the determined cDNA sequence for SSLT-12

SEQ ID NO:221 is the determined cDNA sequence for SSLT-19

SEQ ID NO:222 is the determined cDNA sequence for SSLT-31

SEQ ID NO:223 is the determined cDNA sequence for SSLT-38

SEQ ID NO:224 is the determined cDNA sequence for LT4690-2

SEQ ID NO:225 is the determined cDNA sequence for LT4690-3

SEQ ID NO:226 is the determined cDNA sequence for LT4690-22

SEQ ID NO:227 is the determined cDNA sequence for LT4690-24

SEQ ID NO:228 is the determined cDNA sequence for LT4690-37

SEQ ID NO:229 is the determined cDNA sequence for LT4690-39

SEQ ID NO:230 is the determined cDNA sequence for LT4690-40

SEQ ID NO:232 is the determined cDNA sequence for LT4690-41

SEQ ID NO:232 is the determined cDNA sequence for LT4690-49

SEQ ID NO:233 is the determined 3' cDNA sequence for LT4690-55

SEQ ID NO:234 is the determined 5' cDNA sequence for LT4690-55

SEQ ID NO:235 is the determined cDNA sequence for LT4690-59

SEQ ID NO:236 is the determined cDNA sequence for LT4690-63

SEQ ID NO:237 is the determined cDNA sequence for LT4690-71

SEQ ID NO:238 is the determined cDNA sequence for 2LT-3

SEQ ID NO:239 is the determined cDNA sequence for 2LT-6

SEQ ID NO:240 is the determined cDNA sequence for 2LT-22

SEQ ID NO:241 is the determined cDNA sequence for 2LT-25

SEQ ID NO:242 is the determined cDNA sequence for 2LT-26

SEQ ID NO:243 is the determined cDNA sequence for 2LT-31

SEQ ID NO:244 is the determined cDNA sequence for 2LT-36

SEQ ID NO:245 is the determined cDNA sequence for 2LT-42

SEQ ID NO:246 is the determined cDNA sequence for 2LT-44

SEQ ID NO:247 is the determined cDNA sequence for 2LT-54

SEQ ID NO:248 is the determined cDNA sequence for 2LT-55

SEQ ID NO:249 is the determined cDNA sequence for 2LT-57

SEQ ID NO:250 is the determined cDNA sequence for 2LT-58

SEQ ID NO:251 is the determined cDNA sequence for 2LT-59

SEQ ID NO:252 is the determined cDNA sequence for 2LT-62

SEQ ID NO:253 is the determined cDNA sequence for 2LT-63

SEQ ID NO:254 is the determined cDNA sequence for 2LT-65

SEQ ID NO:255 is the determined cDNA sequence for 2LT-66

SEQ ID NO:256 is the determined cDNA sequence for 2LT-70

SEQ ID NO:257 is the determined cDNA sequence for 2LT-73

SEQ ID NO:258 is the determined cDNA sequence for 2LT-74

SEQ ID NO:259 is the determined cDNA sequence for 2LT-76

SEQ ID NO:260 is the determined cDNA sequence for 2LT-77

SEQ ID NO:261 is the determined cDNA sequence for 2LT-78

SEQ ID NO:262 is the determined cDNA sequence for 2LT-80

SEQ ID NO:263 is the determined cDNA sequence for 2LT-85

SEQ ID NO:264 is the determined cDNA sequence for 2LT-87

SEQ ID NO:265 is the determined cDNA sequence for 2LT-89

SEQ ID NO:266 is the determined cDNA sequence for 2LT-94

SEQ ID NO:267 is the determined cDNA sequence for 2LT-95

SEQ ID NO:268 is the determined cDNA sequence for 2LT-98

SEQ ID NO:269 is the determined cDNA sequence for 2LT-100

SEQ ID NO:270 is the determined cDNA sequence for 2LT-103

SEQ ID NO:271 is the determined cDNA sequence for 2LT-105

SEQ ID NO:272 is the determined cDNA sequence for 2LT-107

SEQ ID NO:273 is the determined cDNA sequence for 2LT-108

SEQ ID NO:274 is the determined cDNA sequence for 2LT-109

SEQ ID NO:275 is the determined cDNA sequence for 2LT-118

SEQ ID NO:276 is the determined cDNA sequence for 2LT-120

SEQ ID NO:277 is the determined cDNA sequence for 2LT-121

SEQ ID NO:278 is the determined cDNA sequence for 2LT-122

SEQ ID NO:279 is the determined cDNA sequence for 2LT-124

SEQ ID NO:280 is the determined cDNA sequence for 2LT-126

SEQ ID NO:281 is the determined cDNA sequence for 2LT-127

SEQ ID NO:282 is the determined cDNA sequence for 2LT-128

SEQ ID NO:283 is the determined cDNA sequence for 2LT-129

SEQ ID NO:284 is the determined cDNA sequence for 2LT-133

SEQ ID NO:285 is the determined cDNA sequence for 2LT-137

SEQ ID NO:286 is the determined cDNA sequence for LT4690-71

SEQ ID NO:287 is the determined cDNA sequence for LT4690-82

SEQ ID NO:288 is the determined full-length cDNA sequence for SSLT-74

SEQ ID NO:289 is the determined cDNA sequence for SSLT-78

DETAILED DESCRIPTION OF THE INVENTION

As noted above, the present invention is generally directed to compositions and methods for the therapy and diagnosis of cancer, such as lung cancer. The compositions described herein may include lung tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a lung tumor protein or a variant thereof. A "lung tumor protein" is a protein that is expressed in lung tumor cells at a level that is at least two fold, and preferably at least five fold, greater than the level of expression in a normal tissue, as determined using a representative assay provided herein. Certain lung tumor proteins are tumor proteins that react detectably (within an immunoassay, such as an ELISA or Western blot) with antisera of a patient afflicted with lung cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human lung tumor proteins. Sequences of polynucleotides encoding specific tumor proteins are provided in SEQ ID NOS:1–31, 49–55, 63,64, 66, 68–72, 78–80, 84–92 and 217–289.

Lung Tumor Protein Polynucleotides

Any polynucleotide that encodes a lung tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a lung tumor protein. More preferably, a polynucleotide encodes an immunogenic portion of a lung tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a lung tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native lung tumor protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 50 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native lung tumor protein (or a complementary sequence). Suitable moderately stringent conditions include prewashing in a solution of 5×SSC, 0.5% SDS, 1.0 mM EDTA (pH 8.0); hybridizing at 5° C.-65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least five fold greater in a lung tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad Sci. USA* 93:10614–10619, 1996 and Heller et al., *Proc. Natl. Acad Sci. USA* 94:2150–2155, 1997). Alternatively, polypeptides may be amplified from cDNA prepared from cells expressing the proteins described herein, such as lung tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a lung tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1: 111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of lung tumor proteins are provided in SEQ ID NO:1–31, 49–55, 63,64, 66, 68–72, 78–80, 84–92 and 217–289. The isolation of these sequences is described in detail below.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a lung tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a lung tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Lung Tumor Polypeptides

Within the context of the present invention, polypeptides may comprise at least an immunogenic portion of a lung tumor protein or a variant thereof, as described herein. As noted above, a "lung tumor protein" is a protein that is expressed by lung tumor cells. Proteins that are lung tumor proteins also react detectably within an immunoassay (such as an ELISA) with antisera from a patient with lung cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a lung tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native lung tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, 125I-labeled Protein A.

As noted above, a composition may comprise a variant of a native lung tumor protein. A polypeptide "variant," as used herein, is a polypeptide that differs from a native lung tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a lung tumor protein. As used herein, an antibody, or antigen-binding fragment thereof, is said to "specifically bind" to a lung tumor protein if it reacts at a detectable level (within, for example, an ELISA) with a lung tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as lung cancer, using the representative assays provided herein. In other words, antibodies or other binding agents that bind to a lung tumor protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a lung tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ system, available from Nexell Therapeutics Inc., Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a lung tumor polypeptide, polynucleotide encoding a lung tumor polypeptide and/or an antigen presenting cell (APC) that expresses such a polypeptide. Such stimulation is performed under conditions and for a time sufficient to permit the generation of T cells that are specific for the polypeptide. Preferably, a lung tumor polypeptide or polynucleotide is present within a delivery vehicle, such as a microsphere, to facilitate the generation of specific T cells.

T cells are considered to be specific for a lung tumor polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a lung tumor polypeptide (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a lung tumor polypeptide, polynucleotide or polypeptide-expressing APC may be $CD4^{30}$ and/or $CD8^+$. Lung tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a lung tumor polypeptide, polynucleotide or APC can be expanded in number either in vitro or in vivo. Proliferation of such T cells in vitro may be accomplished in a variety of ways. For example, the T cells can be re-exposed to a lung tumor polypeptide, or a short peptide corresponding to an immunogenic portion of such a polypeptide, with or without the addition of T cell growth factors, such as interleukin-2, and/or stimulator cells that synthesize a lung tumor polypeptide. Alternatively, one or more T cells that proliferate in the presence of a lung tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.) (see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3DMPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a lung tumor protein (or portion or other variant thereof) such that the lung tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the lung tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as lung cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Suitable dose sizes will vary with the size of the patient, but will typically range from about 0.1 mL to about 50 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a lung tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more lung tumor proteins and/or polynucleotides encoding such proteins in a biological sample (for example, blood, sera, urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a lung tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use lung tumor polypeptides to detect antibodies that bind to such polypeptides in a biological sample. The detection of such lung tumor protein specific antibodies may correlate with the presence of a cancer.

A cancer may also, or alternatively, be detected based on the presence of T cells that specifically react with a lung tumor protein in a biological sample. Within certain methods, a biological sample comprising $CD4^+$ and/or $CD8^+$ T cells isolated from a patient is incubated with a lung tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 μg/ml). It may be desirable to incubate another aliquot of a T cell sample in the absence of lung tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a lung tumor protein in a biological sample. For example, at least two oligonucleotide primers may be employed in a polymerase chain reaction (PCR) based assay to amplify a portion of a lung tumor cDNA derived from a biological sample, wherein at least one of the oligonucleotide primers is specific for (i.e., hybridizes to) a polynucleotide encoding the lung tumor protein. The amplified cDNA is then separated and detected using techniques well known in the art, such as gel electrophoresis. Similarly, oligonucleotide probes that specifically hybridize to a polynucleotide encoding a lung tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a lung tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NOS:1–31, 49–55, 63,64, 66, 68–72, 78–80, 84–92 and 217–289. Techniques for both PCR based assays and hybridization assays are well known in the art (see, for example, Mullis et al., *Cold Spring Harbor Symp. Quant. Biol.,* 51:263, 1987; Erlich ed., PCR Technology, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple lung tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a lung tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a lung tumor protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a lung tumor protein.

The following Examples are offered by way of illustration and not by way of limitation.

EXAMPLES

Example 1

Preparation of Lung Tumor-specific cDNA Sequences Using Differential Display RT-PCR This example illustrates the preparation of cDNA molecules encoding lung tumor-specific polypeptides using a differential display screen.

Tissue samples were prepared from lung tumor and normal tissue of a patient with lung cancer that was confirmed by pathology after removal of samples from the patient. Normal RNA and tumor RNA was extracted from the samples and mRNA was isolated and converted into cDNA using a $(dT)_{12}AG$ (SEQ ID NO:47) anchored 3' primer. Differential display PCR was then executed using a randomly chosen primer (SEQ ID NO:48). Amplification conditions were standard buffer containing 1.5 mM $MgCl_2$, 20 pmol of primer, 500 pmol dNTP and 1 unit of Taq DNA polymerase (Perkin-Elmer, Branchburg, N.J.). Forty cycles of amplification were performed using 94° C. denaturation for 30 seconds, 42° C. annealing for 1 minute and 72° C. extension for 30 seconds. Bands that were repeatedly observed to be specific to the RNA fingerprint pattern of the tumor were cut out of a silver stained gel, subcloned into the pGEM-T vector (Promega, Madison, Wis.) and sequenced. The isolated 3' sequences are provided in SEQ ID NO:1–16.

Comparison of these sequences to those in the public databases using the BLASTN program, revealed no significant homologies to the sequences provided in SEQ ID NO:1–11. To the best of the inventors' knowledge, none of the isolated DNA sequences have previously been shown to be expressed at a greater level in human lung tumor tissue than in normal lung tissue.

Example 2

Use of Patient Sera to Identify DNA Sequences Encoding Lung Tumor Antigens

This example illustrates the isolation of cDNA sequences encoding lung tumor antigens by expression screening of lung tumor samples with autologous patient sera.

A human lung tumor directional cDNA expression library was constructed employing the Lambda ZAP Express expression system (Stratagene, La Jolla, Calif.). Total RNA for the library was taken from a late SCID mouse passaged human squamous epithelial lung carcinoma and poly A+ RNA was isolated using the Message Maker kit (Gibco BRL, Gaithersburg, Md.). The resulting library was screened using *E. coli*-absorbed autologous patient serum, as described in Sambrook et al., (*Molecular Cloning: A Laboratory Manual,* Cold Spring Harbor Laboratories, Cold Spring Harbor, N.Y., 1989), with the secondary antibody being goat anti-human IgG-A-M (H+L) conjugated with alkaline phosphatase, developed with NBT/BCIP (Gibco BRL). Positive plaques expressing immunoreactive antigens were purified. Phagemid from the plaques was rescued and the nucleotide sequences of the clones was determined.

Fifteen clones were isolated, referred to hereinafter as LT86-1–LT86-15. The isolated cDNA sequences for LT86-1–LT86-8 and LT86-10–LT86-15 are provided in SEQ ID NO:17–24 and 26–31, respectively, with the corresponding predicted amino acid sequences being provided in SEQ ID NO:32–39 and 41–46, respectively. The determined cDNA sequence for LT86-9 is provided in SEQ ID NO:25, with the corresponding predicted amino acid sequences from the 3' and 5' ends being provided in SEQ ID NO:40 and 65, respectively. These sequences were compared to those in the gene bank as described above. Clones LT86-3, LT86-6–LT86-9, LT86-11–LT86-13 and LT86. (SEQ ID NO: 19, 22–25, 27–29 and 31, respectively) were found to show some homology to previously identified expressed sequence tags (ESTs), with clones LT86-6, LT86-8, LT86-11, LT86-12 and LT86-15 appearing to be similar or identical to each other. Clone LT86-3 was found to show some homology with a human transcription repressor. Clones LT86-6, 8, 9, 11, 12 and 15 were found to show some homology to a yeast RNA Pol II transcription regulation mediator. Clone LT86-13 was found to show some homology with a *C. elegans* leucine aminopeptidase. Clone LT86-9 appears to contain two inserts, with the 5' sequence showing homology to the previously identified antisense sequence of interferon alpha-induced P27, and the 3' sequence being similar to LT86-6. Clone LT86-14 (SEQ ID NO:30) was found to show some homology to the trithorax gene and has an “RGD” cell attachment sequence and a beta-Lactamase A site which functions in hydrolysis of penicillin. Clones LT86-1, LT86-2, LT86-4, LT86-5 and LT86-10 (SEQ ID NOS:17, 18, 20, 21 and 26, respectively) were found to show homology to previously identified genes. A subsequently determined extended cDNA sequence for LT86-4 is provided in SEQ ID NO:66, with the corresponding predicted amino acid sequence being provided in SEQ ID NO:67.

Subsequent studies led to the isolation of five additional clones, referred to as LT86-20, LT86-21, LT86-22, LT86-26 and LT86-27. The determined 5' cDNA sequences for LT86-20, LT86-22, LT86-26 and LT86-27 are provided in SEQ ID NO:68 and 70–72, respectively, with the determined 3' cDNA sequences for LT86-21 being provided in SEQ ID NO:69. The corresponding predicted amino acid sequences for LT86-20, LT86-21, LT86-22, LT86-26 and LT86-27 are provided in SEQ ID NO:73–77, respectively. LT86-22 and LT86-27 were found to be highly similar to each other. Comparison of these sequences to those in the gene bank as described above, revealed no significant homologies to LT86-22 and LT86-27. LT86-20, LT86-21 and LT86-26 were found to show homology to previously identified genes.

Example 3

Use of Mouse Antistera to Identify DNA Sequences Encoding Lung Tumor Antigens

This example illustrates the isolation of cDNA sequences encoding lung tumor antigens by screening of lung tumor cDNA libraries with mouse anti-tumor sera.

A directional cDNA lung tumor expression library was prepared as described above in Example 2. Sera was obtained from SCID mice containing late passaged human squamous cell and adenocarcinoma tumors. These sera were pooled and injected into normal mice to produce anti-lung tumor serum. Approximately 200,000 PFUs were screened from the unamplified library using this antiserum. Using a goat anti-mouse IgG-A-M (H+L) alkaline phosphatase second antibody developed with NBT/BCIP (BRL Labs.), approximately 40 positive plaques were identified. Phage was purified and phagemid excised for 9 clones with inserts in a pBK-CMV vector for expression in prokaryotic or eukaryotic cells.

The determined cDNA sequences for 7 of the isolated clones (hereinafter referred to as L86S-3, L86S-12, L86S-16, L86S-25, L86S-36, L86S-40 and L86-S46) are provided in SEQ ID NO:49–55, with the corresponding predicted amino acid sequences being provided in SEQ ID NO:56–62, respectively. The 5' cDNA sequences for the remaining 2 clones (hereinafter referred to as L86S-30 and L86S-41) are provided in SEQ ID NO:63 and 64. L86S-36 and L86S-46 were subsequently determined to represent the same gene. Comparison of these sequences with those in the public database as described above, revealed no significant homologies to clones L86S-30, L86S-36 and L86S-46 (SEQ ID NO: 63, 53 and 55, respectively). L86S-16 (SEQ ID NO:51) was found to show some homology to an EST previously identified in fetal lung and germ cell tumor. The remaining clones were found to show at least some degree of homology to previously identified human genes. Subsequently determined extended cDNA sequences for L86S-12, L86S-36 and L86S-46 are provided in SEQ ID NO:78–80, respectively, with the corresponding predicted amino acid sequences being provided in SEQ ID NO:81–83.

Subsequent studies led to the determination of 5' cDNA sequences for an additional nine clones, referred to as L86S-6, L86S-11, L86S-14, L86S-29, L86S-34, L86S-39, L86S-47, L86S-49 and L86S-51 (SEQ ID NO:84–92, respectively). The corresponding predicted amino acid sequences are provided in SEQ ID NO:93–101, respectively. L86S-30, L86S-39 and L86S-47 were found to be similar to each other. Comparison of these sequences with those in the gene bank as described above, revealed no significant homologies to L86S-14. L86S-29 was found to show some homology to a previously identified EST. L86S-6, L86S-11, L86S-34, L86S-39, L86S-47, L86S-49 and L86S-51 were found to show some homology to previously identified genes.

In further studies, a directional cDNA library was constructed using a Stratagene kit with a Lambda Zap Express vector. Total RNA for the library was isolated from two primary squamous lung tumors and poly A+ RNA was isolated using an oligo dT column. Antiserum was developed in normal mice using a pool of sera from three SCID mice implanted with human squamous lung carcinomas. Approximately 700,000 PFUs were screened from the unamplified library with *E. coli* absorbed mouse anti-SCID tumor serum. Positive plaques were identified as described above. Phage was purified and phagemid excised for 180 clones with inserts in a pBK-CMV vector for expression in prokaryotic or eukaryotic cells.

The determined cDNA sequences for 23 of the isolated clones are provided in SEQ ID NO:126–148. Comparison of these sequences with those in the public database as described above revealed no significant homologies to the sequences of SEQ ID NO:139 and 143–148. The sequences of SEQ ID NO:126–138 and 140–142 were found to show homology to previously identified human polynucleotide sequences.

Example 4

Use of Mouse Antisera to Screen Lung Tumor Libraries Prepared From SCID Mice This example illustrates the isolation of cDNA sequences encoding lung tumor antigens by screening of lung tumor cDNA libraries prepared from SCID mice with mouse anti-tumor sera.

A directional cDNA lung tumor expression library was prepared using a Stratagene kit with a Lambda Zap Express vector. Total RNA for the library was taken from a late passaged lung adenocarcinoma grown in SCID mice. Poly A+ RNA was isolated using a Message Maker Kit (Gibco BRL). Sera was obtained from two SCID mice implanted with lung adenocarcinomas. These sera were pooled and injected into normal mice to produce anti-lung tumor serum. Approximately 700,000 PFUs were screened from the unamplified library with *E coli*-absorbed mouse anti-SCID tumor serum. Positive plaques were identified with a goat anti-mouse IgG-A-M (H+L) alkaline phosphatase second antibody developed with NBT/BCIP (Gibco BRL). Phage was purified and phagemid excised for 100 clones with insert in a pBK-CMV vector for expression in prokaryotic or eukaryotic cells.

The determined 5' cDNA sequences for 33 of the isolated clones are provided in SEQ ID NO:149–181. The corresponding predicted amino acid sequences for SEQ ID NO:149, 150, 152–154, 156–158 and 160–181 are provided in SEQ ID NO:182, 183, 186, 188–193 and 194–215, respectively. The clone of SEQ ID NO:151 (referred to as SAL-25) was found to contain two open reading frames (ORFs). The predicted amino acid sequences encoded by these ORFs are provided in SEQ ID NO:184 and 185. The clone of SEQ ID NO:153 (referred to as SAL-50) was found to contain two open reading frames encoding the predicted amino acid sequences of SEQ ID NO:187 and 216. Similarly, the clone of SEQ ID NO:155 (referred to as SAL-66) was found to contain two open reading frames encoding the predicted amino acid sequences of SEQ ID NO:189 and 190. Comparison of the isolated sequences with those in the public database revealed no significant homologies to the sequences of SEQ ID NO:151, 153 and 154. The sequences of SEQ ID NO:149, 152, 156, 157 and 158 were found to show some homology to previously isolated expressed sequence tags (ESTs). The sequences of SEQ ID NO:150, 155 and 159–181 were found to show homology to sequences previously identified in humans.

Using the procedures described above, two directional cDNA libraries (referred to as LT46-90 and LT86-21) were prepared from two late passaged lung squamous carcinomas grown in SCID mice and screened with sera obtained from SCID mice implanted with human squamous lung carcinomas. The determined cDNA sequences for the isolated clones are provided in SEQ ID NO:217–237 and 286–289. SEQ ID NO:286 was found to be a longer sequence of LT4690-71 (SEQ ID NO:237). Comparison of these sequences with those in the public databases revealed no known homologies to the sequences of SEQ ID NO: 219, 220, 225, 226, 287 and 288. The sequences of SEQ ID NO:218, 221, 222 and 224 were found to show some homology to previously identified sequences of unknown function. The sequence of SEQ ID NO:236 was found to show homology to a known mouse mRNA sequence. The sequences of SEQ ID NO:217, 223, 227–237, 286 and 289 showed some homology to known human DNA and/or RNA sequences.

In further studies using the techniques described above, one of the cDNA libraries described above (LT86-21) was screened with *E coli*-absorbed mouse anti-SCID tumor serum. This serum was obtained from normal mice immunized with a pool of 3 sera taken from SCID mice implanted with human squamous lung carcinomas. The determined cDNA sequences for the isolated clones are provided in SEQ ID NO:238–285. Comparison of these sequences with those in the public databases revealed no significant homologies to the sequences of SEQ ID NO:253, 260, 277 and 285. The sequences of SEQ ID NO:249, 250, 256, 266, 276 and 282 were found to show some homology to previously isolated expressed sequence tags (ESTs). The sequences of SEQ ID NO:238–248, 251, 252, 254, 255, 257–259, 261–263, 265, 267–275, 278–281, 283 and 284 were found to show some homology to previously identified DNA or RNA sequences.

Example 5

Determination of Tissue Specificity of Lung Tumor Polypeptides

Using gene specific primers, mRNA expression levels for representative lung tumor polypeptides were examined in a variety of normal and tumor tissues using RT-PCR.

Briefly, total RNA was extracted from a variety of normal and tumor tissues using Trizol reagent. First strand synthesis was carried out using 2 $\mu$g of total RNA with SuperScript II reverse transcriptase (BRL Life Technologies) at 42° C. for one hour. The cDNA was then amplified by PCR with gene-specific primers. To ensure the semiquantitative nature of the RT-PCR, β-actin was used as an internal control for each of the tissues examined. 1 $\mu$l of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous tumor from 3 patients, lung adenocarcinoma, prostate tumor colon tumor and lung tumor), and different normal tissues, including lung from four patients, prostate, brain, kidney, liver, ovary, skeletal muscle, skin, small intestine, myocardium, retina and testes. L86S-46 was found to be expressed at high levels in lung squamous tumor, colon tumor and prostate tumor, and was undetectable in the other tissues examined. L86S-5 was found to be expressed in the lung tumor samples and in 2 out of 4 normal lung samples, but not in the other normal or tumor tissues tested. L86S-16 was found to be expressed in all tissues except normal liver and normal stomach. Using real-time PCR, L86S-46 was found to be over-expressed in lung squamous tissue and normal tonsil, with expression being low or undetectable in all other tissues examined.

Example 6

Isolation of DNA Sequences Encoding Lung Tumor Antigens

DNA sequences encoding antigens potentially involved in squamous cell lung tumor formation were isolated as follows.

A lung tumor directional cDNA expression library was constructed employing the Lambda ZAP Express expression system (Stratagene, La Jolla, Calif.). Total RNA for the library was taken from a pool of two human squamous epithelial lung carcinomas and poly A+ RNA was isolated using oligo-dT cellulose (Gibco BRL, Gaithersburg, Md.). Phagemid were rescued at random and the cDNA sequences of isolated clones were determined.

The determined cDNA sequence for the clone SLT-T1 is provided in SEQ ID NO:102, with the determined 5' cDNA sequences for the clones SLT-T2, SLT-T3, SLT-T5, SLT-T7, SLT-T9, SLT-T10, SLT-T11 and SLT-T12 being provided in SEQ ID NO:103–110, respectively. The corresponding predicted amino acid sequence for SLT-T1, SLT-T2, SLT-T3, SLT-T10 and SLT-T12 are provided in SEQ ID NO:111–115, respectively. Comparison of the sequences for SLT-T2, SLT-T3, SLT-T5, SLT-T7, SLT-T9 and SLT-T11 with those in the public databases as described above, revealed no significant homologies. The sequences for SLT-T10 and SLT-T12 were found to show some homology to sequences previously identified in humans.

The sequence of SLT-T1 was determined to show some homology to a PAC clone of unknown protein function. The cDNA sequence of SLT-T1 (SEQ ID NO:102) was found to contain a mutator (MUTT) domain. Such domains are known to function in removal of damaged guanine from DNA that can cause A to G transversions (see, for example, el-Deiry, W. S., 1997 *Curr. Opin. Oncol.* 9:79–87; Okamoto, K. et al. 1996 *Int. J Cancer* 65:437–41; Wu, C. et al. 1995 *Biochem. Biophys. Res. Commun.* 214:1239–45; Porter, D. W. et al. 1996 *Chem. Res. Toxicol.* 9:1375–81). SLT-T1 may thus be of use in the treatment, by gene therapy, of lung cancers caused by, or associated with, a disruption in DNA repair.

In further studies, DNA sequences encoding antigens potentially involved in adenocarcinoma lung tumor formation were isolated as follows. A human lung tumor directional cDNA expression library was constructed employing the Lambda ZAP Express expression system (Stratagene, La Jolla, Calif.). Total RNA for the library was taken from a late SCID mouse passaged human adenocarcinoma and poly A+ RNA was isolated using the Message Maker kit (Gibco BRL, Gaithersburg, Md.). Phagemid were rescued at random and the cDNA sequences of isolated clones were determined.

The determined 5' cDNA sequences for five isolated clones (referred to as SALT-T3, SALT-T4, SALT-T7, SALT-T8, and SALT-T9) are provided in SEQ ID NO: 116–120, with the corresponding predicted amino acid sequences being provided in SEQ ID NO:121–125. SALT-T3 was found to show 98% identity to the previously identified human transducin-like enhancer protein TLE2. SALT-T4 appears to be the human homologue of the mouse H beta 58 gene. SALT-T7 was found to have 97% identity to human 3-mercaptopyruvate sulfurtransferase and SALT-T8 was found to show homology to human interferon-inducible protein 1-8U. SALT-T9 shows approximately 90% identity to human mucin MUC 5B.

Example 7

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 8

Isolation and Characterization of DNA Sequences Encoding Lung Tumor Antigens by T-Cell Expression Cloning Lung tumor antigens may also be identified by T cell expression cloning. One source of tumor specific T cells is from surgically excised tumors from human patients.

A non-small cell lung carcinoma was minced and enzymatically digested for several hours to release tumor cells and infiltrating lymphocytes (tumor infiltrating T cells, or TILs). The cells were washed in HBSS buffer and passed over a Ficoll (100%/75%/HBSS) discontinuous gradient to separate tumor cells and lymphocytes from non-viable cells. Two bands were harvested from the interfaces; the upper band at the 75%/HBSS interface contained predominantly tumor cells, while the lower band at the 100%/75%/HBSS interface contained a majority of lymphocytes. The TILs were expanded in culture, either in 24-well plates with culture media supplemented with 10 ng/ml IL-7 and 100 U/ml IL-2, or alternatively, 24-well plates that have been pre-coated with the anti-CD3 monoclonal antibody OKT3. The resulting TIL cultures were analyzed by FACS to confirm that a high percentage were CD8+ T cells (>90% of gated population) with only a small percentage of CD4+ cells.

In addition, non-small cell lung carcinoma cells were expanded in culture using standard techniques to establish a tumor cell line, which was later confirmed to be a lung carcinoma cell line by immunohistochemical analysis. This tumor cell line was transduced with a retroviral vector to express human CD80, and characterized by FACS analysis to confirm high expression levels of CD80, and class I and II MHC molecules.

The specificity of the TIL lines to lung tumor was confirmed by INF-γ and/or TNF-γ cytokine release assays. TIL cells from day 21 cultures were co-cultured with either autologous or allogeneic tumor cells, EBV-immortalized LCL, or control cell lines Daudi and K562, and the culture supernatant monitored by ELISA for the presence of cytokines. The TIL specifically recognized autologous tumor but not allogeneic tumor. In addition, there was no recognition of EBV-immortalized LCL or the control cell lines, indicating that the TIL lines are tumor specific and are potentially recognizing a tumor antigen presented by autologous MHC molecules.

The characterized tumor-specific TIL lines were expanded to suitable numbers for T cell expression cloning using soluble anti-CD3 antibody in culture with irradiated EBV transformed LCLs and PBL feeder cells in the presence of 20 U/ml IL-2. Clones from the expanded TIL lines were generated by standard limiting dilution techniques. Specifically, TIL cells were seeded at 0.5 cells/well in a 96-well U bottom plate and stimulated with CD80-transduced autologous tumor cells, EBV transformed LCL, and PBL feeder cells in the presence of 50 U/ml IL-2. These clones were further analyzed for tumor specificity by $^{51}Cr$ microcytotoxicity and IFN-γ bioassays. The MHC restriction element recognized by the TIL clones may be determined by antibody blocking studies.

CTL lines or clones prepared as described above may be employed to identify tumor specific antigens. For example, autologous fibroblasts or LCL from a patient may be transfected or transduced with polynucleotide fragments derived from a lung tumor cDNA library to generate target cells expressing tumor polypeptides. The target cells expressing tumor polypeptides in the context of MHC will be recognized by the CTL line or clone, resulting in T-cell activation which can be monitored by cytokine detection assays. The tumor gene being expressed by the target cell and recognized by the tumor-specific CTL may then be isolated.

From the foregoing, it will be appreciated that, although specific embodiments of the invention have been described herein for the purposes of illustration, various modifications may be made without deviating from the spirit and scope of the invention.

What is claimed is:

1. A method for determining the presence or absence of a cancer in a patient, comprising the steps of:

(a) contacting a biological sample obtained from a patient with an oligonucleotide that hybridizes to a polynucleotide that encodes a lung tumor protein, wherein the tumor protein comprises an amino acid sequence that is encoded by a polynucleotide sequence recited in SEQ ID NO:80 or complement thereof;

(b) detecting in the sample an amount of a polynucleotide that hybridizes to the oligonucleotide; and (c) comparing the amount of polynucleotide that hybridizes to the oligonucleotide to a predetermined cut-off value, and therefrom determining the presence or absence of a cancer in the patient.

2. A method according to claim 1, wherein the amount of polynucleotide that hybridizes to the oligonucleotide is determined using a polymerase chain reaction.

3. A method according to claim 1, wherein the amount of polynucleotide that hybridizes to the oligonucleotide is determined using a hybridization assay.

4. A method for monitoring the progression of a cancer in a patient, comprising the steps of:

(a) contacting a biological sample obtained from a patient with an oligonucleotide that hybridizes to a polynucleotide that encodes a lung tumor protein, wherein the tumor protein comprises an amino acid sequence that is encoded by a polynucleotide sequence recited in SEQ ID NO:80 or complement thereof;

(b) detecting in the sample an amount of a polynucleotide that hybridizes to the oligonucleotide;

(c) repeating steps (a) and (b) using a biological sample obtained from the patient at a subsequent point in time; and (d) comparing the amount of polynucleotide detected in step (c) to the amount detected in step (b) and therefrom monitoring the progression of the cancer in the patient.

5. A method according to claim 4, wherein the amount of polynucleotide that hybridizes to the oligonucleotide is determined using a polymerase chain reaction.

6. A method according to claim 4, wherein the amount of polynucleotide that hybridizes to the oligonucleotide is determined using a hybridization assay.

* * * * *

UNITED STATES PATENT AND TRADEMARK OFFICE

CERTIFICATE OF CORRECTION

PATENT NO. : 6,444,425 B1
DATED : September 3, 2002
INVENTOR(S) : Steven G. Reed et al.

It is certified that error appears in the above-identified patent and that said Letters Patent is hereby corrected as shown below:

Title page,
Item [56], References Cited, OTHER PUBLICATIONS,
"Gure et al., "Human lung cancer antigens recognized by autologous antibodies: definition of a novel cDNA dervied form the tumor suppressor gene locus on chromosome 3p21.3," *Cancer Research,* 58:1034-1041, Mar. 1, 1998." should read -- Gure et al., "Human lung cancer antigens recognized by autologous antibodies: definition of a novel cDNA derived from the tumor suppressor gene locus on chromosome 3p21.3," *Cancer Research,* 58:1034-1041, Mar. 1, 1998. --.

"Heller et al., "Discovery and analysis of inflammatory disease-related genes using cDNA micorarrays," *Proc. Natl. Acad. Sci. USA* 94:2150-2155, Mar. 1997." should read -- Heller et al., "Discovery and analysis of inflammatory disease-related genes using cDNA microarrays," *Proc. Natl. Acad. Sci. USA* 94:2150-2155, Mar. 1997. --.

"Schena et al., "Parallel human genome analysis: mciroarray-based expression monitoring of 1000 genes," *Proc. Natl. Acad. Sci. USA* 93:10614-10619, Oct. 1996." should read -- Schena et al., "Parallel human genome analysis: microarray-based expression monitoring of 1000 genes," *Proc. Natl. Acad. Sci. USA* 93:10614-10619, Oct. 1996. --.

Signed and Sealed this

Twenty-eighth Day of January, 2003

JAMES E. ROGAN
*Director of the United States Patent and Trademark Office*

SEQUENCE LISTING

```
<160> NUMBER OF SEQ ID NOS: 289

<210> SEQ ID NO 1
<211> LENGTH: 339
<212> TYPE: DNA
<213> ORGANISM: Homo sapien

<400> SEQUENCE: 1

gtactcagac aggatagtca tcatgtagca caaagcamat cctgtttcta tacttgtagt     60

ttgctctcac tcagtggcat ratcattact atacagtgta gaatgttrtt atgtagcata    120

gatgtggggt ctctagccca cagctctsta cctttgtcta gcactcctgt cctcatacct    180

ragtggcctg tccatcagca tgtttctcat ctactttgct tgtccagtcc actgtggtcc    240

tcccttgccc tctcccttat gtggcagagt ggaaccagct gtcctgagac ttgagttcaa    300

catctggttc gcccatytgc atgtttgtgg tctgagtac                           339


<210> SEQ ID NO 2
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 2

gtactcagac cacgactgca ttttctccac tgctgacggg tctaatacca gctgcttccc     60

tttcttggag gcagagctng tgaccttgag aaagtgacct gtgaccatca tgtgggtagt    120

gagctgctgc aaggtgtcat gggagctccc acactccatg cactttwaga tctgggactt    180

gcaggcctca ractgccagg tgtagctcgc tccattttgg tagccatagc gsttgttgga    240

ggacaactgc aagttggcgt tcttctgaga agaaaaagaa tctgcaaaag atcctgtggt    300

tgaatcgggg gaacacggcc gattgacatc aaaaacgcgt ttcttagccc gggtgaccat    360
```

-continued

```
tttcgaggaa atggttgggg actggctcct tcaaaggcac tttttggtta tgttttgttt    420

yaatcatgtk gacgctccaa tcttggragg gaatcgaang rantcnccnc caaaacatrc    480

stttcagraa ccttttgarc atcctctttt ttccgtrtcc cggmaargcc cytttccckg    540

ggctttgaaa wyagcctsgt tgggttctta aattaccart ccacnwgttg gaattccccg    600

ggccccctgc ccggktccaa ccaattttgg graaaacccc cncansccgt tkggantgcn    660

acaacntggn ntttttcntt tcgtgntccc ctngaacc                            698
```

<210> SEQ ID NO 3
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 3

```
gtactcagac ccccaacctc gaacagccag aagacaggtt gtctcctggg ccttggacac     60

agccngccag gccattgaag ganaagcaaa gacgaagcga accatctctc tccattgtgg    120

gggccaagta gctgcantan ccttcagtcc cagttgcatt gggttaaaga gctcatacat    180

actatgtgtn aggggtacag aagcttttcc tcatagggca tgagctctcc nagagttgac    240

cttttgcctn aacttggggt ttctgtggtt cataaagttn ggatatgtat tttttttcaa    300

atggaanaaa atccgtattt ggcaaaaaga ctccaggggg atgatactgt ccttgccact    360

tacagtccaa angatnttcc ccaaagaata gacatttttt cctctcatca cttctggatg    420

caaaatcttt tattttttc ctttctcgca ccnccccaga ccccttnnag gttnaaccgc    480

ttcccatctc ccccattcca cacgatnttg aattngcann ncgttgntgg tcgggtcccn    540

nccgaaaggg tntttttatt cggggtnctg anttnnnaac cnctnagttg aatccgcggg    600

gcggccnngn gggttnnacc atgntgggga naactncccn ccgcgnttgg aatgccanag    660

ccttgaaant tttcttttgg tcgccccccn gagattc                             697
```

<210> SEQ ID NO 4
<211> LENGTH: 712
<212> TYPE: DNA
<213> ORGANISM: Homo sapien
<220> FEATURE:
<221> NAME/KEY: misc_feature
<222> LOCATION: (1)...(712)
<223> OTHER INFORMATION: n = A,T,C or G

<400> SEQUENCE: 4

```
gtactcagac aaccaatagg tgtgttyctc anatctgaaa cacaaaaaga ttctagctna     60

taatgttsaa tggttgaggg tttaagtgat cttggtatgt tngatttagc agcgatnggc    120

cgggtgcggt ggctcacgca tgtatcccag cactttggga ggccgaggca ggaggatcac    180

ctgaggtcag gagtttgaga ccagcctggc cgacatggtn aaaccccgtc tctactanga    240

atacanaaat tagcccgggc atagtggcgc gtgcctrtga cctcsgctac tttggggatt    300

ctcctgagga agaattgctt gaactcaggg aagtggargt ttgcagtgag cttaaatcaa    360

gccactggca ctcccagcct gggktaacag agccamgact ctkgccgaaa aaaaaraama    420

cgacggagaa nmagntctgt tattccatgg gaaattkgaa tttccttcyt tkaaatatct    480

taaaatnggt cctcctwaaa aaagttcggc tggggcccgk tggctcacat tttkttaycc    540
```

-continued

```
cycccccttt tggggarggc caarggccgg kttgawtnnc ccttgagggg ccanaactcc    600

agnaaccrgn cccgggccar smgwkgkstr armccctttc cyyccmaraa aawwcsmaaa    660

wwttycccsc cygsykggct ggkasckgtt myyyyygmtm csyagcttgc tt            712
```

<210> SEQ ID NO 5
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 5

```
gtactcagac cacctcacat gcagggtnag aaacatggag tgtgcggcag catcctcctc     60

acatcccttt gtgagcacgg ctgctccgga atactgacca tctgggctag cacgacctaa    120

cagagggttc tgcaggatgt gctattttaa agcagctggg tgcaacttgt gaaaacggga    180

atctngaagc agaacatgtn atcagcgatg gctgggattg gtggacagga ttgacaggag    240

tatttgaggc tctaccaggc ctgtctacag gacagcttca tcgaagggac attttttaac    300

ctgttatttt anatnccaca tatntttttt aatgctnaag catacaggtt gaatttctgg    360

atcgtaacta ctagtgactt ctgaggttta cagttngaat atgttctcnn aggtttatca    420

agttntgtta ttgatgatng gtaatctaca cctctggaag ctgtngaatg tgaaaaagat    480

ncntncanct gaccagtttg nagggcactc tcttctggna agnaatccgn ccaaaaaaat    540

tgtttcnagg gggcntgggg ggtttaaaaa aatgtttctn ttnccntaaa aatgtttacc    600

cnnctattga aaaaatgggg gtcgnggggg gcttnaaatc cccnanttnt gaatnttnta    660

tccggaanct tggtttccc                                                 679
```

<210> SEQ ID NO 6
<211> LENGTH: 369
<212> TYPE: DNA
<213> ORGANISM: Homo sapien
<220> FEATURE:
<221> NAME/KEY: misc_feature
<222> LOCATION: (1)...(369)
<223> OTHER INFORMATION: n = A,T,C or G

<400> SEQUENCE: 6

```
tcagtccagt catgggtcct ataagagaag tcactctgtg agtttccatg gaggaagaaa     60

aagcttcatt tctttaccct gcagcaacag cggagggagg gagagcctat cttctttgca    120

aattcattaa ctttgtggtt gaagggagca gcgtcngaaa ctgctttagc acagtgggag    180

gaaaacaaac agattcatct ccggaaacca aaggaaaggg tragtgggtt tttattagcc    240

agctgtatcc tagatggtca atttccagtg gatgaataca ccttacgtac gtttctcttg    300

cttcctacct nggcctgatc agctnggcac ttraatcatt ccgtnggggt wgctgtnaca    360

ctggactga                                                            369
```

<210> SEQ ID NO 7
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 7

-continued tgctggatra gggatggggc acgggagcac agatmgactt taactgcccc cacgttntcm 60
aggaaaggat tacaggcgtg agccactgcg cccggcctct tctccacttt cataggttcc 120
agtctctggt tcttctttct cagtttgttg tttttgcttc ttaaatmatg gagatnagaa 180
tgaacactac actcggaatc aggaagccct gcctggcgcc tctgtcacct gtctaggggc 240
ttcttctcac tgagtcatcc agca 264

<210> SEQ ID NO 8
<211> LENGTH: 280
<212> TYPE: DNA
<213> ORGANISM: Homo sapien
<220> FEATURE:
<221> NAME/KEY: misc_feature
<222> LOCATION: (1)...(280)
<223> OTHER INFORMATION: n = A,T,C or G

<400> SEQUENCE: 8
acctcaactg cccanaacan aactgttgta caagatttga ggatttaaca atatttcaca 60
tgaaatattt cagacctacg ngagggctta aagacnaatt aaatgagcac cngtgtgccc 120
accgccccna ttaagaatta gagcaagcag tgaggtgaag ccttgtcctt gcttttaaca 180
tagaaagtga tccaaattca ccaaacttga cttnnggttt tgcagtgtgg cctcctgatt 240
ctagacnctg gcgaaacatt tgatgggcaa aaaaaaaaaa 280

<210> SEQ ID NO 9
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 9
tcgtcaactc caggatggct ttgaaaatna atggacacag atctctcctg ttttgatrat 60
ntgcagtgct natgactggc tttgcagttn attttgattc aggcaacaga tgttcctttt 120
ggttccctgt ctcccatggg cgtcatttca tgttgtcctc tgccttcccc cagatattct 180
aagttcagga cacaagcttc tggcccatgc agagcagagg ccatgagggg tcacagcatg 240
ggtacgggag gaaacactgg gctnacccag atnctggact tgagtcttgc ctctgctgct 300
tgctgcacag cttctgtcat ggtgctaaac ctgtgacctg cctcacaggc ttagagcatg 360
cccgtagaag tactctnaac taaratgctt tccacaaatg agatggtttc atgaaaactt 420
caaatagagg gcctgggcaa aaaaaaaaa 449

<210> SEQ ID NO 10
<211> LENGTH: 538
<212> TYPE: DNA
<213> ORGANISM: Homo sapien
<220> FEATURE:
<221> NAME/KEY: misc_feature
<222> LOCATION: (1)...(538)
<223> OTHER INFORMATION: n = A,T,C or G

<400> SEQUENCE: 10
tttttttttt ttcccaaagg cctcaraaca ctagtcttct aattccaagc agaaagttac 60
atccgccggg atacatgcca cttggtttga taaatcaaaa tacagcatcc ttcagatccc 120
tttgctgagc aatacaatta tttgtatatg ttactttttt ttctgtttgg ctnaaagatt 180

-continued

```
tgatatgagc tgaggaaaat gaagccntta ctgctatnag atctnatccc tttccaccac    240

ctttcaggga tnttggcact gcayatattc agaattcccc nnagtcgctn gtgataaaaa    300

tgtcttcaga gatggcagaa tatgtttcct ttggtacatg ttcattaaaa atatacacgt    360

gctcactact gtggatatgt atgtnttgac cgatnacaca ggctgattta gggaagagat    420

aaaagcacac ttngaattta ttagcctttc accnagacta anattctgaa attaagaatg    480

tattccttgg tcaacaattt tcctcttctc ttagccctct tacattgtan tggactga      538


<210> SEQ ID NO 11
<211> LENGTH: 543
<212> TYPE: DNA
<213> ORGANISM: Homo sapien
<220> FEATURE:
<221> NAME/KEY: misc_feature
<222> LOCATION: (1)...(543)
<223> OTHER INFORMATION: n = A,T,C or G

<400> SEQUENCE: 11

tttttttttt ttgcccacag ctgccatctt tgtgtgataa ggccaacctt ctatgggaat     60

caaccctcgc catcccagca aatcccctct ctcccttctc atgggagtgc cttgtattca    120

tcaggcatct gggacttgat gtgggtntgg gatttgaaat cagagcacct nggtctctst    180

caccattctn tcacttatta gctctnacct tgggtnaata cctgccttag tgtcntaggt    240

acaatatgaa tattgtctat ttctcaggga ttgcaatgac nagtnnatna gtgcatgaga    300

gggtaaaacc acagggtact ccgctcctcc naagaatgga gaattttttc tagaagccca    360

natntgcttg gaaggttggc caccnagagc cnnaatcttc ttttatttnc cactgaangc    420

ctaagaggna attctgaact catccccnna tgacctctcc cgaatmagaa tatctctggc    480

acttaccata ttttcttgcc ctcttccact tacnaaactc ctttattcct taacnggacg    540

aaa                                                                  543


<210> SEQ ID NO 12
<211> LENGTH: 329
<212> TYPE: DNA
<213> ORGANISM: Homo sapien

<400> SEQUENCE: 12

cgatgacttg ggcagtgagt gggcctcctg ccaggtggca gggcacagct tagaccaaac     60

ccttggcctc ccccctctgc agstacctct gaccaagaag gaaactagca agcctatgct    120

ggcaagacca taggtggggt gctgggaatc ctcggggccg gctggcaccc actcctggtg    180

ctcaagggag agacccactt gttcagatgc atrggcctca ggcggttcaa ggcrgtctta    240

gagccacaga gtcaaataaa aatcaatttt gagagaccac agcacctgct gctttgatcg    300

tgatgttcaa ggcaagttgc aagtcatcg                                      329


<210> SEQ ID NO 13
<211> LENGTH: 314
<212> TYPE: DNA
<213> ORGANISM: Homo sapien
<220> FEATURE:
<221> NAME/KEY: misc_feature
<222> LOCATION: (1)...(314)
<223> OTHER INFORMATION: n = A,T,C or G

<400> SEQUENCE: 13

cgatgacttg cacccgggag ctgtgacagt ggcctggaag cagatggcag ccccgtcaag     60

gcgggagtgg agaccaccaa accctccaaa cagagcaaca actagtacgc ggccagcagc    120
```

-continued

```
tacctgagcc tgacgcccga gcagtggaag tcccacagaa gctacagctg ccaggtcacg    180

catgaaggga gcaccgtgga gaagacagtg gcccctacag aatgttcata ggttcccnac    240

tctnacccca cccacgggag cctggganctg cangatcccg ggggaagggt ctctctcccc    300

atcccaagtc atcg                                                      314
```

```
<210> SEQ ID NO 14
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 14

cgattacttg cacaatgcan attagaaccc aaatgaaggg tacaacccag atcttctggc     60

ttccagttca gtgctgctgg gtttttctta ctaaaccaaa acaatkaaga gcatagaagg    120

gaagagaaga ataaagtcta ttttggtctt tggtagcchg ggtaangaga atgctstcac    180

tctacnagaa aacccnaagt gaacccggct aatcaggacc gtgcttggga agggagcagg    240

ggcattacct ttcaacacca gaggttcttt gccttctctc tgcagggact cgargactat    300

gtgaagtggc tgggarggca tcactcggct tggttcattg gtrttctcat cataaactat    360

natttctttg gaaaaagatc ctcttgaaag artccttgcc ttccctacag gaaatcaagt    420

ctaggacagt gatcttgccc ctgcttgcas tctccgccgg ctgatcttat csgscccagt    480

tkatgtgsam cgctccttgg atrtkactct tgttttwctc cvaggaaggg gcytgcmagt    540

ccnwtnaatg amssgggccc ttaactccgg scrggtnamy ncttgsctsc rattttgggt    600

ycytcttcyt ttgsccmggt tcktcnaaac cacttngttr aattccccgg sccgcctkgc    660

nggtycaacc wttttgggaa mamcyccccc c                                   691
```

```
<210> SEQ ID NO 15
<211> LENGTH: 355
<212> TYPE: DNA
<213> ORGANISM: Homo sapien
<220> FEATURE:
<221> NAME/KEY: misc_feature
<222> LOCATION: (1)...(355)
<223> OTHER INFORMATION: n = A,T,C or G

<400> SEQUENCE: 15

acctgaactg tgtgttgaag agtgatgtcc tgctgcctgg agctcaagtc actactgatg     60

accgtgccta tgtccgacag ctagttncct ccatggatgt gactgagacc aatgtcttct    120

tcyaccctcg gctcttacct ttgacnaagt ctcccgttga gagtactacc gaaccaccag    180

cagttcgagc ctctnaagag cgtctaagcg atggggatat atatttactg gagaatgggc    240

tcaacctctt cctctgggtg ggagcaagcg tccagcaggg tgttgtccag agccttttca    300

gcgtctcctc cttcagtcag atcaccagtg gtntgagtgt tctgccagtt caggt         355
```

```
<210> SEQ ID NO 16
<211> LENGTH: 522
<212> TYPE: DNA
<213> ORGANISM: Homo sapien
<220> FEATURE:
<221> NAME/KEY: misc_feature
<222> LOCATION: (1)...(522)
<223> OTHER INFORMATION: n = A,T,C or G
```

-continued

<400> SEQUENCE: 16
tcagtccagt gaggtggaag acttcgaggc tcgtgggagc cgcttctcca agtctgctga 60
tgagagacag cgcatgctgg tgcagcgtan ggacgaactc ctccagcaag ctcgcagacg 120
tttcttgaac aaaagttctg aagatgatgc ggcctcagag agcttcctcc cctcggaagg 180
tgcgtcctct gaccccgtga ccctncgtcg aangatgctg gctgccgccg cggaacggan 240
gcttcagaag cagcagacct cctngcgctc ccttgccttc ctcagctgcc tcctgcgccc 300
tgtgcccggc tgactggagg aggcctgtcc aattctgccc gccccatgga aaagcgggct 360
tgactgcatt gccgctgtat naaagcatgt ggtcttacag tgttnggacn gctnatnaat 420
ttnatcctnc tntgtaatac ttcctatgtg acatttctct tccccttgga aacactgcan 480
attttaactg tgagtttgat ctcttctngt gttactggac tg 522

<210> SEQ ID NO 17
<211> LENGTH: 317
<212> TYPE: DNA
<213> ORGANISM: Homo sapien

<400> SEQUENCE: 17
gtgtcgcgaa ttcgcggtgg tgctaagaaa aggaagaaga agtcttacac cactcccaag 60
aaggataagc accagagaaa gaaggttcag ccggccgtcc tgaaatatta taaggtggat 120
gagaatggca aaattagttg ccttcgtcga gagtgcccct ctgatgaatg tggtgctggg 180
gtgtttatgg caagtcactt tgacagacat tattgtggca aatgttgtct gacccactgt 240
ttcaactaac cagaagacaa gtaactgtat gagttaatta aagacatgaa ctaaaaaaaa 300
aaaaaaaaaa actcgag 317

<210> SEQ ID NO 18
<211> LENGTH: 392
<212> TYPE: DNA
<213> ORGANISM: Homo sapien

<400> SEQUENCE: 18
tggagatttc taatgaggtg aggaagttcc gtacattgac agaattgatc ctcgatgctc 60
aggaacatgt taaaaatcct tacaaaggca aaaaactcaa gaaacaccca gacttcccca 120
agaagcccct gaccccttat ttccgcttct tcatggagaa gcgggccaag tatgcgaaac 180
tccaccctca gatgagcaac ctggacctga ccaagattct gtccaagaaa tacaaggagc 240
ttccggagaa gaagaagatg aaatatgttc cggacttcca gagaagagaa acaggagttc 300
gagcgaaacc tggcccgatt cagggaggat cacccccacc ttatccagaa tgccaagaat 360
cggacatccc agagaagccc caagaccccc cg 392

<210> SEQ ID NO 19
<211> LENGTH: 2624
<212> TYPE: DNA
<213> ORGANISM: Homo sapien

<400> SEQUENCE: 19
gaaacagtga gaaggagatt cctgtgctca atgagctgcc agtccccatg gtggcccgct 60
acattcgcat aaaccctcag tcctggtttg ataacgggag catctgcatg aggatggaga 120
tcttgggctg cccactgccg gatcctaata actattatca ccgacgtaat gagatgacca 180
ccacggatga cctggatttt aagcaccaca actattagga aatgcgccag ttgatgaagg 240
ttgtcaatga aatgtgcccc aatattacca ggatttacaa cattggcaaa agccaccagg 300

-continued

```
gcctgaaatt gtatgcggta gagatctctg accatcctgg ggaacatgaa gttggtgagc    360
ccgagttcca ctacatcgca ggggcccacg gcaatgaggt tctgggacga gaactgctgc    420
tgctgctgct gcacttcctc tgccaggaat actcggcgca gaacgcacgc atcgtccgct    480
tggtggagga gactcgaatc cacattctac cctccctcaa tcctgatggc tatgagaagg    540
cctatgaagg aggttccgag ttgggaggct ggtccctggg acgttggacc catgatggca    600
tcgatatcaa caacaacttt ccggatttaa actcgctgct ctgggaggca gaggaccagc    660
agaatgcccc aaggaaggtc cccaaccact acattgccat ccctgagtgg tttctgtctg    720
agaatgccac agtggccaca gagaccagag ccgtcatcgc ctggatggag aagatcccgt    780
ttgtgctggg aggcaaccta caggggggtg agctggtcgt ggcatacccc tatgacatgg    840
tgcggtccct gtggaagacc caggagcaca ccccaacacc tgatgatcat gtgttccgct    900
ggctggcgta ttcctacgcc tccactcacc gcctcatgac agatgccagg aggcgagtgt    960
gccacacgga agattttcag aaggaggagg gcaccgtcaa tggggcttcc tggcacacag   1020
tggctggaag tctaaacgat ttcagctacc tccatacaaa ctgctttgag ctgtccatct   1080
acgtgggctg tgataaatac ccacacgaga gcgagctgcc ggaggaatgg gagaataacc   1140
gggagtctct gattgtgttc atggagcagg ttcatcgagg catcaaaggc atagtgagag   1200
atttacaagg gaaagggatt tcaaatgctg tcatctctgt ggaaggtgtt aaccatgaca   1260
tccggacagc cagcgatggg gattactggc gtctactgaa ccctggcgaa tatgtggtca   1320
cagccaaggc ggaaggcttt atcacttcca ccaagaactg catggttggc tatgatatgg   1380
gagctactcg gtgtgacttc accctcacaa agaccaacct ggctaggata agagaaatta   1440
tggagacatt tgggaagcag cctgtcagcc taccctccag gcgcctgaag ctgcggggac   1500
ggaaaaggcg gcagcgtggg tgaccctgtc ggacacttga gacatacccc agaccgtgca   1560
aataaaaatc cactccagta gtaactctgt agcaggcttt ccctgttgtt ttgactgtaa   1620
ttcaagagac actcaggagc atacctgcat ggcttggctg accccaaagg ggagggctgg   1680
tggctcaggg tgttttgttt tttgtttttt gtttttttcct ttgttctcat ttatccaaat   1740
accttgaaca gagcagcaga gaaaggccgg tggcagtgag ggaattaatt cagtgagtca   1800
gtctgagatt ctaaaaaggg tgcttgacca ctggccagga agggaaatca ggccttcccc   1860
catttgcgtg acattcaagc ttcccagtgc atttgcaagt ggcacagttg acattgcagc   1920
acccagggaa tcctttgccc cagatgttat catttgagat gctcttatgc agcctaagaa   1980
aatccatcct ctctggcccc aggggacaag ccaagctgct atgtacacac tcggtgttct   2040
attgacaata gaggcattta ttaccaagtg tgcatcgctg agtcctaaat cagctctgtt   2100
ccttttttcca acaaagcttg tcttcctaag agcagacaga agtggagagc acccaagaat   2160
gagtgctggg cagcagaccc tgggggaggg ggcttgctat cccagaaagc cctaaaccc    2220
tttgctgctc cattagccct ggggtgagga gagccagaca tgttaggagg ccagagcagt   2280
cagtcagggc atcttggaaa agaccttgaa ggaagcaaac cctgggttcc ttttgctcca   2340
gaatgtgaga gctccaagtt ggccccaatc aggaggggag taatgatgaa catacagacg   2400
gccacatctt gccaatcaag catcatctga tgaaaaagaa agcaatctta ggattacctg   2460
ggacacgtca gtctgggaga ggtggttgaa tcattgtgta agggaatagt gtatctaatc   2520
tgtgttgatc ctgctgcctt gttgacctgg agagaatgaa acaaacaaac acataaacaa   2580
ataaagcaaa tggtaagatt aaaaaaaaaa aaaaaaaact cgag                    2624
```

-continued

<210> SEQ ID NO 20
<211> LENGTH: 488
<212> TYPE: DNA
<213> ORGANISM: Homo sapien

<400> SEQUENCE: 20
ctttcaaccc gcgctcgccg gctccagccc cgcgcgcccc caccccttgc cctcccggcg 60
gctccgcagg gtgaggtggc tttgaccccg ggttgcccgg ccagcacgac cgaggaggtg 120
gctggacagc tggaggatga acggagaagc cgactgcccc acagacctgg aaatggccgc 180
ccccagaggc caagaccgtt ggtcccagga agacatgctg actttgctgg aatgcatgaa 240
gaacaacctt ccatccaatg acagctccca gttcaaaacc acccaaacac acatggaccg 300
ggaaaaagtt gcattgaaag acttttctgg agacatgtgc aagctcaaat gggtcgagat 360
ctctaatgag gtgaggaagt tccgtacatt gacagaattg atcctcgata ctcaggaaca 420
tgtttaaaat ccttacaaag gcaaaaaatc aagaaacacc ccgacttccc cgagaaagcc 480
cctaaccc 488

<210> SEQ ID NO 21
<211> LENGTH: 391
<212> TYPE: DNA
<213> ORGANISM: Homo sapien

<400> SEQUENCE: 21
atggaattgt ggttttctct ttgggatcaa tggtctcaga aattccagag aagaaagctg 60
tggcgattgc tgatgctttg ggcaaaatcc ctcagacagt cctgtggcgg tacactggaa 120
cccgaccatc gaatcttgcg aacaacacga tacttgttca gtggctaccc caaaacgatc 180
tgcttggtca cccaatgacc cgtgcccttta tcacccatgc tagttcccat ggtgttaatg 240
aaagcatatg caatggcgtt cccatggtga tgataccctt atttggtgat cagatggaca 300
atgcaaagcg cagggagact aagggagctg gagtgaccct gaatgttctg gagatgactt 360
ctgaagatct agaagatgct ctgaagagca g 391

<210> SEQ ID NO 22
<211> LENGTH: 1320
<212> TYPE: DNA
<213> ORGANISM: Homo sapien

<400> SEQUENCE: 22
aatctgctgg gaatttcttg ggttgacagc tcttggatcc ctattttgaa cagtggtagt 60
gtcctggatt acttttcaga aagaagtaat cctttttatg acagaacatg taataatgaa 120
gtggtcaaaa tgcagaggct aacattagaa cacttgaatc agatggttgg aatcgagtac 180
atccttttgc atgctcaaga gcccattctt ttcatcattc ggaagcaaca gcggcagtcc 240
cctgcccaag ttatcccact agctgattac tatatcattg ctggagtgat ctatcaggca 300
ccagacttgg gatcagttat aaactctaga gtgcttactg cagtgcatgg tattcagtca 360
gcttttgatg aagctatgtc atactgtcga tatcatcctt ccaaagggta ttggtggcac 420
ttcaaagatc atgaagagca agataaagtc agacctaaag ccaaaaggaa agaagaacca 480
agctctattt ttcagagaca acgtgtggat gctttacttt tagacctcag acaaaaattt 540
ccacccaaat ttgtgcagct aaagcctgga gaaaagcctg ttccagtgga tcaaacaaag 600
aaagaggcag aacctatacc agaaactgta aaacctgagg agaaggagac cacaaagaat 660
gtacaacaga cagtgagtgc taaaggcccc cctgaaaaac ggatgagact tcagtgagta 720

-continued

```
ctggacaaaa gagaagcctg gaagactcct catgctagtt atcatacctc agtactgtgg     780

ctcttgagct ttgaagtact ttattgtaac cttcttattt gtatggaatg cgcttatttt     840

ttgaaaggat attaggccgg atgtggtggc tcacgcctgt aatcccagca ctttgggagg     900

ccatggcggg tggatcactt gaggtcagaa gttcaagacc agcctgacca atatggtgaa     960

accccgtctc tactaaaaat acaaaaatta gccgggcgtg gtggcgggcg cccatagtcc    1020

cagctactcg ggaggctgag acaggagact tgcttgaacc cgggaggtgg aggttgccct    1080

gagctgatca tcctgctgtt gcactccagc ttgggcgaaa gagcgagact ttgtctctat    1140

aaagaaggaa agatattatt cccatcatga tttcttgtga atatttgtaa tatgtttttt    1200

gtaacctttc ctttcccgga cttgagcaac ctacacactc acatgtttaa tggtagatat    1260

gttttaaagc aagataaagg tattggtttt aaaaaaaaaa aaaaaaaaaa aaaactcgag    1320
```

<210> SEQ ID NO 23
<211> LENGTH: 633
<212> TYPE: DNA
<213> ORGANISM: Homo sapien

<400> SEQUENCE: 23

```
ctaagggcag tgaaggtgaa aaccctctca cggtcccagg gagggagaag gaaggcatgc      60

tgatgggggt taagccgggg gaggacgcat cggggcctgc tgaagacctt gtgagaagat     120

ctgagaaaga tactgcagct gttgtctcca gacagggcag ctccctgaac ctctttgaag     180

atgtgcagat cacagaacca gaagctgagc cagagtccaa gtctgaaccg agacctccaa     240

tttcctctcc gagggctccc cagaccagag ctgtcaagcc ccgacttcat cctgtgaagc     300

caatgaatgc cacggccacc aaggttgcta actgcagctt gggaactgcc accatcatcg     360

gtgagaactt gaacaatgag gtcatgatga agaaatacag cccctcggac cctgcatttg     420

catatgcgca gctgacccac gatgagctga ttcagctggt cctcaaacag aaggaaacga     480

taagcaagaa ggagttccag gtccgcgagc tggaagacta cattgacaac ctgctcgtca     540

gggtcatgga agaaaccccc aatatcctcc gcatcccgac tcaggttggc aaaaaagcag     600

gaaagatgta aattagcaga aaaaaaactc gag                                  633
```

<210> SEQ ID NO 24
<211> LENGTH: 1328
<212> TYPE: DNA
<213> ORGANISM: Homo sapien

<400> SEQUENCE: 24

```
gtaaacgctc tcggaattat ggcggcggtg gatatccgag acaatctgct gggaatttct      60

tgggttgaca gctcttggat ccctattttg aacagtggta gtgtcctgga ttacttttca     120

gaaagaagta atcctttttta tgacagaaca tgtaataatg aagtggtcaa aatgcagagg     180

ctaacattag aacacttgaa tcagatggtt ggaatcgagt acatcctttt gcatgctcaa     240

gagcccattc ttttcatcat tcggaagcaa cagcggcagt cccctgccca agttatccca     300

ctagctgatt actatatcat tgctggagtg atctatcagg caccagactt gggatcagtt     360

ataaactcta gagtgcttac tgcagtgcat ggtattcagt cagcttttga tgaagctatg     420

tcatactgtc gatatcatcc ttccaaaggg tattggtggc acttcaaaga tcatgaagag     480

caagataaag tcagacctaa agccaaaagg aaagaagaac caagctctat ttttcagaga     540

caacgtgtgg atgctttact tttagacctc agacaaaaaa tttccaccca aatttgtgca     600
```

-continued

```
gtggatcaaa caaagaaaga ggcagaacct ataccagaaa ctgtaaaacc tgaggagaag    660

gagaccacaa agaatgtaca acagacagtg agtgctaaag gcccccctga aaaacggatg    720

agacttcagt gagtactgga caaaagagaa gcctggaaga ctcctcatgc tagttatcat    780

acctcagtac tgtggctctt gagctttgaa gtactttatt gtaaccttct tatttgtatg    840

gaatgcgctt atttttttga aaggatatta ggccggatgt ggtggctcac gcctgtaatc    900

ccagcacttt gggaggccat ggcgggtgga tcacttgagg tcagaagttc aagaccagcc    960

tgaccaatat ggtgaaaccc cgtctctact aaaaatacaa aaattagccg ggcgtggtgg   1020

cgggcgccca tagtcccagc tactcgggag gctgagacag gagacttgct tgaacccggg   1080

aggtggaggt tgccctgagc tgattatcat gctgttgcac tccagcttgg gcgacagagc   1140

gagactttgt ctcaaaaaag aagaaaagat attattccca tcatgatttc ttgtgaatat   1200

ttgtgatatg tcttctgtaa cctttcctct cccggacttg agcaacctac acactcacat   1260

gtttactggt agatatgttt aaaagcaaaa taaaggtatt tgtataaaaa aaaaaaaaaa   1320

aaactcga                                                            1328
```

<210> SEQ ID NO 25
<211> LENGTH: 1758
<212> TYPE: DNA
<213> ORGANISM: Homo sapien

<400> SEQUENCE: 25

```
gttttttttt tttttttttt aaagagttgc aacaattcat ctttatttct tattttcctc     60

tggagatgca gaatttggta tatttcaccc caagtatatt tgggatagtt ggctcctcgc    120

tgggtcagga tggctgggtg ccttctcccc tggcatggtt ctcttctctg cagggcgagg    180

ggcagggagc tagtaaaacc tcgcaatgac agccgcaatg gcagacccaa tggagcccag    240

gatgaacttg gtcaatccgg agagtccagt tgctcccagt gactgcagag tagccacaag    300

gctgcccgag gcaactccac ccccattggc aatggccgcc gcggacatca tcttggctgc    360

tatggaggac gaggcgattc ccgccgcagt gaagcccatg gcactgagtg gcggcggtgg    420

atatccgaga caatctgctg ggaatttctt gggttgacag ctcttggatc cctattttga    480

acagtggtag tgtcctggat tacttttcag aaagaagtaa tcctttttat gacagaacat    540

gtaataatga agtggtcaaa atgcagaggc taacattaga acacttgaat cagatggttg    600

gaatcgagta catccttttg catgctcaag agcccattct tttcatcatt cggaagcaac    660

agcggcagtc ccctgcccaa gttatcccac tagctgatta ctatatcatt gctggagtga    720

tctatcaggc accagacttg ggatcagtta taaactctag agtgcttact gcagtgcatg    780

gtattcagtc agcttttgat gaagctatgt catactgtcg atatcatcct tccaaagggt    840

attggtggca cttcaaagat catgaagagc aagataaagt cagacctaaa gccaaaagga    900

aagaagaacc aagctctatt tttcagagac aacgtgtgga tgctttactt ttagacctca    960

gacaaaaatt tccacccaaa tttgtgcagc taaagcctgg agaaaagcct gttccagtgg   1020

atcaaacaaa gaaagaggca gaacctatac cagaaactgt aaaacctgag gagaaggaga   1080

ccacaaagaa tgtacaacag acagtgagtg ctaaaggccc ccctgaaaaa cggatgagac   1140

ttcagtgagt actggacaaa agagaagcct ggaagactcc tcatgctagt tatcatacct   1200

cagtactgtg gctcttgagc tttgaagtac tttattgtaa ccttcttatt tgtatggaat   1260

gcgcttattt tttgaaagga tattaggccg gatgtggtgg ctcacgcctg taatcccagc   1320

actttgggag gccatggcgg gtggatcact tgaggtcaga agttcaagac cagcctgacc   1380
```

-continued aatatggtga aaccccgtct ctactaaaaa tacaaaaatt agccgggcgt ggtggcgggc 1440
gcccatagtc ccagctactc gggaggctga gacaggagac ttgcttgaac ccgggaggtg 1500
gaggttgccc tgagctgatt atcatgctgt tgcactccag cttgggcgac agagcgagac 1560
tttgtctcaa aaaagaagaa aagatattat tcccatcatg atttcttgtg aatatttgtt 1620
atatgtcttc tgttaccttt cctctcccgg aattgagcaa cctacacact cacatgttta 1680
ctggtagata tgtttaaaag caaataaagg tattggtata tattgcttca aaaaaaaaaa 1740
aaaaaaaaaa aactcgag 1758

<210> SEQ ID NO 26
<211> LENGTH: 493
<212> TYPE: DNA
<213> ORGANISM: Homo sapien

<400> SEQUENCE: 26
gaggcgagcg gcagggcctg gtggcgagag cgcggctgtc actgcgcccg agcatcccag 60
agctttccga gcggacgagc cggccgtgcc gggcatcccc agcctcgcta ccctcgcagc 120
acacgtcgag ccccgcacag gcaagggtcc ggaacttagc ccaaagcacg tttcccctgg 180
cagcgcagga gacgcccggc cgcgcgccgg cgcacgcccc cctctcctcc tttgttccgg 240
gggtcggcgg ccgctctcct gccagcgtcg ggatctcggc cccgggaggc gggccgtcgg 300
gcgcagccgc gaagattccg ttggaactga cgcagagccg agtgcagaag atctgggtgc 360
ccgtggacca caggccctcg ttgcccagat cctgtgggcc aaagctgacc aactcccccg 420
ccgtcttcgt catggtgggc ctccccgcc cggggcaaga cctacttctc cacgaaagct 480
tactcgctgc ctc 493

<210> SEQ ID NO 27
<211> LENGTH: 1331
<212> TYPE: DNA
<213> ORGANISM: Homo sapien

<400> SEQUENCE: 27
ggtggatatc cgagacaatc tgctgggaat ttcttgggtt gacagctctt ggatccctat 60
tttgaacagt ggtagtgtcc tggattactt ttcagaaaga agtaatcctt tttatgacag 120
aacatgtaat aatgaagtgg tcaaaatgca gaggctaaca ttagaacact tgaatcagat 180
ggttggaatc gagtacatcc ttttgcatgc tcaagagccc attcttttca tcattcggaa 240
gcaacagcgg cagtcccctg cccaagttat cccactagct gattactata tcattgctgg 300
agtgatctat caggcaccag acttgggatc agttataaac tctagagtgc ttactgcagt 360
gcatggtatt cagtcagctt ttgatgaagc tatgtcatac tgtcgatatc atccttccaa 420
agggtattgg tggcacttca aagatcatga agagcaagat aaagtcagac ctaaagccaa 480
aaggaaagaa gaaccaagct ctatttttca gagacaacgt gtggatgctt tacttttaga 540
cctcagacaa aaatttccac ccaaatttgt gcagctaaag cctggagaaa agcctgttcc 600
agtggatcaa acaaagaaag aggcagaacc tataccagaa actgtaaaac ctgaggagaa 660
ggagaccaca aagaatgtac aacagacagt gagtgctaaa ggcccccctg aaaaacggat 720
gagacttcag tgagtactgg acaaaagaga agcctggaag actcctcatg ctagttatca 780
tacctcagta ctgtggctct tgagctttga agtactttat tgtaaccttc ttatttgtat 840
ggaatgcgct tattttttga aaggatatta ggccggatgt ggtggctcac gcctgtaatc 900

-continued ccagcacttt gggaggccat ggcgggtgga tcacttgagg tcagaagttc aagaccagcc 960
tgaccaatat ggtgaaaccc cgtctctact aaaaatacaa aaattagccg ggcgtggtgg 1020
cgggcgccca tagtcccagc tactcgggag gctgagacag gagacttgct tgaacccggg 1080
aggtggaggt tgccctgagc tgattatcat gctgttgcac tccagcttgg gcgacagagc 1140
gagactttgt ctcaaaaaaa gaagaaaaga tattattccc atcatgattt cttgtgaata 1200
tttgttatat gtcttctgta acctttcctc tcccggactt gagcaaccta cacactcaca 1260
tgtttactgg tagatatgtt taaaagcaaa ataaaggtat tggtataaaa aaaaaaaaaa 1320
aaaaactcga g 1331

<210> SEQ ID NO 28
<211> LENGTH: 1333
<212> TYPE: DNA
<213> ORGANISM: Homo sapien

<400> SEQUENCE: 28
cggcggtgga tatccgagac aatctgctgg gaatttcttg ggttgacagc tcttggatcc 60
ctattttgaa cagtggtagt gtcctggatt acttttcaga aagaagtaat cctttttatg 120
acagaacatg taataatgaa gtggtcaaaa tgcagaggct aacattagaa cacttgaatc 180
agatggttgg aatcgagtac atccttttgc atgctcaaga gcccattctt ttcatcattc 240
ggaagcaaca gcggcagtcc cctgcccaag ttatcccact agctgattac tatatcattg 300
ctggagtgat ctatcaggca ccagacttgg gatcagttat aaactctaga gtgcttactg 360
cagtgcatgg tattcagtca gcttttgatg aagctatgtc atactgtcga tatcatcctt 420
ccaaagggta ttggtggcac ttcaaagatc atgaagagca agataaagtc agacctaaag 480
ccaaaaggaa agaagaacca agctctattt ttcagagaca acgtgtggat gctttacttt 540
tagacctcag acaaaaattt ccacccaaat ttgtgcagct aaagcctgga gaaaagcctg 600
ttccagtgga tcaaacaaag aaagaggcag aacctatacc agaaactgta aaacctgagg 660
agaaggagac cacaaagaat gtacaacaga cagtgagtgc taaaggcccc cctgaaaaac 720
ggatgagact tcagtgagta ctggacaaaa gagaagcctg gaagactcct catgctagtt 780
atcatacctc agtactgtgg ctcttgagct ttgaagtact ttattgtaac cttcttattt 840
gtatggaatg cgcttatttt ttgaaaggat attaggccgg atgtggtggc tcacgcctgt 900
aatcccagca ctttgggagg ccatggcggg tggatcactt gaggtcagaa gttcaagacc 960
agcctgacca atatggtgaa accccgtctc tactaaaaat acaaaaatta gccgggcgtg 1020
gtggcgggcg cccatagtcc cagctactcg ggaggctgag acaggagact tgcttgaacc 1080
cgggaggtgg aggttgccct gagctgatta tcatgctgtt gcactccagc ttgggcgaca 1140
gagcgagact ttgtctcaaa aaagaagaaa agatattatt cccatcatga tttcttgtga 1200
atatttgtga tatgtcttct gtaacctttc ctctcccgga cttgagcaac ctacacactc 1260
acatgtttac tggtagatat gtttaaaagc aaaataaagg tatttgtata aaaaaaaaaa 1320
aaaaaaactc gag 1333

<210> SEQ ID NO 29
<211> LENGTH: 813
<212> TYPE: DNA
<213> ORGANISM: Homo sapien

<400> SEQUENCE: 29
ctgagctgca cttcagcgaa ttcacctcgg ctgtggctga catgaagaac tccgtggcgg 60

-continued

```
accgagacaa cagccccagc tcctgtgctg gcctcttcat tgcttcacac atcgggtttg    120
actggcccgg ggtctgggtc cacctggaca tcgctgctcc agtgcatgct ggcgagcgag    180
ccacaggctt tggggtggct ctcctactgg ctctttttgg ccgtgcctcc gaggacccgc    240
tgctgaacct ggtatccccg ctggactgtg aggtggatgc ccaggaaggc gacaacatgg    300
ggcgtgactc caagagacgg aggctcgtgt gagggctact tcccagctgg tgacacaggg    360
ttccttacct cattttgcac tgactgattt taagcaattg aaagattaac taactcttaa    420
gatgagtttg gcttctcctt ctgtgcccag tggtgacagg agtgagccat tcttctctta    480
gaagcagctt aggggcttgg tggggtctgg agaaaattgt cacagacccc ataggtctcc    540
atctgtaagc tctgtccctt gtcctccacc ctggtcttta gagccacctc aggtcaccct    600
ctgtagtgag tgtacttcct gacccaggcc cttgctcaag ctggggctcc ctggggtgtc    660
taaccagccc tgggtagatg tgactggctg ttagggaccc cattctgtga agcaggagac    720
cctcacagct cccaccaacc cccagttcac ttgaagttga attaaatatg gccacaacat    780
aaaaaaaaaa aaaaaaaaaa aaaaaaactc gag                                 813
```

<210> SEQ ID NO 30
<211> LENGTH: 1316
<212> TYPE: DNA
<213> ORGANISM: Homo sapien

<400> SEQUENCE: 30

```
caggcgccca gtcatggccc aagagacagc accaccgtgt ggcccagtct caaggggtga     60
cagtccaatc atagaaaaga tggaaaaaag gacatgtgcc ctgtgccctg aaggccacga    120
gtggagtcaa atatactttt caccatcagg aaatatagtt gctcatgaaa actgtttgct    180
gtattcatca ggactggtgg agtgtgagac tcttgatcta cgtaatacaa ttagaaactt    240
tgatgtcaaa tctgtaaaga aagagatctg gagaggaaga agattgaaat gctcattctg    300
taacaaagga ggcgccaccg tggggtgtga tttatggttc tgtaagaaga gttaccacta    360
tgtctgtgcc aaaaaggacc aagcaattct tcaagttgat ggaaaccatg gaacttacaa    420
attattttgc ccagaacatt ctccagaaca agaagaggcc actgaaagtg ctgatgaccc    480
aagcatgaag aagaagagag gaaaaaacaa acgcctctca tcaggccctc ctgcacagcc    540
aaaaacgatg aaatgtagta acgccaaaag acatatgaca gaagagcctc atggtcacac    600
agatgcagct gtcaaatctc cttttcttaa gaaatgccag gaagcaggac ttcttactga    660
actatttgaa cacatactag aaaatatgga ttcagttcat ggaagacttg tggatgagac    720
tgcctcagag tcggactatg aagggatcga gaccttactg tttgactgtg gattatttaa    780
agacacacta agaaaattcc aagaagtaat caagagtaaa gcttgtgaat gggaagaaag    840
gcaaaggcag atgaagcagc agcttgaggc acttgcagac ttacaacaaa gcttgtgctc    900
atttcaagaa aatggggacc tggactgctc aagttctaca tcaggatcct tgctacctcc    960
tgaggaccac cagtaaaagc tgttcctcag gaaaactgga tggggcctcc atgttctcca   1020
aggatcgagg aagtcttcct gcctaccctg cccaccccag tcaagggcag caacaccaga   1080
gctttgctca gccttaaatg gaatcttaga gctttctctt gcttctgcta ctcctacaga   1140
tggcctcatc atggtctcca ctcagtatta ataactccat cagcatagag caaactcaac   1200
actgtgcatt gcacactgtt accatgggtt tatgctcact atcatatcac attgccaata   1260
tttagcacac ttaataaatg cttgtcaaaa cccaaaaaaa aaaaaaaaaa ctcgag       1316
```

-continued

<210> SEQ ID NO 31
<211> LENGTH: 1355
<212> TYPE: DNA
<213> ORGANISM: Homo sapien

<400> SEQUENCE: 31

```
cggcggtgga tatccgagac aatctgctgg gaatttcttg ggttgacagc tcttggatcc      60

ctattttgaa cagtggtagt gtcctggatt acttttcaga aagaagtaat ccttttttatg     120

acagaacatg taataatgaa gtggtcaaaa tgcagaggct aacattagaa cacttgaatc     180

agatggttgg aatcgagtac atccttttgc atgctcaaga gcccattctt ttcatcattc     240

ggaagcaaca gcggcagtcc cctgcccaag ttatcccact agctgattac tatatcattg     300

ctggagtgat ctatcaggca ccagacttgg gatcagttat aaactctaga gtgcttactg     360

cagtgcatgg tattcagtca gcttttgatg aagctatgtc atactgtcga tatcatcctt     420

ccaaagggta ttggtggcac ttcaaagatc atgaagagca agataaagtc agacctaaag     480

ccaaaaggaa agaagaacca agctctattt ttcagagaca acgtgtggat gctttacttt     540

tagacctcag acaaaaattt ccacccaaat ttgtgcagct aaagcctgga gaaaagcctg     600

ttccagtgga tcaaacaaag aaagaggcag aacctatacc agaaactgta aaacctgagg     660

agaaggagac cacaaagaat gtacaacaga cagtgagtgc taaaggcccc cctgaaaaac     720

ggatgagact tcagtgagta ctggacaaaa gagaagcctg gaagactcct catgctagtt     780

atcatacctc agtactgtgg ctcttgagct ttgaagtact ttattgtaac cttcttattt     840

gtatggaatg cgcttatttt ttgaaaggat attaggccgg atgtggtggc tcacgcctgt     900

aatcccagca ctttgggagg ccatggcggg tggatcactt gaggtcagaa gttcaagacc     960

agcctgacca atatggtgaa accccgtctc tactaaaaat acaaaaatta gccgggcgtg    1020

gtggcgggcg cccatagtcc cagctactcg ggaggctgag acaggagact tgcttgaacc    1080

cgggaggtgg aggttgccct gagctgatta tcatgctgtt gcactccagc ttgggcgaca    1140

gaacgagact ttgtctcaaa aaaagaagaa aagatattat tcccatcatg atttcttgtg    1200

aatatttgtt atatgtcttc tggtaacctt tcctctcccg gacttgaagc aacctcacac    1260

actcacatgt ttactggtag atatgtttta aaagcaaaat aaaggtattt gtttttccaa    1320

aaaaaaaaaa aaaaaaaaaa aaaaaaaaac tcgag                               1355
```

<210> SEQ ID NO 32
<211> LENGTH: 80
<212> TYPE: PRT
<213> ORGANISM: Homo sapien

<400> SEQUENCE: 32

```
Val Ser Arg Ile Arg Gly Gly Ala Lys Lys Arg Lys Lys Lys Ser Tyr
 1               5                  10                  15

Thr Thr Pro Lys Lys Asp Lys His Gln Arg Lys Lys Val Gln Pro Ala
            20                  25                  30

Val Leu Lys Tyr Tyr Lys Val Asp Glu Asn Gly Lys Ile Ser Cys Leu
        35                  40                  45

Arg Arg Glu Cys Pro Ser Asp Glu Cys Gly Ala Gly Val Phe Met Ala
    50                  55                  60

Ser His Phe Asp Arg His Tyr Cys Gly Lys Cys Cys Leu Thr His Cys
65                  70                  75                  80
```

<210> SEQ ID NO 33

-continued

<211> LENGTH: 130
<212> TYPE: PRT
<213> ORGANISM: Homo sapien

<400> SEQUENCE: 33

```
Glu Ile Ser Asn Glu Val Arg Lys Phe Arg Thr Leu Thr Glu Leu Ile
 1               5                  10                  15

Leu Asp Ala Gln Glu His Val Lys Asn Pro Tyr Lys Gly Lys Lys Leu
            20                  25                  30

Lys Lys His Pro Asp Phe Pro Lys Lys Pro Leu Thr Pro Tyr Phe Arg
        35                  40                  45

Phe Phe Met Glu Lys Arg Ala Lys Tyr Ala Lys Leu His Pro Gln Met
    50                  55                  60

Ser Asn Leu Asp Leu Thr Lys Ile Leu Ser Lys Lys Tyr Lys Glu Leu
65                  70                  75                  80

Pro Glu Lys Lys Lys Met Lys Tyr Val Pro Asp Phe Gln Arg Arg Glu
                85                  90                  95

Thr Gly Val Arg Ala Lys Pro Gly Pro Ile Gln Gly Gly Ser Pro Pro
            100                 105                 110

Pro Tyr Pro Glu Cys Gln Glu Ser Asp Ile Pro Glu Lys Pro Gln Asp
        115                 120                 125

Pro Pro
    130
```

<210> SEQ ID NO 34
<211> LENGTH: 506
<212> TYPE: PRT
<213> ORGANISM: Homo sapien

<400> SEQUENCE: 34

```
Asn Ser Glu Lys Glu Ile Pro Val Leu Asn Glu Leu Pro Val Pro Met
 1               5                  10                  15

Val Ala Arg Tyr Ile Arg Ile Asn Pro Gln Ser Trp Phe Asp Asn Gly
            20                  25                  30

Ser Ile Cys Met Arg Met Glu Ile Leu Gly Cys Pro Leu Pro Asp Pro
        35                  40                  45

Asn Asn Tyr Tyr His Arg Arg Asn Glu Met Thr Thr Thr Asp Asp Leu
    50                  55                  60

Asp Phe Lys His His Asn Tyr Lys Glu Met Arg Gln Leu Met Lys Val
65                  70                  75                  80

Val Asn Glu Met Cys Pro Asn Ile Thr Arg Ile Tyr Asn Ile Gly Lys
                85                  90                  95

Ser His Gln Gly Leu Lys Leu Tyr Ala Val Glu Ile Ser Asp His Pro
            100                 105                 110

Gly Glu His Glu Val Gly Glu Pro Glu Phe His Tyr Ile Ala Gly Ala
        115                 120                 125

His Gly Asn Glu Val Leu Gly Arg Glu Leu Leu Leu Leu Leu Leu His
    130                 135                 140

Phe Leu Cys Gln Glu Tyr Ser Ala Gln Asn Ala Arg Ile Val Arg Leu
145                 150                 155                 160

Val Glu Glu Thr Arg Ile His Ile Leu Pro Ser Leu Asn Pro Asp Gly
                165                 170                 175

Tyr Glu Lys Ala Tyr Glu Gly Gly Ser Glu Leu Gly Gly Trp Ser Leu
            180                 185                 190

Gly Arg Trp Thr His Asp Gly Ile Asp Ile Asn Asn Asn Phe Pro Asp
        195                 200                 205
```

-continued

```
Leu Asn Ser Leu Leu Trp Glu Ala Glu Asp Gln Gln Asn Ala Pro Arg
    210                 215                 220

Lys Val Pro Asn His Tyr Ile Ala Ile Pro Glu Trp Phe Leu Ser Glu
225                 230                 235                 240

Asn Ala Thr Val Ala Thr Glu Thr Arg Ala Val Ile Ala Trp Met Glu
                245                 250                 255

Lys Ile Pro Phe Val Leu Gly Gly Asn Leu Gln Gly Gly Glu Leu Val
            260                 265                 270

Val Ala Tyr Pro Tyr Asp Met Val Arg Ser Leu Trp Lys Thr Gln Glu
        275                 280                 285

His Thr Pro Thr Pro Asp Asp His Val Phe Arg Trp Leu Ala Tyr Ser
    290                 295                 300

Tyr Ala Ser Thr His Arg Leu Met Thr Asp Ala Arg Arg Arg Val Cys
305                 310                 315                 320

His Thr Glu Asp Phe Gln Lys Glu Glu Gly Thr Val Asn Gly Ala Ser
                325                 330                 335

Trp His Thr Val Ala Gly Ser Leu Asn Asp Phe Ser Tyr Leu His Thr
            340                 345                 350

Asn Cys Phe Glu Leu Ser Ile Tyr Val Gly Cys Asp Lys Tyr Pro His
        355                 360                 365

Glu Ser Glu Leu Pro Glu Glu Trp Glu Asn Asn Arg Glu Ser Leu Ile
    370                 375                 380

Val Phe Met Glu Gln Val His Arg Gly Ile Lys Gly Ile Val Arg Asp
385                 390                 395                 400

Leu Gln Gly Lys Gly Ile Ser Asn Ala Val Ile Ser Val Glu Gly Val
                405                 410                 415

Asn His Asp Ile Arg Thr Ala Ser Asp Gly Asp Tyr Trp Arg Leu Leu
            420                 425                 430

Asn Pro Gly Glu Tyr Val Val Thr Ala Lys Ala Glu Gly Phe Ile Thr
        435                 440                 445

Ser Thr Lys Asn Cys Met Val Gly Tyr Asp Met Gly Ala Thr Arg Cys
    450                 455                 460

Asp Phe Thr Leu Thr Lys Thr Asn Leu Ala Arg Ile Arg Glu Ile Met
465                 470                 475                 480

Glu Thr Phe Gly Lys Gln Pro Val Ser Leu Pro Ser Arg Arg Leu Lys
                485                 490                 495

Leu Arg Gly Arg Lys Arg Arg Gln Arg Gly
            500                 505
```

<210> SEQ ID NO 35
<211> LENGTH: 96
<212> TYPE: PRT
<213> ORGANISM: Homo sapien

<400> SEQUENCE: 35

```
Met Asn Gly Glu Ala Asp Cys Pro Thr Asp Leu Glu Met Ala Ala Pro
 1               5                  10                  15

Arg Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Gln Phe Lys Thr
        35                  40                  45

Thr Gln Thr His Met Asp Arg Glu Lys Val Ala Leu Lys Asp Phe Ser
    50                  55                  60

Gly Asp Met Cys Lys Leu Lys Trp Val Glu Ile Ser Asn Glu Val Arg
```

-continued

```
65                  70                  75                  80

Lys Phe Arg Thr Leu Thr Glu Leu Ile Leu Asp Thr Gln Glu His Val
                85                  90                  95


<210> SEQ ID NO 36
<211> LENGTH: 129
<212> TYPE: PRT
<213> ORGANISM: Homo sapien

<400> SEQUENCE: 36

Gly Ile Val Val Phe Ser Leu Gly Ser Met Val Ser Glu Ile Pro Glu
 1               5                  10                  15

Lys Lys Ala Val Ala Ile Ala Asp Ala Leu Gly Lys Ile Pro Gln Thr
            20                  25                  30

Val Leu Trp Arg Tyr Thr Gly Thr Arg Pro Ser Asn Leu Ala Asn Asn
        35                  40                  45

Thr Ile Leu Val Gln Trp Leu Pro Gln Asn Asp Leu Leu Gly His Pro
    50                  55                  60

Met Thr Arg Ala Phe Ile Thr His Ala Ser Ser His Gly Val Asn Glu
65                  70                  75                  80

Ser Ile Cys Asn Gly Val Pro Met Val Met Ile Pro Leu Phe Gly Asp
                85                  90                  95

Gln Met Asp Asn Ala Lys Arg Arg Glu Thr Lys Gly Ala Gly Val Thr
            100                 105                 110

Leu Asn Val Leu Glu Met Thr Ser Glu Asp Leu Glu Asp Ala Leu Lys
        115                 120                 125

Ser


<210> SEQ ID NO 37
<211> LENGTH: 238
<212> TYPE: PRT
<213> ORGANISM: Homo sapien

<400> SEQUENCE: 37

Asn Leu Leu Gly Ile Ser Trp Val Asp Ser Ser Trp Ile Pro Ile Leu
 1               5                  10                  15

Asn Ser Gly Ser Val Leu Asp Tyr Phe Ser Glu Arg Ser Asn Pro Phe
            20                  25                  30

Tyr Asp Arg Thr Cys Asn Asn Glu Val Val Lys Met Gln Arg Leu Thr
        35                  40                  45

Leu Glu His Leu Asn Gln Met Val Gly Ile Glu Tyr Ile Leu Leu His
    50                  55                  60

Ala Gln Glu Pro Ile Leu Phe Ile Ile Arg Lys Gln Gln Arg Gln Ser
65                  70                  75                  80

Pro Ala Gln Val Ile Pro Leu Ala Asp Tyr Tyr Ile Ile Ala Gly Val
                85                  90                  95

Ile Tyr Gln Ala Pro Asp Leu Gly Ser Val Ile Asn Ser Arg Val Leu
            100                 105                 110

Thr Ala Val His Gly Ile Gln Ser Ala Phe Asp Glu Ala Met Ser Tyr
        115                 120                 125

Cys Arg Tyr His Pro Ser Lys Gly Tyr Trp Trp His Phe Lys Asp His
    130                 135                 140

Glu Glu Gln Asp Lys Val Arg Pro Lys Ala Lys Arg Lys Glu Glu Pro
145                 150                 155                 160

Ser Ser Ile Phe Gln Arg Gln Arg Val Asp Ala Leu Leu Leu Asp Leu
                165                 170                 175
```

-continued

```
Arg Gln Lys Phe Pro Pro Lys Phe Val Gln Leu Lys Pro Gly Glu Lys
            180                 185                 190

Pro Val Pro Val Asp Gln Thr Lys Lys Glu Ala Glu Pro Ile Pro Glu
        195                 200                 205

Thr Val Lys Pro Glu Glu Lys Glu Thr Thr Lys Asn Val Gln Gln Thr
    210                 215                 220

Val Ser Ala Lys Gly Pro Pro Glu Lys Arg Met Arg Leu Gln
225                 230                 235


<210> SEQ ID NO 38
<211> LENGTH: 202
<212> TYPE: PRT
<213> ORGANISM: Homo sapien

<400> SEQUENCE: 38

Lys Gly Ser Glu Gly Glu Asn Pro Leu Thr Val Pro Gly Arg Glu Lys
 1               5                  10                  15

Glu Gly Met Leu Met Gly Val Lys Pro Gly Glu Asp Ala Ser Gly Pro
            20                  25                  30

Ala Glu Asp Leu Val Arg Arg Ser Glu Lys Asp Thr Ala Ala Val Val
        35                  40                  45

Ser Arg Gln Gly Ser Ser Leu Asn Leu Phe Glu Asp Val Gln Ile Thr
    50                  55                  60

Glu Pro Glu Ala Glu Pro Glu Ser Lys Ser Glu Pro Arg Pro Pro Ile
65                  70                  75                  80

Ser Ser Pro Arg Ala Pro Gln Thr Arg Ala Val Lys Pro Arg Leu His
                85                  90                  95

Pro Val Lys Pro Met Asn Ala Thr Ala Thr Lys Val Ala Asn Cys Ser
            100                 105                 110

Leu Gly Thr Ala Thr Ile Ile Gly Glu Asn Leu Asn Asn Glu Val Met
        115                 120                 125

Met Lys Lys Tyr Ser Pro Ser Asp Pro Ala Phe Ala Tyr Ala Gln Leu
    130                 135                 140

Thr His Asp Glu Leu Ile Gln Leu Val Leu Lys Gln Lys Glu Thr Ile
145                 150                 155                 160

Ser Lys Lys Glu Phe Gln Val Arg Glu Leu Glu Asp Tyr Ile Asp Asn
                165                 170                 175

Leu Leu Val Arg Val Met Glu Glu Thr Pro Asn Ile Leu Arg Ile Pro
            180                 185                 190

Thr Gln Val Gly Lys Lys Ala Gly Lys Met
        195                 200


<210> SEQ ID NO 39
<211> LENGTH: 243
<212> TYPE: PRT
<213> ORGANISM: Homo sapien

<400> SEQUENCE: 39

Val Asn Ala Leu Gly Ile Met Ala Ala Val Asp Ile Arg Asp Asn Leu
 1               5                  10                  15

Leu Gly Ile Ser Trp Val Asp Ser Ser Trp Ile Pro Ile Leu Asn Ser
            20                  25                  30

Gly Ser Val Leu Asp Tyr Phe Ser Glu Arg Ser Asn Pro Phe Tyr Asp
        35                  40                  45

Arg Thr Cys Asn Asn Glu Val Val Lys Met Gln Arg Leu Thr Leu Glu
    50                  55                  60
```

-continued

```
His Leu Asn Gln Met Val Gly Ile Glu Tyr Ile Leu Leu His Ala Gln
65                  70                  75                  80

Glu Pro Ile Leu Phe Ile Ile Arg Lys Gln Gln Arg Gln Ser Pro Ala
                85                  90                  95

Gln Val Ile Pro Leu Ala Asp Tyr Tyr Ile Ile Ala Gly Val Ile Tyr
            100                 105                 110

Gln Ala Pro Asp Leu Gly Ser Val Ile Asn Ser Arg Val Leu Thr Ala
        115                 120                 125

Val His Gly Ile Gln Ser Ala Phe Asp Glu Ala Met Ser Tyr Cys Arg
    130                 135                 140

Tyr His Pro Ser Lys Gly Tyr Trp Trp His Phe Lys Asp His Glu Glu
145                 150                 155                 160

Gln Asp Lys Val Arg Pro Lys Ala Lys Arg Lys Glu Glu Pro Ser Ser
                165                 170                 175

Ile Phe Gln Arg Gln Arg Val Asp Ala Leu Leu Leu Asp Leu Arg Gln
            180                 185                 190

Lys Ile Ser Thr Gln Ile Cys Ala Val Asp Gln Thr Lys Lys Glu Ala
        195                 200                 205

Glu Pro Ile Pro Glu Thr Val Lys Pro Glu Glu Lys Glu Thr Thr Lys
    210                 215                 220

Asn Val Gln Gln Thr Val Ser Ala Lys Gly Pro Pro Glu Lys Arg Met
225                 230                 235                 240

Arg Leu Gln


<210> SEQ ID NO 40
<211> LENGTH: 245
<212> TYPE: PRT
<213> ORGANISM: Homo sapien

<400> SEQUENCE: 40

Ala Ala Val Asp Ile Arg Asp Asn Leu Leu Gly Ile Ser Trp Val Asp
 1               5                  10                  15

Ser Ser Trp Ile Pro Ile Leu Asn Ser Gly Ser Val Leu Asp Tyr Phe
            20                  25                  30

Ser Glu Arg Ser Asn Pro Phe Tyr Asp Arg Thr Cys Asn Asn Glu Val
        35                  40                  45

Val Lys Met Gln Arg Leu Thr Leu Glu His Leu Asn Gln Met Val Gly
    50                  55                  60

Ile Glu Tyr Ile Leu Leu His Ala Gln Glu Pro Ile Leu Phe Ile Ile
65                  70                  75                  80

Arg Lys Gln Gln Arg Gln Ser Pro Ala Gln Val Ile Pro Leu Ala Asp
                85                  90                  95

Tyr Tyr Ile Ile Ala Gly Val Ile Tyr Gln Ala Pro Asp Leu Gly Ser
            100                 105                 110

Val Ile Asn Ser Arg Val Leu Thr Ala Val His Gly Ile Gln Ser Ala
        115                 120                 125

Phe Asp Glu Ala Met Ser Tyr Cys Arg Tyr His Pro Ser Lys Gly Tyr
    130                 135                 140

Trp Trp His Phe Lys Asp His Glu Glu Gln Asp Lys Val Arg Pro Lys
145                 150                 155                 160

Ala Lys Arg Lys Glu Glu Pro Ser Ser Ile Phe Gln Arg Gln Arg Val
                165                 170                 175

Asp Ala Leu Leu Leu Asp Leu Arg Gln Lys Phe Pro Pro Lys Phe Val
            180                 185                 190
```

-continued

```
Gln Leu Lys Pro Gly Glu Lys Pro Val Pro Val Asp Gln Thr Lys Lys
        195                 200                 205

Glu Ala Glu Pro Ile Pro Glu Thr Val Lys Pro Glu Glu Lys Glu Thr
    210                 215                 220

Thr Lys Asn Val Gln Gln Thr Val Ser Ala Lys Gly Pro Pro Glu Lys
225                 230                 235                 240

Arg Met Arg Leu Gln
                245


<210> SEQ ID NO 41
<211> LENGTH: 163
<212> TYPE: PRT
<213> ORGANISM: Homo sapien

<400> SEQUENCE: 41

Gly Glu Arg Gln Gly Leu Val Ala Arg Ala Arg Leu Ser Leu Arg Pro
 1               5                  10                  15

Ser Ile Pro Glu Leu Ser Glu Arg Thr Ser Arg Pro Cys Arg Ala Ser
            20                  25                  30

Pro Ala Ser Leu Pro Ser Gln His Thr Ser Ser Pro Ala Gln Ala Arg
        35                  40                  45

Val Arg Asn Leu Ala Gln Ser Thr Phe Pro Leu Ala Ala Gln Glu Thr
    50                  55                  60

Pro Gly Arg Ala Pro Ala His Ala Pro Leu Ser Ser Phe Val Pro Gly
65                  70                  75                  80

Val Gly Gly Arg Ser Pro Ala Ser Val Gly Ile Ser Ala Pro Gly Gly
                85                  90                  95

Gly Pro Ser Gly Ala Ala Ala Lys Ile Pro Leu Glu Leu Thr Gln Ser
            100                 105                 110

Arg Val Gln Lys Ile Trp Val Pro Val Asp His Arg Pro Ser Leu Pro
        115                 120                 125

Arg Ser Cys Gly Pro Lys Leu Thr Asn Ser Pro Ala Val Phe Val Met
    130                 135                 140

Val Gly Leu Pro Arg Pro Gly Gln Asp Leu Leu Leu His Glu Ser Leu
145                 150                 155                 160

Leu Ala Ala


<210> SEQ ID NO 42
<211> LENGTH: 243
<212> TYPE: PRT
<213> ORGANISM: Homo sapien

<400> SEQUENCE: 42

Val Asp Ile Arg Asp Asn Leu Leu Gly Ile Ser Trp Val Asp Ser Ser
 1               5                  10                  15

Trp Ile Pro Ile Leu Asn Ser Gly Ser Val Leu Asp Tyr Phe Ser Glu
            20                  25                  30

Arg Ser Asn Pro Phe Tyr Asp Arg Thr Cys Asn Asn Glu Val Val Lys
        35                  40                  45

Met Gln Arg Leu Thr Leu Glu His Leu Asn Gln Met Val Gly Ile Glu
    50                  55                  60

Tyr Ile Leu Leu His Ala Gln Glu Pro Ile Leu Phe Ile Ile Arg Lys
65                  70                  75                  80

Gln Gln Arg Gln Ser Pro Ala Gln Val Ile Pro Leu Ala Asp Tyr Tyr
                85                  90                  95
```

-continued

```
Ile Ile Ala Gly Val Ile Tyr Gln Ala Pro Asp Leu Gly Ser Val Ile
            100                 105                 110

Asn Ser Arg Val Leu Thr Ala Val His Gly Ile Gln Ser Ala Phe Asp
        115                 120                 125

Glu Ala Met Ser Tyr Cys Arg Tyr His Pro Ser Lys Gly Tyr Trp Trp
    130                 135                 140

His Phe Lys Asp His Glu Glu Gln Asp Lys Val Arg Pro Lys Ala Lys
145                 150                 155                 160

Arg Lys Glu Glu Pro Ser Ser Ile Phe Gln Arg Gln Arg Val Asp Ala
                165                 170                 175

Leu Leu Leu Asp Leu Arg Gln Lys Phe Pro Pro Lys Phe Val Gln Leu
            180                 185                 190

Lys Pro Gly Glu Lys Pro Val Pro Val Asp Gln Thr Lys Lys Glu Ala
        195                 200                 205

Glu Pro Ile Pro Glu Thr Val Lys Pro Glu Glu Lys Glu Thr Thr Lys
    210                 215                 220

Asn Val Gln Gln Thr Val Ser Ala Lys Gly Pro Pro Glu Lys Arg Met
225                 230                 235                 240

Arg Leu Gln


<210> SEQ ID NO 43
<211> LENGTH: 244
<212> TYPE: PRT
<213> ORGANISM: Homo sapien

<400> SEQUENCE: 43

Ala Val Asp Ile Arg Asp Asn Leu Leu Gly Ile Ser Trp Val Asp Ser
 1               5                  10                  15

Ser Trp Ile Pro Ile Leu Asn Ser Gly Ser Val Leu Asp Tyr Phe Ser
            20                  25                  30

Glu Arg Ser Asn Pro Phe Tyr Asp Arg Thr Cys Asn Asn Glu Val Val
        35                  40                  45

Lys Met Gln Arg Leu Thr Leu Glu His Leu Asn Gln Met Val Gly Ile
    50                  55                  60

Glu Tyr Ile Leu Leu His Ala Gln Glu Pro Ile Leu Phe Ile Ile Arg
65                  70                  75                  80

Lys Gln Gln Arg Gln Ser Pro Ala Gln Val Ile Pro Leu Ala Asp Tyr
                85                  90                  95

Tyr Ile Ile Ala Gly Val Ile Tyr Gln Ala Pro Asp Leu Gly Ser Val
            100                 105                 110

Ile Asn Ser Arg Val Leu Thr Ala Val His Gly Ile Gln Ser Ala Phe
        115                 120                 125

Asp Glu Ala Met Ser Tyr Cys Arg Tyr His Pro Ser Lys Gly Tyr Trp
    130                 135                 140

Trp His Phe Lys Asp His Glu Glu Gln Asp Lys Val Arg Pro Lys Ala
145                 150                 155                 160

Lys Arg Lys Glu Glu Pro Ser Ser Ile Phe Gln Arg Gln Arg Val Asp
                165                 170                 175

Ala Leu Leu Leu Asp Leu Arg Gln Lys Phe Pro Pro Lys Phe Val Gln
            180                 185                 190

Leu Lys Pro Gly Glu Lys Pro Val Pro Val Asp Gln Thr Lys Lys Glu
        195                 200                 205

Ala Glu Pro Ile Pro Glu Thr Val Lys Pro Glu Glu Lys Glu Thr Thr
    210                 215                 220
```

-continued

```
Lys Asn Val Gln Gln Thr Val Ser Ala Lys Gly Pro Pro Glu Lys Arg
225                 230                 235                 240

Met Arg Leu Gln


<210> SEQ ID NO 44
<211> LENGTH: 109
<212> TYPE: PRT
<213> ORGANISM: Homo sapien

<400> SEQUENCE: 44

Glu Leu His Phe Ser Glu Phe Thr Ser Ala Val Ala Asp Met Lys Asn
 1               5                  10                  15

Ser Val Ala Asp Arg Asp Asn Ser Pro Ser Ser Cys Ala Gly Leu Phe
            20                  25                  30

Ile Ala Ser His Ile Gly Phe Asp Trp Pro Gly Val Trp Val His Leu
        35                  40                  45

Asp Ile Ala Ala Pro Val His Ala Gly Glu Arg Ala Thr Gly Phe Gly
    50                  55                  60

Val Ala Leu Leu Leu Ala Leu Phe Gly Arg Ala Ser Glu Asp Pro Leu
65                  70                  75                  80

Leu Asn Leu Val Ser Pro Leu Asp Cys Glu Val Asp Ala Gln Glu Gly
                85                  90                  95

Asp Asn Met Gly Arg Asp Ser Lys Arg Arg Arg Leu Val
            100                 105


<210> SEQ ID NO 45
<211> LENGTH: 324
<212> TYPE: PRT
<213> ORGANISM: Homo sapien

<400> SEQUENCE: 45

Arg Arg Pro Val Met Ala Gln Glu Thr Ala Pro Pro Cys Gly Pro Val
 1               5                  10                  15

Ser Arg Gly Asp Ser Pro Ile Ile Glu Lys Met Glu Lys Arg Thr Cys
            20                  25                  30

Ala Leu Cys Pro Glu Gly His Glu Trp Ser Gln Ile Tyr Phe Ser Pro
        35                  40                  45

Ser Gly Asn Ile Val Ala His Glu Asn Cys Leu Leu Tyr Ser Ser Gly
    50                  55                  60

Leu Val Glu Cys Glu Thr Leu Asp Leu Arg Asn Thr Ile Arg Asn Phe
65                  70                  75                  80

Asp Val Lys Ser Val Lys Lys Glu Ile Trp Arg Gly Arg Arg Leu Lys
                85                  90                  95

Cys Ser Phe Cys Asn Lys Gly Gly Ala Thr Val Gly Cys Asp Leu Trp
            100                 105                 110

Phe Cys Lys Lys Ser Tyr His Tyr Val Cys Ala Lys Lys Asp Gln Ala
        115                 120                 125

Ile Leu Gln Val Asp Gly Asn His Gly Thr Tyr Lys Leu Phe Cys Pro
    130                 135                 140

Glu His Ser Pro Glu Gln Glu Glu Ala Thr Glu Ser Ala Asp Asp Pro
145                 150                 155                 160

Ser Met Lys Lys Lys Arg Gly Lys Asn Lys Arg Leu Ser Ser Gly Pro
                165                 170                 175

Pro Ala Gln Pro Lys Thr Met Lys Cys Ser Asn Ala Lys Arg His Met
            180                 185                 190

Thr Glu Glu Pro His Gly His Thr Asp Ala Ala Val Lys Ser Pro Phe
```

-continued

```
        195                 200                 205

Leu Lys Lys Cys Gln Glu Ala Gly Leu Leu Thr Glu Leu Phe Glu His
    210                 215                 220

Ile Leu Glu Asn Met Asp Ser Val His Gly Arg Leu Val Asp Glu Thr
225                 230                 235                 240

Ala Ser Glu Ser Asp Tyr Glu Gly Ile Glu Thr Leu Leu Phe Asp Cys
                245                 250                 255

Gly Leu Phe Lys Asp Thr Leu Arg Lys Phe Gln Glu Val Ile Lys Ser
            260                 265                 270

Lys Ala Cys Glu Trp Glu Glu Arg Gln Arg Gln Met Lys Gln Gln Leu
        275                 280                 285

Glu Ala Leu Ala Asp Leu Gln Gln Ser Leu Cys Ser Phe Gln Glu Asn
    290                 295                 300

Gly Asp Leu Asp Cys Ser Ser Ser Thr Ser Gly Ser Leu Leu Pro Pro
305                 310                 315                 320

Glu Asp His Gln


<210> SEQ ID NO 46
<211> LENGTH: 244
<212> TYPE: PRT
<213> ORGANISM: Homo sapien

<400> SEQUENCE: 46

Ala Val Asp Ile Arg Asp Asn Leu Leu Gly Ile Ser Trp Val Asp Ser
 1               5                  10                  15

Ser Trp Ile Pro Ile Leu Asn Ser Gly Ser Val Leu Asp Tyr Phe Ser
            20                  25                  30

Glu Arg Ser Asn Pro Phe Tyr Asp Arg Thr Cys Asn Asn Glu Val Val
        35                  40                  45

Lys Met Gln Arg Leu Thr Leu Glu His Leu Asn Gln Met Val Gly Ile
    50                  55                  60

Glu Tyr Ile Leu Leu His Ala Gln Glu Pro Ile Leu Phe Ile Ile Arg
65                  70                  75                  80

Lys Gln Gln Arg Gln Ser Pro Ala Gln Val Ile Pro Leu Ala Asp Tyr
                85                  90                  95

Tyr Ile Ile Ala Gly Val Ile Tyr Gln Ala Pro Asp Leu Gly Ser Val
            100                 105                 110

Ile Asn Ser Arg Val Leu Thr Ala Val His Gly Ile Gln Ser Ala Phe
        115                 120                 125

Asp Glu Ala Met Ser Tyr Cys Arg Tyr His Pro Ser Lys Gly Tyr Trp
    130                 135                 140

Trp His Phe Lys Asp His Glu Glu Gln Asp Lys Val Arg Pro Lys Ala
145                 150                 155                 160

Lys Arg Lys Glu Glu Pro Ser Ser Ile Phe Gln Arg Gln Arg Val Asp
                165                 170                 175

Ala Leu Leu Leu Asp Leu Arg Gln Lys Phe Pro Pro Lys Phe Val Gln
            180                 185                 190

Leu Lys Pro Gly Glu Lys Pro Val Pro Val Asp Gln Thr Lys Lys Glu
        195                 200                 205

Ala Glu Pro Ile Pro Glu Thr Val Lys Pro Glu Glu Lys Glu Thr Thr
    210                 215                 220

Lys Asn Val Gln Gln Thr Val Ser Ala Lys Gly Pro Pro Glu Lys Arg
225                 230                 235                 240

Met Arg Leu Gln
```

-continued

<210> SEQ ID NO 47
<211> LENGTH: 14
<212> TYPE: DNA
<213> ORGANISM: Homo sapien

<400> SEQUENCE: 47 ttttttttt ttag 14

<210> SEQ ID NO 48
<211> LENGTH: 10
<212> TYPE: DNA
<213> ORGANISM: Homo sapien

<400> SEQUENCE: 48
cttcaacctc 10

<210> SEQ ID NO 49
<211> LENGTH: 496
<212> TYPE: DNA
<213> ORGANISM: Homo sapien

<400> SEQUENCE: 49
gcaccatgta ccgagcactt cggctcctcg cgcgctcgcg tcccctcgtg cgggctccag 60
ccgcagcctt agcttcggct cccggcttgg gtggcgcggc cgtgccctcg ttttggcctc 120
cgaacgcggc tcgaatggca agccaaaatt ccttccggat agaatatgat acctttggtg 180
aactaaaggt gccaaatgat aagtattatg gcgcccagac cgtgagatct acgatgaact 240
ttaagattgg aggtgtgaca gaacgcatgc caaccccagt tattaaagct tttggcatct 300
tgaagcgagc ggccgctgaa gtaaaccagg attatggtct tgatccaaag attgctaatg 360
caataatgaa ggcagcagat gaggtagctg aaggtaaatt aaatgatcat tttcctctcg 420
tggtatggca gactggatca ggaactcaga caaatatgaa tgtaaatgaa gtcattagcc 480
aatagagcaa ttgaaa 496

<210> SEQ ID NO 50
<211> LENGTH: 499
<212> TYPE: DNA
<213> ORGANISM: Homo sapien

<400> SEQUENCE: 50
agaaaaagtc tatgtttgca gaaatacaga tccaagacaa agacaggatg ggcactgctg 60
gaaaagttat taaatgcaaa gcagctgtgc tttgggagca gaagcaaccc ttctccattg 120
aggaaataga agttgcccca ccaaagacta aagaagttcg cattaagatt ttggccacag 180
gaatctgtcg cacagatgac catgtgataa aaggaacaat ggtgtccaag tttccagtga 240
ttgtgggaca tgaggcaact gggattgtag agagcattgg agaaggagtg actacagtga 300
aaccaggtga caaagtcatc cctctctttc tgccacaatg tagagaatgc aatgcttgtc 360
gcaacccaga tggcaacctt tgcattagga gcgatattac tggtcgtgga gtactggctg 420
atggcaccac cagatttaca tgcaagggcg aaccagtcca ccacttcatg aacaccagta 480
catttaccga gtacacagt 499

<210> SEQ ID NO 51
<211> LENGTH: 887
<212> TYPE: DNA
<213> ORGANISM: Homo sapien -continued

<400> SEQUENCE: 51

```
gagtctgagc agaaaggaaa agcagccttg gcagccacgt tagaggaata caaagccaca     60
gtggccagtg accagataga gatgaatcgc ctgaaggctc agctggagaa tgaaaagcag    120
aaagtggcag agctgtattc tatccataac tctggagaca aatctgatat tcaggacctc    180
ctggagagtg tcaggctgga caaagaaaaa gcagagactt tggctagtag cttgcaggaa    240
gatctggctc atacccgaaa tgatgccaat cgattacagg atgccattgc taaggtagag    300
gatgaatacc gagccttcca agaagaagct aagaaacaaa ttgaagattt gaatatgacg    360
ttagaaaaat taagatcaga cctggatgaa aaagaaacag aaaggagtga catgaaagaa    420
accatctttg aacttgaaga tgaagtagaa caacatcgtg ctgtgaaact tcatgacaac    480
ctcattattt ctgatctaga gaatacagtt aaaaaactcc aggaccaaaa gcacgacatg    540
gaaagagaaa taaagacact ccacagaaga cttcgggaag aatctgcgga atggcggcag    600
tttcaggctg atctccagac tgcagtagtc attgcaaatg acattaaatc tgaagcccaa    660
gaggagattg gtgatctaaa gcgccggtta catgaggctc aagaaaaaaa tgagaaactc    720
acaaaagaat tggaggaaat aaagtcacgc aagcaagagg aggagcgagg cgggtataca    780
attacatgaa tgccgttgag agagatttgg cagccttaag gcagggaatg ggactgagta    840
gaaggtcctc gacttcctca gagccaactc ctacagtaaa aaccctc                  887
```

<210> SEQ ID NO 52
<211> LENGTH: 491
<212> TYPE: DNA
<213> ORGANISM: Homo sapien

<400> SEQUENCE: 52

```
ggcacgagct tttccaaaaa tcatgctgct cctttctcta aagttcttac attttataga     60
aaggaacctt tcactcttga ggcctactac agctctcctc aggatttgcc ctatccagat    120
cctgctatag ctcagttttc agttcagaaa gtcactcctc agtctgatgg ctccagttca    180
aaagtgaaag tcaaagttcg agtaaatgtc catggcattt tcagtgtgtc cagtgcatct    240
ttagtggagg ttcacaagtc tgaggaaaat gaggagccaa tggaaacaga tcagaatgca    300
aaggaggaag agaagatgca agtggaccag gaggaaccac atgttgaaga gcaacagcag    360
cagacaccag gcagaaaata aggcagagtc tgaagaaatg gagacctctc aagctggatc    420
caaggataaa aagatggacc aaccacccca agccaagaag gcaaaagtga agaccagtac    480
tgtggacctg g                                                         491
```

<210> SEQ ID NO 53
<211> LENGTH: 787
<212> TYPE: DNA
<213> ORGANISM: Homo sapien

<400> SEQUENCE: 53

```
aagcagttga gtaggcagaa aaaagaacct cttcattaag gattaaaatg tataggccag     60
cacgtgtaac ttcgacttca agatttctga atccatatgt agtatgtttc attgtcgtcg    120
caggggtagt gatcctggca gtcaccatag ctctacttgt ttactttttta gcttttgatc   180
aaaaatctta cttttatagg agcagttttc aactcctaaa tgttgaatat aatagtcagt    240
taaattcacc agctacacag gaatacagga ctttgagtgg aagaattgaa tctctgatta    300
ctaaaacatt caaagaatca aatttaagaa atcagttcat cagagctcat gttgccaaac    360
tgaggcaaga tggtagtggt gtgagagcgg atgttgtcat gaaatttcaa ttcactagaa    420
```

-continued ataacaatgg agcatcaatg aaaagcagaa ttgagtctgt tttacgacaa atgctgaata 480
actctggaaa cctggaaata aacccttcaa ctgagataac atcacttact gaccaggctg 540
cagcaaattg gcttattaat gaatgtgggg ccggtccaga cctaataaca ttgtctgagc 600
agagaatcct tggaggcact gaggctgagg agggaagctg gccgtggcaa gtcagtctgc 660
ggctcaataa tgcccaccac tgtggaggca gcctgatcaa taacatgtgg atcctgacag 720
cagctcactg cttcagaagc aactctaatc ctcgtgactg gattgccacg tctggtattt 780
ccacaac 787

<210> SEQ ID NO 54
<211> LENGTH: 386
<212> TYPE: DNA
<213> ORGANISM: Homo sapien

<400> SEQUENCE: 54
ggcattttca gtgtgtccag tgcatcttta gtggaggttc acaagtctga ggaaaatgag 60
gagccaatgg aaacagatca gaatgcaaag gaggaagaga agatgcaagt ggaccaggag 120
gaaccacatg ttgaagagca acagcagcag acaccagcag aaaataaggc agagtctgaa 180
gaaatggaga cctctcaagc tggatccaag gataaaaaga tggaccaacc accccaagcc 240
aagaaggcaa aagtgaagac cagtactgtg gacctgccaa tcgagaatca gctattatgg 300
cagatagaca gagagatgct caacttgtac attgaaaatg agggtaagat gatcatgcag 360
gataaactgg agaaggagcg gaatga 386

<210> SEQ ID NO 55
<211> LENGTH: 1462
<212> TYPE: DNA
<213> ORGANISM: Homo sapien

<400> SEQUENCE: 55
aagcagttga gtaggcagaa aaaagaacct cttcattaag gattaaaatg tataggccag 60
cacgtgtaac ttcgacttca agatttctga atccatatgt agtatgtttc attgtcgtcg 120
caggggtagt gatcctggca gtcaccatag ctctacttgt ttactttta gcttttgatc 180 aaaaatctta cttttatagg agcagttttc aactcctaaa tgttgaatat aatagtcagt 240
taaattcacc agctacacag gaatacagga ctttgagtgg aagaattgaa tctctgatta 300
ctaaaacatt caaagaatca aatttaagaa atcagttcat cagagctcat gttgccaaac 360
tgaggcaaga tggtagtggt gtgagagcgg atgttgtcat gaaatttcaa ttcactagaa 420
ataacaatgg agcatcaatg aaaagcagaa ttgagtctgt tttacgacaa atgctgaata 480
actctggaaa cctggaaata aacccttcaa ctgagataac atcacttact gaccaggctg 540
cagcaaattg gcttattaat gaatgtgggg ccggtccaga cctaataaca ttgtctgagc 600
agagaatcct tggaggcact gaggctgagg agggaagctg gccgtggcaa gtcagtctgc 660
ggctcaataa tgcccaccac tgtggaggca gcctgatcaa taacatgtgg atcctgacag 720
cagctcactg cttcagaagc aactctaatc ctcgtgactg gattgccacg tctggtattt 780
ccacaacatt tcctaaacta agaatgagag taagaaatat tttaattcat aacaattata 840
aatctgcaac tcatgaaaat gacattgcac ttgtgagact tgagaacagt gtcaccttta 900
ccaaagatat ccatagtgtg tgtctcccag ctgctaccca gaatattcca cctggctcta 960
ctgcttatgt aacaggatgg ggcgctcaag aatatgctgg ccacacagtt ccagagctaa 1020

-continued

```
ggcaaggaca ggtcagaata ataagtaatg atgtatgtaa tgcaccacat agttataatg   1080

gagccatctt gtctggaatg ctgtgtgctg gagtacctca aggtggagtg gacgcatgtc   1140

agggtgactc tggtggccca ctagtacaag aagactcacg gcggctttgg tttattgtgg   1200

ggatagtaag ctggggagat cagtgtggcc tgccggataa gccaggagtg tatactcgag   1260

tgacagcata cattgactgg attaggcaac aaactgggat ctagtgcaac aagtgcatcc   1320

ctgttgcaaa gtctgtatgc aggtgtgcct gtcttaaatt ccaaagcttt acatttcaac   1380

tgaaaaagaa actagaaatg tcctaattta acatcttgtt acataaatat ggtttaacaa   1440

aaaaaaaaaa aaaaaactcg ag                                            1462
```

```
<210> SEQ ID NO 56
<211> LENGTH: 159
<212> TYPE: PRT
<213> ORGANISM: Homo sapien

<400> SEQUENCE: 56

Thr Met Tyr Arg Ala Leu Arg Leu Leu Ala Arg Ser Arg Pro Leu Val
 1               5                  10                  15

Arg Ala Pro Ala Ala Ala Leu Ala Ser Ala Pro Gly Leu Gly Gly Ala
            20                  25                  30

Ala Val Pro Ser Phe Trp Pro Pro Asn Ala Ala Arg Met Ala Ser Gln
        35                  40                  45

Asn Ser Phe Arg Ile Glu Tyr Asp Thr Phe Gly Glu Leu Lys Val Pro
    50                  55                  60

Asn Asp Lys Tyr Tyr Gly Ala Gln Thr Val Arg Ser Thr Met Asn Phe
65                  70                  75                  80

Lys Ile Gly Gly Val Thr Glu Arg Met Pro Thr Pro Val Ile Lys Ala
                85                  90                  95

Phe Gly Ile Leu Lys Arg Ala Ala Ala Glu Val Asn Gln Asp Tyr Gly
            100                 105                 110

Leu Asp Pro Lys Ile Ala Asn Ala Ile Met Lys Ala Ala Asp Glu Val
        115                 120                 125

Ala Glu Gly Lys Leu Asn Asp His Phe Pro Leu Val Val Trp Gln Thr
    130                 135                 140

Gly Ser Gly Thr Gln Thr Asn Met Asn Val Asn Glu Val Ile Ser
145                 150                 155


<210> SEQ ID NO 57
<211> LENGTH: 165
<212> TYPE: PRT
<213> ORGANISM: Homo sapien

<400> SEQUENCE: 57

Lys Lys Ser Met Phe Ala Glu Ile Gln Ile Gln Asp Lys Asp Arg Met
 1               5                  10                  15

Gly Thr Ala Gly Lys Val Ile Lys Cys Lys Ala Ala Val Leu Trp Glu
            20                  25                  30

Gln Lys Gln Pro Phe Ser Ile Glu Glu Ile Glu Val Ala Pro Pro Lys
        35                  40                  45

Thr Lys Glu Val Arg Ile Lys Ile Leu Ala Thr Gly Ile Cys Arg Thr
    50                  55                  60

Asp Asp His Val Ile Lys Gly Thr Met Val Ser Lys Phe Pro Val Ile
65                  70                  75                  80

Val Gly His Glu Ala Thr Gly Ile Val Glu Ser Ile Gly Glu Gly Val
                85                  90                  95
```

-continued

```
Thr Thr Val Lys Pro Gly Asp Lys Val Ile Pro Leu Phe Leu Pro Gln
            100                 105                 110

Cys Arg Glu Cys Asn Ala Cys Arg Asn Pro Asp Gly Asn Leu Cys Ile
        115                 120                 125

Arg Ser Asp Ile Thr Gly Arg Gly Val Leu Ala Asp Gly Thr Thr Arg
    130                 135                 140

Phe Thr Cys Lys Gly Glu Pro Val His His Phe Met Asn Thr Ser Thr
145                 150                 155                 160

Phe Thr Glu Tyr Thr
                165


<210> SEQ ID NO 58
<211> LENGTH: 259
<212> TYPE: PRT
<213> ORGANISM: Homo sapien

<400> SEQUENCE: 58

Glu Ser Glu Gln Lys Gly Lys Ala Ala Leu Ala Ala Thr Leu Glu Glu
 1               5                  10                  15

Tyr Lys Ala Thr Val Ala Ser Asp Gln Ile Glu Met Asn Arg Leu Lys
            20                  25                  30

Ala Gln Leu Glu Asn Glu Lys Gln Lys Val Ala Glu Leu Tyr Ser Ile
        35                  40                  45

His Asn Ser Gly Asp Lys Ser Asp Ile Gln Asp Leu Leu Glu Ser Val
    50                  55                  60

Arg Leu Asp Lys Glu Lys Ala Glu Thr Leu Ala Ser Ser Leu Gln Glu
65                  70                  75                  80

Asp Leu Ala His Thr Arg Asn Asp Ala Asn Arg Leu Gln Asp Ala Ile
                85                  90                  95

Ala Lys Val Glu Asp Glu Tyr Arg Ala Phe Gln Glu Glu Ala Lys Lys
            100                 105                 110

Gln Ile Glu Asp Leu Asn Met Thr Leu Glu Lys Leu Arg Ser Asp Leu
        115                 120                 125

Asp Glu Lys Glu Thr Glu Arg Ser Asp Met Lys Glu Thr Ile Phe Glu
    130                 135                 140

Leu Glu Asp Glu Val Glu Gln His Arg Ala Val Lys Leu His Asp Asn
145                 150                 155                 160

Leu Ile Ile Ser Asp Leu Glu Asn Thr Val Lys Lys Leu Gln Asp Gln
                165                 170                 175

Lys His Asp Met Glu Arg Glu Ile Lys Thr Leu His Arg Arg Leu Arg
            180                 185                 190

Glu Glu Ser Ala Glu Trp Arg Gln Phe Gln Ala Asp Leu Gln Thr Ala
        195                 200                 205

Val Val Ile Ala Asn Asp Ile Lys Ser Glu Ala Gln Glu Glu Ile Gly
    210                 215                 220

Asp Leu Lys Arg Arg Leu His Glu Ala Gln Glu Lys Asn Glu Lys Leu
225                 230                 235                 240

Thr Lys Glu Leu Glu Glu Ile Lys Ser Arg Lys Gln Glu Glu Glu Arg
                245                 250                 255

Gly Gly Tyr


<210> SEQ ID NO 59
<211> LENGTH: 125
<212> TYPE: PRT
<213> ORGANISM: Homo sapien
```

-continued

<400> SEQUENCE: 59

```
Gly Thr Ser Phe Ser Lys Asn His Ala Ala Pro Phe Ser Lys Val Leu
 1               5                  10                  15

Thr Phe Tyr Arg Lys Glu Pro Phe Thr Leu Glu Ala Tyr Tyr Ser Ser
            20                  25                  30

Pro Gln Asp Leu Pro Tyr Pro Asp Pro Ala Ile Ala Gln Phe Ser Val
        35                  40                  45

Gln Lys Val Thr Pro Gln Ser Asp Gly Ser Ser Ser Lys Val Lys Val
    50                  55                  60

Lys Val Arg Val Asn Val His Gly Ile Phe Ser Val Ser Ser Ala Ser
65                  70                  75                  80

Leu Val Glu Val His Lys Ser Glu Glu Asn Glu Glu Pro Met Glu Thr
                85                  90                  95

Asp Gln Asn Ala Lys Glu Glu Glu Lys Met Gln Val Asp Gln Glu Glu
            100                 105                 110

Pro His Val Glu Glu Gln Gln Gln Gln Thr Pro Gly Arg
        115                 120                 125
```

<210> SEQ ID NO 60
<211> LENGTH: 246
<212> TYPE: PRT
<213> ORGANISM: Homo sapien

<400> SEQUENCE: 60

```
Met Tyr Arg Pro Ala Arg Val Thr Ser Thr Ser Arg Phe Leu Asn Pro
 1               5                  10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240
```

-continued

```
Thr Ser Gly Ile Ser Thr
                245


<210> SEQ ID NO 61
<211> LENGTH: 128
<212> TYPE: PRT
<213> ORGANISM: Homo sapien

<400> SEQUENCE: 61

Gly Ile Phe Ser Val Ser Ser Ala Ser Leu Val Glu Val His Lys Ser
 1               5                  10                  15

Glu Glu Asn Glu Glu Pro Met Glu Thr Asp Gln Asn Ala Lys Glu Glu
            20                  25                  30

Glu Lys Met Gln Val Asp Gln Glu Glu Pro His Val Glu Glu Gln Gln
        35                  40                  45

Gln Gln Thr Pro Ala Glu Asn Lys Ala Glu Ser Glu Glu Met Glu Thr
    50                  55                  60

Ser Gln Ala Gly Ser Lys Asp Lys Lys Met Asp Gln Pro Pro Gln Ala
65                  70                  75                  80

Lys Lys Ala Lys Val Lys Thr Ser Thr Val Asp Leu Pro Ile Glu Asn
                85                  90                  95

Gln Leu Leu Trp Gln Ile Asp Arg Glu Met Leu Asn Leu Tyr Ile Glu
            100                 105                 110

Asn Glu Gly Lys Met Ile Met Gln Asp Lys Leu Glu Lys Glu Arg Asn
        115                 120                 125


<210> SEQ ID NO 62
<211> LENGTH: 418
<212> TYPE: PRT
<213> ORGANISM: Homo sapien

<400> SEQUENCE: 62

Met Tyr Arg Pro Ala Arg Val Thr Ser Thr Ser Arg Phe Leu Asn Pro
 1               5                  10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190
```

-continued

```
Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Ile Asp Trp Ile Arg Gln Gln Thr
                405                 410                 415

Gly Ile


<210> SEQ ID NO 63
<211> LENGTH: 776
<212> TYPE: DNA
<213> ORGANISM: Homo sapien

<400> SEQUENCE: 63

cacagatggt gatagaggaa tccatcttgc agtcagataa agccctcact gatagagaga     60

aggcagtagc agtggatcgg gccaagaagg aggcagctga gaaggaacag gaacttttaa    120

aacagaaatt acaggagcag ccagcaacag atggaggctc aagataagag tcgcaaggaa    180

aactagccaa ctgaaggaga agctgcagat ggagagagaa cacctactga gagagcagat    240

tatgatgttg gagcacacgc agaaggtcca aaatgattgg cttcatgaag gatttaagaa    300

gaagtatgag gagatgaatg cagagataag tcaatttaaa cgtatgattg atactacaaa    360

aaatgatgat actccctgga ttgcacgaac cttggacaac cttgccgatg agctaactgc    420

aatattgtct gctcctgcta aattaattgg tcatggtgtc aaaggtgtga gctcactctt    480

taaaaagcat aagctcccct tttaaggata ttatagattg tacatatatg ctttggacta    540

tttttgatct gtatgttttt cattttcatt cagcaagttt tttttttttt tcagagtctt    600

actctgttgc ccaggctgga gtacagtggt gcaatctcag ctcactgcaa cctctgcctc    660

ctgggttcaa gagattcacc tgcctcagcc ccctagtagc tgggattata ggtgtacacc    720

accacaccca gctaattttt gtatttttag tagagatggg gtttcactat gttggc        776
```

-continued

<210> SEQ ID NO 64
<211> LENGTH: 160
<212> TYPE: DNA
<213> ORGANISM: Homo sapien

<400> SEQUENCE: 64
gcagcgctct cggttgcagt acccactgga aggacttagg cgctcgcgtg gacaccgcaa 60
gcccctcagt agcctcggcc caagaggcct gctttccact cgctagcccc gccgggggtc 120
cgtgtcctgt ctcggtggcc ggacccgggc ccgagcccga 160

<210> SEQ ID NO 65
<211> LENGTH: 72
<212> TYPE: PRT
<213> ORGANISM: Homo sapien

<400> SEQUENCE: 65

Leu Ser Ala Met Gly Phe Thr Ala Ala Gly Ile Ala Ser Ser Ser Ile
1 5 10 15

Ala Ala Lys Met Met Ser Ala Ala Ala Ile Ala Asn Gly Gly Gly Val
20 25 30

Ala Ser Gly Ser Leu Val Ala Thr Leu Gln Ser Leu Gly Ala Thr Gly
35 40 45

Leu Ser Gly Leu Thr Lys Phe Ile Leu Gly Ser Ile Gly Ser Ala Ile
50 55 60

Ala Ala Val Ile Ala Arg Phe Tyr
65 70

<210> SEQ ID NO 66
<211> LENGTH: 2581
<212> TYPE: DNA
<213> ORGANISM: Homo sapien

<400> SEQUENCE: 66
ctttcaaccc gcgctcgccg gctccagccc cgcgcgcccc cacccccttgc cctcccggcg 60 gctccgcagg gtgaggtggc tttgaccccg ggttgcccgg ccagcacgac cgaggaggtg 120
gctggacagc tggaggatga acggagaagc cgactgcccc acagacctgg aaatggccgc 180
ccccaaaggc caagaccgtt ggtcccagga agacatgctg actttgctgg aatgcatgaa 240
gaacaacctt ccatccaatg acagctccaa gttcaaaacc accgaatcac acatggactg 300
ggaaaaagta gcatttaaag acttttctgg agacatgtgc aagctcaaat gggtggagat 360
ttctaatgag gtgaggaagt tccgtacatt gacagaattg atcctcgatg ctcaggaaca 420
tgttaaaaat ccttacaaag gcaaaaaact caagaaacac ccagacttcc caaagaagcc 480
cctgacccct tatttccgct tcttcatgga gaagcgggcc aagtatgcga aactccaccc 540
tgagatgagc aacctggacc taaccaagat tctgtccaag aaatacaagg agcttccgga 600
gaagaagaag atgaaatata ttcaggactt ccagagagag aaacaggagt tcgagcgaaa 660
cctggcccga ttcagggagg atcaccccga cctaatccag aatgccaaga aatcggacat 720
cccagagaag cccaaaaccc cccagcagct gtggtacacc cacgagaaga aggtgtatct 780
caaagtgcgg ccagatgcca ctacgaagga ggtgaaggac tccctgggga agcagtggtc 840
tcagctctcg gacaaaaaga ggctgaaatg gattcataag gccctggagc agcggaagga 900
gtacgaggag atcatgagag actatatcca gaagcaccca gagctgaaca tcagtgagga 960
gggtatcacc aagtccaccc tcaccaaggc cgaacgccag ctcaaggaca agtttgacgg 1020

-continued

```
gcgacccacc aagccacctc cgaacagcta ctcgctgtac tgcgcagagc tcatggccaa   1080

catgaaggac gtgcccagca cagagcgcat ggtgctgtgc agccagcagt ggaagctgct   1140

gtcccagaag gagaaggacg cctatcacaa gaagtgtgat cagaaaaaga aagattacga   1200

ggtggagctg ctccgtttcc tcgagagcct gcctgaggag gagcagcagc gggtcttggg   1260

ggaagagaag atgctgaaca tcaacaagaa gcaggccacc agccccgcct ccaagaagcc   1320

agcccaggaa gggggcaagg gcggctccga gaagcccaag cggcccgtgt cggccatgtt   1380

catcttctcg gaggagaaac ggcggcagct gcaggaggag cggcctgagc tctccgagag   1440

cgagctgacc cgcctgctgg cccgaatgtg gaacgacctg tctgagaaga agaaggccaa   1500

gtacaaggcc cgagaggcgg cgctcaaggc tcagtcggag aggaagcccg gcggggagcg   1560

cgaggaacgg ggcaagctgc ccgagtcccc caaaagagct gaggagatct ggcaacagag   1620

cgttatcggc gactacctgg cccgcttcaa gaatgaccgg gtgaaggcct tgaaagccat   1680

ggaaatgacc tggaataaca tggaaaagaa ggagaaactg atgtggatta agaaggcagc   1740

cgaagaccaa aagcgatatg agagagagct gagtgagatg cgggcacctc cagctgctac   1800

aaattcttcc aagaagatga aattccaggg agaacccaag aagcctccca tgaacggtta   1860

ccagaagttc tcccaggagc tgctgtccaa tggggagctg aaccacctgc cgctgaagga   1920

gcgcatggtg gagatcggca gtcgctggca gcgcatctcc cagagccaga aggagcacta   1980

caaaaagctg gccgaggagc agcaaaagca gtacaaggtg cacctggacc tctgggttaa   2040

gagcctgtct ccccaggacc gtgcagcata taaagagtac atctccaata aacgtaagag   2100

catgaccaag ctgcgaggcc caaaccccaa atccagccgg actactctgc agtccaagtc   2160

ggagtccgag gaggatgatg aagaggatga ggatgacgag gacgaggatg aagaagagga   2220

agatgatgag aatggggact cctctgaaga tggcggcgac tcctctgagt ccagcagcga   2280

ggacgagagc gaggatgggg atgagaatga agaggatgac gaggacgaag acgacgacga   2340

ggatgacgat gaggatgaag ataatgagtc cgagggcagc agctccagct cctcctcctt   2400

aggggactcc tcagactttg actccaactg aggcttagcc ccaccccagg ggagccaggg   2460

agagcccagg agctcccctc cccaactgac cacctttgtt tcttccccat gttctgtccc   2520

ttgcccccct ggcctccccc actttctttc tttctttaaa aaaaaaaaaa aaaaactcga   2580

g                                                                   2581
```

<210> SEQ ID NO 67
<211> LENGTH: 764
<212> TYPE: PRT
<213> ORGANISM: Homo sapien

<400> SEQUENCE: 67

```
Met Asn Gly Glu Ala Asp Cys Pro Thr Asp Leu Glu Met Ala Ala Pro
 1               5                  10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95
```

-continued

```
Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Ala Thr Thr Lys
    210                 215                 220

Glu Val Lys Asp Ser Leu Gly Lys Gln Trp Ser Gln Leu Ser Asp Lys
225                 230                 235                 240

Lys Arg Leu Lys Trp Ile His Lys Ala Leu Glu Gln Arg Lys Glu Tyr
                245                 250                 255

Glu Glu Ile Met Arg Asp Tyr Ile Gln Lys His Pro Glu Leu Asn Ile
            260                 265                 270

Ser Glu Glu Gly Ile Thr Lys Ser Thr Leu Thr Lys Ala Glu Arg Gln
        275                 280                 285

Leu Lys Asp Lys Phe Asp Gly Arg Pro Thr Lys Pro Pro Pro Asn Ser
    290                 295                 300

Tyr Ser Leu Tyr Cys Ala Glu Leu Met Ala Asn Met Lys Asp Val Pro
305                 310                 315                 320

Ser Thr Glu Arg Met Val Leu Cys Ser Gln Gln Trp Lys Leu Leu Ser
                325                 330                 335

Gln Lys Glu Lys Asp Ala Tyr His Lys Lys Cys Asp Gln Lys Lys Lys
            340                 345                 350

Asp Tyr Glu Val Glu Leu Leu Arg Phe Leu Glu Ser Leu Pro Glu Glu
        355                 360                 365

Glu Gln Gln Arg Val Leu Gly Glu Glu Lys Met Leu Asn Ile Asn Lys
    370                 375                 380

Lys Gln Ala Thr Ser Pro Ala Ser Lys Lys Pro Ala Gln Glu Gly Gly
385                 390                 395                 400

Lys Gly Gly Ser Glu Lys Pro Lys Arg Pro Val Ser Ala Met Phe Ile
                405                 410                 415

Phe Ser Glu Glu Lys Arg Arg Gln Leu Gln Glu Glu Arg Pro Glu Leu
            420                 425                 430

Ser Glu Ser Glu Leu Thr Arg Leu Leu Ala Arg Met Trp Asn Asp Leu
        435                 440                 445

Ser Glu Lys Lys Lys Ala Lys Tyr Lys Ala Arg Glu Ala Ala Leu Lys
    450                 455                 460

Ala Gln Ser Glu Arg Lys Pro Gly Gly Glu Arg Glu Glu Arg Gly Lys
465                 470                 475                 480

Leu Pro Glu Ser Pro Lys Arg Ala Glu Glu Ile Trp Gln Gln Ser Val
                485                 490                 495

Ile Gly Asp Tyr Leu Ala Arg Phe Lys Asn Asp Arg Val Lys Ala Leu
            500                 505                 510
```

-continued

```
Lys Ala Met Glu Met Thr Trp Asn Asn Met Glu Lys Lys Glu Lys Leu
        515                 520                 525

Met Trp Ile Lys Lys Ala Ala Glu Asp Gln Lys Arg Tyr Glu Arg Glu
    530                 535                 540

Leu Ser Glu Met Arg Ala Pro Pro Ala Ala Thr Asn Ser Ser Lys Lys
545                 550                 555                 560

Met Lys Phe Gln Gly Glu Pro Lys Lys Pro Pro Met Asn Gly Tyr Gln
                565                 570                 575

Lys Phe Ser Gln Glu Leu Leu Ser Asn Gly Glu Leu Asn His Leu Pro
            580                 585                 590

Leu Lys Glu Arg Met Val Glu Ile Gly Ser Arg Trp Gln Arg Ile Ser
        595                 600                 605

Gln Ser Gln Lys Glu His Tyr Lys Lys Leu Ala Glu Glu Gln Gln Lys
    610                 615                 620

Gln Tyr Lys Val His Leu Asp Leu Trp Val Lys Ser Leu Ser Pro Gln
625                 630                 635                 640

Asp Arg Ala Ala Tyr Lys Glu Tyr Ile Ser Asn Lys Arg Lys Ser Met
                645                 650                 655

Thr Lys Leu Arg Gly Pro Asn Pro Lys Ser Ser Arg Thr Thr Leu Gln
            660                 665                 670

Ser Lys Ser Glu Ser Glu Glu Asp Asp Glu Glu Asp Glu Asp Asp Glu
        675                 680                 685

Asp Glu Asp Glu Glu Glu Glu Asp Asp Glu Asn Gly Asp Ser Ser Glu
    690                 695                 700

Asp Gly Gly Asp Ser Ser Glu Ser Ser Ser Glu Asp Glu Ser Glu Asp
705                 710                 715                 720

Gly Asp Glu Asn Glu Glu Asp Asp Glu Asp Glu Asp Asp Asp Glu Asp
                725                 730                 735

Asp Asp Glu Asp Glu Asp Asn Glu Ser Glu Gly Ser Ser Ser Ser Ser
            740                 745                 750

Ser Ser Leu Gly Asp Ser Ser Asp Phe Asp Ser Asn
        755                 760
```

<210> SEQ ID NO 68
<211> LENGTH: 434
<212> TYPE: DNA
<213> ORGANISM: Homo sapien

<400> SEQUENCE: 68

```
ctaagatgct ggatgctgaa gacatcgtcg gaactgcccg gccagatgag aaagccatta     60

tgacttatgt gtctagcttc tatcatgcct tctctggagc ccagaaggca gaaacagcag    120

ccaatcgcat ctgcaaagtg ttggcggtca atcaagagaa cgagcagctt atggaagact    180

atgagaagct ggccagtgat ctgttggagt ggatccgccg caccatccca tggctggaga    240

atcgggtgcc tgagaacacc atgcatgcca tgcagcagaa gctggaggac ttccgagact    300

atagacgcct gcacaagccg cccaaggtgc aggagaagtg ccagctggag atcaacttta    360

acacgctgca gaccaaactg cggctcagca accggcctgc cttcatgccc tccgagggca    420

ggatggtctc ggat                                                      434
```

<210> SEQ ID NO 69
<211> LENGTH: 244
<212> TYPE: DNA
<213> ORGANISM: Homo sapien

<400> SEQUENCE: 69

-continued

```
aggcagcatg ctcgttgaga gtcatcacca ctccctaatc tcaagtacgc agggacacaa     60

acactgcgga aggccgcagg gtcctctgcc taggaaaacc agagaccttt gttcacttgt    120

ttatgtgctg accttccctc cactattgtc ctgtgaccct gccaaatccc cctttgtgag    180

aaacacccaa gaatgatcaa taaaaaataa attaatttag gaaaaaaaaa aaaaaaaact    240

cgag                                                                 244


<210> SEQ ID NO 70
<211> LENGTH: 437
<212> TYPE: DNA
<213> ORGANISM: Homo sapien

<400> SEQUENCE: 70

ctgggacggg agcgtccagc gggactcgaa ccccagatgt gaaggcgttt ctggaaagtc     60

cttggtccct ggatccagcg tcggccagcc cagagcccgt gccgcacatc cttgcgtcct    120

ccaggcagtg ggaccccgcg agctgcacgt ccctgggcac ggacaagtgt gaggcactgt    180

tggggctgtg ccaggtgcgg ggtgggctgc cccctttctc agaaccttcc agcctggtgc    240

cgtggccccc aggccggagt cttcctaagg ctgtgaggcc acccctgtcc tggcctccgt    300

tctcgcagca gcagaccttg cccgtgatga gcggggaggc ccttggctgg ctgggccagg    360

ctggttccct ggccatgggg gctgcacctc tgggggagcc agccaaggag gaccccatgc    420

tggcgcagga agccggg                                                   437


<210> SEQ ID NO 71
<211> LENGTH: 271
<212> TYPE: DNA
<213> ORGANISM: Homo sapien

<400> SEQUENCE: 71

gcgcagagtt ctgtcgtcca ccatcgagtg aggaagagag cattggttcc cctgagatag     60

aagagatggc tctcttcagt gcccagtctc catacattaa cccgatcatc cccctttactg   120

gaccaatcca aggagggctg caggagggac ttcaggtgac cctccagggg actaccgaga    180

gttttgcaca aaagtttgtg gtgaactttt cagaacagct tcaatggaga tgacttggcc    240

ttccacttca accccggtta tgaggaagga g                                   271


<210> SEQ ID NO 72
<211> LENGTH: 290
<212> TYPE: DNA
<213> ORGANISM: Homo sapien

<400> SEQUENCE: 72

ccgagcccta cccggaggtc tccagaatcc ccaccgtcag gggatgcaac ggctccctgt     60

ctggtgccct ctcctgctgc gaggactcgg cccagggctc gggcccgccc aaggccccta    120

cggtggccga gggtcccagc tcctgccttc ggcggaacgt gatcagcgag agggagcgca    180

ggaagcggat gtcgttgagc tgtgagcgtc tgcgggccct gctgccccag ttcgatggcc    240

ggcgggagga catggcctcg gtcctggaga tgtctgttgc aattcctgcg               290


<210> SEQ ID NO 73
<211> LENGTH: 144
<212> TYPE: PRT
<213> ORGANISM: Homo sapien

<400> SEQUENCE: 73
```

-continued

```
Lys Met Leu Asp Ala Glu Asp Ile Val Gly Thr Ala Arg Pro Asp Glu
 1               5                  10                  15

Lys Ala Ile Met Thr Tyr Val Ser Ser Phe Tyr His Ala Phe Ser Gly
            20                  25                  30

Ala Gln Lys Ala Glu Thr Ala Ala Asn Arg Ile Cys Lys Val Leu Ala
        35                  40                  45

Val Asn Gln Glu Asn Glu Gln Leu Met Glu Asp Tyr Glu Lys Leu Ala
    50                  55                  60

Ser Asp Leu Leu Glu Trp Ile Arg Arg Thr Ile Pro Trp Leu Glu Asn
65                  70                  75                  80

Arg Val Pro Glu Asn Thr Met His Ala Met Gln Gln Lys Leu Glu Asp
                85                  90                  95

Phe Arg Asp Tyr Arg Arg Leu His Lys Pro Pro Lys Val Gln Glu Lys
            100                 105                 110

Cys Gln Leu Glu Ile Asn Phe Asn Thr Leu Gln Thr Lys Leu Arg Leu
        115                 120                 125

Ser Asn Arg Pro Ala Phe Met Pro Ser Glu Gly Arg Met Val Ser Asp
    130                 135                 140


<210> SEQ ID NO 74
<211> LENGTH: 64
<212> TYPE: PRT
<213> ORGANISM: Homo sapien

<400> SEQUENCE: 74

Gly Ser Met Leu Val Glu Ser His His His Ser Leu Ile Ser Ser Thr
 1               5                  10                  15

Gln Gly His Lys His Cys Gly Arg Pro Gln Gly Pro Leu Pro Arg Lys
            20                  25                  30

Thr Arg Asp Leu Cys Ser Leu Val Tyr Val Leu Thr Phe Pro Pro Leu
        35                  40                  45

Leu Ser Cys Asp Pro Ala Lys Ser Pro Phe Val Arg Asn Thr Gln Glu
    50                  55                  60


<210> SEQ ID NO 75
<211> LENGTH: 145
<212> TYPE: PRT
<213> ORGANISM: Homo sapien

<400> SEQUENCE: 75

Gly Thr Gly Ala Ser Ser Gly Thr Arg Thr Pro Asp Val Lys Ala Phe
 1               5                  10                  15

Leu Glu Ser Pro Trp Ser Leu Asp Pro Ala Ser Ala Ser Pro Glu Pro
            20                  25                  30

Val Pro His Ile Leu Ala Ser Ser Arg Gln Trp Asp Pro Ala Ser Cys
        35                  40                  45

Thr Ser Leu Gly Thr Asp Lys Cys Glu Ala Leu Leu Gly Leu Cys Gln
    50                  55                  60

Val Arg Gly Gly Leu Pro Pro Phe Ser Glu Pro Ser Ser Leu Val Pro
65                  70                  75                  80

Trp Pro Pro Gly Arg Ser Leu Pro Lys Ala Val Arg Pro Pro Leu Ser
                85                  90                  95

Trp Pro Pro Phe Ser Gln Gln Gln Thr Leu Pro Val Met Ser Gly Glu
            100                 105                 110

Ala Leu Gly Trp Leu Gly Gln Ala Gly Ser Leu Ala Met Gly Ala Ala
        115                 120                 125
```

-continued

```
Pro Leu Gly Glu Pro Ala Lys Glu Asp Pro Met Leu Ala Gln Glu Ala
    130                 135                 140

Gly
145


<210> SEQ ID NO 76
<211> LENGTH: 69
<212> TYPE: PRT
<213> ORGANISM: Homo sapien

<400> SEQUENCE: 76

Ala Glu Phe Cys Arg Pro Pro Ser Ser Glu Glu Glu Ser Ile Gly Ser
 1               5                  10                  15

Pro Glu Ile Glu Glu Met Ala Leu Phe Ser Ala Gln Ser Pro Tyr Ile
            20                  25                  30

Asn Pro Ile Ile Pro Phe Thr Gly Pro Ile Gln Gly Gly Leu Gln Glu
        35                  40                  45

Gly Leu Gln Val Thr Leu Gln Gly Thr Thr Glu Ser Phe Ala Gln Lys
    50                  55                  60

Phe Val Val Asn Phe
65


<210> SEQ ID NO 77
<211> LENGTH: 96
<212> TYPE: PRT
<213> ORGANISM: Homo sapien

<400> SEQUENCE: 77

Glu Pro Tyr Pro Glu Val Ser Arg Ile Pro Thr Val Arg Gly Cys Asn
 1               5                  10                  15

Gly Ser Leu Ser Gly Ala Leu Ser Cys Cys Glu Asp Ser Ala Gln Gly
            20                  25                  30

Ser Gly Pro Pro Lys Ala Pro Thr Val Ala Glu Gly Pro Ser Ser Cys
        35                  40                  45

Leu Arg Arg Asn Val Ile Ser Glu Arg Glu Arg Arg Lys Arg Met Ser
    50                  55                  60

Leu Ser Cys Glu Arg Leu Arg Ala Leu Leu Pro Gln Phe Asp Gly Arg
65                  70                  75                  80

Arg Glu Asp Met Ala Ser Val Leu Glu Met Ser Val Ala Ile Pro Ala
                85                  90                  95


<210> SEQ ID NO 78
<211> LENGTH: 2076
<212> TYPE: DNA
<213> ORGANISM: Homo sapien

<400> SEQUENCE: 78

agaaaaagtc tatgtttgca gaaatacaga tccaagacaa agacaggatg ggcactgctg      60

gaaaagttat taaatgcaaa gcagctgtgc tttgggagca gaagcaaccc ttctccattg     120

aggaaataga agttgcccca ccaaagacta aagaagttcg cattaagatt ttggccacag     180

gaatctgtcg cacagatgac catgtgataa aaggaacaat ggtgtccaag tttccagtga     240

ttgtgggaca tgaggcaact gggattgtag agagcattgg agaaggagtg actacagtga     300

aaccaggtga caaagtcatc cctctctttc tgccacaatg tagagaatgc aatgcttgtc     360

gcaacccaga tggcaacctt tgcattagga gcgatattac tggtcgtgga gtactggctg     420

atggcaccac cagatttaca tgcaagggca aaccagtcca ccacttcatg aacaccagta     480
```

-continued

```
catttaccga gtacacagtg gtggatgaat cttctgttgc taagattgat gatgcagctc    540
ctcctgagaa agtctgttta attggctgtg ggttttccac tggatatggc gctgctgtta    600
aaactggcaa ggtcaaacct ggttccactt gcgtcgtctt tggcctgaga ggagttggcc    660
tgtcagtcat catgggctgt aagtcagctg gtgcatctag gatcattggg attgacctca    720
acaaagacaa atttgagaag gccatggctg taggtgccac tgagtgtatc agtcccaagg    780
actctaccaa acccatcagt gaggtgctgt cagaaatgac aggcaacaac gtgggataca    840
cctttgaagt tattgggcat cttgaaacca tgattgatgc cctggcatcc tgccacatga    900
actatgggac cagcgtggtt gtaggagttc ctccatcagc caagatgctc acctatgacc    960
cgatgttgct cttcactgga cgcacatgga agggatgtgt ctttggaggt ttgaaaagca   1020
gagatgatgt cccaaaacta gtgactgagt tcctggcaaa gaaatttgac ctggaccagt   1080
tgataactca tgtcttacca tttaaaaaaa tcagtgaagg atttgagctg ctcaattcag   1140
gacaaagcat tcgaacggtc ctgacgtttt gagatccaaa gtggcaggag gtctgtgttg   1200
tcatggtgaa ctggagtttc tcttgtgaga gttccctcat ctgaaatcat gtatctgtct   1260
cacaaataca agcataagta gaagatttgt tgaagacata gaacccttat aaagaattat   1320
taacctttat aaacatttaa agtcttgtga gcacctggga attagtataa taacaatgtt   1380
aatatttttg atttacattt tgtaaggcta taattgtatc ttttaagaaa acatacactt   1440
ggatttctat gttgaaatgg agatttttaa gagttttaac cagctgctgc agatatatat   1500
ctcaaaacag atatagcgta taaagatata gtaaatgcat ctcctagagt aatattcact   1560
taacacattg aaactattat tttttagatt tgaatataaa tgtatttttt aaacacttgt   1620
tatgagttaa cttggattac attttgaaat cagttcattc catgatgcat attactggat   1680
tagattaaga aagacagaaa agattaaggg acgggcacat ttttcaacga ttaagaatca   1740
tcattacata acttggtgaa actgaaaaag tatatcatat gggtacacaa ggctatttgc   1800
cagcatatat taatatttta gaaaatattc cttttgtaat actgaatata aacatagagc   1860
tagaatcata ttatcatact tatcataatg ttcaatttga tacagtagaa ttgcaagtcc   1920
ttaagtccct attcactgtg cttagtagtg actccattta ataaaaagtg tttttagttt   1980
ttaacaacta cactgatgta tttatatata tttataacat gttaaaaatt tttaaggaaa   2040
ttaaaaatta tataaaaaaa aaaaaaaaaa ctcgag                             2076
```

<210> SEQ ID NO 79
<211> LENGTH: 2790
<212> TYPE: DNA
<213> ORGANISM: Homo sapien

<400> SEQUENCE: 79

```
aagcagttga gtaggcagaa aaaagaacct cttcattaag gattaaaatg tataggccag     60
cacgtgtaac ttcgacttca agatttctga atccatatgt agtatgtttc attgtcgtcg    120
caggggtagt gatcctggca gtcaccatag ctctacttgt ttacttttta gcttttgatc    180
aaaaatctta cttttatagg agcagttttc aactcctaaa tgttgaatat aatagtcagt    240
taaattcacc agctacacag gaatacagga ctttgagtgg aagaattgaa tctctgatta    300
ctaaaacatt caaagaatca aatttaagaa atcagttcat cagagctcat gttgccaaac    360
tgaggcaaga tggtagtggt gtgagagcgg atgttgtcat gaaatttcaa ttcactagaa    420
ataacaatgg agcatcaatg aaaagcagaa ttgagtctgt tttacgacaa atgctgaata    480
actctggaaa cctggaaata aacccttcaa ctgagataac atcacttact gaccaggctg    540
```

-continued

```
cagcaaattg gcttattaat gaatgtgggg ccggtccaga cctaataaca ttgtctgagc    600
agagaatcct tggaggcact gaggctgagg agggaagctg gccgtggcaa gtcagtctgc    660
ggctcaataa tgcccaccac tgtggaggca gcctgatcaa taacatgtgg atcctgacag    720
cagctcactg cttcagaagc aactctaatc ctcgtgactg gattgccacg tctggtattt    780
ccacaacatt tcctaaacta agaatgagag taagaaatat tttaattcat aacaattata    840
aatctgcaac tcatgaaaat gacattgcac ttgtgagact tgagaacagt gtcaccttta    900
ccaaagatat ccatagtgtg tgtctcccag ctgctaccca gaatattcca cctggctcta    960
ctgcttatgt aacaggatgg ggcgctcaag aatatgctgg ccacacagtt ccagagctaa   1020
ggcaaggaca ggtcagaata ataagtaatg atgtatgtaa tgcaccacat agttataatg   1080
gagccatctt gtctggaatg ctgtgtgctg gagtacctca aggtggagtg gacgcatgtc   1140
agggtgactc tggtggccca ctagtacaag aagactcacg gcggctttgg tttattgtgg   1200
ggatagtaag ctggggagat cagtgtggcc tgccggataa gccaggagtg tatactcgag   1260
tgacagccta ccttgactgg attaggcaac aaactgggat ctagtgcaac aagtgcatcc   1320
ctgttgcaaa gtctgtatgc aggtgtgcct gtcttaaatt ccaaagcttt acatttcaac   1380
tgaaaaagaa actagaaatg tcctaattta acatcttgtt acataaatat ggtttaacaa   1440
acactgttta acctttcttt attattaaag gttttctatt ttctccagag aactatatga   1500
atgttgcata gtactgtggc tgtgtaacag aagaaacaca ctaaactaat tacaaagtta   1560
acaatttcat tacagttgtg ctaaatgccc gtagtgagaa gaacaggaac cttgagcatg   1620
tatagtagag gaacctgcac aggtctgatg ggtcagaggg gtcttctctg ggtttcactg   1680
aggatgagaa gtaagcaaac tgtggaaaca tgcaaaggaa aaagtgatag aataatattc   1740
aagacaaaaa gaacagtatg aggcaagaga aatagtatgt atttaaaatt tttggttact   1800
caatatctta tacttagtat gagtcctaaa attaaaaatg tgaaactgtt gtactatacg   1860
tataacctaa ccttaattat tctgtaagaa catgcttcca taggaaatag tggataattt   1920
tcagctattt aaggcaaaag ctaaaatagt tcactcctca actgagaccc aaagaattat   1980
agatattttt catgatgacc catgaaaaat atcactcatc tacataaagg agagactata   2040
tctattttat agagaagcta agaaatatac ctacacaaac ttgtcaggtg ctttacaact   2100
acatagtact ttttaacaac aaaataataa ttttaagaat gaaaaattta atcatcggga   2160
agaacgtccc actacagact tcctatcact ggcagttata tttttgagcg taaaagggtc   2220
gtcaaacgct aaatctaagt aatgaattga aagtttaaag agggggaaga gttggtttgc   2280
aaaggaaaag tttaaatagc ttaatatcaa tagaatgatc ctgaagacag aaaaaacttt   2340
gtcactcttc ctctctcatt ttctttctct ctctctcccc ttctcataca catgcctccc   2400
cgaccaaaga atataatgta aattaaatcc actaaaatgt aatggcatga aaatctctgt   2460
agtctgaatc actaatattc ctgagttttt atgagctcct agtacagcta aagtttgcct   2520
atgcatgatc atctatgcgt cagagcttcc tccttctaca agctaactcc ctgcatctgg   2580
gcatcaggac tgctccatac atttgctgaa aacttcttgt atttcctgat gtaaaattgt   2640
gcaaacacct acaataaagc catctacttt tagggaaagg gagttgaaaa tgcaaccaac   2700
tcttggcgaa ctgtacaaac aaatctttgc tatactttat ttcaaataaa ttctttttga   2760
aatgaaaaaa aaaaaaaaaa aaaactcgag                                    2790
```

<210> SEQ ID NO 80

-continued

<211> LENGTH: 1460
<212> TYPE: DNA
<213> ORGANISM: Homo sapien

<400> SEQUENCE: 80
ctcaaagcag ttgagtaggc agaaaaaaga acctcttcat taaggattaa aatgtatagg 60
ccagcacgtg taacttcgac ttcaagattt ctgaatccat atgtagtatg tttcattgtc 120
gtcgcagggg tagtgatcct ggcagtcacc atagctctac ttgtttactt tttagctttt 180
gatcaaaaat cttactttta taggagcagt tttcaactcc taaatgttga atataatagt 240
cagttaaatt caccagctac acaggaatac aggactttga gtggaagaat tgaatctctg 300
attactaaaa cattcaaaga atcaaattta agaaatcagt tcatcagagc tcatgttgcc 360
aaactgaggc aagatggtag tggtgtgaga gcggatgttg tcatgaaatt tcaattcact 420
agaaataaca atggagcatc aatgaaaagc agaattgagt ctgttttacg acaaatgctg 480
aataactctg gaaacctgga aataaaccct tcaactgaga taacatcact tactgaccag 540
gctgcagcaa attggcttat taatgaatgt ggggccggtc cagacctaat aacattgtct 600
gagcagagaa tccttggagg cactgaggct gaggagggaa gctggccgtg gcaagtcagt 660
ctgcggctca ataatgccca ccactgtgga ggcagcctga tcaataacat gtggatcctg 720
acagcagctc actgcttcag aagcaactct aatcctcgtg actggattgc cacgtctggt 780
atttccacaa catttcctaa actaagaatg agagtaagaa atattttaat tcataacaat 840
tataaatctg caactcatga aaatgacatt gcacttgtga gacttgagaa cagtgtcacc 900
tttaccaaag atatccatag tgtgtgtctc ccagctgcta cccagaatat tccacctggc 960
tctactgctt atgtaacagg atggggcgct caagaatatg ctggccacac agttccagag 1020
ctaaggcaag gacaggtcag aataataagt aatgatgtat gtaatgcacc acatagttat 1080
aatggagcca tcttgtctgg aatgctgtgt gctggagtac ctcaaggtgg agtggacgca 1140
tgtcagggtg actctggtgg cccactagta caagaagact cacggcggct ttggtttatt 1200
gtggggatag taagctgggg agatcagtgt ggcctgccgg ataagccagg agtgtatact 1260
cgagtgacag cctaccttga ctggattagg caacaaactg ggatctagtg caacaagtgc 1320
atccctgttg caaagtctgt atgcaggtgt gcctgtctta aattccaaag ctttacattt 1380
caactgaaaa agaaactaga aatgtcctaa tttaacatct tgttacataa atatggttta 1440
acaaaaaaaa aaaaaaaaaa 1460

<210> SEQ ID NO 81
<211> LENGTH: 386
<212> TYPE: PRT
<213> ORGANISM: Homo sapien

<400> SEQUENCE: 81

Met Phe Ala Glu Ile Gln Ile Gln Asp Lys Asp Arg Met Gly Thr Ala
1 5 10 15

Gly Lys Val Ile Lys Cys Lys Ala Ala Val Leu Trp Glu Gln Lys Gln
20 25 30

Pro Phe Ser Ile Glu Glu Ile Glu Val Ala Pro Pro Lys Thr Lys Glu
35 40 45

Val Arg Ile Lys Ile Leu Ala Thr Gly Ile Cys Arg Thr Asp Asp His
50 55 60

Val Ile Lys Gly Thr Met Val Ser Lys Phe Pro Val Ile Val Gly His
65 70 75 80

-continued

```
Glu Ala Thr Gly Ile Val Glu Ser Ile Gly Glu Gly Val Thr Thr Val
                85                  90                  95

Lys Pro Gly Asp Lys Val Ile Pro Leu Phe Leu Pro Gln Cys Arg Glu
            100                 105                 110

Cys Asn Ala Cys Arg Asn Pro Asp Gly Asn Leu Cys Ile Arg Ser Asp
        115                 120                 125

Ile Thr Gly Arg Gly Val Leu Ala Asp Gly Thr Thr Arg Phe Thr Cys
    130                 135                 140

Lys Gly Lys Pro Val His His Phe Met Asn Thr Ser Thr Phe Thr Glu
145                 150                 155                 160

Tyr Thr Val Val Asp Glu Ser Ser Val Ala Lys Ile Asp Asp Ala Ala
                165                 170                 175

Pro Pro Glu Lys Val Cys Leu Ile Gly Cys Gly Phe Ser Thr Gly Tyr
            180                 185                 190

Gly Ala Ala Val Lys Thr Gly Lys Val Lys Pro Gly Ser Thr Cys Val
        195                 200                 205

Val Phe Gly Leu Arg Gly Val Gly Leu Ser Val Ile Met Gly Cys Lys
    210                 215                 220

Ser Ala Gly Ala Ser Arg Ile Ile Gly Ile Asp Leu Asn Lys Asp Lys
225                 230                 235                 240

Phe Glu Lys Ala Met Ala Val Gly Ala Thr Glu Cys Ile Ser Pro Lys
                245                 250                 255

Asp Ser Thr Lys Pro Ile Ser Glu Val Leu Ser Glu Met Thr Gly Asn
            260                 265                 270

Asn Val Gly Tyr Thr Phe Glu Val Ile Gly His Leu Glu Thr Met Ile
        275                 280                 285

Asp Ala Leu Ala Ser Cys His Met Asn Tyr Gly Thr Ser Val Val Val
    290                 295                 300

Gly Val Pro Pro Ser Ala Lys Met Leu Thr Tyr Asp Pro Met Leu Leu
305                 310                 315                 320

Phe Thr Gly Arg Thr Trp Lys Gly Cys Val Phe Gly Gly Leu Lys Ser
                325                 330                 335

Arg Asp Asp Val Pro Lys Leu Val Thr Glu Phe Leu Ala Lys Lys Phe
            340                 345                 350

Asp Leu Asp Gln Leu Ile Thr His Val Leu Pro Phe Lys Lys Ile Ser
        355                 360                 365

Glu Gly Phe Glu Leu Leu Asn Ser Gly Gln Ser Ile Arg Thr Val Leu
    370                 375                 380

Thr Phe
385


<210> SEQ ID NO 82
<211> LENGTH: 418
<212> TYPE: PRT
<213> ORGANISM: Homo sapien

<400> SEQUENCE: 82

Met Tyr Arg Pro Ala Arg Val Thr Ser Thr Ser Arg Phe Leu Asn Pro
 1               5                  10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60
```

-continued

```
Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile


<210> SEQ ID NO 83
<211> LENGTH: 418
<212> TYPE: PRT
<213> ORGANISM: Homo sapien

<400> SEQUENCE: 83

Met Tyr Arg Pro Ala Arg Val Thr Ser Thr Ser Arg Phe Leu Asn Pro
 1               5                  10                  15
```

-continued

```
Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile
```

-continued

<210> SEQ ID NO 84
<211> LENGTH: 489
<212> TYPE: DNA
<213> ORGANISM: Homo sapien

<400> SEQUENCE: 84
aaaagggtaa gcttgatgat taccaggaac gaatgaacaa aggggaaagg cttaatcaag 60
atcagctgga tgccgtttct aagtaccagg aagtcacaaa taatttggag tttgcaaaag 120
aattacagag gagtttcatg gcactaagtc aagatattca gaaaacaata aagaagacag 180
cacgtcggga gcagcttatg agagaagaag ctgaacagaa acgtttaaaa actgtacttg 240
agctacagta tgttttggac aaattgggag atgatgaagt gcggactgac ctgaaacaag 300
gtttgaatgg agtgccaata ttgtccgaag aggagttgtc attgttggat gaattctata 360
agctagtaga ccctgaacgg gacatgagct tgaggttgaa tgaacagtat gaacatgcct 420
ccattcacct gtgggacctg ctggaaggga aggaaaaacc tgtatgtgga accacctata 480
aagttctaa 489

<210> SEQ ID NO 85
<211> LENGTH: 304
<212> TYPE: DNA
<213> ORGANISM: Homo sapien

<400> SEQUENCE: 85
gggacctgga ggaggccacg ctgcagcatg aagccacagc agccaccctg aggaagaagc 60
acgcggacag cgtggccgag ctcggggagc agatcgacaa cctgcagcgg gtgaagcaga 120
agctggagaa ggagaagagc gagatgaaga tggagatcga tgacctcgct tgtaacatgg 180
aggtcatctc caaatctaag ggaaaccttg agaagatgtg ccgcacactg gaggaccaag 240
tgagtgagct gaagacccag gaggaggaac agcagcggct gatcaatgaa ctgactgcgc 300
agag 304

<210> SEQ ID NO 86
<211> LENGTH: 296
<212> TYPE: DNA
<213> ORGANISM: Homo sapien

<400> SEQUENCE: 86
gaaaatcctt cctttgaatg ggaatctcca agcagttgaa ttgggcgaaa aaagaacctc 60
ttccttaagg attaaaatgt ttagggcaac acgtgttact tccacttcca gatttctgaa 120
tccatatgtt gtatgtttcc ttgtcctccc aggggttgtg atcctggcag tccccatagc 180
tctacttgtt tactttttag cttttgatca aaaatcttac ttttattgga gcaattttcc 240
actcccaaat gttgaatata atagtccgtt taattccccc gcttcaccgg gaattc 296

<210> SEQ ID NO 87
<211> LENGTH: 904
<212> TYPE: DNA
<213> ORGANISM: Homo sapien

<400> SEQUENCE: 87
gtgtccagga aacgattcat gaacataaca agcttgctgc aaattcagat catctcatgc 60
agattcaaaa atgtgagttg gtcttgatcc acacctaccc agttggtgaa gacagccttg 120
tatctgatcg ttctaaaaaa gagttgtccc cggttttaac cagtgaagtt catagtgttc 180
gtgcaggacg gcatcttgct accaaattga atattttagt acagcaacat tttgacttgg 240

-continued cttcaactac tattacaaat attccaatga aggaagaaca gcatgctaac acatctgcca 300
attatgatgt ggagctactt catcacaaag atgcacatgt agatttcctg aaaagtggtg 360
attcgcatct aggtggcggc agtcgagaag gctcgtttaa agaaacaata acattaaagt 420
ggtgtacacc aaggacaaat aacattgaat tacactattg tactggagct tatcggattt 480
cacctgtaga tgtaaatagt agaccttcct cctgccttac taattttctt ctaaatggtc 540
gttctgtttt attggaacaa ccacgaaagt caggttctaa agtcattagt catatgctta 600
gtagccatgg aggagagatt tttttgcacg tccttagcag ttctcgatcc attctagaag 660
atccaccttc aattagtgaa ggatgtggag gaagagttac agactaccgg attacagatt 720
ttggtgaatt tatgagggga aaacagatta actccttttc tacaccccag atataaaatc 780
gatggaagtc ttgaggtccc tttggaaccg agccaaaaga tcagttaaaa aaacataccc 840
gttactggcc tatgatttca aaaacccacc atttttaaca tgcaagcggt agttccgtta 900
acca 904

<210> SEQ ID NO 88
<211> LENGTH: 387
<212> TYPE: DNA
<213> ORGANISM: Homo sapien

<400> SEQUENCE: 88
cgtctctccc ccagtttgcc gttcacccgg agcgctcggg acttgccgat agtggtgacg 60
gcggcaacat gtctgtggct ttcgcggccc cgaggcagcg aggcaagggg gagatcactc 120
ccgctgcgat tcagaagatg ttggatgaca ataaccatct tattcagtgt ataatggact 180
ctcagaataa aggaaagacc tcagagtgtt ctcagtatca gcagatgttg cacacaaact 240
tggtatacct tgctacaata gcagattcta atcaaaatat gcagtctctt ttaccagcac 300
cacccacaca gaatatgcct atgggtcctg gagggatgaa tcagagcggg cctcccccac 360
ctccacgctc tcacaacatg ccttcaa 387

<210> SEQ ID NO 89
<211> LENGTH: 481
<212> TYPE: DNA
<213> ORGANISM: Homo sapien

<400> SEQUENCE: 89
tgttcttgga cctgcggtgc tatagagcag gctcttctag gttggcagtt gccatggaat 60
ctggacccaa aatgttggcc cccgtttgcc tggtggaaaa taacaatgag cagctattgg 120
tgaaccagca agctatacag attcttgaaa agatttctca gccagtggtg gtggtggcca 180
ttgtaggact gtaccgtaca gggaaatcct acttgatgaa ccatctggca ggacagaatc 240
atggcttccc tctgggctcc acggtgcagt ctgaaaccaa gggcatctgg atgtggtgcg 300
tgccccaccc atccaagcca aaccacaccc tggtccttct ggacaccgaa ggtctgggcg 360
atgtggaaaa gggtgaccct aagaatgact cctggatctt tgccctggct gtgctcctgt 420
gcagcacctt tgtctacaac agcatgagca ccatcaacca ccaggccctg gagcagctgc 480
a 481

<210> SEQ ID NO 90
<211> LENGTH: 491
<212> TYPE: DNA
<213> ORGANISM: Homo sapien

<400> SEQUENCE: 90

-continued

```
tgaaaactgt tcttggacct gcggtgctat agagcaggtt ggcagttgcc atggaatctg     60
gacccaaaat gttggccccc gtttgcctgg tggaaaataa caatgagcag ctattggtga    120
accagcaagc tatacagatt cttgaaaaga tttctcagcc agtggtggtg gtggccattg    180
taggactgta ccgtacaggg aaatcctact tgatgaacca tctggcagga cagaatcatg    240
gcttccctct gggctccacg gtgcagtctg aaaccaaggg catctggatg tggtgcgtgc    300
cccacccatc caagccaaac cacaccctgg tccttctgga caccgaaggt ctgggcgatg    360
tggaaaaggg tgaccctaag aatgactcct ggatctttgc cctggctgtg ctcctgtgca    420
gcacctttgt ctacaacagc atgagcacca tcaaccacca agccctggag cagctgcatt    480
atgtgacgga c                                                          491
```

<210> SEQ ID NO 91
<211> LENGTH: 488
<212> TYPE: DNA
<213> ORGANISM: Homo sapien

<400> SEQUENCE: 91

```
ttcgacagtc agccgcatct tcttttgcgt cgccagccga gccacatcgc tcagacacca     60
tggggaaggt gaaggtcgga gtcaacggat ttggtcgtat tgggcgcctg gtcaccaggg    120
ctgcttttaa ctctggtaaa gtggatattg ttgccatcaa tgaccccttc attgacctca    180
actacatggt ttacatgttc caatatgatt ccacccatgg caaattccat ggcaccgtcg    240
aggctgagaa cgggaagctt gtcatcaatg gaaatcccat caccatcttc caggagcgag    300
atccctccaa aatcaagtgg ggcgatgctg gcgctgagta cgtcgtggag tccactggcg    360
tcttcaccac catggagaag gctggggctc atttgcaggg gggagccaaa agggtcatca    420
tctctgcccc tctgctgatg ccccatgttc gtcatgggtg tgaaccatga gaagtatgac    480
acagcctc                                                              488
```

<210> SEQ ID NO 92
<211> LENGTH: 384
<212> TYPE: DNA
<213> ORGANISM: Homo sapien

<400> SEQUENCE: 92

```
gacagtcagc cgcatcttct tttgcgtcgc cagccgagcc acatcgctca gacaccatgg     60
ggaaggtgaa ggtcggagtc aacggatttg gtcgtattgg gcgcctggtc accagggctg    120
cttttaactc tggtaaagtg gatattgttg ccatcaatga ccccttcatt gacctcaact    180
acatggttta catgttccaa tatgattcca cccatggcaa attccatggc accgtcgagg    240
ctgagaacgg gaagcttgtc atcaatggaa atcccatcac catcttccag gagcgagatc    300
cctccaaaat caagtggggc gatactggcg ctgagtacgt cgtggagtcc actggcgtct    360
tcaccaccat ggagaaggct gggg                                            384
```

<210> SEQ ID NO 93
<211> LENGTH: 162
<212> TYPE: PRT
<213> ORGANISM: Homo sapien

<400> SEQUENCE: 93

```
Lys Gly Lys Leu Asp Asp Tyr Gln Glu Arg Met Asn Lys Gly Glu Arg
 1               5                  10                  15

Leu Asn Gln Asp Gln Leu Asp Ala Val Ser Lys Tyr Gln Glu Val Thr
```

-continued

```
            20                  25                  30

Asn Asn Leu Glu Phe Ala Lys Glu Leu Gln Arg Ser Phe Met Ala Leu
        35                  40                  45

Ser Gln Asp Ile Gln Lys Thr Ile Lys Lys Thr Ala Arg Arg Glu Gln
    50                  55                  60

Leu Met Arg Glu Glu Ala Glu Gln Lys Arg Leu Lys Thr Val Leu Glu
65                  70                  75                  80

Leu Gln Tyr Val Leu Asp Lys Leu Gly Asp Asp Glu Val Arg Thr Asp
                85                  90                  95

Leu Lys Gln Gly Leu Asn Gly Val Pro Ile Leu Ser Glu Glu Glu Leu
            100                 105                 110

Ser Leu Leu Asp Glu Phe Tyr Lys Leu Val Asp Pro Glu Arg Asp Met
        115                 120                 125

Ser Leu Arg Leu Asn Glu Gln Tyr Glu His Ala Ser Ile His Leu Trp
    130                 135                 140

Asp Leu Leu Glu Gly Lys Glu Lys Pro Val Cys Gly Thr Thr Tyr Lys
145                 150                 155                 160

Val Leu


<210> SEQ ID NO 94
<211> LENGTH: 100
<212> TYPE: PRT
<213> ORGANISM: Homo sapien

<400> SEQUENCE: 94

Asp Leu Glu Glu Ala Thr Leu Gln His Glu Ala Thr Ala Ala Thr Leu
 1               5                  10                  15

Arg Lys Lys His Ala Asp Ser Val Ala Glu Leu Gly Glu Gln Ile Asp
            20                  25                  30

Asn Leu Gln Arg Val Lys Gln Lys Leu Glu Lys Glu Lys Ser Glu Met
        35                  40                  45

Lys Met Glu Ile Asp Asp Leu Ala Cys Asn Met Glu Val Ile Ser Lys
    50                  55                  60

Ser Lys Gly Asn Leu Glu Lys Met Cys Arg Thr Leu Glu Asp Gln Val
65                  70                  75                  80

Ser Glu Leu Lys Thr Gln Glu Glu Glu Gln Gln Arg Leu Ile Asn Glu
                85                  90                  95

Leu Thr Ala Gln
            100


<210> SEQ ID NO 95
<211> LENGTH: 99
<212> TYPE: PRT
<213> ORGANISM: Homo sapien

<400> SEQUENCE: 95

Lys Ile Leu Pro Leu Asn Gly Asn Leu Gln Ala Val Glu Leu Gly Glu
 1               5                  10                  15

Lys Arg Thr Ser Ser Leu Arg Ile Lys Met Phe Arg Ala Thr Arg Val
            20                  25                  30

Thr Ser Thr Ser Arg Phe Leu Asn Pro Tyr Val Val Cys Phe Leu Val
        35                  40                  45

Leu Pro Gly Val Val Ile Leu Ala Val Pro Ile Ala Leu Leu Val Tyr
    50                  55                  60

Phe Leu Ala Phe Asp Gln Lys Ser Tyr Phe Tyr Trp Ser Asn Phe Pro
65                  70                  75                  80
```

-continued

```
Leu Pro Asn Val Glu Tyr Asn Ser Pro Phe Asn Ser Pro Ala Ser Pro
                85                  90                  95

Gly Ile Pro


<210> SEQ ID NO 96
<211> LENGTH: 257
<212> TYPE: PRT
<213> ORGANISM: Homo sapien

<400> SEQUENCE: 96

Val Gln Glu Thr Ile His Glu His Asn Lys Leu Ala Ala Asn Ser Asp
 1               5                  10                  15

His Leu Met Gln Ile Gln Lys Cys Glu Leu Val Leu Ile His Thr Tyr
            20                  25                  30

Pro Val Gly Glu Asp Ser Leu Val Ser Asp Arg Ser Lys Lys Glu Leu
        35                  40                  45

Ser Pro Val Leu Thr Ser Glu Val His Ser Val Arg Ala Gly Arg His
    50                  55                  60

Leu Ala Thr Lys Leu Asn Ile Leu Val Gln Gln His Phe Asp Leu Ala
65                  70                  75                  80

Ser Thr Thr Ile Thr Asn Ile Pro Met Lys Glu Glu Gln His Ala Asn
                85                  90                  95

Thr Ser Ala Asn Tyr Asp Val Glu Leu Leu His His Lys Asp Ala His
            100                 105                 110

Val Asp Phe Leu Lys Ser Gly Asp Ser His Leu Gly Gly Gly Ser Arg
        115                 120                 125

Glu Gly Ser Phe Lys Glu Thr Ile Thr Leu Lys Trp Cys Thr Pro Arg
    130                 135                 140

Thr Asn Asn Ile Glu Leu His Tyr Cys Thr Gly Ala Tyr Arg Ile Ser
145                 150                 155                 160

Pro Val Asp Val Asn Ser Arg Pro Ser Ser Cys Leu Thr Asn Phe Leu
                165                 170                 175

Leu Asn Gly Arg Ser Val Leu Leu Glu Gln Pro Arg Lys Ser Gly Ser
            180                 185                 190

Lys Val Ile Ser His Met Leu Ser Ser His Gly Gly Glu Ile Phe Leu
        195                 200                 205

His Val Leu Ser Ser Ser Arg Ser Ile Leu Glu Asp Pro Pro Ser Ile
    210                 215                 220

Ser Glu Gly Cys Gly Gly Arg Val Thr Asp Tyr Arg Ile Thr Asp Phe
225                 230                 235                 240

Gly Glu Phe Met Arg Gly Lys Gln Ile Asn Ser Phe Ser Thr Pro Gln
                245                 250                 255

Ile


<210> SEQ ID NO 97
<211> LENGTH: 128
<212> TYPE: PRT
<213> ORGANISM: Homo sapien

<400> SEQUENCE: 97

Ser Leu Pro Gln Phe Ala Val His Pro Glu Arg Ser Gly Leu Ala Asp
 1               5                  10                  15

Ser Gly Asp Gly Gly Asn Met Ser Val Ala Phe Ala Ala Pro Arg Gln
            20                  25                  30

Arg Gly Lys Gly Glu Ile Thr Pro Ala Ala Ile Gln Lys Met Leu Asp
```

-continued

```
        35                  40                  45

Asp Asn Asn His Leu Ile Gln Cys Ile Met Asp Ser Gln Asn Lys Gly
    50                  55                  60

Lys Thr Ser Glu Cys Ser Gln Tyr Gln Gln Met Leu His Thr Asn Leu
65                  70                  75                  80

Val Tyr Leu Ala Thr Ile Ala Asp Ser Asn Gln Asn Met Gln Ser Leu
                85                  90                  95

Leu Pro Ala Pro Pro Thr Gln Asn Met Pro Met Gly Pro Gly Gly Met
            100                 105                 110

Asn Gln Ser Gly Pro Pro Pro Pro Pro Arg Ser His Asn Met Pro Ser
        115                 120                 125


<210> SEQ ID NO 98
<211> LENGTH: 159
<212> TYPE: PRT
<213> ORGANISM: Homo sapien

<400> SEQUENCE: 98

Phe Leu Asp Leu Arg Cys Tyr Arg Ala Gly Ser Ser Arg Leu Ala Val
 1               5                  10                  15

Ala Met Glu Ser Gly Pro Lys Met Leu Ala Pro Val Cys Leu Val Glu
            20                  25                  30

Asn Asn Asn Glu Gln Leu Leu Val Asn Gln Gln Ala Ile Gln Ile Leu
        35                  40                  45

Glu Lys Ile Ser Gln Pro Val Val Val Val Ala Ile Val Gly Leu Tyr
    50                  55                  60

Arg Thr Gly Lys Ser Tyr Leu Met Asn His Leu Ala Gly Gln Asn His
65                  70                  75                  80

Gly Phe Pro Leu Gly Ser Thr Val Gln Ser Glu Thr Lys Gly Ile Trp
                85                  90                  95

Met Trp Cys Val Pro His Pro Ser Lys Pro Asn His Thr Leu Val Leu
            100                 105                 110

Leu Asp Thr Glu Gly Leu Gly Asp Val Glu Lys Gly Asp Pro Lys Asn
        115                 120                 125

Asp Ser Trp Ile Phe Ala Leu Ala Val Leu Leu Cys Ser Thr Phe Val
    130                 135                 140

Tyr Asn Ser Met Ser Thr Ile Asn His Gln Ala Leu Glu Gln Leu
145                 150                 155


<210> SEQ ID NO 99
<211> LENGTH: 147
<212> TYPE: PRT
<213> ORGANISM: Homo sapien

<400> SEQUENCE: 99

Met Glu Ser Gly Pro Lys Met Leu Ala Pro Val Cys Leu Val Glu Asn
 1               5                  10                  15

Asn Asn Glu Gln Leu Leu Val Asn Gln Gln Ala Ile Gln Ile Leu Glu
            20                  25                  30

Lys Ile Ser Gln Pro Val Val Val Val Ala Ile Val Gly Leu Tyr Arg
        35                  40                  45

Thr Gly Lys Ser Tyr Leu Met Asn His Leu Ala Gly Gln Asn His Gly
    50                  55                  60

Phe Pro Leu Gly Ser Thr Val Gln Ser Glu Thr Lys Gly Ile Trp Met
65                  70                  75                  80

Trp Cys Val Pro His Pro Ser Lys Pro Asn His Thr Leu Val Leu Leu
```

-continued

```
                85                  90                  95

Asp Thr Glu Gly Leu Gly Asp Val Glu Lys Gly Asp Pro Lys Asn Asp
            100                 105                 110

Ser Trp Ile Phe Ala Leu Ala Val Leu Leu Cys Ser Thr Phe Val Tyr
        115                 120                 125

Asn Ser Met Ser Thr Ile Asn His Gln Ala Leu Glu Gln Leu His Tyr
    130                 135                 140

Val Thr Asp
145


<210> SEQ ID NO 100
<211> LENGTH: 124
<212> TYPE: PRT
<213> ORGANISM: Homo sapien

<400> SEQUENCE: 100

Met Gly Lys Val Lys Val Gly Val Asn Gly Phe Gly Arg Ile Gly Arg
 1               5                  10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Glu Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro
        115                 120


<210> SEQ ID NO 101
<211> LENGTH: 127
<212> TYPE: PRT
<213> ORGANISM: Homo sapien

<400> SEQUENCE: 101

Gln Ser Ala Ala Ser Ser Phe Ala Ser Pro Ala Glu Pro His Arg Ser
 1               5                  10                  15

Asp Thr Met Gly Lys Val Lys Val Gly Val Asn Gly Phe Gly Arg Ile
            20                  25                  30

Gly Arg Leu Val Thr Arg Ala Ala Phe Asn Ser Gly Lys Val Asp Ile
        35                  40                  45

Val Ala Ile Asn Asp Pro Phe Ile Asp Leu Asn Tyr Met Val Tyr Met
    50                  55                  60

Phe Gln Tyr Asp Ser Thr His Gly Lys Phe His Gly Thr Val Glu Ala
65                  70                  75                  80

Glu Asn Gly Lys Leu Val Ile Asn Gly Asn Pro Ile Thr Ile Phe Gln
                85                  90                  95

Glu Arg Asp Pro Ser Lys Ile Lys Trp Gly Asp Thr Gly Ala Glu Tyr
            100                 105                 110

Val Val Glu Ser Thr Gly Val Phe Thr Thr Met Glu Lys Ala Gly
        115                 120                 125
```

-continued

<210> SEQ ID NO 102
<211> LENGTH: 1225
<212> TYPE: DNA
<213> ORGANISM: Homo sapien

<400> SEQUENCE: 102
atggcggcgc ggtcgtcgtc gggggtggcg gcggcagagg gggcggcggc cctggcggca 60
gcggagacgg cagccgtgac ggtggcagcg gcggcgcggg acctgggcct gggggaatga 120
ggcggccgcg gcgggccagc ggcggagccg tgtagcggag aagctccccc tccctgcttc 180
ccttggccga gccgggggcg cgcgcgcacg cggccgtcca gagcgggctc cccacccctc 240
gactcctgcg acccgcaccg cacccccacc cgggcccgga ggatgatgaa gctcaagtcg 300
aaccagaccc gcacctacga cggcgacggc tacaagaagc gggccgcatg cctgtgtttc 360
cgcagcgaga gcgaggagga ggtgctactc gtgagcagta gtcgccatcc agacagatgg 420
attgtccctg gaggaggcat ggagcccgag gaggagccaa gtgtggcagc agttcgtgaa 480
gtctgtgagg aggctggagt aaaagggaca ttgggaagat tagttggaat ttttgagaac 540
caggagagga agcacaggac gtatgtctat gtgctcattg tcactgaagt gctggaagac 600
tgggaagatt cagttaacat tggaaggaag agggaatggt ttaaaataga agacgccata 660
aaagtgctgc agtatcacaa acccgtgcag gcatcatatt ttgaaacatt gaggcaaggc 720
tactcagcca acaatggcac cccagtcgtg gccaccacat actcggtttc tgctcagagc 780
tcgatgtcag gcatcagatg actgaagact tcctgtaaga gaaatggaaa ttggaaacta 840
gactgaagtg caaatcttcc ctctcaccct ggctctttcc acttctcaca ggcctcctct 900
ttcaaataag gcatggtggg cagcaaagaa agggtgtatt gataatgttg ctgtttggtg 960
ttaagtgatg gggctttttc ttctgttttt attgagggtg ggggttgggt gtgtaatttg 1020
taagtacttt tgtgcatgat ctgtccctcc ctcttcccac ccctgcagtc ctctgaagag 1080
aggccaacag ccttcccctg ccttggattc tgaagtgttc ctgtttgtct tatcctggcc 1140
ctggccagac gttttctttg atttttaatt tttttttttt attaaaagat accagtatga 1200
gaaaaaaaaa aaaaaaaaac tcgag 1225

<210> SEQ ID NO 103
<211> LENGTH: 741
<212> TYPE: DNA
<213> ORGANISM: Homo sapien

<400> SEQUENCE: 103
agaaacctca atcggattca gcaaaggaat ggtgttatta tcactacata ccaaatgtta 60
atcaataact ggcagcaact ttcaagcttt aggggccaag agtttgtgtg ggactatgtc 120
atcctcgatg aagcacataa aataaaaacc tcatctacta agtcagcaat atgtgctcgt 180
gctattcctg caagtaatcg cctcctcctc acaggaaccc caatccagaa taatttacaa 240
gaactatggt ccctatttga ttttgcttgt caagggtccc tgctgggaac attaaaaact 300
tttaagatgg agtatgaaaa tcctattact agagcaagag agaaggatgc taccccagga 360
gaaaaagcct tgggatttaa aatatctgaa aacttaatgg caatcataaa accctatttt 420
ctcaggagga ctaaagaaga cgtacagaag aaaaagtcaa gcaacccaga ggccagactt 480
aatgaaaaga atccagatgt tgatgccatt tgtgaaatgc cttccctttc caggagaaat 540
gatttaatta tttggatacg acttgtgcct ttacaagaag aaatatacag gaaatttgtg 600
tctttagatc atatcaagga gttgctaatg gagacgcgct cacctttggc tgagctaggt 660

-continued gtcttaaaga agctgtgtga tcatcctagg ctgctgtctg cacgggcttg ttgtttgcta 720
aatcttggga cattctctgc t 741

<210> SEQ ID NO 104
<211> LENGTH: 321
<212> TYPE: DNA
<213> ORGANISM: Homo sapien

<400> SEQUENCE: 104
ttgctctgcg tcatcaaaga caccaaactg ctgtgctata aaagttccaa ggaccagcag 60
cctcagatgg aactgccact ccaaggctgt aacattacgt acatcccgaa agacagcaaa 120
aagaagaagc acgagctgaa gattactcag cagggcacgg acccgcttgt tctcgccgtc 180
cagagcaagg aacaggccga gcagtggctg aaggtgatca aagaagccta cagtggttgt 240
agtggccccg tggattcaga gtgtcctcct ccaccaagct ccccggtgca caaggcagaa 300
ctggagaaga aactgtcttc a 321

<210> SEQ ID NO 105
<211> LENGTH: 389
<212> TYPE: DNA
<213> ORGANISM: Homo sapien

<400> SEQUENCE: 105
cagcactggc cacactataa aattcaggtt cagaaaaaca gggtaagtca cagacagcaa 60
cgcttccagc atttattttc tttgcaccca tgggcaattt gagaaaattt acctttagaa 120
cgaactctgt taaaggtaca gacagtacaa tactttttat tcagaaggtt tctgcataaa 180
ggtgatagtc ttttgactta atatattatt gtctcctgcc ttgtgtttct ggaatgaatg 240
aaggtcatta tttagaagat aatctgggtt gtatttgtgt cgtcagattg aattttcatt 300
gcacatgcta cttaatgtct ttaccaaata ataacaaagg gaaagaaaac caaatataga 360
tgtataataa ggaaaagctg gcctataga 389

<210> SEQ ID NO 106
<211> LENGTH: 446
<212> TYPE: DNA
<213> ORGANISM: Homo sapien

<400> SEQUENCE: 106
gccacatttg ccctggtcat agtttaaaca ccaggtcctg tgtcacatct ttttggtgcc 60
acaagtatca ctccattgtt cagagagtaa tgtattagtt ctgcccaatt cattcttcac 120
ttttatttct tccatttcat tagcatttat atcagctcaa gaagttaagg ttagaaaatt 180
ttccacttca aattttcagt acagaaatgt gctgtgatgt ttgacaagac tatttcatag 240
taagtgagtt aatgtttatt ggcctctgct ctcctctgtg tcagacctag gaagcctgag 300
gattacttag ttgttctgtc tctgggtcca caggcagaat ttggcccatc caaagactgg 360
ccaagtgcca aaaaaaggcc tgattaggcc ctgaaattca gtgaaattct gcctgaagaa 420
acctcttatt gaatttgaaa accata 446

<210> SEQ ID NO 107
<211> LENGTH: 467
<212> TYPE: DNA
<213> ORGANISM: Homo sapien

<400> SEQUENCE: 107
ccgccgctgc cgtcgccttc ctgggattgg agtctcgagc tttcttcgtt cgttcgccgg 60

-continued

```
cgggttcgcg cccttctcgc gcctcggggc tgcgaggctg gggaaggggt tggagggggc    120

tgttgatcgc cgcgtttaag ttgcgctcgg ggcggccatg tcggccggcg aggtcgagcg    180

cctagtgtcg gagctgagcg gcgggaccgg aggggatgag gaggaagagt ggctctatgg    240

cgatgaagat gaagttgaaa ggccagaaga agaaaatgcc agtgctaatc ctccatctgg    300

aattgaagat gaaactgctg aaaatggtgt accaaaaccg aaagtgactg agaccgaaga    360

tgatagtgat agtgacagcg atgatgatga agatgatgtg catgtcacta taggagacat    420

taaaacggga gcaccacagt atgggagtta tggtacagca cctgtaa                  467
```

<210> SEQ ID NO 108
<211> LENGTH: 491
<212> TYPE: DNA
<213> ORGANISM: Homo sapien

<400> SEQUENCE: 108

```
gaaagataca acttccccaa cccaaacccg tttgtggagg acgacatgga taagaatgaa     60

atcgcctctg ttgcgtaccg ttaccgcagg tggaagcttg gagatgatat tgaccttatt    120

gtccgttgtg agcacgatgg cgtcatgact ggagccaacg gggaagtgtc cttcatcaac    180

atcaagacac tcaatgagtg ggattccagg cactgtaatg gcgttgactg gcgtcagaag    240

ctggactctc agcgaggggc tgtcattgcc acggagctga agaacaacag ctacaagttg    300

gcccggtgga cctgctgtgc tttgctggct ggatctgagt acctcaagct tggttatgtg    360

tctcggtacc acgtgaaaga ctcctcacgc cacgtcatcc taggcaccca gcagttcaag    420

cctaatgagt ttgccagcca gatcaacctg agcgtggaga atgcctgagg cattttacgc    480

tgcgtcattg a                                                         491
```

<210> SEQ ID NO 109
<211> LENGTH: 489
<212> TYPE: DNA
<213> ORGANISM: Homo sapien

<400> SEQUENCE: 109

```
ctcagatagt actgaaccct ttatcaacta tgttttttca gtctgacaac caaggcggct     60

actaagtgac taaggggcag gtagtataca gtgtggataa gcaggacaaa ggggtgattc    120

acatcccagg caggacagag caggagatca tgagatttca tcactcagga tggcttgtga    180

tttattttat tttattcttt tttttttttg agatggagtc tcactcttgc ccaggctgga    240

gtgcagtggt gcgatcttgg ctcactgcaa cctctgcctc ctgggttcaa gcagttctcc    300

tgcctcagcc tcccaagtag ctgggattac aggcgtccgc caccatgccc agccaatttt    360

tgtactttta gtagagatgg ggtttcacca tgttggccag gctggtctcg aactcctgac    420

ctcaggtgat ccactcgcct cggcctccca aagtgctggg attataggca tgcgccacca    480

tgcccgggc                                                            489
```

<210> SEQ ID NO 110
<211> LENGTH: 391
<212> TYPE: DNA
<213> ORGANISM: Homo sapien

<400> SEQUENCE: 110

```
gcggagtccg ctggctgacc cgagcgctgg tctccgccgg gaaccctggg gcatggagag     60

gtctgagtac ctcggccgcg gcgcacgctg catcgcggag ccaggctgcc gctgtcccag    120
```

-continued

```
tggagttcca ggagcaccac ctgagtgagg tgcagaatat ggcatctgag gagaagctgg    180

agcaggtgct gagttccatg aaggagaaca aagtggccat cattggaaag attcataccc    240

cgatggagta taagggggag ctagcctcct atgatatgcg gctgaggcgt aagttggact    300

tatttgccaa cgtaatccat gtgaagtcac ttcctgggta tatgactcgg cacaacaatc    360

tagacctggt gatcattcga gagcagacag a                                   391
```

```
<210> SEQ ID NO 111
<211> LENGTH: 172
<212> TYPE: PRT
<213> ORGANISM: Homo sapien

<400> SEQUENCE: 111

Met Met Lys Leu Lys Ser Asn Gln Thr Arg Thr Tyr Asp Gly Asp Gly
 1               5                  10                  15

Tyr Lys Lys Arg Ala Ala Cys Leu Cys Phe Arg Ser Glu Ser Glu Glu
            20                  25                  30

Glu Val Leu Leu Val Ser Ser Ser Arg His Pro Asp Arg Trp Ile Val
        35                  40                  45

Pro Gly Gly Gly Met Glu Pro Glu Glu Glu Pro Ser Val Ala Ala Val
    50                  55                  60

Arg Glu Val Cys Glu Glu Ala Gly Val Lys Gly Thr Leu Gly Arg Leu
65                  70                  75                  80

Val Gly Ile Phe Glu Asn Gln Glu Arg Lys His Arg Thr Tyr Val Tyr
                85                  90                  95

Val Leu Ile Val Thr Glu Val Leu Glu Asp Trp Glu Asp Ser Val Asn
            100                 105                 110

Ile Gly Arg Lys Arg Glu Trp Phe Lys Ile Glu Asp Ala Ile Lys Val
        115                 120                 125

Leu Gln Tyr His Lys Pro Val Gln Ala Ser Tyr Phe Glu Thr Leu Arg
    130                 135                 140

Gln Gly Tyr Ser Ala Asn Asn Gly Thr Pro Val Val Ala Thr Thr Tyr
145                 150                 155                 160

Ser Val Ser Ala Gln Ser Ser Met Ser Gly Ile Arg
                165                 170


<210> SEQ ID NO 112
<211> LENGTH: 247
<212> TYPE: PRT
<213> ORGANISM: Homo sapien

<400> SEQUENCE: 112

Arg Asn Leu Asn Arg Ile Gln Gln Arg Asn Gly Val Ile Ile Thr Thr
 1               5                  10                  15

Tyr Gln Met Leu Ile Asn Asn Trp Gln Gln Leu Ser Ser Phe Arg Gly
            20                  25                  30

Gln Glu Phe Val Trp Asp Tyr Val Ile Leu Asp Glu Ala His Lys Ile
        35                  40                  45

Lys Thr Ser Ser Thr Lys Ser Ala Ile Cys Ala Arg Ala Ile Pro Ala
    50                  55                  60

Ser Asn Arg Leu Leu Leu Thr Gly Thr Pro Ile Gln Asn Asn Leu Gln
65                  70                  75                  80

Glu Leu Trp Ser Leu Phe Asp Phe Ala Cys Gln Gly Ser Leu Leu Gly
                85                  90                  95

Thr Leu Lys Thr Phe Lys Met Glu Tyr Glu Asn Pro Ile Thr Arg Ala
            100                 105                 110
```

-continued

Arg Glu Lys Asp Ala Thr Pro Gly Glu Lys Ala Leu Gly Phe Lys Ile
115 120 125

Ser Glu Asn Leu Met Ala Ile Ile Lys Pro Tyr Phe Leu Arg Arg Thr
130 135 140

Lys Glu Asp Val Gln Lys Lys Lys Ser Ser Asn Pro Glu Ala Arg Leu
145 150 155 160

Asn Glu Lys Asn Pro Asp Val Asp Ala Ile Cys Glu Met Pro Ser Leu
165 170 175

Ser Arg Arg Asn Asp Leu Ile Ile Trp Ile Arg Leu Val Pro Leu Gln
180 185 190

Glu Glu Ile Tyr Arg Lys Phe Val Ser Leu Asp His Ile Lys Glu Leu
195 200 205

Leu Met Glu Thr Arg Ser Pro Leu Ala Glu Leu Gly Val Leu Lys Lys
210 215 220

Leu Cys Asp His Pro Arg Leu Leu Ser Ala Arg Ala Cys Cys Leu Leu
225 230 235 240

Asn Leu Gly Thr Phe Ser Ala
245

<210> SEQ ID NO 113
<211> LENGTH: 107
<212> TYPE: PRT
<213> ORGANISM: Homo sapien

<400> SEQUENCE: 113

Leu Leu Cys Val Ile Lys Asp Thr Lys Leu Leu Cys Tyr Lys Ser Ser
1 5 10 15

Lys Asp Gln Gln Pro Gln Met Glu Leu Pro Leu Gln Gly Cys Asn Ile
20 25 30

Thr Tyr Ile Pro Lys Asp Ser Lys Lys Lys Lys His Glu Leu Lys Ile
35 40 45

Thr Gln Gln Gly Thr Asp Pro Leu Val Leu Ala Val Gln Ser Lys Glu
50 55 60

Gln Ala Glu Gln Trp Leu Lys Val Ile Lys Glu Ala Tyr Ser Gly Cys
65 70 75 80

Ser Gly Pro Val Asp Ser Glu Cys Pro Pro Pro Pro Ser Ser Pro Val
85 90 95

His Lys Ala Glu Leu Glu Lys Lys Leu Ser Ser
100 105

<210> SEQ ID NO 114
<211> LENGTH: 155
<212> TYPE: PRT
<213> ORGANISM: Homo sapien

<400> SEQUENCE: 114

Glu Arg Tyr Asn Phe Pro Asn Pro Asn Pro Phe Val Glu Asp Asp Met
1 5 10 15

Asp Lys Asn Glu Ile Ala Ser Val Ala Tyr Arg Tyr Arg Arg Trp Lys
20 25 30

Leu Gly Asp Asp Ile Asp Leu Ile Val Arg Cys Glu His Asp Gly Val
35 40 45

Met Thr Gly Ala Asn Gly Glu Val Ser Phe Ile Asn Ile Lys Thr Leu
50 55 60

Asn Glu Trp Asp Ser Arg His Cys Asn Gly Val Asp Trp Arg Gln Lys
65 70 75 80

-continued

```
Leu Asp Ser Gln Arg Gly Ala Val Ile Ala Thr Glu Leu Lys Asn Asn
                85                  90                  95

Ser Tyr Lys Leu Ala Arg Trp Thr Cys Cys Ala Leu Leu Ala Gly Ser
            100                 105                 110

Glu Tyr Leu Lys Leu Gly Tyr Val Ser Arg Tyr His Val Lys Asp Ser
        115                 120                 125

Ser Arg His Val Ile Leu Gly Thr Gln Gln Phe Lys Pro Asn Glu Phe
    130                 135                 140

Ala Ser Gln Ile Asn Leu Ser Val Glu Asn Ala
145                 150                 155


<210> SEQ ID NO 115
<211> LENGTH: 129
<212> TYPE: PRT
<213> ORGANISM: Homo sapien

<400> SEQUENCE: 115

Gly Val Arg Trp Leu Thr Arg Ala Leu Val Ser Ala Gly Asn Pro Gly
 1               5                  10                  15

Ala Trp Arg Gly Leu Ser Thr Ser Ala Ala Ala His Ala Ala Ser Arg
            20                  25                  30

Ser Gln Ala Ala Ala Val Pro Val Glu Phe Gln Glu His His Leu Ser
        35                  40                  45

Glu Val Gln Asn Met Ala Ser Glu Glu Lys Leu Glu Gln Val Leu Ser
    50                  55                  60

Ser Met Lys Glu Asn Lys Val Ala Ile Ile Gly Lys Ile His Thr Pro
65                  70                  75                  80

Met Glu Tyr Lys Gly Glu Leu Ala Ser Tyr Asp Met Arg Leu Arg Arg
                85                  90                  95

Lys Leu Asp Leu Phe Ala Asn Val Ile His Val Lys Ser Leu Pro Gly
            100                 105                 110

Tyr Met Thr Arg His Asn Asn Leu Asp Leu Val Ile Ile Arg Glu Gln
        115                 120                 125

Thr


<210> SEQ ID NO 116
<211> LENGTH: 550
<212> TYPE: DNA
<213> ORGANISM: Homo sapien

<400> SEQUENCE: 116

gaattcggca ccagcctcag agccccccag cccggctacc accccctgcg gaaaggtacc     60

catctgcatt cctgcccgtc gggacctggt ggacagtcca gcctccttgg cctctagcct    120

tggctcaccg ctgcctagag ccaaggagct catcctgaat gaccttcccg ccagcactcc    180

tgcctccaaa tcctgtgact cctccccgcc ccaggacgct tccacccccca ggcccagctc    240

ggccagtcac ctctgccagc ttgctgccaa gccagcacct tccacggaca gcgtcgccct    300

gaggagcccc ctgactctgt ccagtccctt caccacgtcc ttcagcctgg gctcccacag    360

cactctcaac ggagacctct ccgtgcccag ctcctacgtc agcctccacc tgtcccccca    420

ggtcagcagc tctgtggtgt acggacgctc ccccgtgatg gcatttgagt ctcatcccca    480

tctccgaggg tcatccgtct cttcctccct acccagcatc cctgggggaa agccggccta    540

ctccttccac                                                           550
```

-continued

<210> SEQ ID NO 117
<211> LENGTH: 154
<212> TYPE: DNA
<213> ORGANISM: Homo sapien

<400> SEQUENCE: 117
ttctgaggga aagccgagtg gagtgggcga cccggcggcg gtgacaatga gttttcttgg 60
aggctttttt ggtcccattt gtgagattga tgttgccctt aatgatgggg aaaccaggaa 120
aatggcagaa atgaaaactg aggatggcaa agta 154

<210> SEQ ID NO 118
<211> LENGTH: 449
<212> TYPE: DNA
<213> ORGANISM: Homo sapien

<400> SEQUENCE: 118
gaattcggca ccagggcccg cagcccgagt gtcgccgcca tggcttcgcc gcagctctgc 60
cgcgcgctgg tgtcggcgca atgggtggcg gaggcgctgc gggccccgcg cgctgggcag 120
cctctgcagc tgctggacgc ctcctggtac ctgccgaagc tggggcgcga cgcgcgacgc 180
gagttcgagg agcgccacat cccgggcgcc gctttcttcg acatcgacca gtgcagcgac 240
cgcacctcgc cctacgacca catgctgccc ggggccgagc atttcgcgga gtacgcaggc 300
cgcctgggcg tgggcgcggc cacccacgtc gtgatctacg acgccagcga ccagggcctc 360
tactccgccc cgcgcgtctg gtggatgttc cgcgccttcg gccaccacgc cgtgtcactg 420
cttgatggcg gcctccgcca ctggctgcg 449

<210> SEQ ID NO 119
<211> LENGTH: 642
<212> TYPE: DNA
<213> ORGANISM: Homo sapien

<400> SEQUENCE: 119
gaattcggca cgagcagtaa cccgaccgcc gctggtcttc gctggacacc atgaatcaca 60
ctgtccaaac cttcttctct cctgtcaaca gtggccagcc ccccaactat gagatgctca 120
aggaggagca cgaggtggct gtgctggggg cgccccacaa ccctgctccc ccgacgtcca 180
ccgtgatcca catccgcagc gagacctccg tgcccgacca tgtcgtctgg tccctgttca 240
acaccctctt catgaacccc tgctgcctgg gcttcatagc attcgcctac tccgtgaagt 300
ctagggacag gaagatggtt ggcgacgtga ccggggccca ggcctatgcc tccaccgcca 360
agtgcctgaa catctgggcc ctgattctgg gcatcctcat gaccattctg ctcatcgtca 420
tcccagtgct gatcttccag gcctatggat agatcaggag gcatcactga ggccaggagc 480
tctgcccatg acctgtatcc cacgtactcc aacttccatt cctcgccctg cccccggagc 540
cgagtcctgt atcagccctt tatcctcaca cgcttttcta caatggcatt caataaagtg 600
cacgtgtttc tggtgaaaaa aaaaaaaaaa aaaaaactcg ag 642

<210> SEQ ID NO 120
<211> LENGTH: 603
<212> TYPE: DNA
<213> ORGANISM: Homo sapien

<400> SEQUENCE: 120
gaattcggca cgagccacaa cagccactac gactgcatcc actggatcca cggccacccc 60
gtcctccacc ccgggaacag ctccccctcc caaagtgctg accagcccgg ccaccacacc 120

-continued

```
catgtccacc atgtccacaa tccacacctc ctctactcca gagaccaccc acacctccac    180

agtgctgacc accacagcca ccatgacaag ggccaccaat tccacggcca caccctcctc    240

cactctgggg acgacccgga tcctcactga gctgaccaca acagccacta caactgcagc    300

cactggatcc acggccaccc tgtcctccac cccagggacc acctggatcc tcacagagcc    360

gagcactata gccaccgtga tggtgcccac cggttccacg gccaccgcct cctccactct    420

gggaacagct cacaccccca aagtggtgac caccatggcc actatgccca cagccactgc    480

ctccacggtt cccagctcgt ccaccgtggg gaccacccgc acccctgcag tgctccccag    540

cagcctgcca accttcagcg tgtccactgt gtcctcctca gtcctcacca ccctgagacc    600

cac                                                                   603


<210> SEQ ID NO 121
<211> LENGTH: 178
<212> TYPE: PRT
<213> ORGANISM: Homo sapien

<400> SEQUENCE: 121

Ser Glu Pro Pro Ser Pro Ala Thr Thr Pro Cys Gly Lys Val Pro Ile
 1               5                  10                  15

Cys Ile Pro Ala Arg Arg Asp Leu Val Asp Ser Pro Ala Ser Leu Ala
            20                  25                  30

Ser Ser Leu Gly Ser Pro Leu Pro Arg Ala Lys Glu Leu Ile Leu Asn
        35                  40                  45

Asp Leu Pro Ala Ser Thr Pro Ala Ser Lys Ser Cys Asp Ser Ser Pro
    50                  55                  60

Pro Gln Asp Ala Ser Thr Pro Arg Pro Ser Ser Ala Ser His Leu Cys
65                  70                  75                  80

Gln Leu Ala Ala Lys Pro Ala Pro Ser Thr Asp Ser Val Ala Leu Arg
                85                  90                  95

Ser Pro Leu Thr Leu Ser Ser Pro Phe Thr Thr Ser Phe Ser Leu Gly
            100                 105                 110

Ser His Ser Thr Leu Asn Gly Asp Leu Ser Val Pro Ser Ser Tyr Val
        115                 120                 125

Ser Leu His Leu Ser Pro Gln Val Ser Ser Ser Val Val Tyr Gly Arg
    130                 135                 140

Ser Pro Val Met Ala Phe Glu Ser His Pro His Leu Arg Gly Ser Ser
145                 150                 155                 160

Val Ser Ser Ser Leu Pro Ser Ile Pro Gly Gly Lys Pro Ala Tyr Ser
                165                 170                 175

Phe His


<210> SEQ ID NO 122
<211> LENGTH: 36
<212> TYPE: PRT
<213> ORGANISM: Homo sapien

<400> SEQUENCE: 122

Met Ser Phe Leu Gly Gly Phe Phe Gly Pro Ile Cys Glu Ile Asp Val
 1               5                  10                  15

Ala Leu Asn Asp Gly Glu Thr Arg Lys Met Ala Glu Met Lys Thr Glu
            20                  25                  30

Asp Gly Lys Val
        35
```

-continued

<210> SEQ ID NO 123
<211> LENGTH: 136
<212> TYPE: PRT
<213> ORGANISM: Homo sapien

<400> SEQUENCE: 123

```
Met Ala Ser Pro Gln Leu Cys Arg Ala Leu Val Ser Ala Gln Trp Val
 1               5                  10                  15

Ala Glu Ala Leu Arg Ala Pro Arg Ala Gly Gln Pro Leu Gln Leu Leu
            20                  25                  30

Asp Ala Ser Trp Tyr Leu Pro Lys Leu Gly Arg Asp Ala Arg Arg Glu
        35                  40                  45

Phe Glu Glu Arg His Ile Pro Gly Ala Ala Phe Phe Asp Ile Asp Gln
    50                  55                  60

Cys Ser Asp Arg Thr Ser Pro Tyr Asp His Met Leu Pro Gly Ala Glu
65                  70                  75                  80

His Phe Ala Glu Tyr Ala Gly Arg Leu Gly Val Gly Ala Ala Thr His
                85                  90                  95

Val Val Ile Tyr Asp Ala Ser Asp Gln Gly Leu Tyr Ser Ala Pro Arg
            100                 105                 110

Val Trp Trp Met Phe Arg Ala Phe Gly His His Ala Val Ser Leu Leu
        115                 120                 125

Asp Gly Gly Leu Arg His Trp Leu
    130                 135
```

<210> SEQ ID NO 124
<211> LENGTH: 133
<212> TYPE: PRT
<213> ORGANISM: Homo sapien

<400> SEQUENCE: 124

```
Met Asn His Thr Val Gln Thr Phe Phe Ser Pro Val Asn Ser Gly Gln
 1               5                  10                  15

Pro Pro Asn Tyr Glu Met Leu Lys Glu Glu His Glu Val Ala Val Leu
            20                  25                  30

Gly Ala Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130
```

<210> SEQ ID NO 125
<211> LENGTH: 195
<212> TYPE: PRT
<213> ORGANISM: Homo sapien

<400> SEQUENCE: 125

```
Thr Thr Ala Thr Thr Thr Ala Ser Thr Gly Ser Thr Ala Thr Pro Ser
 1               5                  10                  15
```

-continued

```
Ser Thr Pro Gly Thr Ala Pro Pro Pro Lys Val Leu Thr Ser Pro Ala
            20                  25                  30

Thr Thr Pro Met Ser Thr Met Ser Thr Ile His Thr Ser Ser Thr Pro
        35                  40                  45

Glu Thr Thr His Thr Ser Thr Val Leu Thr Thr Thr Ala Thr Met Thr
    50                  55                  60

Arg Ala Thr Asn Ser Thr Ala Thr Pro Ser Ser Thr Leu Gly Thr Thr
65                  70                  75                  80

Arg Ile Leu Thr Glu Leu Thr Thr Thr Ala Thr Thr Thr Ala Ala Thr
                85                  90                  95

Gly Ser Thr Ala Thr Leu Ser Ser Thr Pro Gly Thr Thr Trp Ile Leu
            100                 105                 110

Thr Glu Pro Ser Thr Ile Ala Thr Val Met Val Pro Thr Gly Ser Thr
        115                 120                 125

Ala Thr Ala Ser Ser Thr Leu Gly Thr Ala His Thr Pro Lys Val Val
    130                 135                 140

Thr Thr Met Ala Thr Met Pro Thr Ala Thr Ala Ser Thr Val Pro Ser
145                 150                 155                 160

Ser Ser Thr Val Gly Thr Thr Arg Thr Pro Ala Val Leu Pro Ser Ser
                165                 170                 175

Leu Pro Thr Phe Ser Val Ser Thr Val Ser Ser Ser Val Leu Thr Thr
            180                 185                 190

Leu Arg Pro
        195


<210> SEQ ID NO 126
<211> LENGTH: 509
<212> TYPE: DNA
<213> ORGANISM: Homo sapien

<400> SEQUENCE: 126

gaattcggca cgagccaagt acccccctgag gaatctgcag cctgcatctg agtacaccgt     60

atccctcgtg gccataaagg gcaaccaaga gagccccaaa gccactggag tctttaccac    120

actgcagcct gggagctcta ttccacctta caacaccgag gtgactgaga ccaccattgt    180

gatcacatgg acgcctgctc caagaattgg ttttaagctg ggtgtacgac caagccaggg    240

aggagaggca ccacgagaag tgacttcaga ctcaggaagc atcgttgtgt ccggcttgac    300

tccaggagta gaatacgtct acaccatcca agtcctgaga gatggacagg aaagagatgc    360

gccaattgta aacaaagtgg tgacaccatt gtctccacca acaaacttgc atctggaggc    420

aaaccctgac actggagtgc tcacagtctc ctggagagga gcaccacccc agacattact    480

gggtatagaa ttaccacaac ccctacaaa                                      509


<210> SEQ ID NO 127
<211> LENGTH: 500
<212> TYPE: DNA
<213> ORGANISM: Homo sapien

<400> SEQUENCE: 127

gaattcggca cgagccactg atgtccgggg agtcagccag gagcttgggg aagggaagcg     60

cgcccccggg gccggtcccg gagggctcga tccgcatcta cagcatgagg ttctgcccgt    120

ttgctgagag gacgcgtcta gtcctgaagg ccaagggaat caggcatgaa gtcatcaata    180

tcaacctgaa aaataagcct gagtggttct ttaagaaaaa tccctttggt ctggtgccag    240
```

-continued

```
ttctggaaaa cagtcagggt cagctgatct acgagtctgc catcacctgt gagtacctgg    300

atgaagcata cccagggaag aagctgttgc cggatgaccc ctatgagaaa gcttgccaga    360

agatgatctt agagttgttt tctaaggtgc catccttggt aggaagcttt attagaagcc    420

aaaataaaga agactatgct ggcctaaaag aagaatttcg taaagaattt accaagctag    480

aggaggttct gactaataag                                                500
```

<210> SEQ ID NO 128
<211> LENGTH: 500
<212> TYPE: DNA
<213> ORGANISM: Homo sapien

<400> SEQUENCE: 128

```
agctttcctc tgctgccgct cggtcacgct tgtgcccgaa ggaggaaaca gtgacagacc     60

tggagactgc agttctctat ccttcacaca gctctttcac catgcctgga tcacttcctt    120

tgaatgcaga agcttgctgg ccaaaagatg tgggaattgt tgcccttgag atctattttc    180

cttctcaata tgttgatcaa gcagagttgg aaaaatatga tggtgtagat gctggaaagt    240

ataccattgg cttgggccag gccaagatgg gcttctgcac agatagagaa gatattaact    300

ctctttgcat gactgtggtt cagaatctta tggagagaaa taacctttcc tatgattgca    360

ttgggcggct ggaagttgga acagagacaa tcatcgacaa atcaaagtct gtgaagacta    420

atttgatgca gctgtttgaa gagtctggga atacagatat agaaggaatc gacacaacta    480

atgcatgcta tggaggcaca                                                500
```

<210> SEQ ID NO 129
<211> LENGTH: 497
<212> TYPE: DNA
<213> ORGANISM: Homo sapien

<400> SEQUENCE: 129

```
gaattcggca cgagcagagg tctccagagc cttctctctc ctgtgcaaaa tggcaactct     60

taaggaaaaa ctcattgcac cagttgcgga agaagaggca acagttccaa acaataagat    120

cactgtagtg ggtgttggac aagttggtat ggcgtgtgct atcagcattc tgggaaagtc    180

tctggctgat gaacttgctc ttgtggatgt tttggaagat aagcttaaag gagaaatgat    240

ggatctgcag catgggagct tatttcttca gacacctaaa attgtggcag ataaagatta    300

ttctgtgacc gccaattcta agattgtagt ggtaactgca ggagtccgtc agcaagaagg    360

ggagagtcgg ctcaatctgg tgcagagaaa tgttaatgtc ttcaaattca ttattcctca    420

gatcgtcaag tacagtcctg attgcatcat aattgtggtt tccaacccag tggacattct    480

tacgtatgtt acctgga                                                   497
```

<210> SEQ ID NO 130
<211> LENGTH: 383
<212> TYPE: DNA
<213> ORGANISM: Homo sapien

<400> SEQUENCE: 130

```
gaattcggca cgagggccgc ggctgccgac tgggtcccct gccgctgtcg ccaccatggc     60

tccgcaccgc cccgcgcccg cgctgctttg cgcgctgtcc ctggcgctgt gcgcgctgtc    120

gctgcccgtc cgcgcggcca ctgcgtcgcg gggggcgtcc caggcggggg cgccccaggg    180

gcgggtgccc gaggcgcggc ccaacagcat ggtggtggaa caccccgagt tcctcaaggc    240

agggaaggag cctggcctgc agatctggcg tgtggagaaa gttcgatctg gtggcccgtg    300
```

cccaccaacc tttatggaga cttcttcacg ggcgacgcct acgtcatcct gaagacagtg    360
cagcttaaga acggaaaatc ttg    383

<210> SEQ ID NO 131
<211> LENGTH: 509
<212> TYPE: DNA
<213> ORGANISM: Homo sapien

<400> SEQUENCE: 131
gaattcggca cgagagtcag ccgcatcttc ttttgcgtcg ccagccgagc cacatcgctc     60
agacaccatg gggaaggtga aggtcggagt caacggattt ggtcgtattg ggcgcctggt    120
caccagggct gcttttaact ctggtaaagt ggatattgtt gccatcaatg accccttcat    180
tgacctcaac tacatggttt acatgttcca atatgattcc acccatggca aattccatgg    240
caccgtcaag gctgagaacg ggaagcttgt catcaatgga aatcccatca ccatcttcca    300
ggagcgagat ccctccaaaa tcaagtgggg cgatgctggc gctgagtacg tcgtggagtc    360
cactggccgt cttcaccacc atggagaagg ctggggctca tttgcagggg ggagccaaaa    420
gggtcatcat ctctgccccc tctgctgacg cccccatgtt cgtcatgggt gtgaaccatg    480
agaagtatga caacagcctc aagatcatc    509

<210> SEQ ID NO 132
<211> LENGTH: 357
<212> TYPE: DNA
<213> ORGANISM: Homo sapien

<400> SEQUENCE: 132
gaattcggca cgagtaagaa gaagccccta gaccacagct ccacaccatg gactggacct     60
ggaggatcct cttcttggtg gcagcagcaa caggtgccca ctcccaggtg caactggtgc    120
aatctgggtc tgagttgaag aagcctgggg cctcagtgaa ggtttcctgc aaggcttctg    180
gacacatctt cagtatctat ggtttgaatt gggtgcgaca ggcccctggt caaggccttg    240
agtggatggg atggatcaaa gtcgacactg cgaacccaac gtatgcccag ggcttcacag    300
gacgatttgt cttctccctg gacacctctg tcagcacggc atatctgcag atcagca    357

<210> SEQ ID NO 133
<211> LENGTH: 468
<212> TYPE: DNA
<213> ORGANISM: Homo sapien

<400> SEQUENCE: 133
gaattcggca cgaggcgccc cgaaccgtcc tcctgctgct ctcggcggcc ctggccctga     60
ccgagacctg ggccggctcc cactccatga ggtatttcga caccgccatg tcccggcccg    120
gccgcgggga gccccgcttc atctcagtgg gctacgtgga cgacacgcag ttcgtgaggt    180
tcgacagcga cgccgcgagt ccgagagagg agccgcgggc gccgtggata gagcaggagg    240
ggccggagta ttgggaccgg aacacacaga tcttcaagac caacacacag actgaccgag    300
agagcctgcg gaacctgcgc ggctactaca accagagcga ggccgggtct cacaccctcc    360
agagcatgta cggctgcgac gtggggccgg acgggcgcct cctccgcggg cataaccagt    420
acgcctacga cggcaaggat tacatcgccc tgaacgagga cctgcgct    468

<210> SEQ ID NO 134
<211> LENGTH: 214
<212> TYPE: DNA

-continued

<213> ORGANISM: Homo sapien

<400> SEQUENCE: 134
gaattcggca cgagctgcgt cctgctgagc tctgttctct ccagcacctc ccaacccact 60
agtgcctggt tctcttgctc caccaggaac aagccaccat gtctcgccag tcaagtgtgt 120
ccttccggag cgggggcagt cgtagcttca gcaccgcctc tgccatcacc ccgtctgtct 180
cccgcaccag cttcacctcc gtgtcccggt ccgg 214

<210> SEQ ID NO 135
<211> LENGTH: 355
<212> TYPE: DNA
<213> ORGANISM: Homo sapien

<400> SEQUENCE: 135
gaattcggca cgaggtgaac aggacccgtc gccatgggcc gtgtgatccg tggacagagg 60
aagggcgccg ggtctgtgtt ccgcgcgcac gtgaagcacc gtaaaggcgc tgcgcgcctg 120
cgcgccgtgg atttcgctga gcggcacggc tacatcaagg gcatcgtcaa ggacatcatc 180
cacgacccgg gccgcggcgc gcccctcgcc aaggtggtct tccgggatcc gtatcggttt 240
aagaagcgga cggagctgtt cattgccgcc gagggcattc acacgggcca gtttgtgtat 300
tgcggcaaga aggcccagct caacattggc aatgtgctcc ctgtgggcac catgc 355

<210> SEQ ID NO 136
<211> LENGTH: 242
<212> TYPE: DNA
<213> ORGANISM: Homo sapien

<400> SEQUENCE: 136
gaattcggca cgagccagct cctaaccgcg agtgatccgc cagcctccgc ctcccgaggt 60
gcccggattg cagacggagt ctccttcact cagtgctcaa tggtgcccag gctggagtgc 120
agtggtgtga tctcggctcg ctacaacatc cacctcccag cagcctgcct tggcctccca 180
aagtgccgag attgcagctc tctgcccggc cgccacccct gtctgggaag tgaggatgct 240
gt 242

<210> SEQ ID NO 137
<211> LENGTH: 424
<212> TYPE: DNA
<213> ORGANISM: Homo sapien

<400> SEQUENCE: 137
gaattcggca cgagcccaga tcccgaggtc cgacagcgcc cggcccagat ccccacgcct 60
gccaggagca agccgagagc cagccggccg gcgcactccg actccgagca gtctctgtcc 120
ttcgacccga gccccgcgcc ctttccggga cccctgcccc gcgggcagcg ctgccaacct 180
gccggccatg gagaccccgt cccagcggcg cgccacccgc agcggggcgc aggccagctc 240
cactccgctg tcgcccaccc gcatcacccg gctgcaggag aaggaggacc tgcaggagct 300
caatgatcgc ttggcggtct acatcgaccg tgtgcgctcg ctggaaacgg agaacgcagg 360
gctgcgcctt cgcatcaccg agtctgaaga ggtggtcagc cgcgaggtgt ccggcatcaa 420
ggcc 424

<210> SEQ ID NO 138
<211> LENGTH: 448
<212> TYPE: DNA
<213> ORGANISM: Homo sapien -continued

<400> SEQUENCE: 138
gaattcggca cgagcctgtg ttccaggagc cgaatcagaa atgtcatcct caggcacgcc 60
agacttacct gtcctactca ccgatttgaa gattcaatat actaagatct tcataaacaa 120
tgaatggcat gattcagtga gtggcaagaa atttcctgtc tttaatcctg caactgagga 180
ggagctctgc caggtagaag aaggagataa ggaggatgtt gacaaggcag tgaaggccgc 240
aagacaggct tttcagattg gatccccgtg gcgtactatg gatgcttccg agagggggcg 300
actattatac aagttggctg atttaatcga aagagatcgt ctgctgctgg ccgacaatgg 360
agtcaatgaa tggtggaaaa ctctattcca atgcatatct gaatgattta gcaggctgca 420
tcaaaacatt gcgctactgt gcaggttg 448

<210> SEQ ID NO 139
<211> LENGTH: 510
<212> TYPE: DNA
<213> ORGANISM: Homo sapien

<400> SEQUENCE: 139
gaattcggca cgaggttccg tgcagctcac ggagaagcga atggacaaag tcggcaagta 60
ccccaaggag ctgcgcaagt gctgcgagga cggcatgcgg gagaacccca tgaggttctc 120
gtgccagcgc cggacccgtt tcatctccct ggcgaggcgt gcaagaaggt cttcctggac 180
tgctgcaact acatcacaga gctgcggcgg cagcacgcgc gggccagcca cctggcctgc 240
caggagtaac ctggatgagg acatcattgc agaagagaac atcgtttccc gaagtgagtt 300
cccagagagc tggctgtgga acgttgagga cttgaaagag ccaccgaaaa atggaatctc 360
tacgaagctc atgaatatat ttttgaaaga ctccatcacc acgtgggaga ttctggctgt 420
gagcatgtcg gacaagaaag ggatctgtgt ggcagacccc ttcgaggtca cagtaatgca 480
ggacttcttc atcgacctgc ggctacccta 510

<210> SEQ ID NO 140
<211> LENGTH: 360
<212> TYPE: DNA
<213> ORGANISM: Homo sapien

<400> SEQUENCE: 140
gaattcggca cgagcggtaa ctaccccggc tgcgcacagc tcggcgctcc ttcccgctcc 60
ctcacacacc ggcctcagcc cgcaccggca gtagaagatg gtgaaagaaa caacttacta 120
cgatgttttg ggggtcaaac ccaatgctac tcaggaagaa ttgaaaaagg cttataggaa 180
actggctttg aagtaccatc ctgataagaa cccaaatgaa ggagagaagt ttaaacagat 240
ttctcaagct tacgaagttc tctctgatgc aaagaaaagg gaattatatg acaaaggagg 300
agaacaggca attaaagagg gtggagcagg tggcggtttt ggctccccca tggacatctt 360

<210> SEQ ID NO 141
<211> LENGTH: 483
<212> TYPE: DNA
<213> ORGANISM: Homo sapien

<400> SEQUENCE: 141
gaattcggca cgagagcaga ggctgatctt tgctggaaaa cagctggaag atgggctgca 60
ccctgtctga ctacaacatc cagaaagagt ccaccctgca cctggtgctc cgtctcagag 120
gtgggatgca aatcttcgtg aagacactca ctggcaagac catcaccctt gaggtggagc 180

-continued

```
ccagtgacac catcgagaac gtcaaagcaa agatccagga caaggaaggc attcctcctg    240

accagcagag gttgatcttt gccggaaagc agctggaaga tgggcgcacc ctgtctgact    300

acaacatcca gaaagagtct accctgcacc tggtgctccg tctcagaggt gggatgcaga    360

tcttcgtgaa gaccctgact ggtaagacca tcaccctcga ggtggagccc agtgacacca    420

tcgagaatgt caaggcaaag atccaagata aggaaggcat tcctcctgat cagcagaggt    480

tga                                                                   483
```

<210> SEQ ID NO 142
<211> LENGTH: 500
<212> TYPE: DNA
<213> ORGANISM: Homo sapien

<400> SEQUENCE: 142

```
gaattcggca cgaggcggcg acgaccgccg ggagcgtgtg cagcggcggc ggcggaagtg     60

gccggcgagc ccggtccccg ccggcaccat gcttcccttg tcactgctga agacggctca    120

gaatcacccc atgttggtgg agctgaaaaa tggggagacg tacaatggac acctggtgag    180

ctgcgacaac tggatgaaca ttaacctgcg agaagtcatc tgcacgtcca gggacgggga    240

caagttctgg cggatgcccg agtgctacat ccgcggcagc accatcaagt acctgcgcat    300

ccccgacgag atcatcgaca tggtcaagga ggaggtggtg gccaagggcc gcggccgcgg    360

aggcctgcag cagcagaagc agcagaaagg ccgcggcatg ggcggcgctg gccgaggtgt    420

gtttggtggc cggggccgag gtgggatccc gggcacaggc agaagccagc cagagaagaa    480

gcctggcaga caggcgggca                                                 500
```

<210> SEQ ID NO 143
<211> LENGTH: 400
<212> TYPE: DNA
<213> ORGANISM: Homo sapien

<400> SEQUENCE: 143

```
gaattcggca cgagctcgga tgtcagcagg cgtcccaacc cagcaggaac tggctcaatt     60

ctcagaagaa agcgatcggc cccgaggcag gaaggccggc tccggtgcag ggcgcgccgc    120

ctgcgggctg cttcgggcca gggtcgaccc gagggccagc gcaagcagcg gcaacaggag    180

cgccaggagg acatgaggct ctgcctgcag tcagcaactt ggaatattca gacttcagac    240

cagcatcaca gattataacc ctccgtaaat catctgcatc ccagctccca tcaaaagcca    300

gcctgaagga cccatggaca cgtgactcca gtgttctcaa caacatctta gatcaagttg    360

gtttgcacaa catttgcatc tacttgggac aaagcaagaa                           400
```

<210> SEQ ID NO 144
<211> LENGTH: 243
<212> TYPE: DNA
<213> ORGANISM: Homo sapien

<400> SEQUENCE: 144

```
gaattcggca cgagccagct cctaaccgcg agtgatccgc cagcctccgc ctcccgaggt     60

gcccggattg cagacggagt ctccttcact cagtgctcaa tggtgcccag gctggagtgc    120

agtggtgtga tctcggctcg ctacaacatc cacctcccag cagcctgcct tggcctccca    180

aagtgccgag attgcagcct ctgcccggcc gtcaccccgt ctgggaagtg aggagcgttt    240

ctg                                                                   243
```

-continued

<210> SEQ ID NO 145
<211> LENGTH: 450
<212> TYPE: DNA
<213> ORGANISM: Homo sapien

<400> SEQUENCE: 145
gaattcggca cgaggacagc aggaccgtgg aggccgcggc aggggtggca gtggtggcgg 60
cggcggcggc ggcggtggtg gttacaaccg cagcagtggt ggctatgaac ccagaggtcg 120
tggaggtggc cgtggaggca gaggtggcat gggcggaagt gaccgtggtg gcttcaataa 180
atttggtggc cctcgggacc aaggatcacg tcatgactcc gaacaggata attcagacaa 240
caacaccatc tttgtgcaag gcctgggtga gaatgttaca attgagtctg tggctgatta 300
cttcaagcag attggtatta ttaagacaaa caagaaaacg ggacagccca tgattaattt 360
gtacacagac agggaaactg gcaagctgaa gggagaggca acggtctctt ttgatgaccc 420
accttcagct aaagcagcct attgactggt 450

<210> SEQ ID NO 146
<211> LENGTH: 451
<212> TYPE: DNA
<213> ORGANISM: Homo sapien

<400> SEQUENCE: 146
gaattcggca cgagccatcg agtccctgcc tttcgacttg cagagaaatg tctcgctgat 60
gcgggagatc gacgcgaaat accaagagat cctgaaggag ctagacgagt gctacgagcg 120
cttcagtcgc gagacagacg gggcgcagaa gcggcggatg ctgcactgtg tgcagcgcgc 180
gctgatccgc accaggagct gggcgacgag aagatccaga tcgtgagcca gatggtggag 240
ctggtggaga accgcacgcg gcaggtggac agccacgtgg agctgttcga ggcgcagcag 300
gagctgggcg acacagcggg caacagcggc aaggctggcg cggacaggcc caaaggcgag 360
gcggcagcgc aggctgacaa gcccaacagc aagcgctcac ggcggcagcg caacaacgag 420
aaccgtgaga acgcgtccag caaccacgac c 451

<210> SEQ ID NO 147
<211> LENGTH: 400
<212> TYPE: DNA
<213> ORGANISM: Homo sapien

<400> SEQUENCE: 147
gaattcggca cgagctcgga tgtcagcagg cgtcccaacc cagcaggaac tggctcaatt 60
ctcagaagaa agcgatcggc cccgaggcag gaaggccggc tccggtgcag ggcgcgccgc 120
ctgcgggctg cttcgggcca gggtcgaccc gagggccagc gcaagcagcg gcaacaggag 180
cgccaggagg acatgaggct ctgcctgcag tcagcaactt ggaatattca gacttcagac 240
cagcatcaca gattataacc ctccgtaaat catctgcatc ccagctccca tcaaaagcca 300
gcctgaagga cccatggaca cgtgactcca gtgttctcaa caacatctta gatcaagttg 360
gtttgcacaa catttgcatc tacttgggac aaagcaagaa 400

<210> SEQ ID NO 148
<211> LENGTH: 503
<212> TYPE: DNA
<213> ORGANISM: Homo sapien

<400> SEQUENCE: 148
aaaagaattc ggcacgagcg gcgccgctca tccccctctc ccagcagatt cccactggaa 60

-continued

```
attcgttgta tgaatcttat tacaagcagg tcgatccggc atacacaggg agggtggggg    120

cgagtgaagc tgcgcttttt ctaaagaagt ctggcctctc ggacattatc cttgggaaga    180

tatgggactt ggccgatcca gaaggtaaag ggttcttgga caaacagggt ttctatgttg    240

cactgagact ggtggcctgt gcacagagtg gccatgaagt taccttgagc aatctgaatt    300

tgagcatgcc accgcctaaa tttcacgaca ccagcagccc tctgatggtc acaccgccct    360

ctgcagaggc ccactgggct gtgagggtgg aagaaaaggc caaatttgat gggatttttg    420

aaagcctctt gcccatcaat ggtttgctct ctggagacaa agtcaagcca gtcctcatga    480

actcaaagct gcctcttgat gtc                                             503
```

<210> SEQ ID NO 149
<211> LENGTH: 1061
<212> TYPE: DNA
<213> ORGANISM: Homo sapien

<400> SEQUENCE: 149

```
gaattcggca cgaggccttt tccagcaacc ccaaggtcca ggtggaggcc atcgaagggg     60

gagccctgca gaagctgctg gtcatcctgg ccacggagca gccgctcact gcaaagaaga    120

aggtcctgtt tgcactgtgc tccctgctgc gccacttccc ctatgcccag cggcagttcc    180

tgaagctcgg ggggctgcag gtcctgagga ccctggtgca ggagaagggc acggaggtgc    240

tcgccgtgcg cgtggtcaca ctgctctacg acctggtcac ggagaagatg ttcgccgagg    300

aggaggctga gctgacccag gagatgtccc cagagaagct gcagcagtat cgccaggtac    360

acctcctgcc aggcctgtgg gaacagggct ggtgcgagat cacggcccac ctcctggcgc    420

tgcccgagca tgatgcccgt gagaaggtgc tgcagacact gggcgtcctc ctgaccacct    480

gccgggaccg ctaccgtcag gacccccagc tcggcaggac actggccagc ctgcaggctg    540

agtaccaggt gctggccagc ctggagctgc aggatggtga ggacgagggc tacttccagg    600

agctgctggg ctctgtcaac agcttgctga aggagctgag atgaggcccc acaccagtac    660

tggactggga tgccgctagt gaggctgagg ggtgccagcg tgggtgggct tctcaggcag    720

gaggacatct tggcagtgct ggcttggcca ttaaatggaa acctgaaggc catcctcttt    780

ctgctgtgtg tctgtgtaga ctgggcacag ccctgtggcc ggggggtcag gtgagtggtt    840

gggtgatggg ctctgctgac gtgcagggct cagcccaggg catccaggaa caggctccag    900

ggcaggaacc tgggcccagg agttgcaagt ctctgcttct taccaagcag cagctctgta    960

ccttgggaag tcgcttaatt gctctgagct tgtttcctca tctgtcagga gtgccattaa   1020

aggagaaaaa tcacgtaaaa aaaaaaaaaa aaaaactcga g                       1061
```

<210> SEQ ID NO 150
<211> LENGTH: 781
<212> TYPE: DNA
<213> ORGANISM: Homo sapien

<400> SEQUENCE: 150

```
gaattcggca cgagaaatgg cggcaggggt cgaagcggca gccgaagtgg cggcgacaga     60

acccaaaatg gaggaagaga gcggcgcgcc ctgcgtgccg agcggcaacg gagctccggg    120

cccgaagggt gaagaacgac ctactcagaa tgagaagagg aaggagaaaa acataaaaag    180

aggaggcaat cgctttgagc catattccaa cccaactaaa agatacagag ccttcattac    240

aaatatacct tttgatgtga aatggcagtc acttaaagac ctggttaaag aaaaagttgg    300

tgaggtaaca tacgtggagc tcttaatgga cgctgaagga aagtcaaggg gatgtgctgt    360
```

-continued

```
tgttgaattc aagatggagg agagcatgaa aaaagctgct gaagttctaa acaagcatag    420
tctgagtgga aggccactga aagtcaagga agatcctgat ggtgaacatg caaggagagc    480
aatgcaaaag gctggaagac ttggaagcac agtatttgta gcaaatctgg attataaagt    540
tggctggaag aaactgaagg aagtatttag tatggctggt gtggtggtcc gagcagacat    600
tctggaagat aaagatggga aaagtcgtgg aataggcatt gtgacttttg aacagtccat    660
tgaagctgtg caagcaatat ctatgtttaa tggccagttg ctgtttgata gaccgatgca    720
cgtcaagatg gatgagaggg ctttaccaaa gggagacttt tttcctcctg aacgccacag    780
c                                                                    781
```

<210> SEQ ID NO 151
<211> LENGTH: 3275
<212> TYPE: DNA
<213> ORGANISM: Homo sapien

<400> SEQUENCE: 151

```
cttaagtgga tcctgcatca ggagggagca gacaccggag aaagaaaaac aagttgtgct     60
gtttgaggaa gcaagttgga cctgcactcc agcctgtgga gatgaaccta ggactgtgat    120
tctgctatcc agtatgttgg ctgaccacag gctcaaactg gaggattata aggatcgcct    180
gaaaagtgga gagcatctta atccagacca gttggaagct gtagagaaat atgaagaagt    240
gctacataat ttggaatttg ccaaggagct tcaaaaaacc ttttctgggt tgagcctaga    300
tctactaaaa gcgcaaaaga aggcccagag aagggagcac atgctaaaac ttgaggctga    360
gaagaaaaag cttcgaacta tacttcaagt tcagtatgta ttgcagaact tgacacagga    420
gcacgtacaa aaagacttca aaggggggttt gaatggtgca gtgtatttgc cttcaaaaga    480
acttgactac ctcattaagt tttcaaaact gacctgccct gaaagaaatg aaagtctgag    540
acaaacactt gaaggatcta ctgtctaaat tgctgaactc aggctatttt gaaagtatcc    600
cagttcccaa aaatgccaag gaaaaggaag taccactgga ggaagaaatg ctaatacaat    660
cagagaaaaa aacacaatta tcgaagactg aatctgtcaa agagtcagag tctctaatgg    720
aatttgccca gccagagata caaccacaag agtttcttaa cagacgctat atgacagaag    780
tagattattc aaacaaacaa ggcgaagagc aaccttggga agcagattat gctagaaaac    840
caaatctccc aaaacgttgg gatatgctta ctgaaccaga tggtcaagag aagaaacagg    900
agtcctttaa gtcctgggag gcttctggta agcaccagga ggtatccaag cctgcagttt    960
ccttagaaca gaggaaacaa gacacctcaa aactcaggtc tactctgccg gaagagcaga   1020
agaagcagga gatctccaaa tccaagccat ctcctagcca gtggaagcaa gatacaccta   1080
aatccaaagc agggtatgtt caagaggaac aaaagaaaca ggagacacca aagctgtggc   1140
cagttcagct gcagaaagaa caagatccaa agaagcaaac tccaaagtct tggacacctt   1200
ccatgcagag cgaacagaac accaccaagt catggaccac tcccatgtgt gaagaacagg   1260
attcaaaaca gccagagact ccaaaatcct gggaaaacaa tgttgagagt caaaaacact   1320
ctttaacatc acagtcacag atttctccaa agtcctgggg agtagctaca gcaagcctca   1380
taccaaatga ccagctgctg cccaggaagt tgaacacaga acccaaagat gtgcctaagc   1440
ctgtgcatca gcctgtaggt tcttcctcta cccttccgaa ggatccagta ttgaggaaag   1500
aaaaactgca ggatctgatg actcagattc aaggaacttg taactttatg caagagtctg   1560
ttcttgactt tgacaaacct tcaagtgcaa ttccaacgtc acaaccgcct tcagctactc   1620
```

-continued

```
caggtagccc cgtagcatct aaagaacaaa atctgtccag tcaaagtgat tttcttcaag   1680
agccgttaca ggtatttaac gttaatgcac ctctgcctcc acgaaaagaa caagaaataa   1740
aagaatcccc ttattcacct ggctacaatc aaagttttac cacagcaagt acacaaacac   1800
caccccagtg ccaactgcca tctatacatg tagaacaaac tgtccattct caagagactg   1860
cagcaaatta tcatcctgat ggaactattc aagtaagcaa tggtagcctt gccttttacc   1920
cagcacagac gaatgtgttt cccagaccta ctcagccatt tgtcaatagc cggggatctg   1980
ttagaggatg tactcgtggt gggagattaa taaccaattc ctatcggtcc cctggtggtt   2040
ataaaggttt tgatacttat agaggactcc cttcaatttc caatggaaat tatagccagc   2100
tgcagttcca agctagagag tattctggag caccttattc ccaaagggat aatttccagc   2160
agtgttataa gcgaggaggg acatctggtg gtccacgagc aaattcgaga gcagggtgga   2220
gtgattcttc tcaggtgagc agcccagaaa gagacaacga aacctttaac agtggtgact   2280
ctggacaagg agactcccgt agcatgaccc ctgtggatgt gccagtgaca aatccagcag   2340
ccaccatact gccagtacac gtctaccctc tgcctcagca gatgcgagtt gccttctcag   2400
cagccagaac ctctaatctg gcccctggaa ctttagacca acctattgtg tttgatcttc   2460
ttctgaacaa cttaggagaa acttttgatc ttcagcttgg tagatttaat tgcccagtga   2520
atggcactta cgttttcatt tttcacatgc taaagctggc agtgaatgtg ccactgtatg   2580
tcaacctcat gaagaatgaa gaggtcttgg tatcagccta tgccaatgat ggtgctccag   2640
accatgaaac tgctagcaat catgcaattc ttcagctctt ccagggagac cagatatggt   2700
tacgtctgca caggggagca atttatggaa gtagctggaa atattctacg ttttcaggct   2760
atcttcttta tcaagattga aagtcagtac agtattgaca ataaaaggat ggtgttctaa   2820
ttagtgggat tgaaggaaaa gtagtctttg ccctcatgac tgattggttt aggaaaatgt   2880
ttttgttcct agagggagga ggtccttact tttttgtttt ccttcctgag gtgaaaaatc   2940
aagctgaatg acaattagca ctaatctggc actttataaa ttgtgatgta gcctcgctag   3000
tcaagctgtg aatgtatatt gtttgcactt aatccttaac tgtattaacg ttcagcttac   3060
taaactgact gcctcaagtc caggcaagtt acaatgcctt gttgtgcctc aataaaaaag   3120
ttacatgcaa aaaaaaaaaa aaaaaaaaaa aaaaaaaaaa aaaaaaaaaa aaaaaaaaaa   3180
aaaaaaaaaa aaaaaaaaaa aaaaaaaaaa aaaaaaaaaa aaaaaaaaaa aaaaaaaaaa   3240
aaaaaaaaaa aaaaaaaaaa aaaaaaaaac tcgag                              3275
```

<210> SEQ ID NO 152
<211> LENGTH: 2179
<212> TYPE: DNA
<213> ORGANISM: Homo sapien

<400> SEQUENCE: 152

```
gaattcggca ccaggcacta ttaaatgtga ggcagcctcc atctactaca acatttgtgc     60
tgaatcaaat aaatcatctt ccacccttgg gatctacaat tgtaatgact aaaacaccac    120
ctgtaacaac caacaggcaa accatcactt taactaagtt tatccagact actgcaagca    180
cacgcccgtc agtctcagca ccaacagtac gaaatgccat gacctctgca ccttcaaaag    240
accaagttca gcttaaagat ctactgaaaa ataatagtct taatgaactg atgaaactaa    300
agccacctgc taatattgct cagccagtag caacagcagc tactgatgta agcaatggta    360
cagtaaagaa agagtcttct aataaagaag gagctagaat gtggataaac gacatgaaga    420
tgaggagttt ttccccaacc atgaaggttc ctgttgtaaa agaagatgat gaaccagagg    480
```

-continued

```
aagaagatga agaagaaatg ggtcatgcag aaacctatgc agaatacatg ccaataaaat    540

taaaaattgg cctacgtcat ccagatgctg tagtggaaac cagctcttta tccagtgtta    600

ctcctcctga tgtttggtac aaaacatcca tttctgagga aaccattgat aatggctggt    660

tatcagcatt gcagcttgag gcaattacat atgcagccca gcaacatgaa actttcctac    720

ctaatggaga tcgtgctggc ttcttaatag gtgatggtgc cggtgtagga aaaggaagga    780

cgatagcagg aatcatctat gaaaattatt tgttgagtag aaaacgagca ttgtggttta    840

gtgtttcaaa tgacttaaag tatgatgctg aaagagattt aagggatatt ggagcaaaaa    900

acattttggt tcattcgtta aataagttta aatacggaaa aatttcttcc aaacataatg    960

ggagtgtgaa aaagggtgtt atttttgcta cttactcttc acttattggt gaaagccagt   1020

ctggcggcaa gtataaaact aggttaaaac aacttctgca ttggtgcggt gatgacttcg   1080

atggagtgat agtgtttgat gagtgtcata aagccaaaaa cttatgtcct gttggttctt   1140

caaagccaac caagacaggc ttagcagttt tagagcttca gaacaaattg ccaaaagcca   1200

gagttgttta tgctagtgca actggtgctt ctgaaccacg caacatggcc tatatgaacc   1260

gtcttggcat atggggtgag ggtactccat ttagagaatt cagtgatttt attcaagcag   1320

tagaacggag aggagttggt gccatggaaa tagttgctat ggatatgaag cttagaggaa   1380

tgtacattgc tcgacaactg agctttactg gagtgacctt caaaattgag gaagttcttc   1440

tttctcagag ctacgttaaa atgtataaca aagctgtcaa gctgtgggtc attgccagag   1500

agcggtttca gcaagctgca gatctgattg atgctgagca acgaatgaag aagtccatgt   1560

ggggtcagtt ctggtctgct caccagaggt tcttcaaata cttatgcata gcatccaaag   1620

ttaaaagggt tgtgcaacta gctcgagagg aaatcaagaa tggaaaatgt gttgtaattg   1680

gtctgcagtc tacaggagaa gctagaacat tagaagcttt ggaagagggc gggggagaat   1740

tgaatgattt tgtttcaact gccaaaggtg tgttgcagtc actcattgaa aaacattttc   1800

ctgctccaga caggaaaaaa ctttatagtt tactaggaat cgatttgaca gctccaagta   1860

acaacagttc gccaagagat agtccttgta aagaaaataa aataaagaag cggaaaggtg   1920

aagaaataac tcgagaagcc aaaaaagcac gaaaagtagg tggccttact ggtagcagtt   1980

ctgacgacag tggaagtgaa tctgatgcct ctgataatga agaaagtgac tatgagagct   2040

ctaaaaacat gagttctgga gatgatgacg atttcaaccc atttttagat gagtctaatg   2100

aggatgatga aaatgatccc tggttaatta aaaaaaaaaa aaaaaaaaaa aaaaaaaaaa   2160

aaaaaaaaaa aaactcgag                                                2179
```

```
<210> SEQ ID NO 153
<211> LENGTH: 2109
<212> TYPE: DNA
<213> ORGANISM: Homo sapien

<400> SEQUENCE: 153

cagagagccc caggcatcga ggagaaggcg gcggagaatg gggccctggg gtcccccgag     60

agagaagaga aagtgctgga gaatggggag ctgacacccc caaggaggga ggagaaagcg    120

ctggagaatg gggagctgag gtccccagag gccggggaga aggtgctggt gaatgggggc    180

ctgacacccc caaagagcga ggacaaggtg tcagagaatg gggcctgag attccccagg     240

aacacggaga ggccaccaga gactgggcct tggagagccc cagggccctg ggagaagacg    300

cccgagagtt ggggtccagc ccccacgatc ggggagccag ccccagagac ctctctggag    360
```

-continued

```
agagcccctg cacccagcgc agtggtctcc tcccggaacg gcggggagac agcccctggc    420

ccccttggcc cagcccccaa gaacgggacg ctggaacccg ggaccgagag gagagccccc    480

gagactgggg gggcgccgag agccccaggg gctgggaggc tggacctcgg gagtgggggc    540

cgagccccag tgggcacggg gacggccccc ggcggcggcc ccggaagcgg cgtggacgca    600

aaggccggat gggtagacaa cacgaggccg cagccaccgc cgccaccgct gccaccgcca    660

ccggaggcac agccgaggag gctggagcca gcgcccccga gagccaggcc ggaggtggcc    720

cccgagggag agcccggggc cccagacagc agggccggcg gagacacggc actcagcgga    780

gacggggacc cccccaagcc cgagaggaag ggccccgaga tgccacgact attcttggac    840

ttgggacccc ctcaggggaa cagcgagcag atcaaagcca ggctctcccg gctctcgctg    900

gcgctgccgc cgctcacgct cacgccattc ccggggccgg gcccgcggcg gcccccgtgg    960

gagggcgcgg acgccggggc ggctggcggg gaggccggcg gggcgggagc gccggggccg   1020

gcggaggagg acggggagga cgaggacgag gacgaggagg aggacgagga ggcggcggcg   1080

ccgggcgcgg cggcggggcc gcggggcccc gggagggcgc gagcagcccc ggtgcccgtc   1140

gtggtgagca gcgccgacgc ggacgcggcc cgcccgctgc gggggctgct caagtctccg   1200

cgcggggccg acgagccaga ggacagcgag ctggagagga agcgcaagat ggtctccttc   1260

cacggggacg tgaccgtcta cctcttcgac caggagacgc caaccaacga gctgagcgtc   1320

caggcccccc ccgaggggga cacggacccg tcaacgcctc cagcgccccc gacacctccc   1380

caccccgcca cccccggaga tgggtttccc agcaacgaca gcggctttgg aggcagtttc   1440

gagtgggcgg aggatttccc cctcctcccc cctccaggcc ccccgctgtg cttctcccgc   1500

ttctccgtct cgcctgcgct ggagaccccg gggccacccg cccgggcccc cgacgcccgg   1560

cccgcaggcc ccgtggagaa ttgattcccc gaagacccga ccccgctgca ccctcagaag   1620

aggggttgag aatggaatcc tctgtggatg acggcgccac tgccaccacc gcagacgccg   1680

cctctgggga ggcccccgag gctgggccct cccccctcca ctcccctacc atgtgccaaa   1740

cgggaggccc cgggccccg cccccccagc cccccagatg gctcccctga cccccctgac   1800

cccctcggag ccaaatgagg caggaatccc cccgcccctc catagagagc cgcctttctc   1860

ggaactgaac tgaactcttt tgggcctgga gcccctcgac acagcggagg tccctcctca   1920

cccactcctg gcccaagaca ggggccgcag gcttcgggga cccggacccc ccatttcgcg   1980

tctcccctttt ccctccccag cccggcccct ggaggggcct ctggttcaaa ccttcgcgtg   2040

gcattttcac attatttaaa aaagacaaaa acaacttttt ggaggaaaaa aaaaaaaaaa   2100

aaactcgag                                                          2109
```

<210> SEQ ID NO 154
<211> LENGTH: 1411
<212> TYPE: DNA
<213> ORGANISM: Homo sapien

<400> SEQUENCE: 154

```
gaattcggca ccaggggaga tgaggaagtt cgatgttcct agcatggagt ctacccttaa     60

ccagccagcc atgctagaga cgttatactc agatccacat taccgagccc atttccccaa    120

cccaagacct gatacaaata aggatgtata caaagtattg ccagaatcca agaaggcacc    180

gggcagtggt gcagtatttg agaggaacgg accacatgct agcagtagtg ggtgctccc    240

tttgggactc cagcctgcgc ctggactttc caagtcacta tcctctcagg tgtggcaacc    300

aagtcctgac ccttggcatc ctggagaaca atcctgtgaa ctcagtactt gtcgacagca    360
```

-continued

```
gttggaattg atccgtttac agatggagca aatgcagctt cagaacggag ccatgtgtca    420

ccatcctgct gctttcgctc cattactgcc caccctagag ccagcacagt ggctcagcat    480

cctgaacagt aacgagcatc tcctgaagga gaaggagctc ctcattgaca agcaaaggaa    540

gcatatctct cagctggagc agaaagtgcg agagagtgaa ctgcaagtcc acagtgccct    600

tttgggccgc cctgccccct ttggggatgt ctgcttattg aggctacagg agttgcagcg    660

agagaacact ttcttacggg cacagtttgc acagaagaca gaagccctga gcaaggagaa    720

gatggagctt gaaaagaaac tctctgcatc tgaagttgaa attcagctca ttagggagtc    780

tctaaaagtg acactacaga agcattcgga ggaggggaag aaacaggagg aaagggtcaa    840

aggtcgtgat aaacatatca ataatttgaa aaagaaatgt cagaaggaat cagagcagaa    900

ccgggagaag cagcagcgta ttgaaacctt ggagcgctat ctagctgacc tgcccaccct    960

agaagaccat cagaaacaga cggagcagct taaggacgct gaattaaaga acacagaact   1020

gcaagagaga gtggctgagc tggagacttt gctggaggac acccaggcaa cctgcagaga   1080

gaaggaggtt cagctggaaa gtctgagaca aagagaagca gacctctcct ctgctagaca   1140

taggtaatgc cctgtgtact tgggggaagg agggagttcg gttctggtgc tctgttaact   1200

cttgtgtgtt caacagtgtt catttcaagt tcctttcttc taagagcttt gtgttctttg   1260

aattgaaagt cacttatggc cgggtgtggt ggcgcacacc tttaatccca gcacttggga   1320

gtcagaggca ggctaatttc tgagtttcag gacagccagg gctatacaga gaaaccctgt   1380

ctcaaacaaa aaaaaaaaaa aaaaactcga g                                  1411
```

<210> SEQ ID NO 155
<211> LENGTH: 678
<212> TYPE: DNA
<213> ORGANISM: Homo sapien

<400> SEQUENCE: 155

```
ctggagtgaa gggagctagt ggtaaaggga gctggtggag gggtggcggc aggggtaagg     60

ggcaggggac accctctaga cggagagcgg gctccgaggt cctggctggc cctcggtgcg    120

cccgcccctg tgttggtccc acaatccctg gcaatgagag gccagggttt attggacaga    180

gtcagttgtg gggttcagag ggtcagcaat caatcaatcc tccgaatcca gagatttaga    240

cccagtcgtc cgtattagga ctggaggggg gtcaataggt tcagtgtttg agatgccaag    300

ggaacctgtc ttttgatttg ggttcaaca tacagagttc aggtacctgc aggaatttgc    360

ccccctaggc acagggggtg gtctttacca ttttcgagac cagatcctgg ctgggagccc    420

cgaggcattc ttcgtgctca atgctgatgt ctgctccgac ttccccttga gtgctatgtt    480

ggaagcccac cgacgccagc gtcacccttt cttactcctt ggcactacgg ctaacaggac    540

gcaatccctc aactacggct gcatcgttga gaatccacag acacacgagg tattgcacta    600

tgtggagaaa cccagcacat ttatcagtga catcatcaac tgcggcacct acctcttttc    660

tcctgaagcc ttgaagcc                                                  678
```

<210> SEQ ID NO 156
<211> LENGTH: 2668
<212> TYPE: DNA
<213> ORGANISM: Homo sapien

<400> SEQUENCE: 156

```
gggaaggcgg ctgcgctgct gggcgggggc gggagctgga gccggagctg gagccggggc     60
```

-continued

```
cggggcccgg gtcagcgctt gagccgggag aagagtttga gatcgtggac cgaagccagc   120
tgcccggccc aggcgacctg cggagcgcaa cgaggccgcg ggcggccgag ggctggtcgg   180
cgcccatcct gaccctggca cgcagggcca ccgggaacct gtcggcgagc tgcgggagcg   240
cgctgcgcgc ggccgcgggg ctgggcggcg gggacagcgg ggacggcacg gcgcgcgcag   300
cttctaagtg ccagatgatg gaggagcgtg ccaacctgat gcacatgatg aaactcagca   360
tcaaggtgtt gctccagtcg gctctgagcc tgggccgcag cctggatgcg gaccatgccc   420
ccttgcagca gttctttgta gtgatggagc actgcctcaa acatgggctg aaagttaaga   480
agagttttat tggccaaaat aaatcattct ttggtccttt ggagctggtg gagaaacttt   540
gtccagaagc atcagatata gcgactagtg tcagaaatct tccagaatta aagacagctg   600
tgggaagagg ccgagcgtgg ctttatcttg cactcatgca aaagaaactg gcagattatc   660
tgaaagtgct tatagacaat aaacatctct taagcgagtt ctatgagcct gaggctttaa   720
tgatggagga agaagggatg gtgattgttg gtctgctggt gggactcaat gttctcgatg   780
ccaatctctg cttgaaagga gaagacttgg attctcaggt tggagtaata gatttttccc   840
tctaccttaa ggatgtgcag gatcttgatg gtggcaagga gcatgaaaga attactgatg   900
tccttgatca aaaaaattat gtggaagaac ttaaccggca cttgagctgc acagttgggg   960
atcttcaaac caagatagat ggcttggaaa agactaactc aaagcttcaa gaagagcttt  1020
cagctgcaac agaccgaatt tgctcacttc aagaagaaca gcagcagtta agagaacaaa  1080
atgaattaat tcgagaaaga agtgaaaaga gtgtagagat aacaaaacag gataccaaag  1140
ttgagctgga gacttacaag caaactcggc aaggtctgga tgaaatgtac agtgatgtgt  1200
ggaagcagct aaaagaggag aagaaagtcc ggttggaact ggaaaaagaa ctggagttac  1260
aaattggaat gaaaaccgaa atggaaattg caatgaagtt actggaaaag gacacccacg  1320
agaagcagga cacactagtt gccctccgcc agcagctgga agaagtcaaa gcgattaatt  1380
tacagatgtt tcacaaagct cagaatgcag agagcagttt gcagcagaag aatgaagcca  1440
tcacatcctt tgaaggaaaa accaaccaag ttatgtccag catgaaacaa atggaagaaa  1500
ggttgcagca ctcggagcgg gcgaggcagg gggctgagga gcggagccac aagctgcagc  1560
aggagctggg cgggaggatc ggcgccctgc agctgcagct ctcccagctg cacgagcaat  1620
gctcaagcct ggagaaagaa ttgaaatcag aaaaagagca aagacaggct cttcagcgcg  1680
aattacagca cgagaaagac acttcctctc tactcaggat ggagctgcaa caagtggaag  1740
gactgaaaaa ggagttgcgg gagcttcagg acgagaaggc agagctgcag aagatctgcg  1800
aggagcagga acaagccctc caggaaatgg gcctgcacct cagccagtcc aagctgaaga  1860
tggaagatat aaaagaagtg aaccaggcac tgaagggcca cgcctggctg aaagatgacg  1920
aagcgacaca ctgtaggcag tgtgagaagg agttctccat ttcccggaga aagcaccact  1980
gccggaactg tggccacatc ttctgcaaca cctgctccag caacgagctg gccctgccct  2040
cctaccccaa gccggtgcga gtgtgcgaca gctgccacac cctgctcctg cagcgctgct  2100
cctccacggc ctcctgaacg tccgtcctca ggagcacagc ctcacggaca gtgccaaacc  2160
ctgtgggtct ccaggggctt gggaaatgtg ttctttccca agagtatcaa aggaaagaat  2220
caaatttctt gcccggtcac tggcactcca gaagacagcg tgccggaacc ggcagctctc  2280
acctttctgt gacttgttcg gaattaactc ctctggatgg aaacttccat cttacttggt  2340
tacatcacgg ctctggttca gatacaactt catgattttg ctactatcat ttttcacttt  2400
tcaaagaatt taacctattt tacagcagtt cagttctgct agtgagtagt tttcctctcc  2460
```

-continued taccttcctt ctaaaaacct gattcatgca cagcgtttga cacacatgga gtctgccagt 2520
gtgccttctc tgcttcagac aagagatctg ccatttcatg cccttgtgac tacctatcat 2580
tggccctgca ataaaatcat ttatttttca aaaaaaaaaa aaaaaaaaaa aaaaaaaaaa 2640
aaaaaaaaaa aaaaaaaaaa aactcgag 2668

<210> SEQ ID NO 157
<211> LENGTH: 2313
<212> TYPE: DNA
<213> ORGANISM: Homo sapien

<400> SEQUENCE: 157
gaattcggca ccaggccggg cgggcgcctc agccatggcc ctgcgcaagg aactgctcaa 60
gtccatctgg tacgccttta ccgcgctgga cgtggagaag agtggcaaag tctccaagtc 120
ccagctcaag gtgctgtccc acaacctgta cacggtcctg cacatccccc atgaccccgt 180
ggccctggag gaacacttcc gagatgatga tgacggccct gtgtccagcc agggatacat 240
gccctacctc aacaagtaca tcctggacaa ggtggaggag ggggcttttg ttaaagagca 300
ctttgatgag ctgtgctgga cgctgacggc caagaagaac tatcgggcag atagcaacgg 360
gaacagtatg ctctccaatc aggatgcctt ccgcctctgg tgcctcttca acttcctgtc 420
tgaggacaag taccctctga tcatggttcc tgatgaggtg gaatacctgc tgaaaaaggt 480
actcagcagc atgagcttgg aggtgagctt gggtgagctg gaggagcttc tggcccagga 540
ggcccaggtg gcccagacca ccgggggggct cagcgtctgg cagttcctgg agctcttcaa 600
ttcgggccgc tgcctgcggg gcgtgggccg ggacaccctc agcatggcca tccacgaggt 660
ctaccaggag ctcatccaag atgtcctgaa gcagggctac ctgtggaagc gagggcacct 720
gagaaggaac tgggccgaac gctggttcca gctgcagccc agctgcctct gctactttgg 780
gagtgaagag tgcaaagaga aaaggggcat tatcccgctg gatgcacact gctgcgtgga 840
ggtgctgcca gaccgcgacg gaaagcgctg catgttctgt gtgaagacag ccacccgcac 900
gtatgagatg agcgcctcag acacgcgcca gcgccaggag tggacagctg ccatccagat 960
ggcgatccgg ctgcaggccg aggggaagac gtccctacac aaggacctga agcagaaacg 1020
gcgcgagcag cgggagcagc gggagcggcg ccgggcggcc aaggaagagg agctgctgcg 1080
gctgcagcag ctgcaggagg agaaggagcg gaagctgcag gagctggagc tgctgcagga 1140
ggcgcagcgg caggccgagc ggctgctgca ggaggaggag gaacggcgcc gcagccagca 1200
ccgcgagctg cagcaggcgc tcgagggcca actgcgcgag gcggagcagg cccgggcctc 1260
catgcaggct gagatggagc tgaaggagga ggaggctgcc cggcagcggc agcgcatcaa 1320
ggagctggag gagatgcagc agcggttgca ggaggccctg caactagagg tgaaagctcg 1380
gcgagatgaa gaatctgtgc gaatcgctca gaccagactg ctggaagagg aggaagagaa 1440
gctgaagcag ttgatgcagc tgaaggagga gcaggagcgc tacatcgaac gggcgcagca 1500
ggagaaggaa gagctgcagc aggagatggc acagcagagc cgctccctgc agcaggccca 1560
gcagcagctg gaggaggtgc ggcagaaccg gcagagggct gacgaggatg tggaggctgc 1620
ccagagaaaa ctgcgccagg ccagcaccaa cgtgaaacac tggaatgtcc agatgaaccg 1680
gctgatgcat ccaattgagc ctggagataa gcgtccggtc acaagcagct ccttctcagg 1740
cttccagccc cctctgcttg cccaccgtga ctcctcccta aagcgcctga cccgctgggg 1800
atcccagggc aacaggaccc cctcgcccaa cagcaatgag cagcagaagt ccctcaatgg 1860

-continued

```
tggggatgag gctcctgccc cggcttccac ccctcaggaa gataaactgg atccagcacc   1920

agaaaattag cctctcttag ccccttgttc ttcccaatgt catatccacc aggacctggc   1980

cacagctggc ctgtgggtga tcccagctct tactaggaga gggagctgag gtcctggtgc   2040

caggggccca ggccctccaa ccataaacag tccaggatgg aacctggttc acccttcata   2100

ccagctccaa gccccagacc atgggagctg tctgggatgt tgatccttga gaacttggcc   2160

ctgtgcttta gacccaagga cccgattcct gggctaggaa agagagaaca agcaagccgg   2220

ggctacctgc ccccaggtgg ccaccaagtt gtggaagcac atttctaaat aaaaactgct   2280

cttagaatga aaaaaaaaaa aaaaaaactc gag                                2313
```

<210> SEQ ID NO 158
<211> LENGTH: 2114
<212> TYPE: DNA
<213> ORGANISM: Homo sapien

<400> SEQUENCE: 158

```
gaattcggca cgaggaagaa ctcgcctctg ttgagtgtaa gtagccaaac aataaccaag     60

gagaataaca gaaatgtcca tttggagcac tcagagcaga atcctggttc atcagcaggt    120

gacacctcag cagcgcacca ggtggtttta ggagaaaact tgatagccac agccctttgt    180

ctttctggca gtgggtctca gtctgatttg aaggatgtgg ccagcacagc aggagaggag    240

ggggacacaa gccttcggga gagcctccat ccagtcactc ggtctcttaa ggcagggtgc    300

catactaagc agcttgcctc caggaattgc tctgaagaga aatccccaca aacctccatc    360

ctaaaggaag gtaacaggga cacaagcttg gatttccgac ctgtagtgtc tccagcaaat    420

ggggttgaag gagtccgagt ggatcaggat gatgatcaag atagctcttc cctgaagctt    480

tctcagaaca ttgctgtaca gactgacttt aagacagctg attcagaggt aaacacagat    540

caagatattg aaaagaattt ggataaaatg atgacagaga gaaccctgtt gaaagagcgt    600

taccaggagg tcctggacaa acagaggcaa gtggagaatc agctccaagt gcaattaaag    660

cagcttcagc aaaggagaga agaggaaatg aagaatcacc aggagatatt aaaggctatt    720

caggatgtga caataaagcg ggaagaaaca aagaagaaga tagagaaaga gaagaaggag    780

tttttgcaga aggagcagga tctgaaagct gaaattgaga agctttgtga gaagggcaga    840

agagaggtgt gggaaatgga actggataga ctcaagaatc aggatggcga aataaatagg    900

aacattatgg aagagactga acgggcctgg aaggcagaga tcttatcact agagagccgg    960

aaagagttac tggtactgaa actagaagaa gcagaaaaag aggcagaatt gcaccttact   1020

tacctcaagt caactccccc aacactggag acagttcgtt ccaaacagga gtgggagacg   1080

agactgaatg gagttcggat aatgaaaaag aatgttcgtg accaatttaa tagtcatatc   1140

cagttagtga ggaacggagc caagctgagc agccttcctc aaatccctac tcccacttta   1200

cctccacccc catcagagac agacttcatg cttcaggtgt ttcaacccag tccctctctg   1260

gctcctcgga tgcccttctc cattgggcag gtcacaatgc ccatggttat gcccagtgca   1320

gatccccgct ccttgtcttt cccaatcctg aaccctgccc tttcccagcc cagccagcct   1380

tcctcacccc ttcctggctc ccatggcaga aatagccctg gcttgggttc ccttgtcagc   1440

cctggtgccg aattcggcac gaggtaccac tggtctgtgt gctagaggag ggtgttgcca   1500

tagaaccagt ggccacagtt gtggtggtgg tggtcagcac tgtgggggtg tgggtggtcc   1560

ccgggacgga ggagggggtc accgtgaagc cactggttgt gggtgtggtg gttgtgctga   1620

tccacactgg aggcgtgcgt gccgtccctg ggctgaagga gggggtgact gtgaagcccg   1680
```

-continued tggttgtggt agtcggcact ttggtagtgt gagctgttcc tggggtggaa gagggggtgg 1740
ccacagagcc ggtggccctg gttgtggtgg ccgtggtggt aagcactgtg gaggtgtggg 1800
cagtctctgg agtggaggag ggtgtggctg tggacatggt ggccgtgggt gtggtggtct 1860
gtgataggcg ggtccaggtg gtgcccaggg aggaggaggg gatggctgta aagctggtag 1920
ctgtgggtgt ggtggctgtg cttctcagtg ctggaagggc ggttgcagtc cctggactgg 1980
agaagggagt ggctttggag ctggtgactg tgggtgtcgt ggccgtggtg ctcacatgtg 2040
gggtgccagc agttgcctgg gtggaggagg cggtggccgt ggatccggtg ggcaccgtca 2100
cgggagtact tcta 2114

<210> SEQ ID NO 159
<211> LENGTH: 278
<212> TYPE: DNA
<213> ORGANISM: Homo sapien

<400> SEQUENCE: 159
gaattcggca caggtaactt tgcctggggt atttaaaaaa aaaaaaaaaa aaaaaaaaag 60
tcaaatatct gagtactaat ttcctgaaaa gtatgttccg atagatgaac agatcattaa 120
tgcagaatga gaatcactcc taaaataggt aatggtaaaa attaaattga caattacctc 180
tctctatgca gaaggaaata tcacctatat gacatcatca tcatctattg atacttgctg 240
gcagtgctaa taatggtttt aatgccaatt tgtaagaa 278

<210> SEQ ID NO 160
<211> LENGTH: 848
<212> TYPE: DNA
<213> ORGANISM: Homo sapien

<400> SEQUENCE: 160
gaattcggca cgagccccag aggagctcgg cctgcgctgc gccacgatgt ccggggagtc 60
agccaggagc ttggggaagg gaagcgcgcc cccggggccg gtcccggagg gctcgatccg 120
catctacagc atgaggttct gcccgtttgc tgagaggacg cgtctagtcc tgaaggccaa 180
gggaatcagg catgaagtca tcaatatcaa cctgaaaaat aagcctgagt ggttctttaa 240
gaaaaatccc tttggtctgg tgccagttct ggaaaacagt cagggtcagc tgatctacga 300
gtctgccatc acctgtgagt acctggatga agcataccca gggaagaagc tgttgccgga 360
tgacccctat gagaaagctt gccagaagat gatcttagag ttgttttcta aggtgccatc 420
cttggtagga agctttatta gaagccaaaa taaagaagac tatgctggcc taaaagaaga 480
atttcgtaaa gaatttacca agctagagga ggttctgact aataagaaga cgaccttctt 540
tggtggcaat tctatctcta tgattgatta cctcatctgg ccctggtttg aacggctgga 600
agcaatgaag ttaaatgagt gtgtagacca cactccaaaa ctgaaactgt ggatggcagc 660
catgaaggaa gatcccacag tctcagccct gcttactagt gagaaagact ggcaaggttt 720
cctagagctc tacttacaga acagccctga ggcctgtgac tatgggctct gaagggggca 780
ggagtcagca ataaagctat gtctgatatt ttccttcact aaaaaaaaaa aaaaaaaaaa 840
aactcgag 848

<210> SEQ ID NO 161
<211> LENGTH: 432
<212> TYPE: DNA
<213> ORGANISM: Homo sapien -continued

<400> SEQUENCE: 161
gaattcggca cgagggcaga ccaagatcct ggaggaggac ctggaacaga tcaagctgtc 60
cttgagagag cgaggccggg agctgaccac tcagaggcag ctgatgcagg aacgggcaga 120
ggaagggaag ggcccaagta aagcacagcg cgggagccta gagcacatga agctgatcct 180
gcgtgataag gagaaggagg tggaatgtca gcaggagcat atccatgaac tccaggagct 240
caaagaccag ctggagcagc agctccaggg cctgcacagg aaggtaggtg agaccagcct 300
cctcctgtcc cagcgagagc aggaaatagt ggtcctgcag cagcaactgc aggaagccag 360
ggaacaaggg gagctgaagg agcagtcact tcagagtcaa ctggatgagg cccagagagc 420
cctagcccag ag 432

<210> SEQ ID NO 162
<211> LENGTH: 433
<212> TYPE: DNA
<213> ORGANISM: Homo sapien

<400> SEQUENCE: 162
gattcggcac gagccggagc tgggttgctc ctgctcccgt ctccaagtcc tggtacctcc 60
ttcaagctgg gagagggctc tagtccctgg ttctgaacac tctggggttc tcgggtgcag 120
gccgccatga gcaaacggaa ggcgccgcag gagactctca acgggggaat caccgacatg 180
ctcacagaac tcgcaaactt tgagaagaac gtgagccaag ctatccacaa gtacaatgct 240
tacagaaaag cagcatctgt tatagcaaaa tacccacaca aaataaagag tggagctgaa 300
gctaagaaat tgcctggagt aggaacaaaa attgctgaaa agattgatga gtttttagca 360
actggaaaat tacgtaaact ggaaaagatt cggcaggatg atacgagttc atccatcaat 420
ttcctgactc gag 433

<210> SEQ ID NO 163
<211> LENGTH: 432
<212> TYPE: DNA
<213> ORGANISM: Homo sapien

<400> SEQUENCE: 163
gaattcggca ccagatgagg ccaacgaggt gacggacagc gcgtacatgg gctccgagag 60
cacctacagt gagtgtgaga ccttcacgga cgaggacacc agcaccctgg tgcaccctga 120
gctgcaacct gaaggggacg cagacagtgc cggcggctcg gccgtgccct ctgagtgcct 180
ggacgccatg gaggagcccg accatggtgc cctgctgctg ctcccaggca ggcctcaccc 240
ccatggccag tctgtcatca cggtgatcgg gggcgaggag cactttgagg actacggtga 300
aggcagtgag gcggagctgt ccccagagac cctatgcaac gggcagctgg gctgcagtga 360
ccccgctttc ctcacgccca gtccgacaaa gcggctctcc agcaagaagg tggcaaggta 420
cctgcaccag tc 432

<210> SEQ ID NO 164
<211> LENGTH: 395
<212> TYPE: DNA
<213> ORGANISM: Homo sapien

<400> SEQUENCE: 164
gacacttgaa tcatgggtga cgttaaaaat tttctgtatg cctggtgtgg caaaaggaag 60
atgaccccat cctatgaaat tagagcagtg gggaacaaaa acaggcagaa attcatgtgt 120
gaggttcagg tggaaggtta taattacact ggcatgggaa attccaccaa taaaaaagat 180

-continued

```
gcacaaagca atgctgccag agactttgtt aactatttgg ttcgaataaa tgaaataaag    240

agtgaagaag ttccagcttt tggggtagca tctccgcccc cacttactga tactcctgac    300

actacagcaa atgctgaagg catcttgttg acatcgaata tgactttgat aataaatacc    360

ggttcctgaa aaaaaaaaaa aaaaaaaaac tcgag                               395
```

<210> SEQ ID NO 165
<211> LENGTH: 503
<212> TYPE: DNA
<213> ORGANISM: Homo sapien

<400> SEQUENCE: 165

```
gaattcggca ccaggaacgc tcggtgagag gcggaggagc ggtaactacc ccggttgcgc     60

acagctcggc gctccttccc gctccctcac acaccggcct cagcccgcac cggcagtaga    120

agatggtgaa agaaacaact tactacgatg ttttgggggt caaacccaat gctactcagg    180

aagaattgaa aaaggcttat aggaaactgg ccttgaagta ccatcctgat aagaacccaa    240

atgaaggaga gaagtttaaa cagatttctc aagcttacga agttctctct gatgcaaaga    300

aaagggaatt atatgacaaa ggaggagaac aggcaattaa agagggtgga gcaggtggcg    360

gttttggctc ccccatggac atctttgata tgttttttgg aggaggagga aggatgcaga    420

gagaaaggag aggtaaaaat gttgtacatc agctctcagt aaccctagaa gacttatata    480

atggtgcaac aagaaaactg gct                                            503
```

<210> SEQ ID NO 166
<211> LENGTH: 893
<212> TYPE: DNA
<213> ORGANISM: Homo sapien

<400> SEQUENCE: 166

```
gaattcggca cgagaggaac ttctcttgac gagaagagag accaaggagg ccaagcaggg     60

gctgggccag aggtgccaac atggggaaac tgaggctcgg ctcggaaggg tgagagtgag    120

actacatctc aaaaaaaaaa aaaaaaaaaa aaaagaaaga aaagaaaaga aaaaagaaag    180

aacggaagta gttgtaggta gtggtatggt ggtatgagtc tgttttctgt tacttataac    240

aacaacaaca acaaaaaacg ctgaaactgg gtaatttata aagaaaagga aaaaaagcag    300

aaaaaaatca ggaagaagag aaaggaaaag aagacaaata aatgaaattt atgtattaca    360

gttctgaagg ctgagacatc ccaggtcaag ggtccacact tggcgagggc tttcttgctg    420

gtggagactc tttgtggagt cctgggacag tgcagaagga tcacgcctcc ctaccgctcc    480

aagcccagcc ctcagccatg gcatgccccc tggatcaggc cattggcctc ctcgtggcca    540

tcttccacaa gtactccggc agggagggtg acaagcacac cctgagcaag aaggagctga    600

aggagctgat ccagaaggag ctcaccattg gctcgaagct gcaggatgct gaaattgcaa    660

ggctgatgga agacttggac cggaacaagg accaggaggt gaacttccag gagtatgtca    720

ccttcctggg ggccttggct ttgatctaca atgaagccct caagggctga aaataaatag    780

ggaagatgga gacaccctct gggggtcctc tctgagtcaa atccagtggt gggtaattgt    840

acaataaatt ttttttggtc aaatttaaaa aaaaaaaaaa aaaaaaactc gag           893
```

<210> SEQ ID NO 167
<211> LENGTH: 549
<212> TYPE: DNA
<213> ORGANISM: Homo sapien -continued

<400> SEQUENCE: 167
gaattcggca cgagcccaga tcccgaggtc cgacagcgcc cggcccagat ccccacgcct 60
gccaggagca agccgagagc cagccggccg gcgcactccg actccgagca gtctctgtcc 120
ttcgacccga gccccgcgcc ctttccggga cccctgcccc gcgggcagcg ctgccaacct 180
gccggccatg gagaccccgt cccagcggcg cgccacccgc agcggggcgc aggccagctc 240
cactccgctg tcgcccaccc gcatcacccg gctgcaggag aaggaggacc tgcaggagct 300
caatgatcgc ttggcggtct acatcgaccg tgtgcgctcg ctggaaacgg agaacgcagg 360
gctgcgcctt cgcatcaccg agtctgaaga ggtggtcagc cgcgaggtgt ccggcatcaa 420
ggccgcctac gaggccgagc tcggggatgc ccgcaagacc cttgactcag tagccaagga 480
gcgcgcccgc ctgcagctgg agctgagcaa agtgcgtgaa gagtttaagg agctgaaagc 540
gcgcaatac 549

<210> SEQ ID NO 168
<211> LENGTH: 547
<212> TYPE: DNA
<213> ORGANISM: Homo sapien

<400> SEQUENCE: 168
gaattcggca cgagatggcg gcaggggtcg aagcggcggc ggaggtggcg gcgacggaga 60
tcaaaatgga ggaagagagc ggcgcgcccg gcgtgccgag cggcaacggg gctccgggcc 120
ctaagggtga aggagaacga cctgctcaga atgagaagag gaaggagaaa aacataaaaa 180
gaggaggcaa tcgctttgag ccatatgcca atccaactaa aagatacaga gccttcatta 240
caaacatacc ttttgatgtg aaatggcagt cacttaaaga cctggttaaa gaaaaagttg 300
gtgaggtaac atacgtggag ctcttaatgg acgctgaagg aaagtcaagg ggatgtgctg 360
ttgttgaatt caagatggaa gagagcatga aaaaagctgc ggaagtccta aacaagcata 420
gtctgagcgg aagaccactg aaagtcaaag aagatcctga tggtgaacat gccaggagag 480
caatgcaaaa ggctggaaga cttggaagca cagtatttgt agcaaatctg gattataaag 540
ttggctg 547

<210> SEQ ID NO 169
<211> LENGTH: 547
<212> TYPE: DNA
<213> ORGANISM: Homo sapien

<400> SEQUENCE: 169
gaattcggca ccaggagtcc gactgtgctc gctgctcagc gccgcacccg gaagatgagg 60
ctcgccgtgg gagccctgct ggtctgcgcc gtcctggggc tgtgtctggc tgtccctgat 120
aaaactgtga gatggtgtgc agtgtcggag catgaggcca ctaagtgcca gagtttccgc 180
gaccatatga aaagcgtcat tccatccgat ggtcccagtg ttgcttgtgt gaagaaagcc 240
tcctaccttg attgcatcag ggccattgcg gcaaacgaag cggatgctgt gacactggat 300
gcaggtttgg tgtatgatgc ttacctggct cccaataacc tgaagcctgt ggtggcagag 360
ttctatgggt caaaagagga tccacagact ttctattatg ctgttgctgt ggtgaagaag 420
gatagtggct tccagatgaa ccagcttcga ggcaagaagt cctgccacac gggtctaggc 480
aggtccgctg ggtggaacat ccccataggc ttactttact gtgacttacc tgagccacgt 540
aaacctc 547

-continued

<210> SEQ ID NO 170
<211> LENGTH: 838
<212> TYPE: DNA
<213> ORGANISM: Homo sapien

<400> SEQUENCE: 170
gaattcggca ccagaggagc tcggcctgcg ctgcgccacg atgtccgggg agtcagccag 60
gagcttgggg aagggaagcg cgcccccggg gccggtcccg gagggctcga tccgcatcta 120
cagcatgagg ttctgcccgt ttgctgagag gacgcgtcta gtcctgaagg ccaagggaat 180
caggcatgaa gtcatcaata tcaacctgaa aaataagcct gagtggttct ttaagaaaaa 240
tccctttggt ctggtgccag ttctggaaaa cagtcagggt cagctgatct acgagtctgc 300
catcacctgt gagtacctgg atgaagcata cccagggaag aagctgttgc cggatgaccc 360
ctatgagaaa gcttgccaga agatgatctt agagttgttt tctaaggtgc catccttggt 420
aggaagcttt attagaagcc aaaataaaga agactatgat ggcctaaaag aagaatttcg 480
taaagaattt accaagctag aggaggttct gactaataag aagacgacct tctttggtgg 540
caattctatc tctatgattg attacctcat ctggccctgg tttgaacggc tggaagcaat 600
gaagttaaat gagtgtgtag accacactcc aaaactgaaa ctgtggatgg cagccatgaa 660
ggaagatccc acagtctcag ccctgcttac tagtgagaaa gactggcaag gtttcctaga 720
gctctactta cagaacagcc ctgaggcctg tgactatggg ctctgaaggg ggcaggagtc 780
agcaataaag ctatgtctga tattttcctt cactaaaaaa aaaaaaaaaa aactcgag 838

<210> SEQ ID NO 171
<211> LENGTH: 547
<212> TYPE: DNA
<213> ORGANISM: Homo sapien

<400> SEQUENCE: 171
gaattcggca ccagcgggat ttgggtcgca gttcttgttt gtggattgct gtgatcgtca 60
cttgacaatg cagatcttcg tgaagactct gactggtaag accatcaccc tcgaggttga 120
gcccagtgac accatcgaga atgtcaaggc aaagatccaa gataaggaag gcatccctcc 180
tgaccagcag aggctgatct ttgctggaaa acagctggaa gatgggcgca ccctgtctga 240
ctacaacatc cagaaagagt ccaccctgca cctggtgctc cgtctcagag gtgggatgca 300
aatcttcgtg aagacactca ctggcaagac catcaccctt gaggtcgagc ccagtgacac 360
catcgagaac gtcaaagcaa agatccagga caaggaaggc attcctcctg accagcagag 420
gttgatcttt gccggaaagc agctggaaga tgggcgcacc ctgtctgact acaacatcca 480
gaaagagtct accctgcacc tggtgctccg tctcagaggt gggatgcaga tcttcgtgaa 540
gaccctg 547

<210> SEQ ID NO 172
<211> LENGTH: 608
<212> TYPE: DNA
<213> ORGANISM: Homo sapien

<400> SEQUENCE: 172
gaattcggca ccagagactt ctccctctga ggcctgcgca cccctcctca tcagcctgtc 60
caccctcatc tacaatggtg ccctgccatg tcagtgcaac cctcaaggtt cactgagttc 120
tgagtgcaac cctcatggtg gtcagtgcct gtgcaagcct ggagtggttg ggcgccgctg 180
tgacctctgt gcccctggct actatggctt tggccccaca ggctgtcaag gcgcttgcct 240

-continued gggctgccgt gatcacacag ggggtgagca ctgtgaaagg tgcattgctg gtttccacgg 300
ggacccacgg ctgccatatg gggccagtg ccggccctgt ccctgtcctg aaggccctgg 360
gagccaacgg cactttgcta cttcttgcca ccaggatgaa tattcccagc agattgtgtg 420
ccactgccgg gcaggctata cggggctgcg atgtgaagct tgtgcccctg ggcactttgg 480
ggacccatca aggccaggtg gccggtgcca actgtgtgag tgcagtggga acattgaccc 540
aatggatcct gatgcctgtg acccccacac ggggcaatgc ctgcgctgtt tacaccacac 600
agagggtc 608

<210> SEQ ID NO 173
<211> LENGTH: 543
<212> TYPE: DNA
<213> ORGANISM: Homo sapien

<400> SEQUENCE: 173
gaattcggca ccagagatca tccgccagca gggtctggcc tcctacgact acgtgcgccg 60
ccgcctcacg gctgaggacc tgttcgaggc tcggatcatc tctctcgaga cctacaacct 120
gctccgggag ggcaccagga gcctccgtga ggctctcgag gcggagtccg cctggtgcta 180
cctctatggc acgggctccg tggctggtgt ctacctgccc ggttccaggc agacactgag 240
catctaccag gctctcaaga aagggctgct gagtgccgag gtggcccgcc tgctgctgga 300
ggcacaggca gccacaggct tcctgctgga cccggtgaag ggggaacggc tgactgtgga 360
tgaagctgtg cggaagggcc tcgtggggcc cgaactgcac gaccgcctgc tctcggctga 420
gcgggcggtc accggctacc gtgaccccta caccgagcag accatctcgc tcttccaggc 480
catgaagaag gaactgatcc ctactgagga ggccctgcgg ctgtggatgc ccagctggcc 540
acc 543

<210> SEQ ID NO 174
<211> LENGTH: 548
<212> TYPE: DNA
<213> ORGANISM: Homo sapien

<400> SEQUENCE: 174
gaattcggca cgagaaatgg cggcaggggt cgaagcggcg gcggaggtgg cggcgacgga 60
gatcaaaatg gaggaagaga gcggcgcgcc cggcgtgccg agcggcaacg gggctccggg 120
ccctaagggt gaaggagaac gacctgctca gaatgagaag aggaaggaga aaaacataaa 180
aagaggaggc aatcgctttg agccatatgc caatccaact aaaagataca gagccttcat 240
tacaaacata ccttttgatg tgaaatggca gtcacttaaa gacctggtta aagaaaaagt 300
tggtgaggta acatacgtgg agctcttaat ggacgctgaa ggaaagtcaa ggggatgtgc 360
tgttgttgaa ttcaagatgg aagagagcat gaaaaaagct gcggaagtcc taaacaagca 420
tagtctgagc ggaagaccac tgaaagtcaa agaagatcct gatggtgaac atgccaggag 480
agcaatgcaa aaggtgatgg ctacgactgg tgggatgggt atgggaccag gtggcccagg 540
aatgatta 548

<210> SEQ ID NO 175
<211> LENGTH: 604
<212> TYPE: DNA
<213> ORGANISM: Homo sapien

<400> SEQUENCE: 175
gaattcggca ccagaggacc tccaggacat gttcatcgtc cataccatcg aggagattga 60

-continued gggcctgatc tcagcccatg accagttcaa gtccaccctg ccggacgccg atagggagcg 120
cgaggccatc ctggccatcc acaaggaggc ccagaggatc gctgagagca accacatcaa 180
gctgtcgggc agcaacccct acaccaccgt caccccgcaa atcatcaact ccaagtggga 240
gaaggtgcag cagctggtgc caaaacggga ccatgccctc ctggaggagc agagcaagca 300
gcagtccaac gagcacctgc gccgccagtt cgccagccag gccaatgttg tggggccctg 360
gatccagacc aagatggagg agatcgggcg catctccatt gagatgaacg ggaccctgga 420
ggaccagctg agccacctga agcagtatga acgcagcatc gtggactaca agcccaacct 480
ggacctgctg gagcagcagc accagcttat ccaggaggcc ctcatcttcg acaacaagca 540
caccaactat accatggagc acatccgcgt gggctgggag cagctgctca ccaccattgc 600
ccgg 604

<210> SEQ ID NO 176
<211> LENGTH: 486
<212> TYPE: DNA
<213> ORGANISM: Homo sapien

<400> SEQUENCE: 176
gaattcggca ccagccaagc tcactattga atccacgccg ttcaatgtcg cagaggggaa 60
ggaggttctt ctactcgccc acaacctgcc ccagaatcgt attggttaca gctggtacaa 120
aggcgaaaga gtggatggca acagtctaat tgtaggatat gtaataggaa ctcaacaagc 180
taccccaggg cccgcataca gtggtcgaga gacaatatac cccaatgcat ccctgctgat 240
ccagaacgtc acccagaatg acacaggatt ctatacccta caagtcataa agtcagatct 300
tgtgaatgaa gaagcaaccg gacagttcca tgtatacccg gagctgccca agccctccat 360
ctccagcaac aactccaacc ccgtggagga caaggatgct gtggccttca cctgtgaacc 420
tgaggttcag aacacaacct acctgtggtg ggtaaatggt cagagcctcc cggtcagtcc 480
caaggc 486

<210> SEQ ID NO 177
<211> LENGTH: 387
<212> TYPE: DNA
<213> ORGANISM: Homo sapien

<400> SEQUENCE: 177
gaattcggca ccagggacag cagaccagac agtcacagca gccttgacaa aacgttcctg 60
gaactcaagc tcttctccac agaggaggac agagcagaca gcagagacca tggagtctcc 120
ctcggcccct ccccacagat ggtgcatccc ctggcagagg ctcctgctca cagcctcact 180
tctaaccttc tggaacccgc ccaccactgc caagctcact attgaatcca cgccgttcaa 240
tgtcgcagag gggaaggagg tgcttctact tgtccacaat ctgccccagc atctttttgg 300
ctacagctgg tacaaaggtg aaagagtgga tggcaaccgt caaattatag gatatgtaat 360
aggaactcaa caagctaccc cagggcc 387

<210> SEQ ID NO 178
<211> LENGTH: 440
<212> TYPE: DNA
<213> ORGANISM: Homo sapien

<400> SEQUENCE: 178
gaattcggca cgaggagaag cagaaaaaca aggaatttag ccagacttta gaaaatgaga 60

-continued

```
aaaatacctt actgagtcag atatcaacaa aggatggtga actaaaaatg cttcaggagg    120

aagtaaccaa aatgaacctg ttaaatcagc aaatccaaga agaactctct agagttacca    180

aactaaagga gacagcagaa gaagagaaag atgatttgga agagaggctt atgaatcaat    240

tagcagaact taatggaagc attgggaatt actgtcagga tgttacagat gcccaaataa    300

aaaatgagct attggaatct gaaatgaaga accttaaaaa gtgtgtgagt gaattggaag    360

aagaaaagca gcagttagtc aaggaaaaaa ctaaggtgga atcagaaata cgaaaggaat    420

atttggagaa aatacaaggt                                                440
```

<210> SEQ ID NO 179
<211> LENGTH: 443
<212> TYPE: DNA
<213> ORGANISM: Homo sapien

<400> SEQUENCE: 179

```
gaattcggca ccagcggggg gctacggcgg cggctacggc ggcgtcctga ccgcgtccga     60

cgggctgctg gcgggcaacg agaagctaac catgcagaac ctcaacgacc gcctggcctc    120

ctacctggac aaggtgcgcg ccctggaggc ggccaacggc gagctagagg tgaagatccg    180

cgactggtac cagaagcagg ggcctgggcc ctcccgcgac tacagccact actacacgac    240

catccaggac ctgcgggaca agattcttgg tgccaccatt gagaactcca ggattgtcct    300

gcagatcgac aacgcccgtc tggctgcaga tgacttccga accaagtttg agacggaaca    360

ggctctgcgc atgagcgtgg aggccgacat caacggcctg cgcagggtgc tggatgagct    420

gaccctggcc aggaccgacc tgg                                            443
```

<210> SEQ ID NO 180
<211> LENGTH: 403
<212> TYPE: DNA
<213> ORGANISM: Homo sapien

<400> SEQUENCE: 180

```
gaattcggca cgaggttatg agagtcgact tcaatgttcc tatgaagaac aaccagataa     60

caaacaacca gaggattaag gctgctgtcc caagcatcaa attctgcttg gacaatggag    120

ccaagtcggt agtccttatg agccacctag gccggcctga tggtgtgccc atgcctgaca    180

agtactcctt agagccagtt gctgtagaac tcagatctct gctgggcaag gatgttctgt    240

tcttgaagga ctgtgtaggc ccagaagtgg agaaagcctg tgccaaccca gctgctgggt    300

ctgtcatcct gctggagaac ctccgctttc atgtggagga agaagggaag ggaaaagatg    360

cttctgggaa caaggttaaa gccgagccag ccaaaataga agc                      403
```

<210> SEQ ID NO 181
<211> LENGTH: 493
<212> TYPE: DNA
<213> ORGANISM: Homo sapien

<400> SEQUENCE: 181

```
gaattcggca ccagcagagg tctccagagc cttctctctc ctgtgcaaaa tggcaactct     60

taaggaaaaa ctcattgcac cagttgcgga agaagaggca acagttccaa acaataagat    120

cactgtagtg ggtgttggac aagttggtat ggcgtgtgct atcagcattc tgggaaagtc    180

tctggctgat gaacttgctc ttgtggatgt tttggaagat aagcttaaag gagaaatgat    240

ggatctgcag catgggagct tatttcttca gacacctaaa attgtggcag ataaagatta    300

ttctgtgacc gccaattcta agattgtagt ggtaactgca ggagtccgtc agcaagaagg    360
```

-continued

```
ggagagtcgg ctcaatctgg tgcagagaaa tgttaatgtc ttcaaattca ttattcctca    420

gatcgtcaag tacagtcctg attgcatcat aattgtggtt tccaacccag tggacattct    480

tacgtatgtt acc                                                       493


<210> SEQ ID NO 182
<211> LENGTH: 209
<212> TYPE: PRT
<213> ORGANISM: Homo sapien

<400> SEQUENCE: 182

Ala Phe Ser Ser Asn Pro Lys Val Gln Val Glu Ala Ile Glu Gly Gly
 1               5                  10                  15

Ala Leu Gln Lys Leu Leu Val Ile Leu Ala Thr Glu Gln Pro Leu Thr
            20                  25                  30

Ala Lys Lys Lys Val Leu Phe Ala Leu Cys Ser Leu Leu Arg His Phe
        35                  40                  45

Pro Tyr Ala Gln Arg Gln Phe Leu Lys Leu Gly Gly Leu Gln Val Leu
    50                  55                  60

Arg Thr Leu Val Gln Glu Lys Gly Thr Glu Val Leu Ala Val Arg Val
65                  70                  75                  80

Val Thr Leu Leu Tyr Asp Leu Val Thr Glu Lys Met Phe Ala Glu Glu
                85                  90                  95

Glu Ala Glu Leu Thr Gln Glu Met Ser Pro Glu Lys Leu Gln Gln Tyr
            100                 105                 110

Arg Gln Val His Leu Leu Pro Gly Leu Trp Glu Gln Gly Trp Cys Glu
        115                 120                 125

Ile Thr Ala His Leu Leu Ala Leu Pro Glu His Asp Ala Arg Glu Lys
    130                 135                 140

Val Leu Gln Thr Leu Gly Val Leu Leu Thr Thr Cys Arg Asp Arg Tyr
145                 150                 155                 160

Arg Gln Asp Pro Gln Leu Gly Arg Thr Leu Ala Ser Leu Gln Ala Glu
                165                 170                 175

Tyr Gln Val Leu Ala Ser Leu Glu Leu Gln Asp Gly Glu Asp Glu Gly
            180                 185                 190

Tyr Phe Gln Glu Leu Leu Gly Ser Val Asn Ser Leu Leu Lys Glu Leu
        195                 200                 205

Arg


<210> SEQ ID NO 183
<211> LENGTH: 255
<212> TYPE: PRT
<213> ORGANISM: Homo sapien

<400> SEQUENCE: 183

Met Ala Ala Gly Val Glu Ala Ala Ala Glu Val Ala Ala Thr Glu Pro
 1               5                  10                  15

Lys Met Glu Glu Glu Ser Gly Ala Pro Cys Val Pro Ser Gly Asn Gly
            20                  25                  30

Ala Pro Gly Pro Lys Gly Glu Glu Arg Pro Thr Gln Asn Glu Lys Arg
        35                  40                  45

Lys Glu Lys Asn Ile Lys Arg Gly Gly Asn Arg Phe Glu Pro Tyr Ser
    50                  55                  60

Asn Pro Thr Lys Arg Tyr Arg Ala Phe Ile Thr Asn Ile Pro Phe Asp
65                  70                  75                  80
```

-continued

```
Val Lys Trp Gln Ser Leu Lys Asp Leu Val Lys Glu Lys Val Gly Glu
                85                  90                  95

Val Thr Tyr Val Glu Leu Leu Met Asp Ala Glu Gly Lys Ser Arg Gly
            100                 105                 110

Cys Ala Val Val Glu Phe Lys Met Glu Glu Ser Met Lys Lys Ala Ala
        115                 120                 125

Glu Val Leu Asn Lys His Ser Leu Ser Gly Arg Pro Leu Lys Val Lys
    130                 135                 140

Glu Asp Pro Asp Gly Glu His Ala Arg Arg Ala Met Gln Lys Ala Gly
145                 150                 155                 160

Arg Leu Gly Ser Thr Val Phe Val Ala Asn Leu Asp Tyr Lys Val Gly
                165                 170                 175

Trp Lys Lys Leu Lys Glu Val Phe Ser Met Ala Gly Val Val Val Arg
            180                 185                 190

Ala Asp Ile Leu Glu Asp Lys Asp Gly Lys Ser Arg Gly Ile Gly Ile
        195                 200                 205

Val Thr Phe Glu Gln Ser Ile Glu Ala Val Gln Ala Ile Ser Met Phe
    210                 215                 220

Asn Gly Gln Leu Leu Phe Asp Arg Pro Met His Val Lys Met Asp Glu
225                 230                 235                 240

Arg Ala Leu Pro Lys Gly Asp Phe Phe Pro Pro Glu Arg His Ser
                245                 250                 255


<210> SEQ ID NO 184
<211> LENGTH: 188
<212> TYPE: PRT
<213> ORGANISM: Homo sapien

<400> SEQUENCE: 184

Leu Ser Gly Ser Cys Ile Arg Arg Glu Gln Thr Pro Glu Lys Glu Lys
 1               5                  10                  15

Gln Val Val Leu Phe Glu Glu Ala Ser Trp Thr Cys Thr Pro Ala Cys
            20                  25                  30

Gly Asp Glu Pro Arg Thr Val Ile Leu Leu Ser Ser Met Leu Ala Asp
        35                  40                  45

His Arg Leu Lys Leu Glu Asp Tyr Lys Asp Arg Leu Lys Ser Gly Glu
    50                  55                  60

His Leu Asn Pro Asp Gln Leu Glu Ala Val Glu Lys Tyr Glu Glu Val
65                  70                  75                  80

Leu His Asn Leu Glu Phe Ala Lys Glu Leu Gln Lys Thr Phe Ser Gly
                85                  90                  95

Leu Ser Leu Asp Leu Leu Lys Ala Gln Lys Lys Ala Gln Arg Arg Glu
            100                 105                 110

His Met Leu Lys Leu Glu Ala Glu Lys Lys Lys Leu Arg Thr Ile Leu
        115                 120                 125

Gln Val Gln Tyr Val Leu Gln Asn Leu Thr Gln Glu His Val Gln Lys
    130                 135                 140

Asp Phe Lys Gly Gly Leu Asn Gly Ala Val Tyr Leu Pro Ser Lys Glu
145                 150                 155                 160

Leu Asp Tyr Leu Ile Lys Phe Ser Lys Leu Thr Cys Pro Glu Arg Asn
                165                 170                 175

Glu Ser Leu Arg Gln Thr Leu Glu Gly Ser Thr Val
            180                 185


<210> SEQ ID NO 185
```

-continued

<211> LENGTH: 746
<212> TYPE: PRT
<213> ORGANISM: Homo sapien

<400> SEQUENCE: 185

```
Asp Lys His Leu Lys Asp Leu Leu Ser Lys Leu Leu Asn Ser Gly Tyr
 1               5                  10                  15

Phe Glu Ser Ile Pro Val Pro Lys Asn Ala Lys Glu Lys Glu Val Pro
            20                  25                  30

Leu Glu Glu Glu Met Leu Ile Gln Ser Glu Lys Lys Thr Gln Leu Ser
        35                  40                  45

Lys Thr Glu Ser Val Lys Glu Ser Glu Ser Leu Met Glu Phe Ala Gln
    50                  55                  60

Pro Glu Ile Gln Pro Gln Glu Phe Leu Asn Arg Arg Tyr Met Thr Glu
65                  70                  75                  80

Val Asp Tyr Ser Asn Lys Gln Gly Glu Glu Gln Pro Trp Glu Ala Asp
                85                  90                  95

Tyr Ala Arg Lys Pro Asn Leu Pro Lys Arg Trp Asp Met Leu Thr Glu
            100                 105                 110

Pro Asp Gly Gln Glu Lys Lys Gln Glu Ser Phe Lys Ser Trp Glu Ala
        115                 120                 125

Ser Gly Lys His Gln Glu Val Ser Lys Pro Ala Val Ser Leu Glu Gln
    130                 135                 140

Arg Lys Gln Asp Thr Ser Lys Leu Arg Ser Thr Leu Pro Glu Glu Gln
145                 150                 155                 160

Lys Lys Gln Glu Ile Ser Lys Ser Lys Pro Ser Pro Ser Gln Trp Lys
                165                 170                 175

Gln Asp Thr Pro Lys Ser Lys Ala Gly Tyr Val Gln Glu Glu Gln Lys
            180                 185                 190

Lys Gln Glu Thr Pro Lys Leu Trp Pro Val Gln Leu Gln Lys Glu Gln
        195                 200                 205

Asp Pro Lys Lys Gln Thr Pro Lys Ser Trp Thr Pro Ser Met Gln Ser
    210                 215                 220

Glu Gln Asn Thr Thr Lys Ser Trp Thr Thr Pro Met Cys Glu Glu Gln
225                 230                 235                 240

Asp Ser Lys Gln Pro Glu Thr Pro Lys Ser Trp Glu Asn Asn Val Glu
                245                 250                 255

Ser Gln Lys His Ser Leu Thr Ser Gln Ser Gln Ile Ser Pro Lys Ser
            260                 265                 270

Trp Gly Val Ala Thr Ala Ser Leu Ile Pro Asn Asp Gln Leu Leu Pro
        275                 280                 285

Arg Lys Leu Asn Thr Glu Pro Lys Asp Val Pro Lys Pro Val His Gln
    290                 295                 300

Pro Val Gly Ser Ser Ser Thr Leu Pro Lys Asp Pro Val Leu Arg Lys
305                 310                 315                 320

Glu Lys Leu Gln Asp Leu Met Thr Gln Ile Gln Gly Thr Cys Asn Phe
                325                 330                 335

Met Gln Glu Ser Val Leu Asp Phe Asp Lys Pro Ser Ser Ala Ile Pro
            340                 345                 350

Thr Ser Gln Pro Pro Ser Ala Thr Pro Gly Ser Pro Val Ala Ser Lys
        355                 360                 365

Glu Gln Asn Leu Ser Ser Gln Ser Asp Phe Leu Gln Glu Pro Leu Gln
    370                 375                 380

Val Phe Asn Val Asn Ala Pro Leu Pro Pro Arg Lys Glu Gln Glu Ile
```

-continued

```
385                 390                 395                 400

Lys Glu Ser Pro Tyr Ser Pro Gly Tyr Asn Gln Ser Phe Thr Thr Ala
                405                 410                 415

Ser Thr Gln Thr Pro Pro Gln Cys Gln Leu Pro Ser Ile His Val Glu
            420                 425                 430

Gln Thr Val His Ser Gln Glu Thr Ala Ala Asn Tyr His Pro Asp Gly
        435                 440                 445

Thr Ile Gln Val Ser Asn Gly Ser Leu Ala Phe Tyr Pro Ala Gln Thr
    450                 455                 460

Asn Val Phe Pro Arg Pro Thr Gln Pro Phe Val Asn Ser Arg Gly Ser
465                 470                 475                 480

Val Arg Gly Cys Thr Arg Gly Gly Arg Leu Ile Thr Asn Ser Tyr Arg
                485                 490                 495

Ser Pro Gly Gly Tyr Lys Gly Phe Asp Thr Tyr Arg Gly Leu Pro Ser
            500                 505                 510

Ile Ser Asn Gly Asn Tyr Ser Gln Leu Gln Phe Gln Ala Arg Glu Tyr
        515                 520                 525

Ser Gly Ala Pro Tyr Ser Gln Arg Asp Asn Phe Gln Gln Cys Tyr Lys
    530                 535                 540

Arg Gly Gly Thr Ser Gly Gly Pro Arg Ala Asn Ser Arg Ala Gly Trp
545                 550                 555                 560

Ser Asp Ser Ser Gln Val Ser Ser Pro Glu Arg Asp Asn Glu Thr Phe
                565                 570                 575

Asn Ser Gly Asp Ser Gly Gln Gly Asp Ser Arg Ser Met Thr Pro Val
            580                 585                 590

Asp Val Pro Val Thr Asn Pro Ala Ala Thr Ile Leu Pro Val His Val
        595                 600                 605

Tyr Pro Leu Pro Gln Gln Met Arg Val Ala Phe Ser Ala Ala Arg Thr
    610                 615                 620

Ser Asn Leu Ala Pro Gly Thr Leu Asp Gln Pro Ile Val Phe Asp Leu
625                 630                 635                 640

Leu Leu Asn Asn Leu Gly Glu Thr Phe Asp Leu Gln Leu Gly Arg Phe
                645                 650                 655

Asn Cys Pro Val Asn Gly Thr Tyr Val Phe Ile Phe His Met Leu Lys
            660                 665                 670

Leu Ala Val Asn Val Pro Leu Tyr Val Asn Leu Met Lys Asn Glu Glu
        675                 680                 685

Val Leu Val Ser Ala Tyr Ala Asn Asp Gly Ala Pro Asp His Glu Thr
    690                 695                 700

Ala Ser Asn His Ala Ile Leu Gln Leu Phe Gln Gly Asp Gln Ile Trp
705                 710                 715                 720

Leu Arg Leu His Arg Gly Ala Ile Tyr Gly Ser Ser Trp Lys Tyr Ser
                725                 730                 735

Thr Phe Ser Gly Tyr Leu Leu Tyr Gln Asp
            740                 745


<210> SEQ ID NO 186
<211> LENGTH: 705
<212> TYPE: PRT
<213> ORGANISM: Homo sapien

<400> SEQUENCE: 186

Ala Leu Leu Asn Val Arg Gln Pro Pro Ser Thr Thr Thr Phe Val Leu
 1               5                  10                  15
```

-continued

```
Asn Gln Ile Asn His Leu Pro Pro Leu Gly Ser Thr Ile Val Met Thr
             20                  25                  30

Lys Thr Pro Pro Val Thr Thr Asn Arg Gln Thr Ile Thr Leu Thr Lys
         35                  40                  45

Phe Ile Gln Thr Thr Ala Ser Thr Arg Pro Ser Val Ser Ala Pro Thr
     50                  55                  60

Val Arg Asn Ala Met Thr Ser Ala Pro Ser Lys Asp Gln Val Gln Leu
65                  70                  75                  80

Lys Asp Leu Leu Lys Asn Asn Ser Leu Asn Glu Leu Met Lys Leu Lys
                 85                  90                  95

Pro Pro Ala Asn Ile Ala Gln Pro Val Ala Thr Ala Ala Thr Asp Val
            100                 105                 110

Ser Asn Gly Thr Val Lys Lys Glu Ser Ser Asn Lys Glu Gly Ala Arg
        115                 120                 125

Met Trp Ile Asn Asp Met Lys Met Arg Ser Phe Ser Pro Thr Met Lys
    130                 135                 140

Val Pro Val Val Lys Glu Asp Asp Glu Pro Glu Glu Glu Asp Glu Glu
145                 150                 155                 160

Glu Met Gly His Ala Glu Thr Tyr Ala Glu Tyr Met Pro Ile Lys Leu
                165                 170                 175

Lys Ile Gly Leu Arg His Pro Asp Ala Val Val Glu Thr Ser Ser Leu
            180                 185                 190

Ser Ser Val Thr Pro Pro Asp Val Trp Tyr Lys Thr Ser Ile Ser Glu
        195                 200                 205

Glu Thr Ile Asp Asn Gly Trp Leu Ser Ala Leu Gln Leu Glu Ala Ile
    210                 215                 220

Thr Tyr Ala Ala Gln Gln His Glu Thr Phe Leu Pro Asn Gly Asp Arg
225                 230                 235                 240

Ala Gly Phe Leu Ile Gly Asp Gly Ala Gly Val Gly Lys Gly Arg Thr
                245                 250                 255

Ile Ala Gly Ile Ile Tyr Glu Asn Tyr Leu Leu Ser Arg Lys Arg Ala
            260                 265                 270

Leu Trp Phe Ser Val Ser Asn Asp Leu Lys Tyr Asp Ala Glu Arg Asp
        275                 280                 285

Leu Arg Asp Ile Gly Ala Lys Asn Ile Leu Val His Ser Leu Asn Lys
    290                 295                 300

Phe Lys Tyr Gly Lys Ile Ser Ser Lys His Asn Gly Ser Val Lys Lys
305                 310                 315                 320

Gly Val Ile Phe Ala Thr Tyr Ser Ser Leu Ile Gly Glu Ser Gln Ser
                325                 330                 335

Gly Gly Lys Tyr Lys Thr Arg Leu Lys Gln Leu Leu His Trp Cys Gly
            340                 345                 350

Asp Asp Phe Asp Gly Val Ile Val Phe Asp Glu Cys His Lys Ala Lys
        355                 360                 365

Asn Leu Cys Pro Val Gly Ser Ser Lys Pro Thr Lys Thr Gly Leu Ala
    370                 375                 380

Val Leu Glu Leu Gln Asn Lys Leu Pro Lys Ala Arg Val Val Tyr Ala
385                 390                 395                 400

Ser Ala Thr Gly Ala Ser Glu Pro Arg Asn Met Ala Tyr Met Asn Arg
                405                 410                 415

Leu Gly Ile Trp Gly Glu Gly Thr Pro Phe Arg Glu Phe Ser Asp Phe
            420                 425                 430

Ile Gln Ala Val Glu Arg Arg Gly Val Gly Ala Met Glu Ile Val Ala
```

-continued

```
        435                 440                 445

Met Asp Met Lys Leu Arg Gly Met Tyr Ile Ala Arg Gln Leu Ser Phe
    450                 455                 460

Thr Gly Val Thr Phe Lys Ile Glu Glu Val Leu Leu Ser Gln Ser Tyr
465                 470                 475                 480

Val Lys Met Tyr Asn Lys Ala Val Lys Leu Trp Val Ile Ala Arg Glu
                485                 490                 495

Arg Phe Gln Gln Ala Ala Asp Leu Ile Asp Ala Glu Gln Arg Met Lys
            500                 505                 510

Lys Ser Met Trp Gly Gln Phe Trp Ser Ala His Gln Arg Phe Phe Lys
        515                 520                 525

Tyr Leu Cys Ile Ala Ser Lys Val Lys Arg Val Val Gln Leu Ala Arg
    530                 535                 540

Glu Glu Ile Lys Asn Gly Lys Cys Val Val Ile Gly Leu Gln Ser Thr
545                 550                 555                 560

Gly Glu Ala Arg Thr Leu Glu Ala Leu Glu Glu Gly Gly Gly Glu Leu
                565                 570                 575

Asn Asp Phe Val Ser Thr Ala Lys Gly Val Leu Gln Ser Leu Ile Glu
            580                 585                 590

Lys His Phe Pro Ala Pro Asp Arg Lys Lys Leu Tyr Ser Leu Leu Gly
        595                 600                 605

Ile Asp Leu Thr Ala Pro Ser Asn Asn Ser Ser Pro Arg Asp Ser Pro
    610                 615                 620

Cys Lys Glu Asn Lys Ile Lys Lys Arg Lys Gly Glu Glu Ile Thr Arg
625                 630                 635                 640

Glu Ala Lys Lys Ala Arg Lys Val Gly Gly Leu Thr Gly Ser Ser Ser
                645                 650                 655

Asp Asp Ser Gly Ser Glu Ser Asp Ala Ser Asp Asn Glu Glu Ser Asp
            660                 665                 670

Tyr Glu Ser Ser Lys Asn Met Ser Ser Gly Asp Asp Asp Asp Phe Asn
        675                 680                 685

Pro Phe Leu Asp Glu Ser Asn Glu Asp Asp Glu Asn Asp Pro Trp Leu
    690                 695                 700

Ile
705


<210> SEQ ID NO 187
<211> LENGTH: 595
<212> TYPE: PRT
<213> ORGANISM: Homo sapien

<400> SEQUENCE: 187

Glu Ser Pro Arg His Arg Gly Glu Gly Gly Gly Glu Trp Gly Pro Gly
 1               5                  10                  15

Val Pro Arg Glu Arg Arg Glu Ser Ala Gly Glu Trp Gly Ala Asp Thr
            20                  25                  30

Pro Lys Glu Gly Gly Glu Ser Ala Gly Glu Trp Gly Ala Glu Val Pro
        35                  40                  45

Arg Gly Arg Gly Glu Gly Ala Gly Glu Trp Gly Pro Asp Thr Pro Lys
    50                  55                  60

Glu Arg Gly Gln Gly Val Arg Glu Trp Gly Pro Glu Ile Pro Gln Glu
65                  70                  75                  80

His Gly Glu Ala Thr Arg Asp Trp Ala Leu Glu Ser Pro Arg Ala Leu
                85                  90                  95
```

-continued

```
Gly Glu Asp Ala Arg Glu Leu Gly Ser Ser Pro His Asp Arg Gly Ala
            100                 105                 110

Ser Pro Arg Asp Leu Ser Gly Glu Ser Pro Cys Thr Gln Arg Ser Gly
        115                 120                 125

Leu Leu Pro Glu Arg Arg Gly Asp Ser Pro Trp Pro Pro Trp Pro Ser
    130                 135                 140

Pro Gln Glu Arg Asp Ala Gly Thr Arg Asp Arg Glu Glu Ser Pro Arg
145                 150                 155                 160

Asp Trp Gly Gly Ala Glu Ser Pro Arg Gly Trp Glu Ala Gly Pro Arg
                165                 170                 175

Glu Trp Gly Pro Ser Pro Ser Gly His Gly Asp Gly Pro Arg Arg Arg
            180                 185                 190

Pro Arg Lys Arg Arg Gly Arg Lys Gly Arg Met Gly Arg Gln His Glu
        195                 200                 205

Ala Ala Ala Thr Ala Ala Thr Ala Ala Thr Ala Thr Gly Gly Thr Ala
    210                 215                 220

Glu Glu Ala Gly Ala Ser Ala Pro Glu Ser Gln Ala Gly Gly Gly Pro
225                 230                 235                 240

Arg Gly Arg Ala Arg Gly Pro Arg Gln Gln Gly Arg Arg Arg His Gly
                245                 250                 255

Thr Gln Arg Arg Arg Gly Pro Pro Gln Ala Arg Glu Glu Gly Pro Arg
            260                 265                 270

Asp Ala Thr Thr Ile Leu Gly Leu Gly Thr Pro Ser Gly Glu Gln Arg
        275                 280                 285

Ala Asp Gln Ser Gln Ala Leu Pro Ala Leu Ala Gly Ala Ala Ala Ala
    290                 295                 300

His Ala His Ala Ile Pro Gly Ala Gly Pro Ala Ala Ala Pro Val Gly
305                 310                 315                 320

Gly Arg Gly Arg Arg Gly Gly Trp Arg Gly Gly Arg Arg Gly Gly Ser
                325                 330                 335

Ala Gly Ala Gly Gly Gly Gly Arg Gly Gly Arg Gly Arg Gly Arg Gly
            340                 345                 350

Gly Gly Arg Gly Gly Gly Gly Ala Gly Arg Gly Gly Gly Ala Ala Gly
        355                 360                 365

Pro Arg Glu Gly Ala Ser Ser Pro Gly Ala Arg Arg Gly Glu Gln Arg
    370                 375                 380

Arg Arg Gly Arg Gly Pro Pro Ala Ala Gly Ala Ala Gln Val Ser Ala
385                 390                 395                 400

Arg Gly Arg Arg Ala Arg Gly Gln Arg Ala Gly Glu Glu Ala Gln Asp
                405                 410                 415

Gly Leu Leu Pro Arg Gly Arg Asp Arg Leu Pro Leu Arg Pro Gly Asp
            420                 425                 430

Ala Asn Gln Arg Ala Glu Arg Pro Gly Pro Pro Arg Gly Gly His Gly
        435                 440                 445

Pro Val Asn Ala Ser Ser Ala Pro Asp Thr Ser Pro Pro Arg His Pro
    450                 455                 460

Arg Arg Trp Val Ser Gln Gln Arg Gln Arg Leu Trp Arg Gln Phe Arg
465                 470                 475                 480

Val Gly Gly Gly Phe Pro Pro Pro Pro Pro Ser Arg Pro Pro Ala Val
                485                 490                 495

Leu Leu Pro Leu Leu Arg Leu Ala Cys Ala Gly Asp Pro Gly Ala Thr
            500                 505                 510

Arg Pro Gly Pro Arg Arg Pro Ala Arg Arg Pro Arg Gly Glu Leu Ile
```

-continued

```
        515                 520                 525

Pro Arg Arg Pro Asp Pro Ala Ala Pro Ser Glu Glu Gly Leu Arg Met
    530                 535                 540

Glu Ser Ser Val Asp Asp Gly Ala Thr Ala Thr Thr Ala Asp Ala Ala
545                 550                 555                 560

Ser Gly Glu Ala Pro Glu Ala Gly Pro Ser Pro Ser His Ser Pro Thr
                565                 570                 575

Met Cys Gln Thr Gly Gly Pro Gly Pro Pro Pro Pro Gln Pro Pro Arg
            580                 585                 590

Trp Leu Pro
        595


<210> SEQ ID NO 188
<211> LENGTH: 376
<212> TYPE: PRT
<213> ORGANISM: Homo sapien

<400> SEQUENCE: 188

Glu Met Arg Lys Phe Asp Val Pro Ser Met Glu Ser Thr Leu Asn Gln
 1               5                  10                  15

Pro Ala Met Leu Glu Thr Leu Tyr Ser Asp Pro His Tyr Arg Ala His
            20                  25                  30

Phe Pro Asn Pro Arg Pro Asp Thr Asn Lys Asp Val Tyr Lys Val Leu
        35                  40                  45

Pro Glu Ser Lys Lys Ala Pro Gly Ser Gly Ala Val Phe Glu Arg Asn
    50                  55                  60

Gly Pro His Ala Ser Ser Ser Gly Val Leu Pro Leu Gly Leu Gln Pro
65                  70                  75                  80

Ala Pro Gly Leu Ser Lys Ser Leu Ser Ser Gln Val Trp Gln Pro Ser
                85                  90                  95

Pro Asp Pro Trp His Pro Gly Glu Gln Ser Cys Glu Leu Ser Thr Cys
            100                 105                 110

Arg Gln Gln Leu Glu Leu Ile Arg Leu Gln Met Glu Gln Met Gln Leu
        115                 120                 125

Gln Asn Gly Ala Met Cys His His Pro Ala Ala Phe Ala Pro Leu Leu
    130                 135                 140

Pro Thr Leu Glu Pro Ala Gln Trp Leu Ser Ile Leu Asn Ser Asn Glu
145                 150                 155                 160

His Leu Leu Lys Glu Lys Glu Leu Leu Ile Asp Lys Gln Arg Lys His
                165                 170                 175

Ile Ser Gln Leu Glu Gln Lys Val Arg Glu Ser Glu Leu Gln Val His
            180                 185                 190

Ser Ala Leu Leu Gly Arg Pro Ala Pro Phe Gly Asp Val Cys Leu Leu
        195                 200                 205

Arg Leu Gln Glu Leu Gln Arg Glu Asn Thr Phe Leu Arg Ala Gln Phe
    210                 215                 220

Ala Gln Lys Thr Glu Ala Leu Ser Lys Glu Lys Met Glu Leu Glu Lys
225                 230                 235                 240

Lys Leu Ser Ala Ser Glu Val Glu Ile Gln Leu Ile Arg Glu Ser Leu
                245                 250                 255

Lys Val Thr Leu Gln Lys His Ser Glu Glu Gly Lys Lys Gln Glu Glu
            260                 265                 270

Arg Val Lys Gly Arg Asp Lys His Ile Asn Asn Leu Lys Lys Lys Cys
        275                 280                 285
```

-continued

```
Gln Lys Glu Ser Glu Gln Asn Arg Glu Lys Gln Gln Arg Ile Glu Thr
    290                 295                 300

Leu Glu Arg Tyr Leu Ala Asp Leu Pro Thr Leu Glu Asp His Gln Lys
305                 310                 315                 320

Gln Thr Glu Gln Leu Lys Asp Ala Glu Leu Lys Asn Thr Glu Leu Gln
                325                 330                 335

Glu Arg Val Ala Glu Leu Glu Thr Leu Leu Glu Asp Thr Gln Ala Thr
            340                 345                 350

Cys Arg Glu Lys Glu Val Gln Leu Glu Ser Leu Arg Gln Arg Glu Ala
        355                 360                 365

Asp Leu Ser Ser Ala Arg His Arg
    370                 375


<210> SEQ ID NO 189
<211> LENGTH: 160
<212> TYPE: PRT
<213> ORGANISM: Homo sapien

<400> SEQUENCE: 189

Met Leu Glu Ala His Arg Arg Gln Arg His Pro Phe Leu Leu Leu Gly
 1               5                  10                  15

Thr Thr Ala Asn Arg Thr Gln Ser Leu Asn Tyr Gly Cys Ile Val Glu
            20                  25                  30

Asn Pro Gln Thr His Glu Val Leu His Tyr Val Glu Lys Pro Ser Thr
        35                  40                  45

Phe Ile Ser Asp Ile Ile Asn Cys Gly Ile Tyr Leu Phe Ser Pro Glu
    50                  55                  60

Ala Leu Lys Pro Leu Arg Asp Val Phe Gln Arg Asn Gln Gln Asp Gly
65                  70                  75                  80

Gln Leu Glu Asp Ser Pro Gly Leu Trp Pro Gly Ala Gly Thr Ile Arg
                85                  90                  95

Leu Glu Gln Asp Val Phe Ser Ala Leu Ala Gly Gln Gly Gln Ile Tyr
            100                 105                 110

Val His Leu Thr Asp Gly Ile Trp Ser Gln Ile Lys Ser Ala Gly Ser
        115                 120                 125

Ala Leu Tyr Ala Ser Arg Leu Tyr Leu Ser Arg Tyr Gln Asp Thr His
    130                 135                 140

Pro Glu Arg Leu Ala Lys His Thr Pro Gly Gly Pro Trp Ile Arg Gly
145                 150                 155                 160


<210> SEQ ID NO 190
<211> LENGTH: 146
<212> TYPE: PRT
<213> ORGANISM: Homo sapien

<400> SEQUENCE: 190

Met Asp Pro Arg Ala Ser Leu Leu Leu Leu Gly Asn Val Tyr Ile His
 1               5                  10                  15

Pro Thr Ala Lys Val Ala Pro Ser Ala Val Leu Gly Pro Asn Val Ser
            20                  25                  30

Ile Gly Lys Gly Val Thr Val Gly Glu Gly Val Arg Leu Arg Glu Ser
        35                  40                  45

Ile Val Leu His Gly Ala Thr Leu Gln Glu His Thr Cys Val Leu His
    50                  55                  60

Ser Ile Val Gly Trp Gly Ser Thr Val Gly Arg Trp Ala Arg Val Glu
65                  70                  75                  80
```

-continued

```
Gly Thr Pro Ser Asp Pro Asn Pro Asn Asp Pro Arg Ala Arg Met Asp
                85                  90                  95

Ser Glu Ser Leu Phe Lys Asp Gly Lys Leu Leu Pro Ala Ile Thr Ile
            100                 105                 110

Leu Gly Cys Arg Val Arg Ile Pro Ala Glu Val Leu Ile Leu Asn Ser
        115                 120                 125

Ile Val Leu Pro His Lys Glu Leu Ser Arg Ser Phe Thr Asn Gln Ile
    130                 135                 140

Ile Leu
145


<210> SEQ ID NO 191
<211> LENGTH: 704
<212> TYPE: PRT
<213> ORGANISM: Homo sapien

<400> SEQUENCE: 191

Glu Gly Gly Cys Ala Ala Gly Arg Gly Arg Glu Leu Glu Pro Glu Leu
 1               5                  10                  15

Glu Pro Gly Pro Gly Pro Gly Ser Ala Leu Glu Pro Gly Glu Glu Phe
            20                  25                  30

Glu Ile Val Asp Arg Ser Gln Leu Pro Gly Pro Gly Asp Leu Arg Ser
        35                  40                  45

Ala Thr Arg Pro Arg Ala Ala Glu Gly Trp Ser Ala Pro Ile Leu Thr
    50                  55                  60

Leu Ala Arg Arg Ala Thr Gly Asn Leu Ser Ala Ser Cys Gly Ser Ala
65                  70                  75                  80

Leu Arg Ala Ala Ala Gly Leu Gly Gly Gly Asp Ser Gly Asp Gly Thr
                85                  90                  95

Ala Arg Ala Ala Ser Lys Cys Gln Met Met Glu Glu Arg Ala Asn Leu
            100                 105                 110

Met His Met Met Lys Leu Ser Ile Lys Val Leu Leu Gln Ser Ala Leu
        115                 120                 125

Ser Leu Gly Arg Ser Leu Asp Ala Asp His Ala Pro Leu Gln Gln Phe
    130                 135                 140

Phe Val Val Met Glu His Cys Leu Lys His Gly Leu Lys Val Lys Lys
145                 150                 155                 160

Ser Phe Ile Gly Gln Asn Lys Ser Phe Phe Gly Pro Leu Glu Leu Val
                165                 170                 175

Glu Lys Leu Cys Pro Glu Ala Ser Asp Ile Ala Thr Ser Val Arg Asn
            180                 185                 190

Leu Pro Glu Leu Lys Thr Ala Val Gly Arg Gly Arg Ala Trp Leu Tyr
        195                 200                 205

Leu Ala Leu Met Gln Lys Lys Leu Ala Asp Tyr Leu Lys Val Leu Ile
    210                 215                 220

Asp Asn Lys His Leu Leu Ser Glu Phe Tyr Glu Pro Glu Ala Leu Met
225                 230                 235                 240

Met Glu Glu Glu Gly Met Val Ile Val Gly Leu Leu Val Gly Leu Asn
                245                 250                 255

Val Leu Asp Ala Asn Leu Cys Leu Lys Gly Glu Asp Leu Asp Ser Gln
            260                 265                 270

Val Gly Val Ile Asp Phe Ser Leu Tyr Leu Lys Asp Val Gln Asp Leu
        275                 280                 285

Asp Gly Gly Lys Glu His Glu Arg Ile Thr Asp Val Leu Asp Gln Lys
    290                 295                 300
```

-continued

```
Asn Tyr Val Glu Glu Leu Asn Arg His Leu Ser Cys Thr Val Gly Asp
305                 310                 315                 320

Leu Gln Thr Lys Ile Asp Gly Leu Glu Lys Thr Asn Ser Lys Leu Gln
                325                 330                 335

Glu Glu Leu Ser Ala Ala Thr Asp Arg Ile Cys Ser Leu Gln Glu Glu
            340                 345                 350

Gln Gln Gln Leu Arg Glu Gln Asn Glu Leu Ile Arg Glu Arg Ser Glu
        355                 360                 365

Lys Ser Val Glu Ile Thr Lys Gln Asp Thr Lys Val Glu Leu Glu Thr
    370                 375                 380

Tyr Lys Gln Thr Arg Gln Gly Leu Asp Glu Met Tyr Ser Asp Val Trp
385                 390                 395                 400

Lys Gln Leu Lys Glu Glu Lys Lys Val Arg Leu Glu Leu Glu Lys Glu
                405                 410                 415

Leu Glu Leu Gln Ile Gly Met Lys Thr Glu Met Glu Ile Ala Met Lys
            420                 425                 430

Leu Leu Glu Lys Asp Thr His Glu Lys Gln Asp Thr Leu Val Ala Leu
        435                 440                 445

Arg Gln Gln Leu Glu Glu Val Lys Ala Ile Asn Leu Gln Met Phe His
    450                 455                 460

Lys Ala Gln Asn Ala Glu Ser Ser Leu Gln Gln Lys Asn Glu Ala Ile
465                 470                 475                 480

Thr Ser Phe Glu Gly Lys Thr Asn Gln Val Met Ser Ser Met Lys Gln
                485                 490                 495

Met Glu Glu Arg Leu Gln His Ser Glu Arg Ala Arg Gln Gly Ala Glu
            500                 505                 510

Glu Arg Ser His Lys Leu Gln Gln Glu Leu Gly Gly Arg Ile Gly Ala
        515                 520                 525

Leu Gln Leu Gln Leu Ser Gln Leu His Glu Gln Cys Ser Ser Leu Glu
    530                 535                 540

Lys Glu Leu Lys Ser Glu Lys Glu Gln Arg Gln Ala Leu Gln Arg Glu
545                 550                 555                 560

Leu Gln His Glu Lys Asp Thr Ser Ser Leu Leu Arg Met Glu Leu Gln
                565                 570                 575

Gln Val Glu Gly Leu Lys Lys Glu Leu Arg Glu Leu Gln Asp Glu Lys
            580                 585                 590

Ala Glu Leu Gln Lys Ile Cys Glu Glu Gln Glu Gln Ala Leu Gln Glu
        595                 600                 605

Met Gly Leu His Leu Ser Gln Ser Lys Leu Lys Met Glu Asp Ile Lys
    610                 615                 620

Glu Val Asn Gln Ala Leu Lys Gly His Ala Trp Leu Lys Asp Asp Glu
625                 630                 635                 640

Ala Thr His Cys Arg Gln Cys Glu Lys Glu Phe Ser Ile Ser Arg Arg
                645                 650                 655

Lys His His Cys Arg Asn Cys Gly His Ile Phe Cys Asn Thr Cys Ser
            660                 665                 670

Ser Asn Glu Leu Ala Leu Pro Ser Tyr Pro Lys Pro Val Arg Val Cys
        675                 680                 685

Asp Ser Cys His Thr Leu Leu Leu Gln Arg Cys Ser Ser Thr Ala Ser
    690                 695                 700
```

<210> SEQ ID NO 192
<211> LENGTH: 331

-continued

<212> TYPE: PRT
<213> ORGANISM: Homo sapien

<400> SEQUENCE: 192

```
Arg Ala Gly Ala Ser Ala Met Ala Leu Arg Lys Glu Leu Leu Lys Ser
 1               5                  10                  15

Ile Trp Tyr Ala Phe Thr Ala Leu Asp Val Glu Lys Ser Gly Lys Val
            20                  25                  30

Ser Lys Ser Gln Leu Lys Val Leu Ser His Asn Leu Tyr Thr Val Leu
        35                  40                  45

His Ile Pro His Asp Pro Val Ala Leu Glu Glu His Phe Arg Asp Asp
    50                  55                  60

Asp Asp Gly Pro Val Ser Ser Gln Gly Tyr Met Pro Tyr Leu Asn Lys
65                  70                  75                  80

Tyr Ile Leu Asp Lys Val Glu Glu Gly Ala Phe Val Lys Glu His Phe
                85                  90                  95

Asp Glu Leu Cys Trp Thr Leu Thr Ala Lys Lys Asn Tyr Arg Ala Asp
            100                 105                 110

Ser Asn Gly Asn Ser Met Leu Ser Asn Gln Asp Ala Phe Arg Leu Trp
        115                 120                 125

Cys Leu Phe Asn Phe Leu Ser Glu Asp Lys Tyr Pro Leu Ile Met Val
    130                 135                 140

Pro Asp Glu Val Glu Tyr Leu Leu Lys Lys Val Leu Ser Ser Met Ser
145                 150                 155                 160

Leu Glu Val Ser Leu Gly Glu Leu Glu Glu Leu Leu Ala Gln Glu Ala
                165                 170                 175

Gln Val Ala Gln Thr Thr Gly Gly Leu Ser Val Trp Gln Phe Leu Glu
            180                 185                 190

Leu Phe Asn Ser Gly Arg Cys Leu Arg Gly Val Gly Arg Asp Thr Leu
        195                 200                 205

Ser Met Ala Ile His Glu Val Tyr Gln Glu Leu Ile Gln Asp Val Leu
    210                 215                 220

Lys Gln Gly Tyr Leu Trp Lys Arg Gly His Leu Arg Arg Asn Trp Ala
225                 230                 235                 240

Glu Arg Trp Phe Gln Leu Gln Pro Ser Cys Leu Cys Tyr Phe Gly Ser
                245                 250                 255

Glu Glu Cys Lys Glu Lys Arg Gly Ile Ile Pro Leu Asp Ala His Cys
            260                 265                 270

Cys Val Glu Val Leu Pro Asp Arg Asp Gly Lys Arg Cys Met Phe Cys
        275                 280                 285

Val Lys Thr Ala Thr Arg Thr Tyr Glu Met Ser Ala Ser Asp Thr Arg
    290                 295                 300

Gln Arg Gln Glu Trp Thr Ala Ala Ile Gln Met Ala Ile Arg Leu Gln
305                 310                 315                 320

Ala Glu Gly Lys Thr Ser Leu His Lys Asp Leu
                325                 330
```

<210> SEQ ID NO 193
<211> LENGTH: 475
<212> TYPE: PRT
<213> ORGANISM: Homo sapien

<400> SEQUENCE: 193

```
Lys Asn Ser Pro Leu Leu Ser Val Ser Ser Gln Thr Ile Thr Lys Glu
 1               5                  10                  15
```

-continued

```
Asn Asn Arg Asn Val His Leu Glu His Ser Glu Gln Asn Pro Gly Ser
            20                  25                  30

Ser Ala Gly Asp Thr Ser Ala Ala His Gln Val Val Leu Gly Glu Asn
        35                  40                  45

Leu Ile Ala Thr Ala Leu Cys Leu Ser Gly Ser Gly Ser Gln Ser Asp
    50                  55                  60

Leu Lys Asp Val Ala Ser Thr Ala Gly Glu Glu Gly Asp Thr Ser Leu
65                  70                  75                  80

Arg Glu Ser Leu His Pro Val Thr Arg Ser Leu Lys Ala Gly Cys His
                85                  90                  95

Thr Lys Gln Leu Ala Ser Arg Asn Cys Ser Glu Glu Lys Ser Pro Gln
            100                 105                 110

Thr Ser Ile Leu Lys Glu Gly Asn Arg Asp Thr Ser Leu Asp Phe Arg
        115                 120                 125

Pro Val Val Ser Pro Ala Asn Gly Val Glu Gly Val Arg Val Asp Gln
    130                 135                 140

Asp Asp Asp Gln Asp Ser Ser Ser Leu Lys Leu Ser Gln Asn Ile Ala
145                 150                 155                 160

Val Gln Thr Asp Phe Lys Thr Ala Asp Ser Glu Val Asn Thr Asp Gln
                165                 170                 175

Asp Ile Glu Lys Asn Leu Asp Lys Met Met Thr Glu Arg Thr Leu Leu
            180                 185                 190

Lys Glu Arg Tyr Gln Glu Val Leu Asp Lys Gln Arg Gln Val Glu Asn
        195                 200                 205

Gln Leu Gln Val Gln Leu Lys Gln Leu Gln Gln Arg Arg Glu Glu Glu
    210                 215                 220

Met Lys Asn His Gln Glu Ile Leu Lys Ala Ile Gln Asp Val Thr Ile
225                 230                 235                 240

Lys Arg Glu Glu Thr Lys Lys Lys Ile Glu Lys Glu Lys Lys Glu Phe
                245                 250                 255

Leu Gln Lys Glu Gln Asp Leu Lys Ala Glu Ile Glu Lys Leu Cys Glu
            260                 265                 270

Lys Gly Arg Arg Glu Val Trp Glu Met Glu Leu Asp Arg Leu Lys Asn
        275                 280                 285

Gln Asp Gly Glu Ile Asn Arg Asn Ile Met Glu Glu Thr Glu Arg Ala
    290                 295                 300

Trp Lys Ala Glu Ile Leu Ser Leu Glu Ser Arg Lys Glu Leu Leu Val
305                 310                 315                 320

Leu Lys Leu Glu Glu Ala Glu Lys Glu Ala Glu Leu His Leu Thr Tyr
                325                 330                 335

Leu Lys Ser Thr Pro Pro Thr Leu Glu Thr Val Arg Ser Lys Gln Glu
            340                 345                 350

Trp Glu Thr Arg Leu Asn Gly Val Arg Ile Met Lys Lys Asn Val Arg
        355                 360                 365

Asp Gln Phe Asn Ser His Ile Gln Leu Val Arg Asn Gly Ala Lys Leu
    370                 375                 380

Ser Ser Leu Pro Gln Ile Pro Thr Pro Thr Leu Pro Pro Pro Pro Ser
385                 390                 395                 400

Glu Thr Asp Phe Met Leu Gln Val Phe Gln Pro Ser Pro Ser Leu Ala
                405                 410                 415

Pro Arg Met Pro Phe Ser Ile Gly Gln Val Thr Met Pro Met Val Met
            420                 425                 430

Pro Ser Ala Asp Pro Arg Ser Leu Ser Phe Pro Ile Leu Asn Pro Ala
```

-continued

```
        435                 440                 445

Leu Ser Gln Pro Ser Gln Pro Ser Ser Pro Leu Pro Gly Ser His Gly
    450                 455                 460

Arg Asn Ser Pro Gly Leu Gly Ser Leu Val Ser
465                 470                 475


<210> SEQ ID NO 194
<211> LENGTH: 241
<212> TYPE: PRT
<213> ORGANISM: Homo sapien

<400> SEQUENCE: 194

Met Ser Gly Glu Ser Ala Arg Ser Leu Gly Lys Gly Ser Ala Pro Pro
 1               5                  10                  15

Gly Pro Val Pro Glu Gly Ser Ile Arg Ile Tyr Ser Met Arg Phe Cys
            20                  25                  30

Pro Phe Ala Glu Arg Thr Arg Leu Val Leu Lys Ala Lys Gly Ile Arg
        35                  40                  45

His Glu Val Ile Asn Ile Asn Leu Lys Asn Lys Pro Glu Trp Phe Phe
    50                  55                  60

Lys Lys Asn Pro Phe Gly Leu Val Pro Val Leu Glu Asn Ser Gln Gly
65                  70                  75                  80

Gln Leu Ile Tyr Glu Ser Ala Ile Thr Cys Glu Tyr Leu Asp Glu Ala
                85                  90                  95

Tyr Pro Gly Lys Lys Leu Leu Pro Asp Asp Pro Tyr Glu Lys Ala Cys
            100                 105                 110

Gln Lys Met Ile Leu Glu Leu Phe Ser Lys Val Pro Ser Leu Val Gly
        115                 120                 125

Ser Phe Ile Arg Ser Gln Asn Lys Glu Asp Tyr Ala Gly Leu Lys Glu
    130                 135                 140

Glu Phe Arg Lys Glu Phe Thr Lys Leu Glu Glu Val Leu Thr Asn Lys
145                 150                 155                 160

Lys Thr Thr Phe Phe Gly Gly Asn Ser Ile Ser Met Ile Asp Tyr Leu
                165                 170                 175

Ile Trp Pro Trp Phe Glu Arg Leu Glu Ala Met Lys Leu Asn Glu Cys
            180                 185                 190

Val Asp His Thr Pro Lys Leu Lys Leu Trp Met Ala Ala Met Lys Glu
        195                 200                 205

Asp Pro Thr Val Ser Ala Leu Leu Thr Ser Glu Lys Asp Trp Gln Gly
    210                 215                 220

Phe Leu Glu Leu Tyr Leu Gln Asn Ser Pro Glu Ala Cys Asp Tyr Gly
225                 230                 235                 240

Leu


<210> SEQ ID NO 195
<211> LENGTH: 138
<212> TYPE: PRT
<213> ORGANISM: Homo sapien

<400> SEQUENCE: 195

Gln Thr Lys Ile Leu Glu Glu Asp Leu Glu Gln Ile Lys Leu Ser Leu
 1               5                  10                  15

Arg Glu Arg Gly Arg Glu Leu Thr Thr Gln Arg Gln Leu Met Gln Glu
            20                  25                  30

Arg Ala Glu Glu Gly Lys Gly Pro Ser Lys Ala Gln Arg Gly Ser Leu
        35                  40                  45
```

-continued

```
Glu His Met Lys Leu Ile Leu Arg Asp Lys Glu Lys Glu Val Glu Cys
    50                  55                  60

Gln Gln Glu His Ile His Glu Leu Gln Glu Leu Lys Asp Gln Leu Glu
65                  70                  75                  80

Gln Gln Leu Gln Gly Leu His Arg Lys Val Gly Glu Thr Ser Leu Leu
                85                  90                  95

Leu Ser Gln Arg Glu Gln Glu Ile Val Val Leu Gln Gln Gln Leu Gln
            100                 105                 110

Glu Ala Arg Glu Gln Gly Glu Leu Lys Glu Gln Ser Leu Gln Ser Gln
        115                 120                 125

Leu Asp Glu Ala Gln Arg Ala Leu Ala Gln
    130                 135


<210> SEQ ID NO 196
<211> LENGTH: 102
<212> TYPE: PRT
<213> ORGANISM: Homo sapien

<400> SEQUENCE: 196

Met Ser Lys Arg Lys Ala Pro Gln Glu Thr Leu Asn Gly Gly Ile Thr
 1               5                  10                  15

Asp Met Leu Thr Glu Leu Ala Asn Phe Glu Lys Asn Val Ser Gln Ala
            20                  25                  30

Ile His Lys Tyr Asn Ala Tyr Arg Lys Ala Ala Ser Val Ile Ala Lys
        35                  40                  45

Tyr Pro His Lys Ile Lys Ser Gly Ala Glu Ala Lys Lys Leu Pro Gly
    50                  55                  60

Val Gly Thr Lys Ile Ala Glu Lys Ile Asp Glu Phe Leu Ala Thr Gly
65                  70                  75                  80

Lys Leu Arg Lys Leu Glu Lys Ile Arg Gln Asp Asp Thr Ser Ser Ser
                85                  90                  95

Ile Asn Phe Leu Thr Arg
            100


<210> SEQ ID NO 197
<211> LENGTH: 138
<212> TYPE: PRT
<213> ORGANISM: Homo sapien

<400> SEQUENCE: 197

Glu Ala Asn Glu Val Thr Asp Ser Ala Tyr Met Gly Ser Glu Ser Thr
 1               5                  10                  15

Tyr Ser Glu Cys Glu Thr Phe Thr Asp Glu Asp Thr Ser Thr Leu Val
            20                  25                  30

His Pro Glu Leu Gln Pro Glu Gly Asp Ala Asp Ser Ala Gly Gly Ser
        35                  40                  45

Ala Val Pro Ser Glu Cys Leu Asp Ala Met Glu Glu Pro Asp His Gly
    50                  55                  60

Ala Leu Leu Leu Leu Pro Gly Arg Pro His Pro His Gly Gln Ser Val
65                  70                  75                  80

Ile Thr Val Ile Gly Gly Glu Glu His Phe Glu Asp Tyr Gly Glu Gly
                85                  90                  95

Ser Glu Ala Glu Leu Ser Pro Glu Thr Leu Cys Asn Gly Gln Leu Gly
            100                 105                 110

Cys Ser Asp Pro Ala Phe Leu Thr Pro Ser Pro Thr Lys Arg Leu Ser
        115                 120                 125
```

-continued

```
Ser Lys Lys Val Ala Arg Tyr Leu His Gln
    130                 135


<210> SEQ ID NO 198
<211> LENGTH: 100
<212> TYPE: PRT
<213> ORGANISM: Homo sapien

<400> SEQUENCE: 198

Met Gly Asp Val Lys Asn Phe Leu Tyr Ala Trp Cys Gly Lys Arg Lys
 1               5                  10                  15

Met Thr Pro Ser Tyr Glu Ile Arg Ala Val Gly Asn Lys Asn Arg Gln
            20                  25                  30

Lys Phe Met Cys Glu Val Gln Val Glu Gly Tyr Asn Tyr Thr Gly Met
        35                  40                  45

Gly Asn Ser Thr Asn Lys Lys Asp Ala Gln Ser Asn Ala Ala Arg Asp
    50                  55                  60

Phe Val Asn Tyr Leu Val Arg Ile Asn Glu Ile Lys Ser Glu Glu Val
65                  70                  75                  80

Pro Ala Phe Gly Val Ala Ser Pro Pro Pro Leu Thr Asp Thr Pro Asp
                85                  90                  95

Thr Thr Ala Asn
            100


<210> SEQ ID NO 199
<211> LENGTH: 127
<212> TYPE: PRT
<213> ORGANISM: Homo sapien

<400> SEQUENCE: 199

Met Val Lys Glu Thr Thr Tyr Tyr Asp Val Leu Gly Val Lys Pro Asn
 1               5                  10                  15

Ala Thr Gln Glu Glu Leu Lys Lys Ala Tyr Arg Lys Leu Ala Leu Lys
            20                  25                  30

Tyr His Pro Asp Lys Asn Pro Asn Glu Gly Glu Lys Phe Lys Gln Ile
        35                  40                  45

Ser Gln Ala Tyr Glu Val Leu Ser Asp Ala Lys Lys Arg Glu Leu Tyr
    50                  55                  60

Asp Lys Gly Gly Glu Gln Ala Ile Lys Glu Gly Gly Ala Gly Gly Gly
65                  70                  75                  80

Phe Gly Ser Pro Met Asp Ile Phe Asp Met Phe Phe Gly Gly Gly Gly
                85                  90                  95

Arg Met Gln Arg Glu Arg Arg Gly Lys Asn Val Val His Gln Leu Ser
            100                 105                 110

Val Thr Leu Glu Asp Leu Tyr Asn Gly Ala Thr Arg Lys Leu Ala
        115                 120                 125


<210> SEQ ID NO 200
<211> LENGTH: 90
<212> TYPE: PRT
<213> ORGANISM: Homo sapien

<400> SEQUENCE: 200

Met Ala Cys Pro Leu Asp Gln Ala Ile Gly Leu Leu Val Ala Ile Phe
 1               5                  10                  15

His Lys Tyr Ser Gly Arg Glu Gly Asp Lys His Thr Leu Ser Lys Lys
            20                  25                  30
```

-continued

```
Glu Leu Lys Glu Leu Ile Gln Lys Glu Leu Thr Ile Gly Ser Lys Leu
        35                  40                  45

Gln Asp Ala Glu Ile Ala Arg Leu Met Glu Asp Leu Asp Arg Asn Lys
    50                  55                  60

Asp Gln Glu Val Asn Phe Gln Glu Tyr Val Thr Phe Leu Gly Ala Leu
65                  70                  75                  80

Ala Leu Ile Tyr Asn Glu Ala Leu Lys Gly
                85                  90


<210> SEQ ID NO 201
<211> LENGTH: 120
<212> TYPE: PRT
<213> ORGANISM: Homo sapien

<400> SEQUENCE: 201

Met Glu Thr Pro Ser Gln Arg Arg Ala Thr Arg Ser Gly Ala Gln Ala
 1               5                  10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn
        115                 120


<210> SEQ ID NO 202
<211> LENGTH: 177
<212> TYPE: PRT
<213> ORGANISM: Homo sapien

<400> SEQUENCE: 202

Met Ala Ala Gly Val Glu Ala Ala Ala Glu Val Ala Ala Thr Glu Ile
 1               5                  10                  15

Lys Met Glu Glu Glu Ser Gly Ala Pro Gly Val Pro Ser Gly Asn Gly
            20                  25                  30

Ala Pro Gly Pro Lys Gly Glu Gly Glu Arg Pro Ala Gln Asn Glu Lys
        35                  40                  45

Arg Lys Glu Lys Asn Ile Lys Arg Gly Gly Asn Arg Phe Glu Pro Tyr
    50                  55                  60

Ala Asn Pro Thr Lys Arg Tyr Arg Ala Phe Ile Thr Asn Ile Pro Phe
65                  70                  75                  80

Asp Val Lys Trp Gln Ser Leu Lys Asp Leu Val Lys Glu Lys Val Gly
                85                  90                  95

Glu Val Thr Tyr Val Glu Leu Leu Met Asp Ala Glu Gly Lys Ser Arg
            100                 105                 110

Gly Cys Ala Val Val Glu Phe Lys Met Glu Glu Ser Met Lys Lys Ala
        115                 120                 125

Ala Glu Val Leu Asn Lys His Ser Leu Ser Gly Arg Pro Leu Lys Val
    130                 135                 140
```

-continued

Lys Glu Asp Pro Asp Gly Glu His Ala Arg Arg Ala Met Gln Lys Ala
145 150 155 160

Gly Arg Leu Gly Ser Thr Val Phe Val Ala Asn Leu Asp Tyr Lys Val
165 170 175

Gly

<210> SEQ ID NO 203
<211> LENGTH: 164
<212> TYPE: PRT
<213> ORGANISM: Homo sapien

<400> SEQUENCE: 203

Met Arg Leu Ala Val Gly Ala Leu Leu Val Cys Ala Val Leu Gly Leu
1 5 10 15

Cys Leu Ala Val Pro Asp Lys Thr Val Arg Trp Cys Ala Val Ser Glu
20 25 30

His Glu Ala Thr Lys Cys Gln Ser Phe Arg Asp His Met Lys Ser Val
35 40 45

Ile Pro Ser Asp Gly Pro Ser Val Ala Cys Val Lys Lys Ala Ser Tyr
50 55 60

Leu Asp Cys Ile Arg Ala Ile Ala Ala Asn Glu Ala Asp Ala Val Thr
65 70 75 80

Leu Asp Ala Gly Leu Val Tyr Asp Ala Tyr Leu Ala Pro Asn Asn Leu
85 90 95

Lys Pro Val Val Ala Glu Phe Tyr Gly Ser Lys Glu Asp Pro Gln Thr
100 105 110

Phe Tyr Tyr Ala Val Ala Val Val Lys Lys Asp Ser Gly Phe Gln Met
115 120 125

Asn Gln Leu Arg Gly Lys Lys Ser Cys His Thr Gly Leu Gly Arg Ser
130 135 140

Ala Gly Trp Asn Ile Pro Ile Gly Leu Leu Tyr Cys Asp Leu Pro Glu
145 150 155 160

Pro Arg Lys Pro

<210> SEQ ID NO 204
<211> LENGTH: 241
<212> TYPE: PRT
<213> ORGANISM: Homo sapien

<400> SEQUENCE: 204

Met Ser Gly Glu Ser Ala Arg Ser Leu Gly Lys Gly Ser Ala Pro Pro
1 5 10 15

Gly Pro Val Pro Glu Gly Ser Ile Arg Ile Tyr Ser Met Arg Phe Cys
20 25 30

Pro Phe Ala Glu Arg Thr Arg Leu Val Leu Lys Ala Lys Gly Ile Arg
35 40 45

His Glu Val Ile Asn Ile Asn Leu Lys Asn Lys Pro Glu Trp Phe Phe
50 55 60

Lys Lys Asn Pro Phe Gly Leu Val Pro Val Leu Glu Asn Ser Gln Gly
65 70 75 80

Gln Leu Ile Tyr Glu Ser Ala Ile Thr Cys Glu Tyr Leu Asp Glu Ala
85 90 95

Tyr Pro Gly Lys Lys Leu Leu Pro Asp Asp Pro Tyr Glu Lys Ala Cys
100 105 110

Gln Lys Met Ile Leu Glu Leu Phe Ser Lys Val Pro Ser Leu Val Gly
115 120 125

-continued

```
Ser Phe Ile Arg Ser Gln Asn Lys Glu Asp Tyr Asp Gly Leu Lys Glu
    130                 135                 140

Glu Phe Arg Lys Glu Phe Thr Lys Leu Glu Glu Val Leu Thr Asn Lys
145                 150                 155                 160

Lys Thr Thr Phe Phe Gly Gly Asn Ser Ile Ser Met Ile Asp Tyr Leu
                165                 170                 175

Ile Trp Pro Trp Phe Glu Arg Leu Glu Ala Met Lys Leu Asn Glu Cys
            180                 185                 190

Val Asp His Thr Pro Lys Leu Lys Leu Trp Met Ala Ala Met Lys Glu
        195                 200                 205

Asp Pro Thr Val Ser Ala Leu Leu Thr Ser Glu Lys Asp Trp Gln Gly
    210                 215                 220

Phe Leu Glu Leu Tyr Leu Gln Asn Ser Pro Glu Ala Cys Asp Tyr Gly
225                 230                 235                 240

Leu


<210> SEQ ID NO 205
<211> LENGTH: 160
<212> TYPE: PRT
<213> ORGANISM: Homo sapien

<400> SEQUENCE: 205

Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160


<210> SEQ ID NO 206
<211> LENGTH: 197
<212> TYPE: PRT
<213> ORGANISM: Homo sapien

<400> SEQUENCE: 206

Thr Ser Pro Ser Glu Ala Cys Ala Pro Leu Leu Ile Ser Leu Ser Thr
 1               5                  10                  15

Leu Ile Tyr Asn Gly Ala Leu Pro Cys Gln Cys Asn Pro Gln Gly Ser
            20                  25                  30

Leu Ser Ser Glu Cys Asn Pro His Gly Gly Gln Cys Leu Cys Lys Pro
        35                  40                  45
```

-continued

```
Gly Val Val Gly Arg Arg Cys Asp Leu Cys Ala Pro Gly Tyr Tyr Gly
    50                  55                  60

Phe Gly Pro Thr Gly Cys Gln Gly Ala Cys Leu Gly Cys Arg Asp His
65                  70                  75                  80

Thr Gly Gly Glu His Cys Glu Arg Cys Ile Ala Gly Phe His Gly Asp
                85                  90                  95

Pro Arg Leu Pro Tyr Gly Gly Gln Cys Arg Pro Cys Pro Cys Pro Glu
            100                 105                 110

Gly Pro Gly Ser Gln Arg His Phe Ala Thr Ser Cys His Gln Asp Glu
        115                 120                 125

Tyr Ser Gln Gln Ile Val Cys His Cys Arg Ala Gly Tyr Thr Gly Leu
    130                 135                 140

Arg Cys Glu Ala Cys Ala Pro Gly His Phe Gly Asp Pro Ser Arg Pro
145                 150                 155                 160

Gly Gly Arg Cys Gln Leu Cys Glu Cys Ser Gly Asn Ile Asp Pro Met
                165                 170                 175

Asp Pro Asp Ala Cys Asp Pro His Thr Gly Gln Cys Leu Arg Cys Leu
            180                 185                 190

His His Thr Glu Gly
        195
```

<210> SEQ ID NO 207
<211> LENGTH: 175
<212> TYPE: PRT
<213> ORGANISM: Homo sapien

<400> SEQUENCE: 207

```
Ile Ile Arg Gln Gln Gly Leu Ala Ser Tyr Asp Tyr Val Arg Arg Arg
 1               5                  10                  15

Leu Thr Ala Glu Asp Leu Phe Glu Ala Arg Ile Ile Ser Leu Glu Thr
            20                  25                  30

Tyr Asn Leu Leu Arg Glu Gly Thr Arg Ser Leu Arg Glu Ala Leu Glu
        35                  40                  45

Ala Glu Ser Ala Trp Cys Tyr Leu Tyr Gly Thr Gly Ser Val Ala Gly
    50                  55                  60

Val Tyr Leu Pro Gly Ser Arg Gln Thr Leu Ser Ile Tyr Gln Ala Leu
65                  70                  75                  80

Lys Lys Gly Leu Leu Ser Ala Glu Val Ala Arg Leu Leu Leu Glu Ala
                85                  90                  95

Gln Ala Ala Thr Gly Phe Leu Leu Asp Pro Val Lys Gly Glu Arg Leu
            100                 105                 110

Thr Val Asp Glu Ala Val Arg Lys Gly Leu Val Gly Pro Glu Leu His
        115                 120                 125

Asp Arg Leu Leu Ser Ala Glu Arg Ala Val Thr Gly Tyr Arg Asp Pro
    130                 135                 140

Tyr Thr Glu Gln Thr Ile Ser Leu Phe Gln Ala Met Lys Lys Glu Leu
145                 150                 155                 160

Ile Pro Thr Glu Glu Ala Leu Arg Leu Trp Met Pro Ser Trp Pro
                165                 170                 175
```

<210> SEQ ID NO 208
<211> LENGTH: 177
<212> TYPE: PRT
<213> ORGANISM: Homo sapien

<400> SEQUENCE: 208

-continued

```
Met Ala Ala Gly Val Glu Ala Ala Ala Glu Val Ala Ala Thr Glu Ile
 1               5                  10                  15

Lys Met Glu Glu Glu Ser Gly Ala Pro Gly Val Pro Ser Gly Asn Gly
            20                  25                  30

Ala Pro Gly Pro Lys Gly Glu Gly Glu Arg Pro Ala Gln Asn Glu Lys
        35                  40                  45

Arg Lys Glu Lys Asn Ile Lys Arg Gly Gly Asn Arg Phe Glu Pro Tyr
    50                  55                  60

Ala Asn Pro Thr Lys Arg Tyr Arg Ala Phe Ile Thr Asn Ile Pro Phe
65                  70                  75                  80

Asp Val Lys Trp Gln Ser Leu Lys Asp Leu Val Lys Glu Lys Val Gly
                85                  90                  95

Glu Val Thr Tyr Val Glu Leu Leu Met Asp Ala Glu Gly Lys Ser Arg
            100                 105                 110

Gly Cys Ala Val Val Glu Phe Lys Met Glu Glu Ser Met Lys Lys Ala
        115                 120                 125

Ala Glu Val Leu Asn Lys His Ser Leu Ser Gly Arg Pro Leu Lys Val
    130                 135                 140

Lys Glu Asp Pro Asp Gly Glu His Ala Arg Arg Ala Met Gln Lys Val
145                 150                 155                 160

Met Ala Thr Thr Gly Gly Met Gly Met Gly Pro Gly Gly Pro Gly Met
                165                 170                 175

Ile
```

<210> SEQ ID NO 209
<211> LENGTH: 196
<212> TYPE: PRT
<213> ORGANISM: Homo sapien

<400> SEQUENCE: 209

```
Asp Leu Gln Asp Met Phe Ile Val His Thr Ile Glu Glu Ile Glu Gly
 1               5                  10                  15

Leu Ile Ser Ala His Asp Gln Phe Lys Ser Thr Leu Pro Asp Ala Asp
            20                  25                  30

Arg Glu Arg Glu Ala Ile Leu Ala Ile His Lys Glu Ala Gln Arg Ile
        35                  40                  45

Ala Glu Ser Asn His Ile Lys Leu Ser Gly Ser Asn Pro Tyr Thr Thr
    50                  55                  60

Val Thr Pro Gln Ile Ile Asn Ser Lys Trp Glu Lys Val Gln Gln Leu
65                  70                  75                  80

Val Pro Lys Arg Asp His Ala Leu Leu Glu Glu Gln Ser Lys Gln Gln
                85                  90                  95

Ser Asn Glu His Leu Arg Arg Gln Phe Ala Ser Gln Ala Asn Val Val
            100                 105                 110

Gly Pro Trp Ile Gln Thr Lys Met Glu Glu Ile Gly Arg Ile Ser Ile
        115                 120                 125

Glu Met Asn Gly Thr Leu Glu Asp Gln Leu Ser His Leu Lys Gln Tyr
    130                 135                 140

Glu Arg Ser Ile Val Asp Tyr Lys Pro Asn Leu Asp Leu Leu Glu Gln
145                 150                 155                 160

Gln His Gln Leu Ile Gln Glu Ala Leu Ile Phe Asp Asn Lys His Thr
                165                 170                 175

Asn Tyr Thr Met Glu His Ile Arg Val Gly Trp Glu Gln Leu Leu Thr
            180                 185                 190
```

-continued

Thr Ile Ala Arg
        195

<210> SEQ ID NO 210
<211> LENGTH: 156
<212> TYPE: PRT
<213> ORGANISM: Homo sapien

<400> SEQUENCE: 210

Lys Leu Thr Ile Glu Ser Thr Pro Phe Asn Val Ala Glu Gly Lys Glu
1               5                   10                  15

Val Leu Leu Leu Ala His Asn Leu Pro Gln Asn Arg Ile Gly Tyr Ser
            20                  25                  30

Trp Tyr Lys Gly Glu Arg Val Asp Gly Asn Ser Leu Ile Val Gly Tyr
        35                  40                  45

Val Ile Gly Thr Gln Gln Ala Thr Pro Gly Pro Ala Tyr Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Val Gln Asn Thr Thr Tyr Leu Trp
    130                 135                 140

Trp Val Asn Gly Gln Ser Leu Pro Val Ser Pro Lys
145                 150                 155

<210> SEQ ID NO 211
<211> LENGTH: 92
<212> TYPE: PRT
<213> ORGANISM: Homo sapien

<400> SEQUENCE: 211

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly
                85                  90

<210> SEQ ID NO 212
<211> LENGTH: 142
<212> TYPE: PRT
<213> ORGANISM: Homo sapien

<400> SEQUENCE: 212

Glu Lys Gln Lys Asn Lys Glu Phe Ser Gln Thr Leu Glu Asn Glu Lys
1               5                   10                  15

Asn Thr Leu Leu Ser Gln Ile Ser Thr Lys Asp Gly Glu Leu Lys Met

-continued

```
            20                  25                  30

Leu Gln Glu Glu Val Thr Lys Met Asn Leu Leu Asn Gln Gln Ile Gln
        35                  40                  45

Glu Glu Leu Ser Arg Val Thr Lys Leu Lys Glu Thr Ala Glu Glu Glu
    50                  55                  60

Lys Asp Asp Leu Glu Glu Arg Leu Met Asn Gln Leu Ala Glu Leu Asn
65                  70                  75                  80

Gly Ser Ile Gly Asn Tyr Cys Gln Asp Val Thr Asp Ala Gln Ile Lys
                85                  90                  95

Asn Glu Leu Leu Glu Ser Glu Met Lys Asn Leu Lys Lys Cys Val Ser
            100                 105                 110

Glu Leu Glu Glu Glu Lys Gln Gln Leu Val Lys Glu Lys Thr Lys Val
        115                 120                 125

Glu Ser Glu Ile Arg Lys Glu Tyr Leu Glu Lys Ile Gln Gly
    130                 135                 140


<210> SEQ ID NO 213
<211> LENGTH: 142
<212> TYPE: PRT
<213> ORGANISM: Homo sapien

<400> SEQUENCE: 213

Gly Gly Tyr Gly Gly Gly Tyr Gly Gly Val Leu Thr Ala Ser Asp Gly
 1               5                  10                  15

Leu Leu Ala Gly Asn Glu Lys Leu Thr Met Gln Asn Leu Asn Asp Arg
            20                  25                  30

Leu Ala Ser Tyr Leu Asp Lys Val Arg Ala Leu Glu Ala Ala Asn Gly
        35                  40                  45

Glu Leu Glu Val Lys Ile Arg Asp Trp Tyr Gln Lys Gln Gly Pro Gly
    50                  55                  60

Pro Ser Arg Asp Tyr Ser His Tyr Tyr Thr Thr Ile Gln Asp Leu Arg
65                  70                  75                  80

Asp Lys Ile Leu Gly Ala Thr Ile Glu Asn Ser Arg Ile Val Leu Gln
                85                  90                  95

Ile Asp Asn Ala Arg Leu Ala Ala Asp Asp Phe Arg Thr Lys Phe Glu
            100                 105                 110

Thr Glu Gln Ala Leu Arg Met Ser Val Glu Ala Asp Ile Asn Gly Leu
        115                 120                 125

Arg Arg Val Leu Asp Glu Leu Thr Leu Ala Arg Thr Asp Leu
    130                 135                 140


<210> SEQ ID NO 214
<211> LENGTH: 129
<212> TYPE: PRT
<213> ORGANISM: Homo sapien

<400> SEQUENCE: 214

Val Met Arg Val Asp Phe Asn Val Pro Met Lys Asn Asn Gln Ile Thr
 1               5                  10                  15

Asn Asn Gln Arg Ile Lys Ala Ala Val Pro Ser Ile Lys Phe Cys Leu
            20                  25                  30

Asp Asn Gly Ala Lys Ser Val Val Leu Met Ser His Leu Gly Arg Pro
        35                  40                  45

Asp Gly Val Pro Met Pro Asp Lys Tyr Ser Leu Glu Pro Val Ala Val
    50                  55                  60

Glu Leu Arg Ser Leu Leu Gly Lys Asp Val Leu Phe Leu Lys Asp Cys
```

-continued

```
65                  70                  75                  80

Val Gly Pro Glu Val Glu Lys Ala Cys Ala Asn Pro Ala Ala Gly Ser
                85                  90                  95

Val Ile Leu Leu Glu Asn Leu Arg Phe His Val Glu Glu Glu Gly Lys
            100                 105                 110

Gly Lys Asp Ala Ser Gly Asn Lys Val Lys Ala Glu Pro Ala Lys Ile
        115                 120                 125

Glu


<210> SEQ ID NO 215
<211> LENGTH: 148
<212> TYPE: PRT
<213> ORGANISM: Homo sapien

<400> SEQUENCE: 215

Met Ala Thr Leu Lys Glu Lys Leu Ile Ala Pro Val Ala Glu Glu Glu
 1               5                  10                  15

Ala Thr Val Pro Asn Asn Lys Ile Thr Val Val Gly Val Gly Gln Val
            20                  25                  30

Gly Met Ala Cys Ala Ile Ser Ile Leu Gly Lys Ser Leu Ala Asp Glu
        35                  40                  45

Leu Ala Leu Val Asp Val Leu Glu Asp Lys Leu Lys Gly Glu Met Met
    50                  55                  60

Asp Leu Gln His Gly Ser Leu Phe Leu Gln Thr Pro Lys Ile Val Ala
65                  70                  75                  80

Asp Lys Asp Tyr Ser Val Thr Ala Asn Ser Lys Ile Val Val Val Thr
                85                  90                  95

Ala Gly Val Arg Gln Gln Glu Gly Glu Ser Arg Leu Asn Leu Val Gln
            100                 105                 110

Arg Asn Val Asn Val Phe Lys Phe Ile Ile Pro Gln Ile Val Lys Tyr
        115                 120                 125

Ser Pro Asp Cys Ile Ile Ile Val Val Ser Asn Pro Val Asp Ile Leu
    130                 135                 140

Thr Tyr Val Thr
145


<210> SEQ ID NO 216
<211> LENGTH: 527
<212> TYPE: PRT
<213> ORGANISM: Homo sapien

<400> SEQUENCE: 216

Gln Arg Ala Pro Gly Ile Glu Glu Lys Ala Ala Glu Asn Gly Ala Leu
 1               5                  10                  15

Gly Ser Pro Glu Arg Glu Glu Lys Val Leu Glu Asn Gly Glu Leu Thr
            20                  25                  30

Pro Pro Arg Arg Glu Glu Lys Ala Leu Glu Asn Gly Glu Leu Arg Ser
        35                  40                  45

Pro Glu Ala Gly Glu Lys Val Leu Val Asn Gly Gly Leu Thr Pro Pro
    50                  55                  60

Lys Ser Glu Asp Lys Val Ser Glu Asn Gly Gly Leu Arg Phe Pro Arg
65                  70                  75                  80

Asn Thr Glu Arg Pro Pro Glu Thr Gly Pro Trp Arg Ala Pro Gly Pro
                85                  90                  95

Trp Glu Lys Thr Pro Glu Ser Trp Gly Pro Ala Pro Thr Ile Gly Glu
            100                 105                 110
```

-continued

```
Pro Ala Pro Glu Thr Ser Leu Glu Arg Ala Pro Ala Pro Ser Ala Val
        115                 120                 125

Val Ser Ser Arg Asn Gly Gly Glu Thr Ala Pro Gly Pro Leu Gly Pro
    130                 135                 140

Ala Pro Lys Asn Gly Thr Leu Glu Pro Gly Thr Glu Arg Arg Ala Pro
145                 150                 155                 160

Glu Thr Gly Gly Ala Pro Arg Ala Pro Gly Ala Gly Arg Leu Asp Leu
                165                 170                 175

Gly Ser Gly Gly Arg Ala Pro Val Gly Thr Gly Thr Ala Pro Gly Gly
            180                 185                 190

Gly Pro Gly Ser Gly Val Asp Ala Lys Ala Gly Trp Val Asp Asn Thr
        195                 200                 205

Arg Pro Gln Pro Pro Pro Pro Pro Leu Pro Pro Pro Pro Glu Ala Gln
    210                 215                 220

Pro Arg Arg Leu Glu Pro Ala Pro Pro Arg Ala Arg Pro Glu Val Ala
225                 230                 235                 240

Pro Glu Gly Glu Pro Gly Ala Pro Asp Ser Arg Ala Gly Gly Asp Thr
                245                 250                 255

Ala Leu Ser Gly Asp Gly Asp Pro Pro Lys Pro Glu Arg Lys Gly Pro
            260                 265                 270

Glu Met Pro Arg Leu Phe Leu Asp Leu Gly Pro Pro Gln Gly Asn Ser
        275                 280                 285

Glu Gln Ile Lys Ala Arg Leu Ser Arg Leu Ser Leu Ala Leu Pro Pro
    290                 295                 300

Leu Thr Leu Thr Pro Phe Pro Gly Pro Gly Pro Arg Arg Pro Pro Trp
305                 310                 315                 320

Glu Gly Ala Asp Ala Gly Ala Ala Gly Gly Glu Ala Gly Gly Ala Gly
                325                 330                 335

Ala Pro Gly Pro Ala Glu Glu Asp Gly Glu Asp Glu Asp Glu Asp Glu
            340                 345                 350

Glu Glu Asp Glu Glu Ala Ala Ala Pro Gly Ala Ala Ala Gly Pro Arg
        355                 360                 365

Gly Pro Gly Arg Ala Arg Ala Ala Pro Val Pro Val Val Val Ser Ser
    370                 375                 380

Ala Asp Ala Asp Ala Ala Arg Pro Leu Arg Gly Leu Leu Lys Ser Pro
385                 390                 395                 400

Arg Gly Ala Asp Glu Pro Glu Asp Ser Glu Leu Glu Arg Lys Arg Lys
                405                 410                 415

Met Val Ser Phe His Gly Asp Val Thr Val Tyr Leu Phe Asp Gln Glu
            420                 425                 430

Thr Pro Thr Asn Glu Leu Ser Val Gln Ala Pro Pro Glu Gly Asp Thr
        435                 440                 445

Asp Pro Ser Thr Pro Pro Ala Pro Pro Thr Pro Pro His Pro Ala Thr
    450                 455                 460

Pro Gly Asp Gly Phe Pro Ser Asn Asp Ser Gly Phe Gly Gly Ser Phe
465                 470                 475                 480

Glu Trp Ala Glu Asp Phe Pro Leu Leu Pro Pro Pro Gly Pro Pro Leu
                485                 490                 495

Cys Phe Ser Arg Phe Ser Val Ser Pro Ala Leu Glu Thr Pro Gly Pro
            500                 505                 510

Pro Ala Arg Ala Pro Asp Ala Arg Pro Ala Gly Pro Val Glu Asn
        515                 520                 525
```

-continued

<210> SEQ ID NO 217
<211> LENGTH: 466
<212> TYPE: DNA
<213> ORGANISM: Homo sapien

<400> SEQUENCE: 217
gaatggtgcc tgtcctgctg tctctgctgc tgcttctggg tcctgctgtc ccccaggaga 60
accaagatgg tcgttactct ctgacctata tctacactgg gctgtccaag catgttgaag 120
acgtccccgc gtttcaggcc cttggctcac tcaatgacct ccagttcttt agatacaaca 180
gtaaagacag gaagtctcag cccatgggac tctggagaca ggtggaagga atggaggatt 240
ggaagcagga cagccaactt cagaaggcca gggaggacat ctttatggag accctgaaag 300
acatcgtgga gtattacaac gacagtaacg ggtctcacgt attgcaggga aggtttggtt 360
gtgagatcga gaataacaga agcagcggag cattctggaa atattactat gatggaaagg 420
actacattga attcaacaaa gaaatcccag cctgggtccc cttcga 466

<210> SEQ ID NO 218
<211> LENGTH: 381
<212> TYPE: DNA
<213> ORGANISM: Homo sapien

<400> SEQUENCE: 218
gagtttcctt cgcaagttca tgtggggtac cttcccaggc tgcctggctg accagctggt 60
tttaaagcgc cggggtaacc agttggagat ctgtgccgtg gtcctgaggc agttgtctcc 120
acacaagtac tacttcctcg tgggctacag tgaaactttg ctgtcctact tttacaaatg 180
tcctgtgcga ctccacctcc aaactgtgcc ctcaaaggtt gtgtataagt acctctagaa 240
caatcccctt ttttccatca agctgtagcc tgcagagaat ggaaacgtgg gaaaggaatg 300
gtatgtgggg gaaatgcatc ccctcagagg actgaggcat agtctctcat ctgctattga 360
ataaagacct tctatcttgt a 381

<210> SEQ ID NO 219
<211> LENGTH: 1293
<212> TYPE: DNA
<213> ORGANISM: Homo sapien

<400> SEQUENCE: 219
gaggggaggc gcatggcggg gatggcgctg gcgcgggcct ggaagcagat gtcctggttc 60
tactaccagt acctgctggt cacggcgctc tacatgctgg agccctggga gcggacggtg 120
ttcaattcca tgctggtttc cattgtgggg atggcactat acacaggata cgtcttcatg 180
ccccagcaca tcatggcgat attgcactac tttgaaatcg tacaatgacc aagatgcgac 240
caggatcaga ggttccttgg ggaagaccca ccctacgaag ttggaatgag accatcagat 300
gtgataagaa actcttctag atgtcaacat aaccaacctt ataaagacta aaattcatga 360
gtagaacagg aaaatcatcc tgactcatgt gttgtgttct ttatttttaa ttttcaaaga 420
ggctcttgta tagcagtttt tgtctatttt aacattgtag tcatttgtac tttgatatca 480
gtattttctt aacctttgtg actgtttcaa tattaccccc gtgaaagctt ttcttaatgt 540
aactttgagt acattttaat tgccttctat ttttaaaact caaaatcatt agttgggctt 600
tactgttctt gctattgtat ggcatataca tctgcctgga tatatttcta ctcttgacca 660
aagttttgta aagaacaata taagatttcg ggtaggggta tggggaggga agatatttta 720
ttgagaacta cttaacaaaa gatttatctg taagcttgaa ctcaggagta cagttttagc 780

-continued tatctagact ctaacagctt ttgctttaaa attattaaag tgtttcttaa tgaaaaagaa 840
aagatcttgc taaagttaaa ataaggaaca tttcaccttt taaatattta attcttatgt 900
ggacttattt ccagaaaact ttggtgataa ttcttgagac aaaaggtggt taagtagcat 960
tattatgtaa tgcttatata ccatagagtt tttaatagaa gagaaatcca tttcctccga 1020
gggtcactat taacaatgta cttccttaaa tttagtttaa tgattgtaat gggtgctgca 1080
tttgcacatt gcattaagtt atgatgagac gaattgttgt taaaaattat agcaaaaaga 1140
aatgtaaact tggttaaaat cctttcactc tttgtattgt ttttttaag gtttttattc 1200 cttaaatgta aaatgactac ctaatttttt gatgtaaata cattaaattc aaagagaaaa 1260
aaaatcaaaa aaaaaaaaaa aaaaaaactc gag 1293

<210> SEQ ID NO 220
<211> LENGTH: 983
<212> TYPE: DNA
<213> ORGANISM: Homo sapien

<400> SEQUENCE: 220
caggttattc tgatcctgcc gcctgtcttc cctgtaagag tggagcctcg aggtgtacct 60
taaagtgacc ggaatgttag agatgcaatt tgcagagctg gggcaaggaa gggctccttg 120
tcactgtagt tactttcctt gcagtggcca aatgcccaat aagaaggaat acatgaccac 180
tgctgtgggg agtcagcagg tgcgtgatgc agctggccac actccatcca cggccatgac 240
ataaaacaga caagaagtaa ggctggactg taacacctca aggcctgctc cagtgaccca 300
ctttcttcag agaggctcta ccacacacac aaccaccttc caaatttaca ctcagatcac 360
tacaccatgt ctcccaagtt aaaacatgta tccacctaga ctttaaatgt gctttgtaac 420
tgttgatggc actgtacaga gggccaaagt atttcccatc agatagcatt tttctgaacc 480
catgcctctt gggacgagat cacaggactt gacccatcat caaataggac caggtgacct 540
acagagacat cacaatgatg gcttcctaca gtcaagtcca tttccaataa tgctctcatc 600
taagagaacc catgaacctt atttgaatcc tggttcaaac aaaaacctta aattatttat 660
gagacaatta taaacttgat agattttgat gtgtgaaggt atttatgaat atttttagtc 720
agtgatggta tactgttaag gaaaaggttc atattttagg gacaaaggct gaaacattta 780
tggacagagt gatatgatat ctgggatttg ttttaggatg aagtgggagg gaggaaatga 840
atggaaatag tgttgaaaca gtattggcca cgagtcagct attgtgtgct aagacgctcc 900
tcacaccagt ctactctgta tgtgtttgaa tatctctgta ataaacttaa caaggaaaaa 960
aaaaaaaaaa aaaaaaactc gag 983

<210> SEQ ID NO 221
<211> LENGTH: 373
<212> TYPE: DNA
<213> ORGANISM: Homo sapien

<400> SEQUENCE: 221
cattttatgg gttaattttt tattaaatag caataagata cttttataac tcaataaaat 60
tattcaatga tacattcgga aaataaatgt ataaaatatg aaaaagtact aaaaagcatt 120
tttcagtact tttaggtaag attaatccaa ctaaacacta gcatatgtta tacagtaata 180
ataaggggaa aatacaataa tgttgagaaa gcaaactcaa agcatagatc aatgaaaaaa 240
ttgagaaatg gacataaatg atttagtatt tttaaagaga gtgaaaaatc attattttat 300

-continued

```
gcttttgtgt agcgttagat gaattaaata acatatgcac atatagcttt gcgatacaaa    360

tttccagacc ata                                                       373
```

<210> SEQ ID NO 222
<211> LENGTH: 544
<212> TYPE: DNA
<213> ORGANISM: Homo sapien

<400> SEQUENCE: 222

```
cagagatgct gctgctacaa aggatcggtg taagcagtta acccaggaaa tgatgacaga     60

gaaagaaaga agcaatgtgg ttataacaag gatgaaagat cgaattggaa cattagaaaa    120

ggaacataat gtatttcaaa acaaaataca tgtcagttat caagagactc aacagatgca    180

gatgaagttt cagcaagttc gtgagcagat ggaggcagag atagctcact tgaagcagga    240

aaatggtata ctgagagatg cagtcagcaa cactacaaat caactggaaa gcaagcagtc    300

tgcagaacta aataaactac gccaggatta tgctaggttg gtgaatgagc tgactgagaa    360

aacaggaaag ctacagcaag aggaagtcca aaagaagaat gctgagcaag cagctactca    420

gttgaaggtt caactacaag aagctgagag aaggtgggaa gaagttcaga gctacatcag    480

gaagagaaca gcggaacatg aggcagcaca gctagattta cagagtaaat ttgtggccaa    540

agaa                                                                 544
```

<210> SEQ ID NO 223
<211> LENGTH: 316
<212> TYPE: DNA
<213> ORGANISM: Homo sapien

<400> SEQUENCE: 223

```
gaggcaaggg atatgcttta gtgcctatta tagttaattc ttcaactcca aagtctaaaa     60

cagttgaatc tgctgaagga aaatctgaag aagtaaatga aacattagtt atacccactg    120

aggaagcaga aatggaagaa agtggacgaa gtgcaactcc tgttaactgt gaacagcctg    180

atatcttggt ttcttctaca ccaataaatg aaggacagac tgtgttagac aaggtggctg    240

agcagtgtga acctgctgaa agtcagccag aagcacttct gagaggaaga tgtttgcaag    300

gtaactctaa cagttg                                                    316
```

<210> SEQ ID NO 224
<211> LENGTH: 1583
<212> TYPE: DNA
<213> ORGANISM: Homo sapien

<400> SEQUENCE: 224

```
cagaccacgt ctgccctcgc cgctctagcc ctgcgcccca gcccggccgc ggcacctccg     60

cctcgccgcc gctaggtcgg ccggctccgc ccggctgccg cctaggatga atatcatgga    120

cttcaacgtg aagaagctgg cggccgacgc aggcaccttc ctcagtcgcg ccgtgcagtt    180

cacagaagaa aagcttggcc aggctgagaa gacagaattg gatgctcact tagagaacct    240

ccttagcaaa gctgaatgta ccaaaatatg gacagaaaaa ataatgaaac aaactgaagt    300

gttattgcag ccaaatccaa atgccaggat agaagaattt gtttatgaga aactggatag    360

aaaagctcca agtcgtataa acaacccaga acttttggga caatatatga ttgatgcagg    420

gactgagttt ggcccaggaa cagcttatgg taatgccctt attaaatgtg gagaaaccca    480

aaaaagaatt ggaacagcag acagagaact gattcaaacg tcagccttaa attttcttac    540

tcctttaaga aactttatag aaggagatta caaaacaatt gctaaagaaa ggaaactatt    600
```

-continued

```
gcaaaataag agactggatt tggatgctgc aaaaacgaga ctaaaaaagg caaaagctgc    660
agaaactaga aattcatctg aacaggaatt aagaataact caaagtgaat ttgatcgtca    720
agcagagatt accagacttc tgctagaggg aatcagcagt acacatgccc atcaccttcg    780
ctgtctgaat gactttgtag aagcccagat gacttactat gcacagtgtt accagtatat    840
gttggacctc cagaaacaac tgggaagttt tccatccaat tatcttagta acaacaatca    900
gacttctgtg acacctgtac catcagtttt accaaatgcg attggttctt ctgccatggc    960
ttcaacaagt ggcctagtaa tcacctctcc ttccaacctc agtgacctta aggagtgtag   1020
tggcagcaga aaggccaggg ttctctatga ttatgatgca gcaaacagta ctgaattatc   1080
acttctggca gatgaggtga tcactgtgtt cagtgttgtt ggaatggatt cagactggct   1140
aatgggggaa aggggaaacc agaagggcaa ggtgccaatt acctacttag aactgctcaa   1200
ttaagtaggt ggactatgga aaggttgccc atcatgactt tgtatttata tacaattaac   1260
tctaaataaa gcaggttaag tatcttccat gttaatgtgt taagagactg aaaataccag   1320
ccatcagaaa ctggcctttt tgccaataaa gttgcatggt aaatatttca ttacagaatt   1380
tatgttagag ctttcatgcc aagaatgttt tcttacaaaa ttctcttttt attgaggttt   1440
cactaataag cagcttctac ttttgagcct caacttaaag cagaactgtt ttttactgga   1500
tttttcatta acagcaagct ttttttttta tgtaaaataa atctattgtg aattgaaaaa   1560
aaaaaaaaaa aaaaaaactc gag                                           1583
```

<210> SEQ ID NO 225
<211> LENGTH: 491
<212> TYPE: DNA
<213> ORGANISM: Homo sapien

<400> SEQUENCE: 225

```
gaacaacatc atcttgaatc actagataga ctcttgacgg aaagcaaagg ggaaatgaaa     60
aaggaaaata tgaagaaaga tgaagcttta aaagcattac agaaccaagt atctgaagaa    120
acaatcaagg ttaggcaact agattcagca ttggaaattt gtaaggaaga acttgtcttg    180
catttgaatc aattggaagg aaataaggaa aagtttgaaa aacagttaaa gaagaaatct    240
gaagaggtat attgtttaca gaaagagcta aagataaaaa atcacagtct tcaagagact    300
tctgagcaaa acgttattct acagcatact cttcagcaac agcagcaaat gttacaacaa    360
gagacaatta gaaatggaga gctagaagat actcaaacta aacttgaaaa acaggtgtca    420
aaactggaac aagaacttca aaaacaaagg gaaagttcag ctgaaaagtt gagaaaaatg    480
gaggagaaat g                                                        491
```

<210> SEQ ID NO 226
<211> LENGTH: 483
<212> TYPE: DNA
<213> ORGANISM: Homo sapien

<400> SEQUENCE: 226

```
cagccgcacg ccgcggagca ggggctcgga ggtcccggga ttacggtgct cgagcacgct     60
ggtgggaaag gacccgggac ttgaacagtg ttgtgcggcg ccatgcaggt ctccagcctc    120
aatgaggtga agatttacag cctcagctgc ggcaagtccc ttcctgagtg gctttctgat    180
aggaagaaga gagcgctaca gaagaaagat gtagatgtcc gtaggagaat tgaacttatt    240
caggactttg aaatgcctac tgtgtgtacc actattaagg tgtcaaaaga tggacagtac    300
```

-continued

```
attttagcaa ctggaacata taaacctcgg gttcgatgtt atgacaccta tcaattatcc    360

ttgaagtttg aaaggtgttt agattcagaa gttgtcacct ttgaaatttt gtctgatgac    420

tactcaaaga ttgtcttctt acataatgat agatacattg aatttcattc gcaatcaggt    480

ttt                                                                  483
```

<210> SEQ ID NO 227
<211> LENGTH: 486
<212> TYPE: DNA
<213> ORGANISM: Homo sapien

<400> SEQUENCE: 227

```
gagcctcgct aagctccgac tctgggcggc accgggcgtc ccacgatgcc gaagaacaag     60

aagcggaaca ctccccaccg cggtagcagt gctggcggcg gcgggtcagg agcagccgca    120

gcgacggcgg cgacagcagg tggccagcat cgaaatgttc agccttttag tgatgaagat    180

gcatcaattg aaacagtgag ccattgcagt ggttatagcg atccttccag ttttgctgaa    240

gatggaccag aagtccttga tgaggaagga actcaagaag acctagagta caagttgaag    300

ggattaattg acctaaccct ggataagagt gcgaagacaa ggcaagcagc tcttgaaggt    360

attaaaaatg cactggcttc aaaaatgctg tatgaattta ttctggaaag gagaatgact    420

ttaactgata gcattgaacg ctgcctgaaa aaaggtaaga gtgatgagca acgtgcagct    480

gcagcg                                                               486
```

<210> SEQ ID NO 228
<211> LENGTH: 494
<212> TYPE: DNA
<213> ORGANISM: Homo sapien

<400> SEQUENCE: 228

```
gaggccagga ctccgggaat gcgagcaggc cccttattct cccagtggcc tcggtctgtc     60

cccacagcgg cccggtcagg gttgcccgag ccccaaggcg gggggcggca ccggggtgct    120

gaaagggaca gaatgctttg acctccaagc tgttttaaat ctagtagata agccagatcc    180

tgtgttgcca taagcccttg gcccacattt aagtgggaat gcagctagct tggatgtctg    240

aaactttgta agcgccttct gtctgaatcc tgaacacagg caccaagact actgaagaag    300

ctcgtcattc ttgtgcaggg atagccacac aagcaaacat gtttgcaaaa cttgaaagaa    360

agaaaattgc agaaagaaga cttgctgttc ttaagaggcc caggaaggtg ctacttagga    420

atcccaccgg cttgtgaagc aagggaatca agtttgcctt caatggggaa cttgacttca    480

ggaaaatgaa cttt                                                      494
```

<210> SEQ ID NO 229
<211> LENGTH: 465
<212> TYPE: DNA
<213> ORGANISM: Homo sapien

<400> SEQUENCE: 229

```
gtcagagagc tggtataacc tcctgttgga catgcagaac cgactcaata aggtcatcaa     60

aagcgtgggc aagattgagc actccttctg gagatccttt cacactgagc gaaagacaga    120

accagccaca ggcttcatcg atggtgatct gattgaaagt ttcctagata tcagccgccc    180

taagatgcag gaggttgtgg caaacttgca gtatgatgat ggcagtggta tgaagcggga    240

ggcaactgca gatgacctca tcaaagtcgt ggaggaacta actcggatcc attagccaag    300

gacaggatct cttttcctga ccctcctaaa ggcgttgccc tcctatcctc ccttccttgc    360
```

-continued

```
ccacccttgg tttctttggc atgggaaggt tttccttaac cacttgccct agagccacca    420

gtgaccttgt gtggaaacag ggtttttttt acttaaaaca gttca                   465
```

<210> SEQ ID NO 230
<211> LENGTH: 495
<212> TYPE: DNA
<213> ORGANISM: Homo sapien

<400> SEQUENCE: 230

```
caggggaaag ggtgtttggc cttgaccagc cactgctgac ctcaatctca gacctacaga     60

tggtgaatat ctccctgcga gtgttgtctc gacccaatgc tcaggagctt cctagcatgt    120

accagcgcct agggctggac tacgaggaac gagtgttgcc gtccattgtc aacgaggtgc    180

tcaagagtgt ggtggccaag ttcaatgcct cacagctgat cacccagcgg gcccaggtat    240

ccctgttgat ccgccgggag ctgacagaaa gggccaaagg acttcagcct catcctggat    300

gatgtggcca tcacagactt gagctttagc cgagaagtac acaagctgcc tgtaagaaac    360

ccaaccaagt ggggtgaatt ccaaaaaccc gtgggggtga agggcttctt aagaatgcaa    420

ggaaggagga aaagaattcc atgggggggg ggttccttaa cccaggaaca ggggtttccc    480

ttgaattttt ttcca                                                     495
```

<210> SEQ ID NO 231
<211> LENGTH: 498
<212> TYPE: DNA
<213> ORGANISM: Homo sapien

<400> SEQUENCE: 231

```
ggcagcttct gagaccaggg ttgctccgtc cgtgctccgc ctcgccatga cttcctacag     60

ctatcgccag tcgtcggcca cgtcgtcctt cggaggcctg ggcggcggct ccgtgcgttt    120

tgggccgggg gtcgcttttc gcgcgcccag cattcacggg ggctccggcg gccgcggcgt    180

atccgtgtcc tccgcccgct ttgtgtcctc gtcctcctcg gggggctacg gcggcggcta    240

cggcggcgtc ctgaccgcgt ccgacgggct gctggcgggc aacgagaagc taaccatgca    300

gaacctcaac gaccgcctgc ctcctacctg gacaaagtgc gcgccctgga agcgggcaac    360

ggcgaactta gaggtgaaag aatcccgcga actggtacca aaaacaaggg gcctggggcc    420

ttccgcgact tacagccaac ttactacacc gaacattcaa gaacttgcgg gaacaaaaat    480

ttttggtgcc acccattt                                                  498
```

<210> SEQ ID NO 232
<211> LENGTH: 465
<212> TYPE: DNA
<213> ORGANISM: Homo sapien

<400> SEQUENCE: 232

```
caggccggcc gagtaggaaa gctggaggcg cgggtgggga acatgtctga gtcggagctc     60

ggcaggaagt gggaccggtg tctggcggat gcggtcgtga agataggtac tggttttgga    120

ttaggaattg ttttctcact taccttcttt aaaagaagaa tgtggccatt agccttcggt    180

tctggcatgg gattaggaat ggcttattcc aactgtcagc atgatttcca ggctccatat    240

cttctacatg gaaaatatgt caaagagcag gagcagtgac ttcacctgag aacatcccag    300

cgggaggaca agagaaaatc atgtttattc ctcaggaata cttgaagtgc cctggagtaa    360

actgccattc ttctgtaaca atggtatcag taatgcttta aactccagca cctggttatg    420
```

-continued

```
catttgaaac ccaagtctgg ttcttggttt ggattttctc tctgg                465


<210> SEQ ID NO 233
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 233

cagtaaaaaa ggttatgttt tattaattgc tggacaaccg tgggaaaaca aataagcaat    60

tgacaccacc aaattcttat tacattcaan ataaaanatt tattcacacc acaaaaaagat  120

aatcacaaca aaatatacac taacttaaaa aacaaaagat tatagtgaca taaaatgtta   180

tattctcttt ttaagtgggt aaaagtattt tgtttgcttc tacataaatt tctattcatg   240

ananaataac aaatattaaa atacagtgat agtttgcatt tcttctatag aatgaacata   300

gacataaccc tgaagctttt agtttacagg gagtttccat gaagccacaa actaaactaa   360

ttatca                                                              366


<210> SEQ ID NO 234
<211> LENGTH: 379
<212> TYPE: DNA
<213> ORGANISM: Homo sapien

<400> SEQUENCE: 234

gagggcagcc ctcctacctg cgcacgtggt gccgccgctg ctgcctcccg ctcgccctga    60

acccagtgcc tgcagccatg gctcccggcc agctcgcctt atttagtgtc tctgacaaaa   120

ccggccttgt ggaatttgca agaaacctga ccgctcttgg tttgaatctg gtcgcttccg   180

gagggactgc aaaagctctc agggatgctg gtctggcagt cacagatgtc tctgagttga   240

cgggatttct gaaatgttgg ggggacgtgt gaaaactttg catcctgcac gatcccatgc   300

tggaatccta gctcctaata ttcagaagat aatgcttgac atgcgccaca cttgattcaa   360

tcttataaca attgttgcc                                                379


<210> SEQ ID NO 235
<211> LENGTH: 406
<212> TYPE: DNA
<213> ORGANISM: Homo sapien

<400> SEQUENCE: 235

caggctgcac catgtacccc accttcagtt taaaagaaaa aaaaaatccc cttcactcct    60

actgggaggt gggacccctt tcattttcag ttttgctcat ctagggaaaa taaggctttg   120

gtttccagtt taattgtttt tgaccttcta aaatgttttt atgttagcac tgatagttgg   180

cattactgtt gttaagcact gtgttccaga ccgtgtctga cttagtgtaa cctaggagat   240

tttatagttt tattttaatg aaaccctgat tgacgcacag cagtggggag aacagcgtct   300

tttacctgtc accgaagcca ggaagccccg tttgtaagcg tgtgttgtgg tgctttattg   360

tacatcctcc agtggcgttc tttttactct aatgttcttt tggttt                  406


<210> SEQ ID NO 236
<211> LENGTH: 278
<212> TYPE: DNA
<213> ORGANISM: Homo sapien

<400> SEQUENCE: 236
```

-continued

```
gagattagca cctgtgaaca atgcgttctc tgatgacact ctgagcatgg accaacgcct     60

tcttaagcta attctgcaaa atcacatatt gaaagtaaaa gttggcctta gcgacctcta    120

caatggacag atactggaaa ccattggagg caaacaactc cgagtctttg tgtatcggac    180

ggctatctgc atagaaaact catgcatggt gagaggaagc aagcagggaa ggaacggtgc    240

cattcacata ttccgagaga tcatccaacc agcagaat                            278
```

<210> SEQ ID NO 237
<211> LENGTH: 322
<212> TYPE: DNA
<213> ORGANISM: Homo sapien

<400> SEQUENCE: 237

```
cagggccgtg gcggaggagg agcgctgcac ggtggagcgt cgggccgacc tcacctacgc     60

ggagttcgtg cagcagtacg tgcgcccctg atcgcggagg tcgcgtcctg ttcaccggcc    120

cgtctgcccc gaccgcccaa ggccgccttc ccctgacctc gcgcgcacgc gtggggctgg    180

ggcggcgagg ctggcggtcc ggcctggccg cgactctgcc cttctttcca gaggttccgg    240

gccctgtgct cccgcgacag gttgctggct tcgtttgggg acagagtggt ccggtgagca    300

ccgccaacac ctactcctac ct                                             322
```

<210> SEQ ID NO 238
<211> LENGTH: 613
<212> TYPE: DNA
<213> ORGANISM: Homo sapiens
<220> FEATURE:
<221> NAME/KEY: misc_feature
<222> LOCATION: (399)
<223> OTHER INFORMATION: n=A,T,C or G

<400> SEQUENCE: 238

```
gaattcggca ccagccttct tggatcagga ccagtctcca ccccgtttct acagtggaga     60

tcagcctcct tcttatcttg gtgcaagtgt ggataaactc catcaccctt tagaatttgc    120

agacaaatct cccacacctc ctaatttacc tagcgataaa atctaccctc cttctgggtc    180

ccccgaagag aataccagca cagccaccat gacttacatg acaactactc cagcaacagc    240

ccaaatgagc accaaggaag ccagctggga tgtggctgaa caacccacca ctgctgattt    300

tgctgctgcc acacttcagc gcacgcacag aactaatcgt ccccttcccc ctccgccttc    360

ccagagatct gcagagcagc caccagttgt ggggcaggna caagcagcaa ccaatatagg    420

attaaataat tcccacaagg ttcaaggagt agttccagtt ccagagaggc cacctgaacc    480

tcgagccatg gatgaccctg cgtctgcctt catcagtgac agtggtgctg ctgctgctca    540

gtgtcccatg gctacagctg tccagccagg cctgcctgag aaagtgcggg acggtgcccg    600

ggtcccgctg ctg                                                       613
```

<210> SEQ ID NO 239
<211> LENGTH: 613
<212> TYPE: DNA
<213> ORGANISM: Homo sapiens

<400> SEQUENCE: 239

```
gaattcggca ccaggggaca ctggtgctga gctggatgat gatcagcact ggtctgacag     60

cccgtcggat gctgacagag agctgcgttt gccgtgccca gctgaggggg aagcagagct    120

ggagctgagg gtgtcggaag atgaggagaa gctgcccgcc tcaccgaagc accaagagag    180
```

-continued

```
aggtccctcc caagccacca gccccatccg gtctccccag gaatcagctc ttctgttcat    240

tccagtccac agcccctcaa cagaggggcc ccaactccca cctgtccctg ccgccaccca    300

ggagaaatca cctgaggagc gccttttccc tgagcctttg ctccccaaag agaagcccaa    360

agctgatgcc ccctcggatc tgaaagctgt gcactctccc atccgatcac agccagtgac    420

cctgccagaa gctaggactc ctgtctcacc agggagcccg cagccccagc cacccgtggc    480

ggcctccacg cccccaccca gcgaggtctc cagagccttc tctctcctgt gcaaaatggc    540

aactcttaag gaaaaactca ttgcaccagt tgcggaagaa gaggcaacag ttccaaacaa    600

taagatcact gta                                                       613
```

<210> SEQ ID NO 240
<211> LENGTH: 585
<212> TYPE: DNA
<213> ORGANISM: Homo sapiens

<400> SEQUENCE: 240

```
gaattcggca cgaggtgaga tctacgatga actttaagat tggaggtgtg acagaacgca     60

tgccaacccc agttattaaa gcttttggca tcttgaagcg agcggccgct gaagtaaacc    120

aggattatgg tcttgatcca aagattgcta atgcaataat gaaggcagca gatgaggtag    180

ctgaaggtaa attaaatgat cattttcctc tcgtggtatg gcagactgga tcaggaactc    240

agacaaatat gaatgtaaat gaagtcatta gcaatagagc aattgaaatg ttaggaggtg    300

aacttggcag caagatacct gtgcatccca acgatcatgt taataaaagc cagagctcaa    360

atgatacttt tcccacagca atgcacattg ctgctgcaat agaagttcat gaagtactgt    420

taccaggact acagaagtta catgatgctc ttgatgcaaa atccaaagag tttgcacaga    480

tcatcaagat tggacgtact catactcagg atgctgttcc acttactctt gggcaggaat    540

ttagtggtta tgttcaacaa gtaaaatatg caatgacaag aataa                    585
```

<210> SEQ ID NO 241
<211> LENGTH: 566
<212> TYPE: DNA
<213> ORGANISM: Homo sapiens

<400> SEQUENCE: 241

```
gaattcggca ccaggcgagc tgcacctcga ggtgaaggcc tcactgatga acgatgactt     60

cgagaagatc aagaactggc agaaggaagc ctttcacaag cagatgatgg gcggcttcaa    120

ggagaccaag gaagctgagg acggctttcg gaaggcacag aagccctggg ccaagaagct    180

gaaagaggta gaagcagcaa agaaagccca ccatgcagcg tgcaaagagg agaagctggc    240

tatctcacga gaagccaaca gcaaggcaga cccatccctc aaccctgaac agctcaagaa    300

attgcaagac aaaatagaaa agtgcaagca agatgttctt aagaccaaag agaagtatga    360

gaagtccctg aaggaactcg accagggcac accccagtac atggagaaca tggagcaggt    420

gtttgagcag tgccagcagt tcgaggagaa acgccttcgc ttcttccggg aggttctgct    480

ggaggttcag aagcacctag acctgtccaa tgtggctggc tacaaagcca tttaccatga    540

cctggagcag agcatcagag cagctg                                         566
```

<210> SEQ ID NO 242
<211> LENGTH: 556
<212> TYPE: DNA
<213> ORGANISM: Homo sapiens

<400> SEQUENCE: 242

-continued gaattcggca cgagcaaagg tgaagcagga catgcctccg cccgggggct atgggcccat 60
cgactacaaa cggaacttgc cgcgtcgagg actgtcgggc tacagcatgc tggccatagg 120
gattggaacc ctgatctacg ggcactggag cataatgaag tggaaccgtg agcgcaggcg 180
cctacaaatc gaggacttcg aggctcgcat cgcgctgttg ccactgttac aggcagaaac 240
cgaccggagg accttgcaga tgcttcggga gaacctggag gaggaggcca tcatcatgaa 300
ggacgtgccc gactggaagg tgggggagtc tgtgttccac acaacccgct gggtgccccc 360
cttgatcggg gagctgtacg ggctgcgcac cacagaggag gctctccatg ccagccacgg 420
cttcatgtgg tacacgtagg ccctgtgccc tccggccacc tggatccctg cccctcccca 480
ctgggacgga ataaatgctc tgcagacctg gaaaaaaaaa aaaaaaaaaa aaaaaaaaaa 540
aaaaaaaaaa ctcgag 556

<210> SEQ ID NO 243
<211> LENGTH: 591
<212> TYPE: DNA
<213> ORGANISM: Homo sapiens

<400> SEQUENCE: 243
gtctatgttt gcagaaatac agatccaaga caaagacagg atgggcactg ctggaaaagt 60
tattaaatgc aaagcagctg tgctttggga gcagaagcaa cccttctcca ttgaggaaat 120
agaagttgcc ccaccaaaga ctaaagaagt tcgcattaag attttggcca caggaatctg 180
tcgcacagat gaccatgtga taaaaggaac aatggtgtcc aagtttccag tgattgtggg 240
acatgaggca actgggattg tagagagcat tggagaagga gtgactacag tgaaaccagg 300
tgacaaagtc atccctctct ttctgccaca atgtagagaa tgcaatgctt gtcgcaaccc 360
agatggcaac ctttgcatta ggagcgatat tactggtcgt ggagtactgg ctgatggcac 420
caccagattt acatgcaagg gcaaaccagt ccaccacttc atgaacacca gtacatttac 480
cgagtacaca gtggtggatg aatcttctgt tgctaagatt gatgatgcag ctcctcctga 540
gaaagtctgt ttaattggct gtgggttttc cactggatat ggcgctgctg t 591

<210> SEQ ID NO 244
<211> LENGTH: 594
<212> TYPE: DNA
<213> ORGANISM: Homo sapiens

<400> SEQUENCE: 244
gaattcggca cgagaacaga gtgaactgag catcagtcag aaaaagtcta tgtttgcaga 60
aatacagatc caagacaaag acaggatggg cactgctgga aaagttatta aatgcaaagc 120
agctgtgctt tgggagcaga agcaaccctt ctccattgag gaaatagaag ttgccccacc 180
aaagactaaa gaagttcgca ttaagatttt ggccacagga atctgtcgca cagatgacca 240
tgtgataaaa ggaacaatgg tgtccaagtt tccagtgatt gtgggacatg aggcaactgg 300
gattgtagag agcattggag aaggagtgac tacagtgaaa ccaggtgaca aagtcatccc 360
tctctttctg ccacaatgta gagaatgcaa tgcttgtcgc aacccagatg gcaacctttg 420
cattaggagc gatattactg gtcgtggagt actggctgat ggcaccacca gatttacatg 480
caagggcaaa ccagtccacc acttcatgaa caccagtaca tttaccgagt acacagtggt 540
ggatgaatct tctgttgcta agattgatga tgcagctcct cctgagaaag tctg 594

<210> SEQ ID NO 245

-continued

<211> LENGTH: 615
<212> TYPE: DNA
<213> ORGANISM: Homo sapiens
<220> FEATURE:
<221> NAME/KEY: misc_feature
<222> LOCATION: (105)
<223> OTHER INFORMATION: n=A,T,C or G

<400> SEQUENCE: 245
gtccctttcc tctgctgccg ctcggtcacg cttgtgcccg aaggaggaaa cagtgacaga 60
cctggagact gcagttctct atccttccac agctctttca ccatnctgga tcacttcctt 120
tgaatgcaga agcttgctgg ccaaaagatg tgggaattgt tgcccttgag atctattttc 180
cttctcaata tgttgatcaa gcagagttgg aaaaatatga tggtgtagat gctggaaagt 240
ataccattgg cttgggccag gccaagatgg gcttctgcac agatagagaa gatattaact 300
ctctttgcat gactgtggtt cagaatctta tggagagaaa taacctttcc tatgattgca 360
ttgggcggct ggaagttgga acagagacaa tcatcgacaa atcaaagtct gtgaagacta 420
atttgatgca gctgtttgaa gagtctggga atacagatat agaaggaatc gacacaacta 480
atgcatgcta tggaggcaca gctgctgtct tcaatgcttg ttaactggat tgagtccagc 540
tcttgggatg gacggtatgc cctggtaagt tgcaggagat attgctgtat atgccacagg 600
aaatgctaga cctac 615

<210> SEQ ID NO 246
<211> LENGTH: 546
<212> TYPE: DNA
<213> ORGANISM: Homo sapiens

<400> SEQUENCE: 246
gaattcggca ccaggctgcc tcccgctcgc cctgaaccca gtgcctgcag ccatggctcc 60
cggccagctc gccttattta gtgtctctgc aaaaccggcc ttgtgaattt gcaagaaacc 120
tgaccgctct tggtttgaat ctggtcgctt ccggagggac tgcaaaagct ctcagggatg 180
ctggtctggc agtcagagat gtctctgagt tgacgggatt tcctgaaatg ttggggggac 240
gtgtgaaaac tttgcatcct gcagtccatg ctggaatcct agctcgtaat attccagaag 300
ataatgctga catggccaga cttgatttca atcttataag agttgttgcc tgcaatctct 360
atccctttgt aaagacagtg gcttctccag gtgtaactgt tgaggaggct gtggagcaaa 420
ttgacattgg tggagtaacc ttactgagag ctgcagccaa aaaccacgct cgagtgacag 480
tggtgtgtga accagaggac tatgtgggtg ggtgtccacg gagatgcaga gctccgagag 540
taagga 546

<210> SEQ ID NO 247
<211> LENGTH: 564
<212> TYPE: DNA
<213> ORGANISM: Homo sapiens

<400> SEQUENCE: 247
gaattcggca ccagagatca cgtgcagtga gatgcagcaa aaagttgaac ttctgagata 60
tgaatctgaa aagcttcaac aggaaaattc tattttgaga aatgaaatta ctactttaaa 120
tgaagaagat agcatttcta acctgaaatt agggacatta aatggatctc aggaagaaat 180
gtggcaaaaa acggaaactg taaaacaaga aaatgctgca gttcagaaga tggttgaaaa 240
tttaaagaaa cagatttcag aattaaaaat caaaaaccaa caattggatt tggaaaatac 300
agaacttagc caaaagaact ctcaaaacca ggaaaaactg caagaactta atcaacgtct 360

-continued aacagaaatg ctatgccaga aggaaaaaga gccaggaaac agtgcattgg aggaacggga 420
acaagagaag tttaatctga aagaagaact ggaacgttgt aaagtgcagt cctccacttt 480
agtgtcttct ctggaggcgg agctctctga agttaaaata cagacccata ttgtgcaaca 540
ggaaaaccac cttctcaaag atga 564

<210> SEQ ID NO 248
<211> LENGTH: 434
<212> TYPE: DNA
<213> ORGANISM: Homo sapiens

<400> SEQUENCE: 248
gttcttgttt gtggatcgct gtgatcgtca cttgacaatg cagatcttcg tgaagactct 60
gactggtaag accatcaccc tcgaggttga gcccagtgac accatcgaga atgtcaaggc 120
aaagatccaa gataaggaag gcatccctcc tgaccagcag aggctgatct ttgctggaaa 180
acagctggaa gatgggcgca ccctgtctga ctacaacatc cagaaagagt ccaccctgca 240
cctggtgctc cgtctcagag gtgggatgca aatcttcgtg aagacactca ctggcaagac 300
catcaccctt gaggtggagc ccagtgacac catcgagaac gtcaaagcaa agatccagga 360
caaggaaggc attcctcctg accagcagag gttgatcttt gccggaaagc cagcctggga 420
agatggggcc gcca 434

<210> SEQ ID NO 249
<211> LENGTH: 416
<212> TYPE: DNA
<213> ORGANISM: Homo sapiens

<400> SEQUENCE: 249
gcgggcccag gaggcggcgg cggcggcggc ggacgggccc cccgcggcag acggcgagga 60
cggacaggac ccgcacagca agcacctgta cacggccgac atgttcacgc acgggatcca 120
gagcgccgcg cacttcgtca tgttcttcgc gccctggtgt ggacactgcc agcggctgca 180
gccgacttgg aatgacctgg gagacaaata caacagcatg gaagatgcca aagtctatgt 240
ggctaaagtg gactgcacgg cccactccga cgtgtgctcc gcccaggggg tgcgaggata 300
ccccacctta aagcttttca agccaggcca agaagctgtg aagtaccagg gtcctcggga 360
cttccagaca ctggaaaact ggatgctgca gacactgaac gaggagccag tgacac 416

<210> SEQ ID NO 250
<211> LENGTH: 504
<212> TYPE: DNA
<213> ORGANISM: Homo sapiens

<400> SEQUENCE: 250
gaattcggca cgaggcgggt aacgttatag tatttgtcag aagttggggt ctccgtgggc 60
attgtgatcc gtcccaggca gtggattagg aggccagaag gagatccctt ccacggtgct 120
aggctgagat ggatcctctc agggcccaac agctggctgc ggagctggag gtggagatga 180
tggccgatat gtacaacaga atgaccagtg cctgccaccg gaagtgtgtg cctcctcact 240
acaaggaagc agagctctcc aagggcgagt ctgtgtgcct ggaccgatgt gtctctaagt 300
acctggacat ccatgagcgg atgggcaaaa agttgacaga gttgtctatg caggatgaag 360
agctgatgaa gagggtgcag cagagctctg ggcctgcatg aggtccctgt cagtatacac 420
cctggggtgt accccacccc ttcccacttt aataaacgtg ctccctgttg ggtgtcatct 480

-continued gtgaagactg ccaggcctag ctct 504

<210> SEQ ID NO 251
<211> LENGTH: 607
<212> TYPE: DNA
<213> ORGANISM: Homo sapiens

<400> SEQUENCE: 251
gatgaaaata cacaatttta ctagcaaatg cctctactgt aatcgctatt tacccacaga 60
tactctgctc aaccatatgt taattcatgg tctgtcttgt ccatattgcc gttcaacttt 120
caatgatgtg gaaaagatgg ccgcacacat gcggatggtt cacattgatg aagagatggg 180
acctaaaaca gattctactt tgagttttga tttgacattg cagcagggta gtcacactaa 240
catccatctc ctggtaacta catacaatct gagggatgcc ccagctgaat ctgttgctta 300
ccatgcccaa aataatcctc cagttcctcc aaagccacag ccaaaggttc aggaaaaggc 360
agatatccct gtaaaaagtt cacctcaagc tgcagtgccc tataaaaaag atgttgggaa 420
aaccctttgt cctctttgct tttcaatcct aaaaggaccc atatctgatg cacttgcaca 480
tcacttacga gagaggcacc aagttattca gacggttcat ccagttgaga aaaagctcac 540
ctacaaatgt atccattgcc ttggtgtgta taccagcaac atgaccgcct caactatcac 600
tctgcat 607

<210> SEQ ID NO 252
<211> LENGTH: 618
<212> TYPE: DNA
<213> ORGANISM: Homo sapiens

<400> SEQUENCE: 252
gaattcgcac caggggtcct gctggtcttc gcctttcttc tccgcttcta ccccgtcggc 60
cgctgccact ggggtccctg gccccaccga catggcggcg gtgttgagca agtcctggag 120
cgcacggagc tgaacaagct gcccaagtct gtccagaaca aacttgaaaa gttccttgct 180
gatcagcaat ccgagatcga tggcctgaag gggcggcatg agaaatttaa ggtggagagc 240
gaacaacagt attttgaaat agaaaagagg ttgtcccaca gtcaggagag acttgtgaat 300
gaaacccgag agtgtcaaag cttgcggctt gagctagaga aactcaacaa tcaactgaag 360
gcactaactg agaaaaacaa agaacttgaa attgctcagg atcgcaatat tgccattcag 420
agccaattta caagaacaaa ggaagaatta gaagctgaga aaagagactt aattagaacc 480
aatgagagac tatctcaaga acttgaatac ttaacagagg atgttaaacg tctgaatgaa 540
aaacttaaag aaagcaatac aacaaagggt gaacttcagt taaaattgga tgaacttcaa 600
gcttctgatg tttctgtt 618

<210> SEQ ID NO 253
<211> LENGTH: 1201
<212> TYPE: DNA
<213> ORGANISM: Homo sapiens

<400> SEQUENCE: 253
gaattcggca ccagggtggc gagcgcggct gctgtgctgg ggcgagcagc ggggaccgtg 60
tgtgagtttg gcatgatttg gtcccctggg attctgcctt agcaagaaag aagttggaaa 120
tacttcctgg aagaaaacta aaacaataca aaagccacag cttattgatt gcatgtcagc 180
ccccttacaa atatggacac atttcctagc ctatttccac ctggaggaga tagtaggctg 240
aatcctgagc ctgagttcca aaatatgtta attgatgaaa gggtacgctg tgaacatcat 300

-continued aaacataatt atcaggctct gaaaattgaa cacaaaaggt tgcaggaaga atatgtaaaa 360
tcacaaaatg aacttaaacg tgtattaatt gaaaagcaag caagccagga aaaattccaa 420
ctgctccttg aagacttaag gggagaatta gtagagaaag ctagagacat agaaaaaatg 480
aaactgcagg tactaacacc acaaaaattg gaattggtaa aagcccaact acaacaagaa 540
ttagaagctc caatgcgaga acgttttcgg actcttgatg aagaagtgga aaggtacaga 600
gctgagtata acaagctgcg ctacgagtat acatttctca agtcagagtt tgaacaccag 660
aaagaagagt ttactcgggt ttcagaagaa gagaaaatga aatacaagtc agaggttgca 720
cgactggaga aggacaaaga ggagctacat aaccagctgc ttagtgttga tcccacgaga 780
gacagcaaac gaatggagca acttgttcga gaaaaaaccc atttgcttca gaaattgaaa 840
agtttagagg ctgaagtagc agaattaagg gctgagaaag aaaattctgg tgctcaggta 900
gaaaatgtcc aaagaataca ggtgaggcag ttggctgaga tgcaggctac actcagatcc 960
ttggaggctg aaaagcagtc agctaaacta caagctgagc gtttagaaaa agaactacaa 1020
tcaagcaatg aacagaatac ctgcttaatc agcaaactgc atagagctga ccgagaaatc 1080
agcacactgg ccagtgaagt gaaagagctt aaacatgcaa acaaactaga aataactgac 1140
atcaaactgg aggcagcaag agctaagagt gagctcgaaa gagaaaggaa taagatccaa 1200
a 1201

<210> SEQ ID NO 254
<211> LENGTH: 560
<212> TYPE: DNA
<213> ORGANISM: Homo sapiens

<400> SEQUENCE: 254
gaattcggca ccagtttggg gggtgaggtt taattggaaa tggtctctgg ggactgaaaa 60
ctgatgtttt tgcagattac ctcagggaaa cggaggtttg ttgagttaca gacacattaa 120
accaaaggcc gtgggaaaac ccctctccag ctccagggga ttggtcagga ccacccacta 180
accagtgcct tccttcttaa cattcacttt tagcagcttg tgtttatttt acatgggcag 240
ttttgatggg aaattgccat gaccacaggg gtttggagtt ctgctttttt tttttcttct 300
tctttttcgg gggactgggg gactcctccc aagatcacat tttagcatct ttctctccta 360
ctccatttag aaaaataagt aacaggtgaa atgtggtctc agtgttaacg ggataattct 420
gctaccggct cctccctgat gattctgaaa tacactactg aacgagctct ggctggtcct 480
ttctatcctg gatgtggttc ttctgtgtag caattccttg atgtccagtt tggaaagatg 540
tactcttctc aacaagaaaa 560

<210> SEQ ID NO 255
<211> LENGTH: 612
<212> TYPE: DNA
<213> ORGANISM: Homo sapiens

<400> SEQUENCE: 255
gaattcggca ccaggcgggg cagcagggcc gcggccatgg ggagcttgaa ggaggagctg 60
ctcaaagcca tctggcacgc cttcaccgac tcgaccagga ccacagggca aggtctccaa 120
gtcccagctc aaggtccttt cccataacct gtgcacggtg ctgaaggttc ctcatgaccc 180
agttgccctt gaagagcact tcagggatga tgatgagggt ccagtgtcca accagggcta 240
catgccttat ttaaacaggt tcattttgga aaaggtccaa gacaactttg acaagattga 300

-continued

```
attcaatagg atgtgttgga ccctctgtgt caaaaaaaaa cctcacaaag aatcccctgc    360

tcattacaga agaagatgca tttaaaatat gggttatttt caacttttta tctgaggaca    420

agtatccatt aattattgtg tcagaagaga ttgaatacct gcttaagaag cttacagaag    480

ctatgggagg aggttggcag caagaacaat ttgaacatta taaaatcaac tttgatgaca    540

gtaaaaatgg cctttctgca tgggaactta ttgagcttat tggaaatgga cagtttagca    600

aaggcatgga cc                                                        612
```

<210> SEQ ID NO 256
<211> LENGTH: 1132
<212> TYPE: DNA
<213> ORGANISM: Homo sapiens

<400> SEQUENCE: 256

```
gaattcggca cgaggtctgg gagaggcctc tggagcagga ggcccagtgg ctcttctgac     60

ccaaggcccc gccgtccagc ttctaagtgc cagatgatgg aggagcgtgc caacctgatg    120

cacatgatga aactcagcat caaggtgttg ctccagtcgg ctctgagcct gggccgcagc    180

ctggatgcgg accatgcccc cttgcagcag ttctttgtag tgatggagca ctgcctcaaa    240

catgggctga aagttaagaa gagttttatt ggccaaaata aatcattctt tggtcctttg    300

gagctggtgg agaaactttg tccagaagca tcagatatag cgactagtgt cagaaatctt    360

ccagaattaa agacagctgt gggaagaggc cgagcgtggc tttatcttgc actcatgcaa    420

aagaaactgg cagattatct gaaagtgctt atagacaata aacatctctt aagcgagttc    480

tatgagcctg aggctttaat gatggaggaa gaagggatgg tgattgttgg tctgctggtg    540

ggactcaatg ttctcgatgc caatctctgc ttgaaaggag aagacttgga ttctcaggtt    600

ggagtaatag atttttccct ctaccttaag gatgtgcagg atcttgatgg tggcaaggag    660

catgaaagaa ttactgatgt ccttgatcaa aaaaattatg tggaagaact taaccggcac    720

ttgagctgca cagttgggga tcttcaaacc aagatagatg gcttggaaaa gactaactca    780

aagcttcaag aagagctttc agctgcaaca gaccgaattt gctcacttca agaagaacag    840

cagcagttaa gagaacaaaa tgaattaatt cgagaaagaa gtgaaaagag tgtagagata    900

acaaaacagg ataccaaagt tgagctggag acttacaagc aaactcggca aggtctggat    960

gaaatgtaca gtgatgtgtg gaagcagcta aaagaggaga agaaagtccg gttggaactg   1020

gaaaaagaac tggagttaca aattggaatg aaaaccgaaa tggaaattgc aatgaagtta   1080

ctggaaaagg acacccacga gaagcaggac acactagttg ccctccgcca gc           1132
```

<210> SEQ ID NO 257
<211> LENGTH: 519
<212> TYPE: DNA
<213> ORGANISM: Homo sapiens

<400> SEQUENCE: 257

```
gaattcgtga cacgaggtgc tcgagatgaa ccccagcgcc cccagctacc ccatggcctc     60

tctgtacgtg ggggacctgc accccgacgt gaccgaggcg atgctctacg agaagttcag    120

cccggccggg cccatcctct ccatccgggt ctgcagggac atgatcaccc gccgctcctt    180

gggctacgcg tacgtgaact tccagcagcc ggcggacgcg gaacgtgctt tggacaccat    240

gaattttgat gttataaagg gcaagccagt acgcatcatg tggtctcagc gtgatccatc    300

acttcgcaaa agtggagtag gcaacatatt cattaaaaat ttggacaaat ccatcgacaa    360

taaagcacta tatgatacgt tttctgcgtt tggtaacatc ctttcatgta aggtggtttg    420
```

-continued tgatgaaaat ggctccaagg gctatggatt tgtacacttt gaaacacagg aagcagctga 480
aagagctatt gaaaaaatga atgggatgct tctaaatga 519

<210> SEQ ID NO 258
<211> LENGTH: 596
<212> TYPE: DNA
<213> ORGANISM: Homo sapiens

<400> SEQUENCE: 258
gctttgccaa agacttagaa gctaagcaga aaatgagctt aacatcctgg tttttggtga 60
gcagtggagg cactcgccac aggctgccac gagaaatgat ttttgttgga agagatgact 120
gtgagctcat gttgcagtct cgtagtgtgg ataagcaaca cgctgtcatc aactatgatg 180
cgtctacgga tgagcattta gtgaaggatt tgggcagcct caatgggact tttgtgaatg 240
atgtaaggat tccggaacag acttatatca ccttgaaact tgaagataag ctgagatttg 300
gatatgatac aaatcttttc actgtagtac aaggagaaat gagggtccct gaagaagctc 360
ttaagcatga gaagtttacc attcagcttc agttgtccca aaaatcttca gaatcagaat 420
tatccaaatc tgcaagtgcc aaaagcatag attcaaaggt agcagacgct gctactgaag 480
tgcagcacaa aactactgaa gcactgaaat ccgaggaaaa agccatggat atttctgcta 540
tgccccgtgg tactccatta tatgggcagc cgtcatggtg gggggatgat gaggtg 596

<210> SEQ ID NO 259
<211> LENGTH: 595
<212> TYPE: DNA
<213> ORGANISM: Homo sapiens

<400> SEQUENCE: 259
gaattcggca ccagagaaaa agcttcaagg tatattgagt cagagtcaag ataaatcact 60
tcggagaatt tcagaattaa gagaggagct gcaaatggac cagcaagcaa agaaacatct 120
tcaggacgag tttgatgcat gtttggagga gaaagatcag tatatcagtg ttctccagac 180
tcaggtttct cttctaaagc agcgattaca gaatggccca atgaatgttg atgctcccaa 240
acccctccct cccggggagc tccaggcaga agtgcacggt gacacggaga agatggaggg 300
cgtcggggaa ccagtgggag gtgggacttc cgctaaaacc ctggaaatgc tccagcaaag 360
agtgaaacgt caggagaatc tgcttcagcg ctgtaaggag acaattgggt cccacaagga 420
gcagtgcgca ctgctgctga gtgagaagga ggcactgcag gagcagttgg atgaaaggct 480
gcaggagctg gaaaagatga aggggatggt aataaccgag acgaagcggc aaatgcttga 540
gaccctggaa ctgaaagaag atgaaattgc tcagcttcgt agtcatatca aacag 595

<210> SEQ ID NO 260
<211> LENGTH: 994
<212> TYPE: DNA
<213> ORGANISM: Homo sapiens

<400> SEQUENCE: 260
gaattcggca cgaggcgttg cctgccttct tgctgtctat cagcctttct tgcctcttcc 60
ttttcgcctt ccctgttctt ccctttctca aacaaacaag acatggcaaa ccgcagtcta 120
acccagccct ttgaaattat ccatagtttt acagacagct ccaggccatg agccacaatg 180
tccaaaatta ttcttgagca ctgatataaa ttacttagac cttctttgag ggcagaactc 240
agctgttgct ctcatgatgg gcagtgctgg aaagggttct ggtatgtctt caaaatgagt 300

-continued

```
ccacgagttt actgagtgct tacaggtaaa ggaatgaata taagatgtct ttctgatcag    360

aacaggtgtc ccttcacatg agctttacta gactctggga gggaaaagta gccaagtact    420

tctgaaccat tttttaatac ttgttttgtc atggtgaaat tatagcagtt atcccaaaat    480

gttttaatta tcaaaatact gtcttttaaa aaaaaaaaaa agtaacacct tttaaagcat    540

tagatttcac ttgggtttct tttccaaaaa atgctaggta gacaaggcat tgtaaacatg    600

agtttccttt aagaaccatc agaatataaa tttaacatga agaaaactgc tatatctagt    660

agaaataata tctaaagttt aacaactaaa gtaccctcac agaatagcaa ataccccttct    720

gttctggaca tgggttcaaa tttgaatatg gaaataattt ccttggaagt ccctagaggc    780

aggtcagagg aagtatgcat taagagggaa aggagagaat ggaaataaaa gtcactataa    840

tgcagattta tgccttattt tttagcattt tttaaatgtt gggtctttca aggtgttttt    900

tgctttttat tagatctata taaataagtt aactagcaat ttagttttgt atttaagcta    960

cacttaatct ttttctttgg tgatatttat ttct                                994
```

<210> SEQ ID NO 261
<211> LENGTH: 594
<212> TYPE: DNA
<213> ORGANISM: Homo sapiens
<220> FEATURE:
<221> NAME/KEY: misc_feature
<222> LOCATION: (538)
<223> OTHER INFORMATION: n=A,T,C or G

<400> SEQUENCE: 261

```
gaattcggca ccagtggaga tccagctgaa ccatgccaac cgccaggctg cggaggcaat     60

caggaacctt cggaacaccc agggaatgct gaaggacaca cagctgcacc tggacgatgc    120

tctcagaggc caggacgacc tgaaagagca gctggccatg gttgagcgca gagccaacct    180

gatgcaggct gagatcgagg agctcagggc atccctggaa cagacagaga ggagcaggag    240

agtggccgag caagagctac tggatgccag tgagcgcgtg cagctcctcc acacccagaa    300

caccagcctc atcaacacca agaagaagct ggagacagac atttcccaaa tccagggaga    360

gatggaagac atcgtccagg aagcccgcaa cgcagaagag aaggccaaga aagccatcac    420

tgatgccgcc atgatggcgg aggagctgaa gaaggagcag gacaccagcg cccacctgga    480

gcggatgaag aagaacatgg agcagaccgt gaaggacctg cagcaccgtc tggacgangc    540

tgagcagctt ggcgctgaag ggcgggcaag aagcagatcc agaaactgga ggct          594
```

<210> SEQ ID NO 262
<211> LENGTH: 594
<212> TYPE: DNA
<213> ORGANISM: Homo sapiens

<400> SEQUENCE: 262

```
gaaaaggtgg ctggagccaa aggcatagtc agggttaatg ctcctttttc tttatcccaa     60

atcagatagt gtttaggctt tttcatcaaa tataaaaacc cagcccagtt catggctcat    120

tcggcagcaa ccctgagacg ctttacagct ctagacccta aaaggtcaaa aggccgtctt    180

atgctcaata tacattttat tacccaatct gccccggaca ttaaataaaa ctccaaaaat    240

taaatccggc cctcaaaccc cacaacagga cttaattgac ctcaccttca aggtgtagaa    300

taataaaaaa aaaaagttgc aattccttgc ctccgctgtg agacaaaccc cagccacatc    360

tccagcacac aagaacttcc aaacgcctga accacagcag ccaggcgttc ctccagaacc    420

tcctccccca ggagcttgct acatgtgccg gaaatctggc cactaggcca aggaatgcct    480
```

-continued

```
gcagccccgg attcctccta agccgtgtcc catctgtgcg ggaccccact gaaaatcgga    540

ctgttcaact cacctggcag ccactctcag agaccctgga actctggccc aagg          594
```

<210> SEQ ID NO 263
<211> LENGTH: 506
<212> TYPE: DNA
<213> ORGANISM: Homo sapiens

<400> SEQUENCE: 263

```
gaattcggca cgagcggaaa cttaggggcc acgtgagcca cggccacggc cgcataggca     60

agcaccggaa gcaccccggc ggccgcggta atgctggtgg tctgcatcac caccggatca    120

acttcgacaa ataccaccca ggctactttg ggaaagttgg tatgaagcat taccacttaa    180

agaggaacca gagcttctgc ccaactgtca accttgacaa attgtggact ttggtcagtg    240

aacagacacg ggtgaatgct gctaaaaaca agactggggc tgctcccatc attgatgtgg    300

tgcgatcggg ctactataaa gttctgggaa agggaaagct cccaaagcag cctgtcatcg    360

tgaaggccaa attcttcagc agaagagctg aggagaagat taagagtgtt ggggggggcct    420

gtgtcctggt ggcttgaagc cacatggagg gagtttcatt aaatgctaac tactttttaa    480

aaaaaaaaaa aaaaaaaaaa ctcgag                                         506
```

<210> SEQ ID NO 264
<211> LENGTH: 600
<212> TYPE: DNA
<213> ORGANISM: Homo sapiens
<220> FEATURE:
<221> NAME/KEY: misc_feature
<222> LOCATION: (32)
<223> OTHER INFORMATION: n=A,T,C or G

<400> SEQUENCE: 264

```
ggctcgtgaa cacacactga cagctatagg gnaggcggcg gcaccgtccc cgcttcccct     60

cggcggcggg gtgtcccgtc ggcggccctg aagtgaccca taaacatgtc ttgtgagagg    120

aaaggcctct cggagctgcg atcggagctc tacttcctca tcgcccggtt cctggaagat    180

ggaccctgtc agcaggcggc tcaggtgctg atccgcgagg tggccgagaa ggagctgctg    240

ccccggcgca ccgactggac cgggaaggag catcccagga cctaccagaa tctggtgaag    300

tattacagac acttagcacc tgatcacttg ctgcaaatat gtcatcgact aggacctctt    360

cttgaacaag aaattcctca aagtgttcct ggagtacaaa ctttattagg agctggaaga    420

cagtctttac tacgcacaaa taaaagctgc aagcatgttg tgtggaaagg atctgctctg    480

gctgcgttgc actgtggaag accacctgag tcaccagtta actatggtag cccacccagc    540

attgcggata ctctgttttc aaggaagctg aatgggaaat acagacttga gcgacttgtt    600
```

<210> SEQ ID NO 265
<211> LENGTH: 534
<212> TYPE: DNA
<213> ORGANISM: Homo sapiens

<400> SEQUENCE: 265

```
gaattcggca cgagtgagga gcccatcatg gcgacgcccc ctaagcggcg ggcggtggag     60

gccacggggg agaaagtgct gcgctacgag accttcatca gtgacgtgct gcagcgggac    120

ttgcgaaagg tgctggacca tcgagacaag gtatatgagc agctggccaa ataccttcaa    180

ctgagaaatg tcattgagcg actccaggaa gctaagcact cggagttata tatgcaggtg    240
```

-continued

```
gatttgggct gtaacttctt cgttgacaca gtggtcccag atacttcacg catctatgtg    300

gccctgggat atggtttttt cctggagttg acactggcag aagctctcaa gttcattgat    360

cgtaagagct ctctcctcac agagctcagc aacagcctca ccaaggactc catgaatatc    420

aaagcccata tccacatgtt gctagagggg cttagagaac tacaaggcct gcagaatttc    480

ccagagaagc ctcaccattg acttcttccc cccatcctca gacattaaag agcc          534
```

<210> SEQ ID NO 266
<211> LENGTH: 552
<212> TYPE: DNA
<213> ORGANISM: Homo sapiens

<400> SEQUENCE: 266

```
gaattcggca ccagggcacc tccgcctcgc cgccgctagg tcggccggct ccgcccggct     60

gccgcctagg atgaatatca tggacttcaa cgtgaagaag ctggcggccg acgcaggcac    120

cttcctcagt cgcgccgtgc agttcacaga agaaaagctt ggccaggctg agaagacaga    180

attggatgct cacttagaga acctccttag caaagctgaa tgtaccaaaa tatggacaga    240

aaaaataatg aaacaaactg aagtgttatt gcagccaaat ccaaatgcca ggatagaaga    300

atttgtttat gagaaactgg atagaaaagc tccaagtcgt ataaacaacc cagaactttt    360

gggacaatat atgattgatg cagggactga gtttggccca ggaacagctt atggtaatgc    420

ccttattaaa tgtggagaaa cccaaaaaag aattggaaca gcagacagag aactgattca    480

aacgtcagcc ttaaattttc ttactccttt aagaaacttt atagaaggag attacaaaac    540

aattgctaaa ga                                                        552
```

<210> SEQ ID NO 267
<211> LENGTH: 551
<212> TYPE: DNA
<213> ORGANISM: Homo sapiens

<400> SEQUENCE: 267

```
gaagcctacc agccaggtgc cggccccccc acccccggcc cagccccctc ctgcagcggt     60

ggaagcggct cggcagatcg agcgtgaggc ccagcagcag cagcacctgt accgggtgaa    120

catcaacaac agcatgcccc caggacgcac gggcatgggg accccgggga gccagatggc    180

ccccgtgagc ctgaatgtgc cccgacccaa ccaggtgagc gggcccgtca tgcccagcat    240

gcctcccggg cagtggcagc aggcgcccct tccccagcag cagcccatgc caggcttgcc    300

caggcctgtg atatccatgc aggcccaggc ggccgtggct gggccccgga tgcccagcgt    360

gcagccaccc aggagcatct cacccagcgc tctgcaagac ctgctgcgga ccctgaagtc    420

gcccagctcc cctcagcagc aacagcaggt gctgaacatt ctcaaatcaa acccgcagct    480

aatggcagct ttcatcaaac agcgcacagc caagtacgtg gccaatcagc ccggcatgca    540

gccccagcct g                                                         551
```

<210> SEQ ID NO 268
<211> LENGTH: 573
<212> TYPE: DNA
<213> ORGANISM: Homo sapiens

<400> SEQUENCE: 268

```
gaattcggca ccagggttcc ttgtgggcta gaagaatcct gcaaaaatgt ctctctatcc     60

atctctcgaa gacttgaagg tagacaaagt aattcaggct caaactgctt tttctgcaaa    120

ccctgccaat ccagcaattt tgtcagaagc ttctgctcct atccctcacg atggaaatct    180
```

-continued ctatcccaga ctgtatccag agctctctca atacatgggg ctgagtttaa atgaagaaga 240
aatacgtgca aatgtggccg tggtttctgg tgcaccactt caggggcagt tggtagcaag 300
accttccagt ataaactata tggtggctcc tgtaactggt aatgatgttg gaattcgtag 360
agcagaaatt aagcaaggga ttcgtgaagt cattttgtgt aaggatcaag atggaaaaat 420
tggactcagg cttaaatcaa tagataatgg tatatttgtt cagctagtcc aggctaattc 480
tccagcctca ttggttggtc tgagatttgg ggaccaagta cttcagatca atggtgaaaa 540
ctgtgcagga tggagctctg ataaagcgca caa 573

<210> SEQ ID NO 269
<211> LENGTH: 500
<212> TYPE: DNA
<213> ORGANISM: Homo sapiens

<400> SEQUENCE: 269
gaatcggcac caggaaacct ttattagcag agatagctgg cttggatcag attacgggga 60
atgtggggga gccatgaaga aactaactaa aggggagcct ttggggacca gggggagaca 120
agtcactatt ttgagggaga aagctctgga ttgattctga caggacactt gagtgtgaac 180
tgtccaagct aagcctctgg gtgtgtagag agagccctta cagatagata gcacctttgc 240
tttcagagtg gaaggactag ccactaagga ccagaccaag atgcatgtag gtcactgaca 300
agcacctgat gaagaggagg ggtctcctcc aagtttgtgt ttggaactcc tcctgtgttc 360
aatttcctaa aagccataat ccagcaagct gaactcatga gaaggtctgc ttcatgttga 420
gcatggaaga cagaacacag acggaaactg cagtgatggt gtgaagacac cacggatagg 480
ttaggggcag tgaggaggaa 500

<210> SEQ ID NO 270
<211> LENGTH: 224
<212> TYPE: DNA
<213> ORGANISM: Homo sapiens

<400> SEQUENCE: 270
gaattcggca cgagaagact acaatctcca gggaaacctg gggcgtctcg cgcaaacgtc 60
cataactgaa agtagctaag gcaccccagc cggaggaagt gagctctcct ggggcgtggt 120
tgttcgtgat ccttgcatct gttacttagg gtcaaggctt gggtcttgcc ccgcagaccc 180
ttgggacgac ccggccccag cgcagctatg aacctggagc gagt 224

<210> SEQ ID NO 271
<211> LENGTH: 447
<212> TYPE: DNA
<213> ORGANISM: Homo sapiens

<400> SEQUENCE: 271
gaattcggca cgaggctggg ccgggcccga gcggatcgcg ggctcgggct gcggggctcc 60
ggctgcgggc gctgggccgc gaggcgcgga gcttgggagc ggagcccagg ccgtgccgcg 120
cggcgccatg aagggcaagg aggagaagga gggcggcgca cggctgggcg ctggcggcgg 180
aagccccgag aagagcccga gcgcgcagga gctcaaggag cagggcaatc gtctgttcgt 240
gggccgaaag tacccggagg cggcggcctg ctacggccgc gcgatcaccc ggaacccgct 300
ggtggccgtg tattacacca accgggcctt gtgctacctg aagatgcagc agcacgagca 360
ggccctggcc gactgccggc gcgccctgga gctggacggg cagtctgtga aggcgcactt 420

-continued cttcctgggg cagtgccagc tggagat 447

<210> SEQ ID NO 272
<211> LENGTH: 606
<212> TYPE: DNA
<213> ORGANISM: Homo sapiens

<400> SEQUENCE: 272
gcaactactt atattccttt gatggataat gctgactcaa gtcctgtggt agataagaga 60
gaggttattg atttgcttaa acctgaccaa gtagaaggga tccagaaatc tgggactaaa 120
aaactgaaga ccgaaactga caaagaaaat gctgaagtga agtttaaaga ttttcttctg 180
tccttgaaga ctatgatgtt ttctgaagat gaggctcttt gtgttgtaga cttgctaaag 240
gagaagtctg gtgtaataca agatgcttta aagaagtcaa gtaagggaga attgactacg 300
cttatacatc agcttcaaga aaaggacaag ttactcgctg ctgtgaagga agatgctgct 360
gctacaaagg atcggtgtaa gcagttaacc caggaaatga tgacagagaa agaaagaagc 420
aatgtggtta taacaaggat gaaagatcga attggaacat tagaaaagga acataatgta 480
tttcaaaaca aaatacatgt cagttatcaa gagactcaac agatgcagat gaagtttcag 540
caagttcgtg agcagatgga ggcagagata gctcacttga agcaggaaaa tgggtatact 600
ggagaa 606

<210> SEQ ID NO 273
<211> LENGTH: 598
<212> TYPE: DNA
<213> ORGANISM: Homo sapiens

<400> SEQUENCE: 273
gaattcggca ccaggcccgg tcccgcggtc gcagctccag ccgcctcctc cgcgcagccg 60
ccgcctcagc tgctcgctct gtgggtcggt cctctccggc acttgggctc cagtcgcgcc 120
ctccaagccc ttcaggccgc cccagtgtcc tcctccttct ccggccagac ccagccccgc 180
gaagatggtg gaccgcgagc aactggtgca gaaagcccgg ctggccgagc aggcggagcg 240
ctacgacgac atggccgcgg ccatgaagaa cgtgacagag ctgaatgagc cactgtcgaa 300
tgaggaacga aaccttctgt ctgtggccta caagaacgtt gtgggggcac gccgctcttc 360
ctggagggtc atcagtagca ttgagcagaa gacatctgca gacggcaatg agaagaagat 420
tgagatggtc cgtgcgtacc gggagaagat agagaaggag ttggaggctg tgtgccagga 480
tgtgctgagc ctgctggata actacctgat caagaattgc agcgagaccc agtacgagag 540
caaagtgttc tacctgaaga tgaaagggga ctactaccgc tacctggctg aagtggcc 598

<210> SEQ ID NO 274
<211> LENGTH: 536
<212> TYPE: DNA
<213> ORGANISM: Homo sapiens

<400> SEQUENCE: 274
gcaccaagag actaaacaag aaagtggatc agggaagaag aaagcttcat caaagaaaca 60
aaagacagaa aatgtcttcg tagatgaacc ccttattcat gcaactactt atattccttt 120
gatggataat gctgactcaa gtcctgtggt agataagaga gaggttattg atttgcttaa 180
acctgaccaa gtagaaggga tccagaaatc tgggactaaa aaactgaaga ccgaaactga 240
caaagaaaat gctgaagtga agtttaaaga ttttcttctg tccttgaaga ctatgatgtt 300
ttctgaagat gaggctcttt gtgttgtaga cttgctaaag gagaagtctg gtgtaataca 360

-continued

```
agatgcttta aagaagtcaa gtaagggaga attgactacg cttatacatc agcttcaaga    420

aaaggacaag ttactcgctg ctgtgaagga agatgctgct gctacaaagg atcggtgtaa    480

gcagttaacc caggaaatga tgacagagaa agaaagaagc aatgtggtta taacaa        536
```

<210> SEQ ID NO 275
<211> LENGTH: 494
<212> TYPE: DNA
<213> ORGANISM: Homo sapiens
<220> FEATURE:
<221> NAME/KEY: misc_feature
<222> LOCATION: (379)
<223> OTHER INFORMATION: n=A,T,C or G

<400> SEQUENCE: 275

```
gaattcggca ccagggtcgc ggttcttgtt tgtggatcgc tgtgatcgtc acttgacaat     60

gcagatcttc gtgaagactc tgactggtaa gaccatcacc ctcgaggttg agcccagtga    120

caccatcgag aatgtcaagg caaagatcca agataaggaa ggcatccctc ctgaccagca    180

gaggctgatc tttgctggaa aacagctgga agatgggcgc accctgtctg actacaacat    240

ccagaaagag tccaccctgc acctggtgct ccgtctcaga ggtgggatgc aaatcttcgt    300

gaagacactc actggcaaga ccatcaccct tgaggtggag cccagtgaca ccatcgagaa    360

cgtcaaagca aagatccang acaaggaagg cattcctcct gaccagcaga ggttgatctt    420

tgccggaaag cagctggaag atgggcgcac cctgtctgac tacaacatcc agaaagagtc    480

taccctgcac ctgg                                                      494
```

<210> SEQ ID NO 276
<211> LENGTH: 484
<212> TYPE: DNA
<213> ORGANISM: Homo sapiens

<400> SEQUENCE: 276

```
ggcttttaac cagaagtcaa acctgttcag acagaaggca gtcacagcag aaaaatcttc     60

agacaaaagg cagtcacagg tgtgcaggga gtgtgggcga ggctttagca ggaagtcaca    120

gctcatcata caccagagga cacacacagg agaaaagcct tatgtctgcg gagagtgtgg    180

gcgaggcttt atagttgagt cagtcctccg caaccacctg agtacacact ccggggagaa    240

accttatgtg tgcagccatt gtgggcgagg ctttagctgc aagccatacc tcatcagaca    300

tcagaggaca cacacaaggg agaaatcgtt tatgtgcaca gtgtgtgggc gaggctttcg    360

tgaaaagtca gagctcatta agcaccagag aattcacacg ggggataagc cttatgtgtg    420

cagagattga ggccgaggct ttgtaaagga gatcatgtct caacacacac cagaggatta    480

catt                                                                 484
```

<210> SEQ ID NO 277
<211> LENGTH: 513
<212> TYPE: DNA
<213> ORGANISM: Homo sapiens

<400> SEQUENCE: 277

```
gcttgaggct gccaatcaga gcttggcaga gctgagagat cagcggcagg gggagcgcct     60

ggaacatgca gcagctttgc gggccctaca agatcaggta tccatccaga gtgcagatgc    120

acaggaacaa gtggaagggc ttttggctga gaacaatgcc ttgaggacta gcctggctgc    180

cctggagcag atccaaacag caaagaccca agaactgaat atgctccggg aacagaccac    240
```

-continued

```
tgggctggca gctgagttgc agcagcagca ggctgagtac gaggacctta tgggacagaa    300

agatgacctc aactcccagc tccaggagtc attacgggcc aatagtcgac tgctggaaca    360

acttcaagaa atagggcagg agaaggagca gttgacccag gaattacagg aggctcggaa    420

gagtgcggag aagcggaagg ccatgcttgg atgagctagc aatggaaacg ctgcaagaga    480

agtcccacac aaggaagagc ttgggagcag ttc                                 513
```

```
<210> SEQ ID NO 278
<211> LENGTH: 471
<212> TYPE: DNA
<213> ORGANISM: Homo sapiens

<400> SEQUENCE: 278

gaattcggca ccagccaagg ccctgtccct ggctcgggcc cttgaagagg ccttggaagc     60

caaagaggaa ctcgagcgga ccaacaaaat gctcaaagcc gaaatggaag acctggtcag    120

ctccaaggat gacgtgggca agaacgtcca tgagctggag aagtccaagc gggccctgga    180

gacccagatg gaggagatga agacgcagct ggaagagctg gaggacgagc tgcaagccac    240

ggaggacgcc aaactgcggc tggaagtcaa catgcaggcg ctcaagggcc agttcgaaag    300

ggatctccaa gcccgggacg agcagaatga ggagaagagg aggcaactgc agagacagct    360

tcacgagtat gagacggaac tggaagacga gcgaaagcaa cgtgccctgg cagctgcagc    420

aaagaagaag ctggaagggg acctgaaaga cctggagctt caggccgact t             471
```

```
<210> SEQ ID NO 279
<211> LENGTH: 497
<212> TYPE: DNA
<213> ORGANISM: Homo sapiens
<220> FEATURE:
<221> NAME/KEY: misc_feature
<222> LOCATION: (457)
<223> OTHER INFORMATION: n=A,T,C or G
<220> FEATURE:
<221> NAME/KEY: misc_feature
<222> LOCATION: (471)
<223> OTHER INFORMATION: n=A,T,C or G

<400> SEQUENCE: 279

gaattcggca cgaggccaca gaggcggcgg agagatggcc ttcagcggtt cccaggctcc     60

ctacctgagt ccagctgtcc ccttttctgg gactattcaa ggaggtctcc aggacggact    120

tcagatcact gtcaatggga ccgttctcag ctccagtgga accaggtttg ctgtgaactt    180

tcagactggc ttcagtggaa atgacattgc cttccacttc aaccctcggt ttgaagatgg    240

agggtacgtg gtgtgcaaca cgaggcagaa cggaagctgg gggcccgagg agaggaagac    300

acacatgcct ttccagaagg ggatgccctt tgacctctgc ttcctggtgc agagctcaga    360

tttcaaggtg atggtgaacg ggatcctctt cgtgcagtac ttccaccgcg tgcccttcca    420

ccgtgtggac accatctccg tcaatggctc tgtgcanctg tcctacatca ncttccagac    480

ccagacagtc atccaca                                                   497
```

```
<210> SEQ ID NO 280
<211> LENGTH: 544
<212> TYPE: DNA
<213> ORGANISM: Homo sapiens
<220> FEATURE:
<221> NAME/KEY: misc_feature
<222> LOCATION: (451)
<223> OTHER INFORMATION: n=A,T,C or G

<400> SEQUENCE: 280
```

```
gaattcggca ccagaatagg aacagctccg gtctacagct cccagcgtga gcgacgcaga      60

agacgggtga tttctgcatt tccatctgag gtaccgggtt catctcacta gggagtgcca     120

gacagtgggc gcaggccagt gtgtgtgcgc accgtgcgcg agccgaagca gggcgaggca     180

ttgcctcacc tgggaagcac aaggggtcag ggagttccct ttccgagtca aagaaagggg     240

tgacggacgc acctggaaaa tcgggtcact cccacccgaa tattgtgctt ttcagaccgg     300

cttaagaaac ggcgcaccac gagactatat cccacacctg gctcagaggg tcctacgccc     360

acggaatctc gctgattgct agcacagcag tcttagatca aactgcaagg ggggcaacga     420

ggctgggggga ggggcgcccg ccattgccca ngcttgctta ggtaaacaaa gcagccggga     480

agcttgaact gggtggagcc caccacagct caaggaggcc tgcctgcctc tgtagctcca     540

cctc                                                                  544
```

<210> SEQ ID NO 281
<211> LENGTH: 527
<212> TYPE: DNA
<213> ORGANISM: Homo sapiens
<220> FEATURE:
<221> NAME/KEY: misc_feature
<222> LOCATION: (456)
<223> OTHER INFORMATION: n=A,T,C or G

<400> SEQUENCE: 281

```
gaattcggca cgaggcctcg ctcagctcca acatggcaaa aatctccagc cctacagaga      60

ctgagcggtg catcgagtcc ctgattgctg tcttccagaa gtatgctgga aaggatggtt     120

ataactacac tctctccaag acagagttcc taagcttcat gaatacagaa ctagctgcct     180

tcacaaagaa ccagaaggac cctggtgtcc ttgaccgcat gatgaagaaa ctggacacca     240

acagtgatgg tcagctagat ttctcagaat ttcttaatct gattggtggc ctagctatgg     300

cttgccatga ctccttcctc aaggctgtcc cttcccagaa gcggacctga ggacccccttg     360

gccctggcct tcaaacccac cccctttcct tccagccttt ctgtcatcat ctccacagcc     420

cacccatccc ctgagcacac taaccacctc atgcanggcc cccctgccaa tagtaataaa     480

gcaatgtcct tttttaaaac atgaaaaaaa aaaaaaaaaa actcgag                   527
```

<210> SEQ ID NO 282
<211> LENGTH: 514
<212> TYPE: DNA
<213> ORGANISM: Homo sapiens
<220> FEATURE:
<221> NAME/KEY: misc_feature
<222> LOCATION: (494)
<223> OTHER INFORMATION: n=A,T,C or G

<400> SEQUENCE: 282

```
ggaagactgg agcctttgcg gcggcgctgc ccctcccctg gtccccgcga gctcggaggg      60

cccggctggt gctgcggggg ccccgggagg ttgaaaacta agcatgggga agagctgcaa     120

ggtggtcgtg tgtggccagg cgtctgtggg caaaacttca atcctggagc agcttctgta     180

tgggaaccat gtagtgggtt cggagatgat cgagacgcag gaggacatct acgtgggctc     240

cattgagaca gaccgggggg tgcgagagca ggtgcgtttc tatgacaccc gggggctccg     300

agatggggcc gaactgcccc gacactgctt ctcttgcact gatggctacg tcctggtcta     360

tagcacagat agcagagagt cttttcagcg tgtggagctg ctcaagaagg agattgacaa     420

atccaaggac aagaaggagg tcaccatcgt ggtccttggc aacaagtgtg acttacagga     480
```

-continued gcagcggcgt gtanacccaa atgtggctca acac 514

<210> SEQ ID NO 283
<211> LENGTH: 484
<212> TYPE: DNA
<213> ORGANISM: Homo sapiens

<400> SEQUENCE: 283
gggcgggcgg tggacagtca tggcggcccg gcgcggggct ctcatagtgc tggagggcgt 60
ggaccgcgcc gggaagagca cgcagagccg caagctggtg gaagcgctgt gcgccgcggg 120
ccaccgcgcc gaactgctcc ggttcccgga aagatcaact gaaatcggca aacttctgag 180
ttcctacttg caaaagaaaa gtgacgtgga ggatcactcg gtgcacctgc ttttttctgc 240
aaatcgctgg gaacaagtgc cgttaattaa ggaaaagttg agccagggcg tgaccctcgt 300
cgtggacaga tacgcatttt ctggtgtggc cttcaccggt gccaaggaga atttttccct 360
agactggtgt aaacagccag acgtgggcct tcccaaaccc gacctggtcc tgttcctcca 420
gttacagctg gcggatgctg ccaagcgggg agcgtttggc catgagcgct atgagaacgg 480
ggct 484

<210> SEQ ID NO 284
<211> LENGTH: 514
<212> TYPE: DNA
<213> ORGANISM: Homo sapiens

<400> SEQUENCE: 284
gaattcggca cgaggcggag gccgcggagg ctcctcggtc cttcagcacc cctcggcccg 60
acgcacccac gcccctcacc ccccgagagc cgaaaatgga cccaagtggg gtcaaagtgc 120
tggaaacagc agaggacatc caggagaggc ggcagcaggt cctagaccga taccaccgct 180
tcaaggaact ctcaaccctt aggcgtcaga agctggaaga ttcctatcga ttccagttct 240
ttcaaagaga tgctgaagag ctggagaaat ggatacagga aaaacttcag attgcatctg 300
atgagaatta taaagaccca accaacttgc agggaaagct tcagaagcat caagcatttg 360
aagctgaagt gcaggccaac tcaggagcca ttgttaagct ggatgaaact ggaaacctga 420
tgatctcaga agggcatttt gcatctgaaa ccatacggac ccgtttgatg gagctgcacc 480
gccagtggga attacttttg gagaagatgc gaga 514

<210> SEQ ID NO 285
<211> LENGTH: 383
<212> TYPE: DNA
<213> ORGANISM: Homo sapiens

<400> SEQUENCE: 285
gaattcggca cgaggccggg ctccaccgcg catcctgctc cactctggcg accgcccccg 60
gggcccccgc cgcgggcgcg gcgcccgcca tgggcgagga ggactactat ctggagctgt 120
gcgagcggcc ggtgcagttc gagaaggcga accctgtcaa ctgcgtcttc ttcgatgagg 180
ccaacaagca ggtttttgct gttcgatctg gtggagctac tggcgtggta gttaaaggcc 240
cagatgatag gaatcccatc tcatttagaa tggatgacaa aggagaagtg aagtgcatta 300
agttttcctt agaaaataag atattggctg ttcagaggac ctcaaagact gtggattttt 360
gtaattttat ccctgataat tcc 383

<210> SEQ ID NO 286
<211> LENGTH: 943

-continued

<212> TYPE: DNA
<213> ORGANISM: Homo sapiens

<400> SEQUENCE: 286
gaattcggca ccagggccgt ggcggaggag gagcgctgca cggtggagcg tcgggccgac 60
ctcacctacg cggagttcgt gcagcagtac gtgcgcccct gatcgcggag gtcgcgtcct 120
gttcaccggc ccgtctgccc cgaccgccca aggccgcctt cccctgacct cgcgcgcacg 180
cgtggggctg gggcggcgag gctggcggtc cggcctggcc gcgactctgc ccttctttcc 240
agaggttccg ggccctgtgc tcccgcgaca ggttgctggc ttcgtttggg gacagagtgg 300
tccggctgag caccgccaac acctactcct accacaaagt ggacttgccc ttccaggagt 360
atgtggagca gctgctgcac ccccaggacc ccacctccct gggcaatggt gaggcagccc 420
taggcggcgg tagggggtgg ggacgcttgg agtctccagg tgccaggatc cctgtccccg 480
ccgtctctgt tggcagacac cctgtacttc ttcggggaca acaacttcac cgagtgggcc 540
tctctctttc ggcactactc cccacccccca tttggcctgc tgggaaccgc tccagcttac 600
agctttggaa tcgcaggagc tggctcgggg gtgcccttcc actggcatgg acccgggtac 660
tcagaagtga tctacggtcg taagcgctgg ttcctttacc cacctgagaa gacgccagag 720
ttccacccca acaagaccac actggcctgg ctccgggaca catacccagc cctgccaccg 780
tctgcacggc ccctggagtg taccatccgg gctggtgagg tgctgtactt ccccgaccgc 840
tggtggcatg ctacgctcaa ccttgacacc agcgtcttca tctccacctt cctcggctag 900
ccaaaacagc tggcaggact gccggtcaca caccagcacg tcc 943

<210> SEQ ID NO 287
<211> LENGTH: 1143
<212> TYPE: DNA
<213> ORGANISM: Homo sapiens

<400> SEQUENCE: 287
gaattcggca cgagggaaga acagctgttg gaacaacaag aatatttaga aaaagaaatg 60
gaggaagcaa agaaaatgat atcaggacta caggccttac tgctcaatgg atccttacct 120
gaagatgaac aggagaggcc cttggccctc tgtgaaccag gtgtcaatcc cgaggaacaa 180
ctgattataa tccaaagtcg tctggatcag agtatggagg agaatcagga cttaaagaag 240
gaactgctga aatgtaaaca agaagccaga aacttacagg ggataaagga tgccttgcag 300
cagagattga ctcagcagga cacatctgtt cttcagctca aacaagagct actgagggca 360
aatatggaca aagatgagct gcacaaccag aatgtggatc tgcagaggaa gctagatgag 420
aggaaccggc tcttgggaga atataaaaaa gagctggggc agaaggatcg ccttcttcag 480
cagcaccagg ccaagttaga agaagcactc cggaaactct ctgatgtcag ttaccaccag 540
gtggatctag agcgagagct agaacacaaa gatgtcctct tggctcactg tatgaaaaga 600
gaggcagatg aggcgaccaa ctacaacagt cacaactctc aaagcaatgg ttttctcctt 660
ccaacggcag gaaaaggagc tacttcagtc agcaacagag ggaccagcga cctgcagctt 720
gttcgagatg ctctccgcag cctgcgcaac agcttcagtg gccacgatcc tcagcaccac 780
actattgaca gcttggagca gggcatttct agcctcatgg agcgcctgca tgttatggag 840
acgcagaaga aacaagaaag aaaggttcgg gtcaagtcac ccagaactca agtaggtagt 900
gaataccggg agtcctggcc ccctaactca aagttgcctc actcacagag ctctccaact 960
gtcagcagca cctgtactaa agtgctctat ttcactgacc ggtcacttac gcccttcatg 1020

-continued gtcaatatac caaagaggtt ggaggaggtg acgttaaagg attttaaagc agctattgat 1080
cgggaaggaa atcaccggta tcacttcaaa gcactggatc ctgagtttgg cactgtcaaa 1140
gag 1143

<210> SEQ ID NO 288
<211> LENGTH: 881
<212> TYPE: DNA
<213> ORGANISM: Homo sapiens

<400> SEQUENCE: 288
gtgagagcgg gccgaggaga ttggcgacgg tgtcgcccgt gttttcgttg gcgggtgcct 60
gggctggtgg gaacagccgc ccgaaggaag caccatgatt tcggccgcgc agttgttgga 120
tgagttaatg ggccgggacc gaaacctagc cccggacgag aagcgcagca acgtgcggtg 180
ggaccacgag agcgtttgta aatattatct ctgtggtttt tgtcctgcgg aattgttcac 240
aaatacacgt tctgatcttg gtccgtgtga aaaaattcat gatgaaaatc tacgaaaaca 300
gtatgagaag agctctcgtt tcatgaaagt tggctatgag agagattttt tgcgatactt 360
acagagctta cttgcagaag tagaacgtag gatcagacga ggccatgctc gtttggcatt 420
atctcaaaac cagcagtctt ctggggccgc tggcccaaca ggcaaaaatg aagaaaaaat 480
tcaggttcta acagacaaaa ttgatgtact tctgcaacag attgaagaat tagggtctga 540
aggaaaagta gaagaagccc aggggatgat gaaattagtt gagcaattaa aagaagagag 600
agaactgcta aggtccacaa cgtcgacaat tgaaagcttt gctgcacaag aaaaacaaat 660
ggaagtttgt gaagtatgtg gagccttttt aatagtagga gatgcccagt cccgggtaga 720
tgaccatttg atgggaaaac aacacatggg ctatgccaaa attaaagcta ctgtagaaga 780
attaaaagaa aagttaagga aaagaaccga agaacctgat cgtgatgagc gtctaaaaaa 840
ggagaagcaa gaaagagaaa aaaaaaaaaa aaaaactcga g 881

<210> SEQ ID NO 289
<211> LENGTH: 987
<212> TYPE: DNA
<213> ORGANISM: Homo sapiens

<400> SEQUENCE: 289
gaattcggca cgagggactg tggtttccag gaatggtggc gtctcacgct tcttgtgctt 60
tttcctttgg ggcctccgag cggctggggt tgggggactg ggcaggaggc tccctgtaaa 120
catttggact tgggctgggg caggggctgg tgttgggcaa agctgggggt ccaggctgga 180
gaagcagggg cccctccaga cgcagccttg ggagactcag catgtgcccc cctcccctca 240
tcacagaaca agacaatggt taaaaaccag aacagatgcc cagaaggggg taccatggcc 300
attaccagca tctcagacaa gggcaggctt caaacaggga ggcctgtggc aacccctccc 360
ctacgtctgg agctgagggg acagggggag ctgagaacaa agagaggaaa gaggagaaaa 420
gcggcggggg aacaggcggg gagcgtgatc ttcttgcccc catcttcctc aggggttggg 480
gggtacaaag tcggcggtgg cccatcccgc caggccccgc tgcccctcag aagaggccgc 540
agtccttcag gttgttcttg atgatgacat cggtgacggc gtcaaacacg aactgcacgt 600
tcttggtgtc ggtggcgcac gtgaagtgcg tgtagatctc cttggtgtct ttgcgcttat 660
tcaggtcctc aaacttactc tggatgtagc tggctgcctc atcatatttg ttggcccctg 720
tatactcagg gaagcagatg gtcaggggac tgtgtgtgat cttctcctca aacaggtcct 780
tcttgttgag gaagaggatg atggacgtgt ctgtgaacca cttgttgttg cagatgctat 840

-continued

```
cgaatagctt catgctctca tgcatgcggt tcatctcctc gtcctcagct agcaccaagt    900

cataggcgct caaggctacg cagaagatga tggctgtgac gccctcaaag cagtggatcc    960

acttcttccg ctcagaccgc tgaccac                                        987
```